US012138304B2

United States Patent
Henderson et al.

(10) Patent No.: US 12,138,304 B2
(45) Date of Patent: Nov. 12, 2024

(54) HIV-1 ENVELOPE STABILIZING MUTATIONS

(71) Applicant: Duke University, Durham, NC (US)

(72) Inventors: Rory Henderson, Durham, NC (US); S. Munir Alam, Durham, NC (US); Barton F. Haynes, Durham, NC (US); Kevin J. Wiehe, Durham, NC (US)

(73) Assignee: Duke University, Durham, NC (US)

( * ) Notice: Subject to any disclaimer, the term of this patent is extended or adjusted under 35 U.S.C. 154(b) by 660 days.

(21) Appl. No.: 17/281,918

(22) PCT Filed: Sep. 5, 2019

(86) PCT No.: PCT/US2019/049662
§ 371 (c)(1),
(2) Date: Mar. 31, 2021

(87) PCT Pub. No.: WO2020/072169
PCT Pub. Date: Apr. 9, 2020

(65) Prior Publication Data
US 2021/0379177 A1    Dec. 9, 2021

Related U.S. Application Data

(60) Provisional application No. 62/739,727, filed on Oct. 1, 2018.

(51) Int. Cl.
*A61K 39/12* (2006.01)
*C07K 14/16* (2006.01)
*C12N 7/00* (2006.01)
*C12N 15/63* (2006.01)

(52) U.S. Cl.
CPC ........... *A61K 39/12* (2013.01); *C07K 14/162* (2013.01); *C12N 7/00* (2013.01); *C12N 15/63* (2013.01); *C12N 2740/16122* (2013.01); *C12N 2740/16134* (2013.01)

(58) Field of Classification Search
CPC ...................... A61K 39/12; C12N 2740/16122
See application file for complete search history.

(56) References Cited

U.S. PATENT DOCUMENTS

| | | | |
|---|---|---|---|
| 5,792,459 | A | 8/1998 | Haigwood |
| 7,951,377 | B2 | 5/2011 | Korber et al. |
| 8,071,107 | B2 | 12/2011 | Haynes et al. |
| 9,872,900 | B2 | 1/2018 | Ciaramella et al. |
| 2003/0147888 | A1 | 8/2003 | Haynes et al. |
| 2006/0051373 | A1 | 3/2006 | Olson et al. |
| 2009/0286852 | A1 | 11/2009 | Kariko et al. |
| 2010/0015218 | A1 | 1/2010 | Jadhav et al. |
| 2010/0041875 | A1 | 2/2010 | Dey et al. |
| 2011/0076298 | A1 | 3/2011 | Olson et al. |
| 2011/0250220 | A1 | 10/2011 | Dey et al. |
| 2011/0262488 | A1 | 10/2011 | Phogat et al. |
| 2012/0052090 | A1 | 3/2012 | Tamamura et al. |
| 2013/0111615 | A1 | 5/2013 | Kariko et al. |
| 2013/0197068 | A1 | 8/2013 | Kariko et al. |
| 2013/0261172 | A1 | 10/2013 | Kariko et al. |
| 2014/0328862 | A1 | 11/2014 | Scheid et al. |
| 2015/0038558 | A1 | 2/2015 | Kariko et al. |
| 2016/0032316 | A1 | 2/2016 | Weissman et al. |
| 2016/0271244 | A1 | 9/2016 | Haynes et al. |
| 2017/0043037 | A1 | 2/2017 | Kariko et al. |
| 2017/0233441 | A1 | 8/2017 | Kwong et al. |
| 2017/0327842 | A1 | 11/2017 | Weissman et al. |
| 2017/0369532 | A1 | 12/2017 | Carfi et al. |
| 2018/0028645 | A1 | 2/2018 | Ciaramella et al. |
| 2018/0072777 | A1 | 3/2018 | Rutten et al. |

FOREIGN PATENT DOCUMENTS

| | | |
|---|---|---|
| CA | 2944068 A1 | 10/2015 |
| EP | 0272858 A2 | 6/1988 |
| EP | 1466924 A1 | 10/2004 |
| EP | 1738764 A1 | 1/2007 |
| WO | WO-07/149491 A2 | 12/2007 |
| WO | WO-10/031113 A1 | 3/2010 |
| WO | WO-2013/006688 A2 | 1/2013 |
| WO | WO-14/42669 A1 | 3/2014 |
| WO | WO-14/043386 A1 | 3/2014 |
| WO | WO-2014/172366 A1 | 10/2014 |
| WO | WO-2015/127108 A1 | 8/2015 |
| WO | WO-2015/153638 A1 | 10/2015 |
| WO | WO-16/037154 A1 | 3/2016 |
| WO | WO-2016/149695 A1 | 9/2016 |
| WO | WO-17/151801 A1 | 9/2017 |
| WO | WO-17/0152146 A2 | 9/2017 |

(Continued)

OTHER PUBLICATIONS

Henderson, R., et al., "Disruption of the HIV-1 Envelope allosteric network blocks CD4-induced rearrangements," Nature Communications, vol. 11, No. 520, pp. 1-14 (2020).
"FASTX-Toolkit", downloaded from http://hannonlab.cshl.edu/fastx_toolkit, last retrieved Nov. 4, 2020 (2 total pages).
"Models of SHM Targeting and Substitution—SF5 Mutability Model dataset" last downloaded Feb. 2, 2021 from; http://clip.med.yale.edu/shm/download.php (2 total pages).

(Continued)

*Primary Examiner* — Jeffrey S Parkin
(74) *Attorney, Agent, or Firm* — Baker Donelson

(57) ABSTRACT

The technology is directed to HIV envelopes which comprise sequence modifications wherein these modifications prevent CD4-induced transitions of the HIV envelope. Specifically, the disclosure provides recombinant HIV-1 Env proteins comprising mutations, wherein the envelope is a protomer, and wherein three protomers form a trimer stabilized by the presence of the mutations. Provided also are compositions comprising envelopes of the technology, and methods of use.

12 Claims, 84 Drawing Sheets

Specification includes a Sequence Listing.

(56) References Cited

FOREIGN PATENT DOCUMENTS

| | | |
|---|---|---|
| WO | WO-18/067580 A1 | 4/2018 |
| WO | WO-18/161049 A1 | 9/2018 |
| WO | WO-19/169356 A1 | 9/2019 |
| WO | WO-20/72162 A1 | 4/2020 |
| WO | WO-20/72169 A1 | 4/2020 |

OTHER PUBLICATIONS

Alam, S. M., et al., "Antigenicity and Immunogenicity of RV144 Vaccine AIDSVAX Clade E Envelope Immunogen Is Enhanced by a gp120 N-Terminal Deletion," Journal of Virology, vol. 87, No. 3, pp. 1554-1568 (Feb. 2013).

Alam, S.M., et al., "Human Immunodeficiency Virus Type 1 gp41 Antibodies That Mask Membrane Proximal Region Epitopes: Antibody Binding Kinetics, Induction, and Potential for Regulation in Acute Infection," J. Virol., vol. 82, No. 1, pp. 115-125 (Jan. 2008).

Alam, S.M., et al., "Mimicry of an HIV broadly neutralizing antibody epitope with a synthetic glycopeptide," Sci. Transl. Med., vol. 9, No. 381, eaai7521, Mar. 15, 2017 (Author Manuscript—20 total pages—available in PMC Aug. 18, 2017).

Alam, S.M., et al., "Recognition of synthetic glycopeptides by HIV-1 broadly neutralizing antibodies and their unmutated ancestors," PNAS, vol. 110, No. 45, pp. 18214-18219 (Nov. 5, 2013)—last downloaded Oct. 6, 2020 from https://www.pnas.org/content/110/45/18214 (24 total pages).

Alam, S.M., et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes," J. Immunol., vol. 178, pp. 4424-4435 (accepted for publication Jan. 12, 2007) (13 total pages).

Alam, S. M., et al., "Role of HIV membrane in neutralization by two broadly neutralizing antibodies", PNAS, vol. 106, No. 48, pp. 20234-20239 (Dec. 1, 2009).

Alving, C.R., et al., "Adjuvants for human vaccines," Current Opinion in Immunology, vol. 24, No. 3, pp. 310-315, (Jun. 2012), Author Manuscript available in PMC Jun. 1, 2013 (12 total pages).

Andrabi, R., et al., "Identification of Common Features in Prototype Broadly Neutralizing Antibodies to HIV Envelope V2 Apex to Facilitate Vaccine Design," Immunity, vol. 43, No. 5, pp. 959-973 (Nov. 2015)—Author Manuscript available in PMC Nov. 17, 2016 (25 total pages).

Arnaoty, A., et al., "Novel Approach for the Development of New Antibodies Directed Against Transposase-Derived Proteins Encoded by Human Neogenes," Yves Bigot (ed.), Mobile Genetic Elements: Protocols and Genomic Applications, Methods in Molecular Biology, vol. 859, Chapter 17, pp. 293-305 (2012).

Arnaoty, Ahmed, et al., "Reliability of the nanopheres-DNA immunization technology to produce polyclonal antibodies directed against human neogenic proteins," Mol. Genet. Genomics, vol. 288, pp. 347-363 (2013).

Aussedat, B., et al., "Chemical synthesis of highly congested gp120 V1V2 N-glycopeptide antigens for potential HIV-1-directed vaccines," J. Am. Chem. Soc., vol. 135, No. 35, Sep. 2013 (Author Manuscript—16 total pages—available in PMC Sep. 4, 2014).

Bamrungsap, S. et al., "Nanotechnology in therapeutics: a focus on nanoparticles as a drug delivery system," Nanomedicine, vol. 7, No. 8, pp. 1253-1271 (2012).

Barouch, D. H., et al., "Mosaic HIV-1 Vaccines Expand the Breadth and Depth of Cellular Immune Responses in Rhesus Monkeys," Nature Medicine, vol. 16, No. 3, pp. 319-323, Mar. 2010 (Author Manuscript—15 total pages—available in PMC Sep. 1, 2010).

Batista, F.D., et al., "B cells extract and present immobilized antigen: implications for affinity discrimination," The EMBO Journal, vol. 19, No. 4, pp. 513-520 (2000).

Behrens, A.J., et al. "Composition and Antigenic Effects of Individual Glycan Sites of a Trimeric HIV-1 Envelope Glycoprotein," Cell Rep. vol. 14, pp. 2695-2706 with cover page—13 total pages (Mar. 22, 2016).

Betz, A G., "Passenger transgenes reveal intrinsic specificity of the antibody hypermutation mechanism: Clustering, polarity, and specific hot spots," Proceedings of the National Academy of Sciences of the United States of America, vol. 90, pp. 2385-2388 (Mar. 1993).

Bhattacharya, T., et al., "Founder Effects in the Assessment of HIV Polymorphisms and HLA Allele Associations," Science, vol. 315, No. 5818, pp. 1583-1586, Apr. 2007 (last downloaded Oct. 6, 2020 from https://www.researchgate.net/publication/6442933_Founder_Effects_in_the_Assessment_of_HIV_Polymorphisms_and_HLA_Allele_Associations—10 total pages).

Binley, J.M., et al., "Enhancing the Proteolytic Maturation of Human Immunodeficiency Virus Type 1 Envelope Glycoproteins," Journal of Virology, vol. 76, No. 6, pp. 2606-2616 (Mar. 2002).

Bonsignori, M., et al. "Staged induction of HIV-1 glycan-dependent broadly neutralizing antibodies" Sci Transl Med., vol. 9, No. 381, pp. 1-26, Mar. 15, 2017 (Author Manuscript—available in PMC Aug. 18, 2017—26 total pages).

Bonsignori, M., et al., "Analysis of a Clonal Lineage of HIV-1 Envelope V2/V3 Conformational Epitope-Specific Broadly Neutralizing Antibodies and Their Inferred Unmutated Common Ancestors," Journal of Virology, vol. 85, No. 19, pp. 9998-10009 (Oct. 2011).

Bonsignori, M., et al., "Maturation Pathway from Germline to Broad HIV-1 Neutralizer of a CD4-Mimic Antibody," Cell, vol. 165, pp. 449-463 with cover page—16 total pages (Apr. 7, 2016).

Bonsignori, M., et al., "Two distinct broadly neutralizing antibody specificities of different clonal lineages in a single HIV-1-infected donor: implications for vaccine design," Journal of Virology, vol. 86, No. 8, pp. 4688-4692 (published online Feb. 1, 2012).

Bosch, V., et al., "Mutational Analysis of the Human Immunodeficiency Virus Type 1 env Gene Product Proteolytic Cleavage Site," Journal of Virology, vol. 64, No. 5, pp. 2337-2344 (May 1990).

Bransteitter, R., et al., "Biochemical analysis of Hypermutational Targeting by Wild Type and Mutant Activation-induced Cytidine Deaminase," The Journal of Biological Chemistry, vol. 279, No. 49, pp. 51612-51621 with cover page—11 pages total (Sep. 14, 2004).

Burton D. R. , "Antibody responses to envelope glycoproteins in HIV-1 infection," Nature immunology, vol. 16, No. 6, pp. 571-576, Jun. 2015 (Author Manuscript—17 total pages—available in PMC Apr. 18, 2016).

Burton, D.R., et al. "Broadly Neutralizing Antibodies to HIV and Their Role in Vaccine Design," Annu Rev Immunol, vol. 34, pp. 635-659, May 2016 (Author Manuscript—31 total pages—available in PMC Jul. 6, 2018).

Cany, J., et al., "AFP-specific immunotherapy impairs growth of autochthonous hepatocellular carcinoma in mice," Journal of Hepatology, vol. 54, pp. 115-121 (2011).

Center, R.J., et al., "Oligomeric structure of the human immunodeficiency virus type 1 envelope protein on the virion surface," Journal of Virology, vol. 76, No. 15, pp. 7863-7867 (Aug. 2002).

Chakrabarti, B.K., et al., "Modifications of the Human Immunodeficiency Virus Envelope Glycoprotein Enhance Immunogenicity for Genetic Immunization," Journal of Virology, vol. 76, No. 11, pp. 5357-5368 (Jun. 2002).

Churchyard, G.J., et al., A Phase IIA Randomized Clinical Trial of a Multiclade HIV-1 DNA Prime Followed by a Multiclade rAd5 HIV-1 Vaccine Boost in Healthy Adults (HVTN204), PLoS One, vol. 6, No. 8, e21225, Aug. 2011 (last downloaded on Jan. 19, 2021 from https://journals.plos.org/plosone/article?id=10.1371/journal.pone.0021225—10 total pages).

Cloanalyst Software, Boston University—Microbiology, Laboratory of Computation Immunology, downloaded from http://www.bu.edu/computationalimmunology/research/software (3 total pages) last retrieved Oct. 5, 2020.

Cowell, L. G. and Kepler, T.B., "The nucleotide-replacement spectrum under somatic hypermutation exhibits microsequence dependence that is strand-symmetric and distinct from that under germline mutation," Journal of Immunology, vol. 164, pp. 1971-1976 (2000).

De Taeye, S. W., et al., "Immunogenicity of stabilized HIV-1 envelope trimers with reduced exposure of non-neutralizing epitopes," Cell., vol. 163, No. 7, pp. 1702-1715, Dec. 17, 2015 (Author Manuscript—25 total pages—available in PMC Jan. 29, 2016).

(56) References Cited

OTHER PUBLICATIONS

DeCamp, A., et al. "Global panel of HIV-1 Env reference strains for standardized assessments of vaccine-elicited neutralizing antibodies," J Virol, vol. 88, No. 5, pp. 2489-2507 (Mar. 2014).

Dennison, S.M., et al., "Induction of Antibodies in Rhesus Macaques That Recognize a Fusion-Intermediate Conformation of HIV-1 gp41," Public Library of Science ONE, vol. 6, No. 11, e27824, pp. 1-14 (Nov. 30, 2011).

Dennison, S.M., et al., "Nonneutralizing HIV-1 gp4 | envelope cluster II human monoclonal antibodies show polyreactivity for binding to phospholipids and protein autoantigens," J. Virol. vol., 85, No. 3, pp. 1340-1347 (Feb. 2011).

Dennison, S.M., et al., "Stable Docking of Neutralizing Human Immunodeficiency Virus Type 1 gp41 Membrane-Proximal External Region Monoclonal Antibodies 2F5 and 4E10 Is Dependent on the Membrane Immersion Depth of Their Epitope Regions," Journal of Virology, vol. 83., No. 19, pp. 10211-10223 (Oct. 2009).

Di Noia, J.M., et al., "Molecular mechanisms of antibody somatic hypermutation," Annu Rev Biochem, vol. 76, pp. 1-22 including TOC—25 total pages (published online Feb. 28, 2007).

Doores, K. J., et al., "Two Classes of Broadly Neutralizing Antibodies within a Single Lineage Directed to the High-Mannose Patch of HIV Envelope," Journal of Virology, vol. 89, No. 2, pp. 1105-1118 (Jan. 2015) with Author Correction (Journal of Virology, vol. 89, No. 12, p. 6525, Jun. 2015).

Doria-Rose, N.A., et al., "Developmental pathway for potent V1V2-directed HIV-neutralizing antibodies," Nature, vol. 509, No. 7498, pp. 55-62 (published online Mar. 2, 2014)—Author Manuscript—33 total pages (available in PMC Apr. 13, 2015).

Easterhoff, D., et al. "Boosting of HIV envelope CD4 binding site antibodies with long variable heavy third complementarity determining region in the randomized double blind RV305 HIV-1 vaccine trial," PLoS Pathogens, vol. 13, No. 2, e1006182, pp. 1-21 (Feb. 24, 2017).

Eroshkin, A.M., et al., "bNAber: database of broadly neutralizing HIV antibodies," Nucleic Acids Res, vol. 42, pp. D1133-D1139 (published online Nov. 7, 2013).

Fera, D. and Harrison, S.C., "92BR SOSIP.664 trimer in complex with DH270.1 Fab," EM Data Bank Accession No. EMD-8507 downloaded from EMDataResource https://www.emdataresource.org/EMD-8507 (6 total pages) last retrieved Nov. 3, 2020.

Fera, D., "Affinity maturation in an HIV broadly neutralizing B-cell lineage through reorientation of variable domains," Proceedings of the National Academy of Sciences of the United States of America, vol. 111, No. 28, pp. 10275-10280 (Jul. 15, 2014).

Gao, F. et al., "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).

Gao, F., et al., "Cooperation of B Cell Lineages in Induction of HIV-1-Broadly Neutralizing Antibodies," Cell, vol. 158, pp. 481-491 (Jul. 31, 2014).

Garces, F., et al., "Affinity maturation of a potent family of HIV antibodies is primarily focused on accommodating or avoiding glycans," Immunity, vol. 43, No. 6, pp. 1053-1063, Dec. 2015 (Author Manuscript—22 total pages—available in PMC Dec. 15, 2016).

Garces, F., et al., "Structural evolution of glycan recognition by a family of potent HIV antibodies," Cell, vol. 159, No. 1, pp. 69-79, Sep. 2014 (Author Manuscript—23 total pages—available in PMC Sep. 25, 2015).

GenBank with accession Nos. KY347498 through KY347701 downloaded from https://www.ncbi.nlm.nih.gov/ last retrieved on Nov. 4, 2020 (22 total pages).

GenBank with accession Nos. KY354938 through KY354963 downloaded from https://www.ncbi.nlm.nih.gov/ last retrieved on Nov. 4, 2020 (3 total pages).

Georgiev, I.S., et al., "Antibodies VRC01 and 10E8 neutralize HIV-1 with high breadth and potency even with Ig-framework regions substantially reverted to germline," Journal of Immunology, vol. 192, pp. 1100-1106 with cover page—8 total pages (published online Jan. 3, 2014).

Gnanakaran, S., et al., "Genetic Signatures in the Envelope Glycoproteins of HIV-1 that Associate with Broadly Neutralizing Antibodies," PLoS Computational Biology, vol. 6, No. 10, e1000955, 24 total pages (published Oct. 7, 2010).

Go, E.P., et al., "Comparative Analysis of the Glycosylation Profiles of Membrane-Anchored HIV-1 Envelope Glycoprotein Trimers and Soluble gp140," Journal of Virology, vol. 89, No. 16, pp. 8245-8257 (Aug. 2015).

Goo, L., et al., "Early development of broadly neutralizing antibodies in HIV-I-infected infants," Nature Medicine, vol. 20, No. 6, pp. 655-658 (Jun. 2014), Author Manuscript available in PMC Dec. 1, 2014 (14 total pages).

Gorman, J., et al., "Structures of HIV-1 Env V1V2 with broadly neutralizing antibodies reveal commonalities that enable vaccine design," Nature Structural and Molecular Biology, vol. 23, No. 1, pp. 81-90 (Jan. 2016)—Author Manuscript (34 total pages)—available in PMC Jun. 21, 2016).

Graham, B.S., et al., "DNA Vaccine Delivered by a Needle-Free Injection Device Improves Potency of Priming for Antibody and CD8+ T-Cell Responses after rAd5 Boost in a Randomized Clinical Trial," Public Library of Science ONE, vol. 8, No. 4, e59340, pp. 1-11 (Apr. 8, 2013).

Gray, E.S., et al. "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).

Gray, E. S., et al., "The Neutralization Breadth of HIV-1 Develops Incrementally over Four Years and Is Associated with CD4+ T Cell Decline and High Viral Load during Acute Infection," Journal of Virology, vol. 85, No. 10, pp. 4828-4840 (May 2011).

Guo, H.-G., et al., "Characterization of an HIV-1 Point Mutant Blocked in Envelope Glycoprotein Cleavage," Virology, vol. 174, pp. 217-224 (1990).

Guttman, M., et al., "Antibody potency relates to the ability to recognize the closed, pre-fusion form of HIV Env," Nature Communications, vol. 6, No. 6144, pp. 1-11 (Feb. 5, 2015).

Haynes, B. F., et al., "B-cell-lineage immunogen design in vaccine development with HIV-1 as a case study," Nat. Biotechnol., vol. 30, No. 5, pp. 423-433 (2012)—Author Manuscript available in PMC May 7, 2013 (30 total pages).

Haynes, B.F., et al., "Developing an HIV vaccine," Science, vol. 355, No. 6330, pp. 1129-1130 (Mar. 17, 2017)—Author Manuscript available in PMC Mar. 17, 2018 (5 total pages).

He, L., et al., "Presenting native-like trimeric HIV-1 antigens with self-assembling nanoparticles," Nature Communications, vol. 7, No. 12041, pp. 1-15 (Jun. 28, 2016).

Hraber, P., et al., "Prevalence of broadly neutralizing antibody responses during chronic HIV-1 infection," AIDS, vol. 28, No. 2, pp. 163-169 (Jan. 14, 2014), Author Manuscript available in PMC Jan. 14, 2015 (9 total pages).

Hraber, P., et al., "Longitudinal Antigenic Sequences and Sites from Intra-Host Evolution (LASSIE) Identifies Immune-Selected HIV Variants," Viruses, vol. 7, pp. 5443-5475 (Oct. 21, 2015).

Hwang, J.K., et al., "Sequence Intrinsic Somatic Mutation Mechanisms Contribute to Affinity Maturation of VRC01-class HIV-1 Broadly Neutralizing Antibodies," Proceedings of the National Academy of Sciences of the United States of America, vol. 114, No. 32, pp. 8614-8619 (Aug. 8, 2017).

International Search Report and Written Opinion mailed Aug. 23, 2017 by U.S. Patent and Trademark Office as International Searching Authority for International Patent Application No. PCT/US2017/020823 (15 total pages).

International Search Report and Written Opinion mailed Feb. 1, 2018 by U.S. Patent and Trademark Office as International Searching Authority for International Patent Application No. PCT/US2017/054956 (14 total pages).

Jardine, J.G., et al., "Minimally Mutated HIV-1 Broadly Neutralizing Antibodies to Guide Reductionist Vaccine Design," PLOS Pathogens, vol. 12, No. 8, e1005815, pp. 1-33 (Aug. 25, 2016).

(56) References Cited

OTHER PUBLICATIONS

Julien, J.-P., et al., "Broadly Neutralizing Antibody PGT121 Allosterically Modulates CD4 Binding via Recognition of the HIV-1 gp120 V3 Base and Multiple Surrounding Glycans," Public Library of Science Pathogens, vol. 9, No. 5: e1003342, pp. 1-15 (May 2, 2013).
Keele, B. F., et al., "Identification and characterization of transmitted and early founder virus envelopes in primary HIV-1 infection," Proceedings of the National Academy of Sciences of the United States of America, vol. 105, No. 21, pp. 7552-7557 (May 27, 2008).
Kelsoe, G., et al., "Host controls of HIV broadly neutralizing antibody development," Immunology Review, vol. 275, No. 1, pp. 79-88 (Jan. 2017), Author Manuscript—19 total pages—available in PMC Jun. 21, 2017.
Kepler, T.B., "Reconstructing a B-cell clonal lineage. I. Statistical inference of unobserved ancestors," F1000 Research 2013, vol. 2, No. 103, 12 total pages (last updated Jan. 22, 2014).
Kepler, T.B., et al., "Immunoglobulin gene insertions and deletions in the affinity maturation of HIV-1 broadly reactive neutralizing antibodies," Cell Host & Microbe, vol. 16, pp. 304-313 (Sep. 10, 2014).
Kepler, T.B., et al., "Reconstructing a B-Cell Clonal Lineage. II. Mutation, Selection, and Affinity Maturation," Frontiers in Immunology, vol. 5, Article 170, pp. 1-10 (Apr. 2014).
Kibler, K. V., et al., "Improved NYVAC-based vaccine vectors," Public Library of Science ONE, vol. 6, No. 11: e25674, pp. 1-13, (Nov. 9, 2011).
Kirchherr, J. L., et al., "High throughput functional analysis of HIV-1 env genes without cloning," Journal of Virological Methods, vol. 143, No. 1, pp. 104-111, Jul. 2007 (Author Manuscript—18 total pages—available in PMC Jul. 1, 2008).
Klein, F., et al., "Somatic Mutations of the Immunoglobulin Framework Are Generally Required for Broad and Potent HIV-1 Neutralization", Cell, vol. 153, pp. 126-138 (Mar. 28, 2013).
Kong, L., et al., "Complete epitopes for vaccine design derived from a crystal structure of the broadly neutralizing antibodies PGT128 and 8ANC195 in complex with an HIV-1 Env trimer," Acta Crystallographica, Section D, Biological Crystallography, vol. D71, pp. 2099-2108 (2015).
Kong, L., et al., "Supersite of immune vulnerability on the glycosylated face of HIV-1 envelope glycoprotein gp120," Nature Structural Molecular Biology, vol. 20, No. 7, pp. 796-803, Jul. 2013 (Author Manuscript—22 total pages—available in PMC Jan. 1, 2014).
Kwon, Y.-D., et al., "Crystal structure, conformational fixation, and entry-related interactions of mature ligand-free HIV-1 Env," Nature Structural Molecular Biology, vol. 22, No. 7, pp. 522-531, Jul. 2015 (Author Manuscript—30 total pages—available in PMC Jan. 8, 2016).
Lee, J. H., et al., "Model Building and Refinement of a Natively Glycosylated HIV-1 Env Protein by High-Resolution Cryoelectron Microscopy," Structure, vol. 23, pp. 1943-1951 with cover page—10 total pages (Oct. 6, 2015).
Li, M., et al., "Human Immunodeficiency Virus Type 1 env Clones from Acute and Early Subtype B Infections for Standardized Assessments of Vaccine-Elicited Neutralizing Antibodies," J. Virol., vol. 79, No. 16, pp. 10108-10125 (Aug. 2005).
Li, Y., et al., "Control of expression, glycosylation, and secretion of HIV-1 gp120 by homologous and heterologous signal sequences," Virology, vol. 204, pp. 266-278 (accepted Jun. 23, 1994).
Li, Y., et al., "Effects of inefficient cleavage of the signal sequence of HIV-1 gp120 on its association with calnexin, folding, and intracellular transport," Proceedings of the National Academy of Sciences of the United States of America, vol. 93, pp. 9606-9611 (Sep. 1996).
Liao, H .- X., et al., "A group M consensus envelope glycoprotein induces antibodies that neutralize subsets of subtype B and C HIV-1 primary viruses," Virology, vol. 353, pp. 268-282 (available online Jul. 7, 2006).
Liao, H.X., et al., "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 with Supplementary Materials—34 total pages (Apr. 2013).
Liao, H.X., et al., "Co-evolution of a broadly neutralizing HIV-1 antibody and founder virus," Nature, vol. 496, No. 7446, pp. 469-476, Apr. 25, 2013 (Author Manuscript—25 total pages—available in PMC Oct. 25, 2013).
Liao, H.X., et al., "Vaccine induction of antibodies against a structurally heterogeneous site of immune pressure within HIV-1 envelope protein variable regions 1 and 2," Immunity, vol. 38, No. 1, pp. 176-186, Jan. 24, 2013 (Author Manuscript—21 total pages—available in PMC Jan. 24, 2014).
Loughran, G., et al., "Evidence of efficient stop codon readthrough in four mammalian genes," Nucleic Acids Research, vol. 42, No. 14, pp. 8928-8938 (published online Jul. 10, 2014).
Mascola, J. R. and Haynes, B.F., "HIV-1 neutralizing antibodies: understanding nature's pathways," Immunological Reviews, vol. 254, No. 1, pp. 225-244, Jul. 2013 (Author Manuscript—29 pages—available in PMC Jul. 1, 2014).
McCune, J.M., et al., "Endoproteolytic Cleavage of gp160 Is Required for the Activation of Human Immunodeficiency Virus," Cell, vol. 53, pp. 55-67 (Apr. 8, 1988).
Mcguire, A.T., et al., "Engineering HIV envelope protein to activate germline B cell receptors of broadly neutralizing anti-CD4 binding site antibodies", The Journal of Experimental Medicine, vol. 210, No. 4, pp. 655-663 (Mar. 25, 2013).
Moody, M.A., et al., "Toll-Like Receptor 7 /8 (TLR7/8) and TLR9 Agonists Cooperate To Enhance HIV-1 Envelope Antibody Responses in Rhesus Macaques," J. Virol., vol. 88, No. 6, pp. 3329-3339 (Mar. 2014).
Moore, P. L. et al., "Evolution of an HIV glycan-dependent broadly neutralizing antibody epitope through immune escape," Nat. Med. Vol.18, No. 11, pp. 1688-1692 (Nov. 2012)—Author Manuscript—12 total pages—available in PMC Nov. 9, 2012.
Mouquet, H., et al., "Complex-type N-glycan recognition by potent broadly neutralizing HIV antibodies," Proceedings of the National Academy of Sciences of the United States of America, pp. E3268-E3277, https://www.pnas.org/content/109/47/E3268 (published online Oct. 30, 2012).
Muenchhoff, M., et al., "Non-progressing HIV-infected children share fundamental immunological features of non-pathogenic SIV infection," Sci Transl Med, vol. 8, No. 358: 358ra125 (published Sep. 28, 2016), Author Manuscript—25 total pages (available Aug. 12, 2018).
Munro, J.B., et al., "Conformational dynamics of single HIV-1 envelope trimers on the surface of native virions," Science, vol. 346, Issue 6210, pp. 759-763, Nov. 7, 2014, with Supplementary Materials: pp. 1-27 and cover pages (34 total pages).
Neuberger, M.S., et al., "Monitoring and interpreting the intrinsic features of somatic hypermutation," Immunol. Rev., vol. 162, pp. 107-116 (1998).
Nickle D. C., L. Heath, "HIV-Specific Probabilistic Models of Protein Evolution," PloS One, Issue 6, e503, pp. 1-11 (Jun. 2007).
Pancera, M., et al. "Structure and immune recognition of trimeric prefusion HIV-1 Env", Nature, vol. 514, No. 7523, pp. 455-461, Oct. 2014 (Author Manuscript—43 total pages—available in PMC Apr. 23, 2015).
Pancera, M., et al., "N332-Directed Broadly Neutralizing Antibodies Use Diverse Modes of HIV-1 recognition: Inferences from Heavy-Light Chain Complementation of Function," Plos One, vol. 8, No. 2, e55701, 11 total pages (published Feb. 19, 2013).
Parren, P.W.H.I., et al., "Antibody Neutralization-Resistant Primary Isolates of Human Immunodeficiency Virus Type 1," Journal of Virology, vol. 72, No. 12, pp. 10270-10274 (Dec. 1998).
Pejchal, R., et al., "A potent and broad neutralizing antibody recognizes and penetrates the HIV glycan shield," Science, vol. 334, No. 6059, pp. 1097-1103, Oct. 2011 (Author Manuscript—13 total pages—available in PMC Nov. 25, 2012).
Perreau, M., et al., "DNA/NYVAC Vaccine Regimen Induces HIV-Specific CD4 and CD8 T-Cell Responses in Intestinal Mucosa," Journal of Virology, vol. 85, No. 19, pp. 9854-9862 (Oct. 2011).
Poignard, P., et al., "Heterogeneity of envelope molecules expressed on primary human immunodeficiency virus type 1 particles as

(56) References Cited

OTHER PUBLICATIONS probed by the binding of neutralizing and nonneutralizing antibodies.," Journal of Virology, vol. 77, No. 1, pp. 353-365 (Jan. 2003).
Proft, T., et al., "Sortase-mediated protein ligation: an emerging biotechnology tool for protein modification and immobilisation," Biotechnol. Lett., vol. 32, No. 1, pp. 1-10 (published online Sep. 1, 2009).
Protein Data Bank (PDB) ID 4LST, downloaded from https://www.rcsb.org/structure/4LST, last retrieved Nov. 4, 2020 (7 total pages).
Protein Data Bank (PDB) ID 4QHL, downloaded from https://www.rcsb.org/structure/4QHL, last retrieved Nov. 4, 2020 (4 total pages).
Protein Data Bank Accession Code 5TPL, downloaded from https://www.rcsb.org/structure/5TPL, last retrieved Feb. 2, 2021 (4 total pages).
Protein Data Bank Accession Code 5TPP, downloaded from https://www.rcsb.org/structure/5TPP, last retrieved Feb. 2, 2021 (4 total pages).
Protein Data Bank Accession Code 5TQA, downloaded from https://www.rcsb.org/structure/5TQA, last retrieved Feb. 2, 2021 (4 total pages).
Protein Data Bank Accession Code 5TRP, downloaded from https://www.rcsb.org/structure/5TRP, last retrieved Feb. 2, 2021 (4 total pages).
Protein Data Bank Accession Code 5U0R, downloaded from https://www.rcsb.org/structure/5U0R, last retrieved Feb. 2, 2021 (4 total pages).
Protein Data Bank Accession Code 5U0U, downloaded from https://www.rcsb.org/structure/5U0U, last retrieved Feb. 2, 2021 (4 total pages).
Protein Data Bank Accession Code 5U15, downloaded from https://www.rcsb.org/structure/5U15, last retrieved Feb. 2, 2021 (4 total pages).
Rerks-Ngam, S., et al., "Vaccination with ALVAC and AIDSVAX to prevent HIV-1 infection in Thailand," The New England Journal of Medicine, vol. 361, pp. 2209-2220, Dec. 3, 2009, last retrieved Oct. 6, 2020 from https://www.nejm.org/doi/10.1056/NEJMoa0908492?url_ver=Z39.88-2003&rfr_id=ori:rid:crossref.org&rfr_dat=cr_pubOwww.ncbi.nlm.nih.gov (22 total pages).
Ringe, R.P., et al., "Influences on the Design and Purification of Soluble, Recombinant Native-Like HIV-1 Envelope Glycoprotein Trimers," Journal of Virology, vol. 89, No. 23, pp. 12189-12210 (Dec. 2015).
Salazar-Gonzalez, J F., et al., "Genetic identity, biological phenotype, and evolutionary pathways of transmitted/founder viruses in acute and early HIV-1 infection," The Journal of Experimental Medicine, vol. 206, No. 6, pp. 1273-1289 (Jun. 8, 2009).
Sanders, R.W., et al., "A Next-Generation Cleaved, Soluble HIV-1 Env Trimer, BG505 SOSIP.664 gp140, Expresses Multiple Epitopes for Broadly Neutralizing but Not Non-Neutralizing Antibodies," PLOS—Pathogens, vol. 9, Issue 9, e1003618, pp. 1-20 (published Sep. 19, 2013).
Santra, S., et al., "Mosaic Vaccines Elicit CD8+ T lymphocyte Responses in Monkeys that Confer Enhanced Immune Coverage of Diverse HIV Strains," Nat. Med., vol. 16, No. 3, pp. 324-328, Mar. 2010 (Author Manuscript—13 total pages—available in PMC Sep. 1, 2010).
Sarzotti-Kelsoe, M., et al., "Optimization and validation of the TZM-bl assay for standardized assessments of neutralizing antibodies against HIV-1," J Immunol Methods, pp. 131-146, doi:10.1016/j.jim.2013.11.022 (Jul. 2014), Author Manuscript—37 total pages (available in PMC Jul. 1, 2015).
Saunders, K.O., "Vaccine Elicitation of High Mannose-Dependent Neutralizing Antibodies against the V3-Glycan Broadly Neutralizing Epitope in Nonhuman Primates," Cell Rep. vol. 18, No. 9, pp. 2175-2188 (Feb. 28, 2017), Author Manuscript—25 total pages (available in PMC Apr. 28, 2017).
Scheid, J.F., et al., "Sequence and structural convergence of broad and potent HIV antibodies that mimic CD4 binding," Science, vol. 333, No. 6049, pp. 1633-1637 (Sep. 16, 2011)—Author Manuscript available in PMC May 15, 2012 (11 total pages).

Schmohl, L., and Schwarzer, D., "Sortase-mediated ligations for the site-specific modification of proteins," Current Opinion in Chemical Biology, vol. 22, pp. 122-128 (available online Oct. 6, 2014).
Seaman, M. S., et al., "Tiered Categorization of a Diverse Panel of HIV-1 Env Pseudoviruses for Assessment of Neutralizing Antibodies," Journal of Virology, vol. 84, No. 3, pp. 1439-1452 (Feb. 2010).
Sharma, S., et al., "Cleavage-Independent HIV-1 Env Trimers Engineered as Soluble Native Spike Mimetics for Vaccine Design," Cell Reports, vol. 11, pp. 539-550 with cover pages—13 total pages (Apr. 28, 2015).
Shaw, G.M. and Hunter, Eric, "HIV transmission," Cold Spring Harbor Perspectives in Medicine, vol. 2, a006965, pp. 1-23 (2012).
Sheng, Z., et al., "Gene-Specific Substitution Profiles Describe the Types and Frequencies of Amino Acid Changes during Antibody Somatic Hypermutation," Front. Immunol., vol. 8, No. 537, published online May 10, 2017, last downloaded Oct. 7, 2020 from <https://www.ncbi.nlm.nih.gov/pmc/articles/PMC5424261/>—27 total pages.
Simonich, C.A., et al., "HIV-1 Neutralizing Antibodies with Limited Hypermutation from an Infant," Cell, vol. 166, No. 1, pp. 77-87 (Jun. 30, 2016), Author Manuscript—16 total pages (available in PMC Jun. 30, 2017).
Sliepen, K., et al., "Presenting native-like HIV-1 envelope trimers on ferritin nanoparticles improves their immunogenicity," Retrovirology, vol. 12, No. 82, 5 total pages (2015).
Sok, D., "Promiscuous glycan site recognition by antibodies to the high-mannose patch of gp120 broadens neutralization of HIV," Science Translational Medicine, vol. 6, No. 236, 236ra263, May 14, 2014 (Author Manuscript—26 total pages—available in PMC Nov. 14, 2014).
Sok, D., "The effects of somatic hypermutation on neutralization and binding in the PGT121 family of broadly neutralizing HIV antibodies," PLoS—Pathogens, vol. 9, No. 11, e1003754, pp. 1-20 (published Nov. 21, 2013).
Steichen, J.M, et al., "HIV Vaccine Design to Target Germline Precursors of Glycan-Dependent Broadly Neutralizing Antibodies," Immunity, vol. 45, pp. 483-496 with cover page—15 total pages (Sep. 20, 2016).
Stewart-Jones, G.B., "Trimeric HIV-1-Env Structures Define Glycan Shields from Clades A, B, and G," Cell, vol. 165, pp. 813-826 (May 5, 2016) with cover page, pp. S1-S10, and Supplemental Information (cover page with pp. 1-23)—49 total pages.
Tabata, et al., "Development of a Sortase A-mediated Peptide-labeled Liposome Applicable to Drug-delivery Systems," Anticancer Research, vol. 35, pp. 4411-4417 (2015).
Teng, G., et al., "Immunoglobulin somatic hypermutation," Annu Rev Genet, vol. 41, pp. 107-120 (Jun. 4, 2007).
Tomaras, G.D., et al., "Initial B-Cell Responses to Transmitted Human Immunodeficiency Virus Type 1: Virion-Binding Immunoglobulin M (IgM) and IgG Antibodies Followed by Plasma Anti-gp41 Antibodies with Ineffective Control of Initial Viremia," Journal of Virology, vol. 82, No. 24, pp. 12449-12463 (Dec. 2008).
Tsukiji, S., et al., "Sortase-Mediated Ligation: A Gift from Gram-Positive Bacteria to Protein Engineering," ChemBioChem, vol. 10, pp. 787-798 (published online Feb. 6, 2009).
Wagh, K., et al., "Optimal Combinations of Broadly Neutralizing Antibodies for Prevention and Treatment of HIV-1 Clade C Infection," Public Library of Science Pathogens, vol. 12, No. 3: e1005520, pp. 1-27 (Mar. 30, 2016).
Walker, L.M., et al., "Broad and potent neutralizing antibodies from an African donor reveal a new HIV-1 vaccine target," Science, vol. 326, pp. 285-289 (Oct. 9, 2009) with correction dated Feb. 19, 2010.
Walker, L.M., et al., "Broad neutralization coverage of HIV by multiple highly potent antibodies," Nature, vol. 477, No. 7365, pp. 466-470, Sep. 22, 2011 (Author Manuscript—14 total pages—available in PMC Jul. 10, 2012).
West, Jr., A.P., et al., "Structural basis for germ-line gene usage of a potent class of antibodies targeting the CD4-binding site of HIV-1 gp120", Proceedings of the National Academy of Sciences, vol. 109, No. 30, pp. E2083-E2090 (published online Jun. 27, 2012).
Williams, W. B., et al., "Diversion of HIV-1 vaccine-induced immunity by gp41-microbiota cross-reactive antibodies," Science,

(56) References Cited

OTHER PUBLICATIONS vol. 349, No. 6249, aab1253, Aug. 14, 2015 (Author Manuscript—23 total pages—available in PMC Aug. 14, 2016).
Wu, X., et al., "Maturation and Diversity of the VRC01-Antibody Lineage over 15 Years of Chronic HIV-1 Infection," Cell, vol. 161, No. 3, pp. 470-485 (Apr. 23, 2015)—Author Manuscript available in PMC Apr. 23, 2016 (31 total pages).
Yaari, G et al., "Models of Somatic Hypermutation Targeting and Substitution Based on Synonymous Mutations from High-Throughput Immunoglobulin Sequencing Data," Frontiers in Immunology, vol. 4, No. 358, pp. 1-19 (published online Nov. 15, 2013).
Yang. X., et al., "Antibody binding is a dominant determinant of the efficiency of human immunodeficiency virus type 1 neutralization," Journal of Virology, vol. 80, No. 22, p. 11404-11408 (Nov. 2006).
Yeap, L.-S., et al., "Sequence-intrinsic mechanisms that target AID mutational outcomes on antibody genes," Cell, vol. 163, No. 5, pp. 1124-1137, Nov. 19, 2015 (Author Manuscript—26 total pages—available in PMC Nov. 19, 2016).
Yoon, H., et al., "CATNAP: a tool to compile, analyze and tally neutralizing antibody panels," Nucleic Acids Res., vol. 43 (Web Server issue), pp. W213-W219—10 total pages (Jun./Jul. 2015).
Yu, J.-S., et al., "Generation of Mucosal Anti-Human Immunodeficiency Virus Type 1 T-Cell Responses by Recombinant *Mycobacterium smegmatis*," Clinical and Vaccine Immunology, vol. 13, No. 11, pp. 1204-1211 (Nov. 2006).
Yu, J.-S., et al., "Recombinant Mycobacterium bovis Bacillus Calmette-Guerin Elicits Human Immunodeficiency Virus Type 1 Envelope-Specific T Lymphocytes at Mucosal Sites," Clinical and Vaccine Immunology, vol. 14, No. 7, pp. 886-893 (Jul. 2007).
Yu, L., et al., "Immunologic Basis for Long HCDR3s in Broadly Neutralizing Antibodies Against HIV-1," Front Immunol., vol. 5, No. 250, pp. 1-15 (published online Jun. 2, 2014).
Zhou, T, et al., "Multi-donor analysis reveals structural elements, genetic determinants, and maturation pathway for HIV-1 neutralization by VRC01-class antibodies," Immunity, vol. 39, No. 2, pp. 245-258, published online Aug. 1, 2013 (Author Manuscript—17 total pages—available in PMC Apr. 14, 2014).
Zhou, T., et al., "Structural basis for broad and potent neutralization of HIV-1 by antibody VRC01," Science, vol. 329, No. 5993, pp. 811-817 (Aug. 13, 2010)—Author Manuscript available in PMC Aug. 13, 2011 (19 total pages).
Sanders, R.W., et al., "HIV-1 neutralizing antibodies induced by native-like envelope trimers," Science, vol. 349, Issue 6244, p. 154 with aac4223-1-aac4223-10 and cover pages—13 total pages (Jul. 10, 2015).
Afonine, P.V., et al., "Real-space refinement in PHENIX for cryo-EM and crystallography," Acta Crystallographica Section D, Structural Biology, vol. 74, pp. 531-544 (accepted Apr. 27, 2018).
Altschul, Stephen F., et al., "Basic Local Alignment Search Tool," J. Mol. Biol., vol. 215, pp. 403-410 (1990).
Altschul, Stephen F., et al., "Issues in searching molecular sequence databases", Nature Genetics, vol. 6, pp. 119-129 (Feb. 1994).
Barad, B.A., et al., "EMRinger: side chain-directed model and map validation for 3D Electron Cryomicroscopy," Nature Methods, vol. 12, No. 10. pp. 943-946 (Oct. 2015)—Author Manuscript available in PMC Apr. 1, 2016 (13 total pages).
Barnes, C.O., et al., "Structural characterization of a highly-potent V3-glycan broadly neutralizing antibody bound to natively-glycosylated HIV-1 envelope," Nature Communications, vol. 9, No. 1251, pp. 1-12 (2018).
Bartesaghi, A., et al., "Atomic Resolution Cryo-EM Structure of B-Galactosidase," Structure, vol. 26, pp. 848-856 with pp. e1-e3 (Jun. 5, 2018).
Cao, J., et al., "Effects of amino acid changes in the extracellular domain of the human immunodeficiency virus type 1 gp41 envelope glycoprotein," Journal of virology 67, No. 5, 2747-2755 (May 1993).
Cao, L., et al., "Differential processing of HIV envelope glycans on the virus and soluble recombinant trimer," Nature Communications, vol. 9, No. 3693, pp. 1-14 (2018).

Chan, D.C., et al., "HIV Entry and Its Inhibition," Cell 93, vol. 3, No. 5, pp. 681-684 (May 29, 1998).
Chen, V.B., et al., "MolProbity: all-atom structure validation for macromolecular crystallography," Acta Crystallographica Section D, Biological Crystallography, vol. 66, pp. 12-21 (2010).
Chuang, G.-Y., et al., "Structure-Based Design of a Soluble Prefusion-Closed HIV-1 Env Trimer with Reduced CD4 Affinity and Improved Immunogenicity," Journal of Virology, vol. 91, No. 10, e02268-16, pp. 1-18 (May 2017).
Corpet, Florence, "Multiple sequence alignment with hierarchical clustering," Nucleic Acids Research, vol. 16, No. 22, pp. 10881-10890 (1988).
Cowell, L.G., et al., "The Nucleotide-Replacement Spectrum Under Somatic Hypermutation Exhibits Microsequence Dependence That Is Strand-Symmetric and Distinct from That Under Germline Mutation," Journal of Immunology, vol. 164, pp. 1971-1976 with cover page—7 total pages (2000).
Crooks, E.T., et al., "Vaccine-Elicited Tier 2 HIV-1 Neutralizing Antibodies Bind to Quaternary Epitopes Involving Glycan-Deficient Patches Proximal to the CD4 Binding Site," Public Library of Science Pathogens, vol. 11, No. 5, e1004932, pp. 1-34 (May 29, 2015).
De Taeye, SW et al., HIV-1 envelope trimer design and immunization strategies to induce broadly neutrailizing antibodies, Trends in Immunology, vol. 37, No. 3, pp. 221-232 (Mar. 2016)—Author Manuscript available in PMC Jun. 2, 2017 (19 total pages).
Ding, S., et al., "A Highly Conserved gp120 Inner Domain Residue Modulates Env Conformation and Trimer Stability," Journal of Virology, vol. 90, No. 19, pp. 8395-8409 (Oct. 2016).
Dingens, A.S., et al., "Complete functional mapping of infection- and vaccine-elicited antibodies against the fusion peptide of HIV," Public Library of Science Pathogens, vol. 14, No. 7, e1007159, pp. 1-16 (Jul. 5, 2018).
Doran, R.C., et al., "Characterization of a monoclonal antibody to a novel glycan-dependent epitope in the V1/V2 domain of the HIV-1 envelope protein, gp120," Molecular Immunology, vol. 62, No. 1, pp. 219-226 (available online Jul. 11, 2014).
Doria-Rose, N.A., "A short segment of the HIV-1 gp120 V1/V2 region is a major determinant of resistance to V1/V2 neutralizing antibodies," Journal of Virology, vol. 86, No. 15, pp. 8319-8323 (Aug. 2012).
Emsley, P., et al., "Features and development of Coot," Acta Crystallographica Section D, Biological Crystallography, vol. D66, pp. 486-501 (accepted Feb. 26, 2010).
Finzi, A., et al., "Topological Layers in the HIV-1 gp120 Inner Domain Regulate gp41 Interaction and CD4-Triggered Conformational Transitions," Molecular Cell, vol. 37, No. 5, pp. 656-667 (Mar. 12, 2010).
Gardner, M.R., et al., "AAV-expressed eCD4-Ig provides durable protection from multiple SHIV challenges," Nature, vol. 519, No. 7541, pp. 87-91 (Mar. 5, 2015)—Author Manuscript available in PMC Sep. 5, 2015 (30 total pages).
Grant, T., et al., "Measuring the optimal exposure for single particle cryo-EM using a 2.6 Å reconstruction of rotavirus VP6," eLife, vol. 4, No. e06980, pp. 1-19 (May 29, 2015).
Grant, T., et al., "cisTEM, user-friendly software for single-particle image processing," eLife, vol. 7, No. e35383, pp. 1-24 (Mar. 7, 2018).
Gristick, H.B., et al., "Natively glycosylated HIV-1 Env structure reveals new mode for antibody recognition of the CD4-binding site," Nature Structural & Molecular Biology, vol. 23, No. 10, pp. 906-915 (Oct. 2016)—Author Manuscript available in PMC Apr. 1, 2017 (24 total pages).
Grupping, K., et al., "MiniCD4 protein resistance mutations affect binding to the HIV-1 gp120 CD4 binding site and decrease entry efficiency," Retrovirology, vol. 9, No. 36, pp. 1-16 (2012).
Harrison, S.C., "Viral membrane fusion," Nature Structural & Molecular Biology, vol. 15, No. 7, pp. 690-698 (Jul. 2008).
He, L., et al., "HIV-1 vaccine design through minimizing envelope metastability," Science Advances, vol. 4, eaau6769, pp. 1-19 with cover page—20 total pages (Nov. 21, 2018).

(56) References Cited

OTHER PUBLICATIONS

Herschhorn, A., et al., "The ß20-ß21 of gp120 is a regulatory switch for HIV-1 Env conformational transitions," Nature Communications, vol. 8, No. 1049, pp. 1-12 (2017).
Higgins, D.G. and Sharp, P.M., "CLUSTAL: a package for performing multiple sequence alignment on a microcomputer," Gene, vol. 73, pp. 237-244 (1988).
Higgins, D.G., et al., "Fast and sensitive multiple sequence alignments on a microcomputer," CABIOS Communications, vol. 5, No. 2, pp. 151-153 (1989).
Huang, J., et al., "Identification of a CD4-Binding-Site Antibody to HIV that Evolved Near-Pan Neutralization Breadth," Immunity, vol. 45, No. 5, pp. 1108-1121 with cover page—15 total pages (Nov. 15, 2016).
Humphrey, W., et al., "VMD: Visual molecular dynamics," Journal of Molecular Graphics, vol. 14, pp. 33-38 (Feb. 1996).
Ingale, J., et al., "High-Density Array of Well-Ordered HIV-1 Spikes on Synthetic Liposomal Nanoparticles Efficiently Activate B Cells," Cell Reports, vol. 15, pp. 1986-1999 with cover pages—15 total pages (May 31, 2016).
International Seach Report and Written Opinion issued by U.S. Patent and Trademark Office as International Application No. PCT/US18/20788 on Jul. 2, 2018 (14 total pages).
International Seach Report and Written Opinion issued by U.S. Patent and Trademark Office as International Application No. PCT/US2019/049431 on Feb. 4, 2020 (11 total pages).
International Seach Report and Written Opinion issued by U.S. Patent and Trademark Office as International Application No. PCT/US2019/049662 on Feb. 11, 2020 (17 total pages).
International Seach Report and Written Opinion issued by U.S. Patent and Trademark Office as International Application No. PCT/US2019/020436 on Jul. 22, 2019 (12 total pages).
Juette, M.F., et al., "Single-molecule imaging of non-equilibrium molecular ensembles on the millisecond timescale," Nature Methods, vol. 13, No. 4, pp. 341-344 (Apr. 2016)—Author Manuscript available in PMC Aug. 15, 2016 (14 total pages).
Kong, L., et al., "Uncleaved prefusion-optimized gp140 trimers derived from analysis of HIV-1 envelope metastability," Nature Communications, vol. 7, No. 12040, pp. 1-15 (Jun. 28, 2016).
Korber, B., et al., "Polyvalent vaccine approaches to combat HIV-1 diversity," Immunological Reviews, vol. 275, pp. 230-244 (2017).
Kulp, D.W., et al., "Structure-based design of native-like HIV-1 envelope trimers to silence non-neutralizing epitopes and eliminate CD4 binding," Nature Communications, vol. 8, No. 1655, pp. 1-14 (2017).
Kwong, P.D., et al., "Structure of an HIV gp120 envelope glycoprotein in complex with the CD4 receptor and a neutralizing human antibody," Nature, vol. 393, No. 6686, pp. 648-659 (Jun. 18, 1998)—Author Manuscript available in PMC Oct. 6, 2017 (29 total pages).
Langley, D.R., et al., "Homology Models of the HIV-1 Attachment Inhibitor BMS-626529 Bound to gp120 Suggest a Unique Mechanism of Action," Proteins, vol. 83, pp. 331-350 (2015).
Lee, J.H., et al., "A Broadly Neutralizing Antibody Targets the Dynamic HIV Envelope Trimer Apex via a Long, Rigidified, and Anionic-Hairpin Structure," Immunity, vol. 46, pp. 690-702 with cover page—14 total pages (Apr. 18, 2017).
Lee, J.H., et al., "Cryo-EM structure of a native, fully glycosylated, cleaved HIV-1 envelope trimer," Science, vol. 351, No. 6277, pp. 1043-1048 with cover page—7 total pages (Mar. 4, 2016).
Lemmin, T., et al., "Microsecond Dynamics and Network Analysis of the HIV-1 Sosip Env Trimer Reveal Collective Behavior and Conserved Microdomains of the Glycan Shield," Structure, vol. 25, No. 10, pp. 1631-1639 with pp. e1-e2 and cover page—12 total pages (Oct. 3, 2017).
Liu, J., et al., "Molecular architecture of native HIV-1 gp120 trimers," Nature, vol. 455, pp. 109-113 with "Methods" (6 total pages) Sep. 4, 2008.
Liu, Q., et al., "Quaternary contact in the initial interaction of CD4 with the HIV-1 envelope trimer," Nature Structural & Molecular Biology, vol. 24, No. 4, Apr. 2017, pp. 370-378 with "Online Methods" and "Corrigendum: Quaternary contact in the initial interaction of CD4 with the HIV-1 envelope trimer," published online Feb. 20, 2017; corrected after print Apr. 27, 2017 (13 total pages).
Lu, M., et al., "Associating HIV-1 envelope glycoprotein structures with states on the virus observed by smFRET," Nature, vol. 568, No. 7752, pp. 415-419 (Apr. 10, 2019) available in PMC Oct. 10, 2019 (36 total pages).
Ma, B.J., et al., "Envelope Deglycosylation Enhances Antigenicity of HIV1 gp41 Epitopes for Both Broad Neutralizing Antibodies and Their Unmutated Ancestor Antibodies," Public Library of Science Pathogens, vol. 7, No. 9, e1002200, pp. 1-16 (Sep. 1, 2011).
Ma, X., et al., "HIV-1 Env trimer opens through an asymmetric intermediate in which individual protomers adopt distinct conformations," eLife, vol. 7, No. e34271, pp. 1-18 (Mar. 21, 2018).
Martinez-Murillo, P., et al., "Particulate Array of Well-Ordered HIV Clade C Env Trimers Elicits Neutralizing Antibodies that Display a Unique V2 Cap Approach," Immunity, vol. 46, pp. 804-817 with pp. e1-e7 (May 16, 2017).
McLellan, J.S., et al., "Structure of HIV-1 gp120 V1/V2 domain with broadly neutralizing antibody PG9," Nature, vol. 480, pp. 336-343 with "Methods" (10 total pages) Dec. 15, 2011.
Meanwell, N.A., et al., "Inhibitors of HIV-1 Attachment: The Discovery and Development of Temsavir and its Prodrug Fostemsavir," Journal of Medicinal Chemistry, vol. 61, pp. 62-80 (Dec. 22, 2017).
Mo, H., et al., "Conserved residues in the coiled-coil pocket of human immunodeficiency virus type 1 gp41 are essential for viral replication and interhelical interaction," Virology, vol. 329, pp. 319-327 (available online Sep. 25, 2004).
Munro, J.B., et al., "Structure and Dynamics of the Native HIV-1 Env Trimer," Journal of Virology, vol. 89, No. 11, pp. 5752-5755 (Jun. 2015).
Munro, S. et al. "Use of peptide tagging to detect proteins expressed from cloned genes: deletion mapping functional domains of *Drosophila* hsp70", The EMBO Journal, vol. 3, No. 13, pp. 3087-3093 (1984).
Needleman, S.B., et al. "A General Method Applicable to the Search for Similarities in the Amino Acid Sequence of Two Proteins" J. Mol. Biol., vol. 48, pp. 443-453 (1970).
Ozorowski, G., et al., "Open and closed structures reveal allostery and pliability in the HIV-1 envelope spike," Nature, vol. 547, pp. 360-363 with "Methods" (16 total pages), Jul. 20, 2017.
Pancera, M., et al., "Crystal structures of trimeric HIV envelope with entry inhibitors BMS-378806 and BMS-626529," Nature Chemical Biology, vol. 13, No. 10, pp. 1115-1122 (Oct. 2017)—Author Manuscript available in PMC Feb. 21, 2018 (24 total pages).
Pancera, M., et al., "Structure of HIV-1 gp120 with gp41-interactive region reveals layered envelope architecture and basis of conformational mobility," Proceedings of the National Academy of Sciences of the United States of America, vol. 107, No. 3, pp. 1166-1171 (Jan. 19, 2010).
Pancera, M., et.al., "Structure and immune recognition of trimeric pre-fusion HIV-1 Env," Nature, vol. 514, No. 7523, pp. 455-461 (Oct. 23, 2014)—Author Manuscript available in PMC Apr. 23, 2015, pp. 1-42 with cover page 43 total pages.
Pearson, W. R., et al., "Improved tools for biological sequence comparison," Proc. Natl. Acad. Sci. U.S.A., vol. 85, pp. 2444-2448 (Apr. 1988).
Pettersen, E.F., et al., "UCSF Chimera—A Visualization System for Exploratory Research and Analysis," Journal of Computational Chemistry, vol. 25, pp. 1605-1612 (2004).
Powell, R.L.R., et al., "Plasticity and Epitope Exposure of the HIV-1 Envelope Trimer," Journal of Virology, vol. 91, No. 17, e00410-00417, pp. 1-17 (Sep. 2017).
Pritz, S., et al., "Synthesis of Biologically Active Peptide Nucleic Acid-Peptide Conjugates by Sortase-Mediated Ligation," Journal of Organic Chemistry, vol. 72, pp. 3909-3912 (Published on Web Apr. 14, 2007).
Pugach, P., et al., "A Native-Like SOSIP.664 Trimer Based on an HIV-1 Subtype B env Gene," Journal of Virology, vol. 89, No. 6, pp. 3380-3395 (Mar. 2015).

(56) References Cited

OTHER PUBLICATIONS

Punjani, A., et al., "cryoSPARC: algorithms for rapid unsupervised cryo-EM structure determination," Nature Methods, vol. 14, No. 3, pp. 290-296 with "Online Methods" (8 total pages), Mar. 2017.
Rantalainen, K., et al., "Co-evolution of HIV Envelope and Apex-Targeting Neutralizing Antibody Lineage Provides Benchmarks for Vaccine Design," Cell Reports, vol. 23, pp. 3249-3261 with cover page—14 total pages (Jun. 12, 2018).
Rohou, A., et al., "CTFFIND4: Fast and accurate defocus estimation from electron micrographs," Journal of Structural Biology, vol. 192, No. 2, pp. 216-221 (Nov. 2015)—Author Manuscript available in PMC Sep. 25, 2019 (18 total pages).
Saunders, K.O., et al., "Vaccine Induction of Heterologous Tier 2 HIV-1 Neutralizing Antibodies in Animal Models," Cell Reports, vol. 21, pp. 3681-3690 (Dec. 26, 2017).
Scharf, L., et al., "Broadly Neutralizing Antibody 8ANC195 Recognizes Closed and Open States of HIV-1 Env," Cell, vol. 162, pp. 1379-1390 with cover page—13 total pages (Sep. 10, 2015).
Shaik, M.M., et al., "Structural basis of coreceptor recognition by HIV-1 envelope spike," Nature, vol. 565, No. 7739, pp. 318-323 (Jan. 2019)—Author Manuscript available in PMC Jun. 12, 2019 (34 total pages).
Smith, T. F., et al., "Comparison of Biosequences," Adv. Appl. Math., vol. 2, pp. 482-489 (1981).
Stamatatos, L., et al., "An Envelope Modification That Renders a Primary, Neutralization-Resistant Clade B Human Immunodeficiency Virus Type 1 Isolate Highly Susceptible to Neutralization by Sera from Other Clades," Journal of Virology, vol. 72, No. 10, pp. 7840-7845 (Oct. 1998).
Tang, G., et al., "EMAN2: An Extensible Image Processing Suite for Electron Microscopy," Journal of Structural Biology, Article in Press: 2006 (accepted May 31, 2006), doi:10.1016/j.jsb.2006.05.009, pp. 1-9.
Torrents de la Peña, A., et al., "Improving the Immunogenicity of Native-like HIV-1 Envelope Trimers by Hyperstabilization," Cell Reports, vol. 20, pp. 1805-1817 with cover page—14 total pages (Aug. 22, 2017).
Tran, E.E.H., et al., "Structural Mechanism of Trimeric HIV-1 Envelope Glycoprotein Activation," Public Library of Science Pathogens, vol. 8, Issue 7, e1002797, pp. 1-18 (Jul. 12, 2012).
Tria, G., et al., "Advanced ensemble modelling of flexible macromolecules using X-ray solution scattering," International Union of Crystallography Journal, vol. 2, pp. 207-217 (accepted Jan. 30, 2015).
Voss, J.E., et al., "Elicitation of Neutralizing Antibodies Targeting the V2 Apex of the HIV Envelope Trimer in a Wild-Type Animal Model," Cell Reports, vol. 21, pp. 222-235 with cover page—15 total pages (Oct. 3, 2017).
Wagh, K., et al., "Completeness of HIV-1 Envelope Glycan Shield at Transmission Determines Neutralization Breadth," Cell Reports, vol. 25, pp. 893-908 with pp. e1-e7 and cover page—24 total pages (Oct. 23, 2018).
Wang, H., et al., "Cryo-EM structure of a CD4-bound open HIV-1 envelope trimer reveals structural rearrangements of the gp120 V1V2 loop," Proceedings of the National Academy of Sciences of the United States of America, pp. E7151-E7158, https://doi.org/10.1073/pnas.1615939113 (published online Oct. 31, 2016).
Wang, H., et al., "Partially Open HIV-1 Envelope Structures Exhibit Conformational Changes Relevant for Coreceptor Binding and Fusion," Cell Host & Microbe, vol. 24, pp. 579-592 with pp. e1-e4 and cover page—19 total pages (Oct. 10, 2018).
Wang, R.Y.-R., et al., "Automated structure refinement of macromolecular assemblies from cryo-EM maps using Rosetta," eLife, vol. 5, No. e17219, pp. 1-22 (Sep. 26, 2016).
Wang, W., et al., "A systematic study of the N-glycosylation sites of HIV-1 envelope protein on infectivity and antibody-mediated neutralization," Retrovirology, vol. 10, No. 14, pp. 1-14 (2013).
Ward, A.B., et al., "Insights Into the Trimeric HIV-1 Envelope Glycoprotein Structure," Trends in Biochemical Sciences, vol. 40, No. 2, pp. 101-107 (Feb. 2015)—Author Manuscript available in PMC Feb. 1, 2016 (16 total pages).
Ward, A.B., et al., "The HIV-1 envelope glycoprotein structure: nailing down a moving target," Immunological Reviews, vol. 275, pp. 21-32 (2017).
Weissenhorn, W., et al., "Atomic structure of the ectodomain from HIV-1 gp41," Nature, 387, pp. 426-430 (May 22, 1997).
Xu, K., et al., "Epitope-based vaccine design yields fusion peptide-directed antibodies that neutralize diverse strains of HIV-1," Nature Medicine, vol. 24, Jun. 2018, pp. 857-867 with "Methods" and "Nature Research: Life Sciences Reporting Summary—Jun. 2017" (19 total pages).
Zhang, P., et al., "Interdomain Stabilization Impairs CD4 Binding and Improves Immunogenicity of the HIV-1 Envelope Trimer," Cell Host & Microbe, vol. 23, No. pp. 832-844 with cover page and pp. e1-e6—20 total pages (Jun. 13, 2018).
Zhou, T., et al., "Quantification of the Impact of the HIV-1-Glycan Shield on Antibody Elicitation," Cell Reports, vol. 19, pp. 719-732 with cover page—15 total pages (Apr. 25, 2017).
Zolla-Pazner, S., et al., "Structure/Function Studies Involving the V3 Region of the HIV-1 Envelope Delineate Multiple Factors That Affect Neutralization Sensitivity," Journal of Virology, vol. 90, No. 2, pp. 636-649 (Jan. 2016).

BG505-WT
ETTLFCASDAKAYETEKHNVWATHACVPTDPNPQEIHLENVTEEFNMWKNNMVEQ
MHTDIISLWDQSLKPCVKLT...TSAITQACPKVSFEPIPIHYCAPAGFAILKCKDKKFN
GTGPCPSVSTVQCTHGIKPVVSTQLLLNGSLAEEEVMIRSENITNNAKNILVQFNTP
VQINCTRPNNNTRKSIRIGPGQAFYATGDIIG...GEFFYCNTSGLFNSTWISNTSVQG
SNSTGSNDSITLPCRIKQIINMW (SEQ ID NOS 11-13)

BG505-F14
ETTLFCASDAKAYETEKHNIWATHACVPTDPNPQEIHLENVTEEFNMWKNNMVEQ
MHTDIISLWDQSLKPCVKLT...TSAITQVCPKLSFEPIPIHYCAPAGFAILKCKDKKFN
GTGPCPSVSTVQCTHGIKPVLSTQLLLNGSLAEEEVMIRSENITNNAKNILVQFNTP
VQINCTRPNNNTRKSIRIGPGQAFYATGDIIG...GEFFYCNTSGLFNSTWISNTSVQG
SNSTGSNDSITLPCRIKQIINMW (SEQ ID NOS 14-16)

BG505-F14/Vt8
ETTLFCASDAKAYETEKHNIWATHACVPTDPNPQEIHLENVTEEFNMWKNNMVEQ
MHTDIISLWDQSLKPCVKLT...TSAITMVCPKLSFEPIPIHYCAPAGFAILKCKDKKFN
GTGPCPSVSTVQCTHGIKPVLSTQLLLNGSLAEEEVMIRSENITNNAKNILVQFNTP
VQINCTRPLNLTRKSIRIGPGQAFYAMGDIIG...GEFFYCNTSGLFNSTWISNTSVQG
SNSTGSNDSITLPCRIKMIINMW (SEQ ID NOS 17-19)

Figure 1F

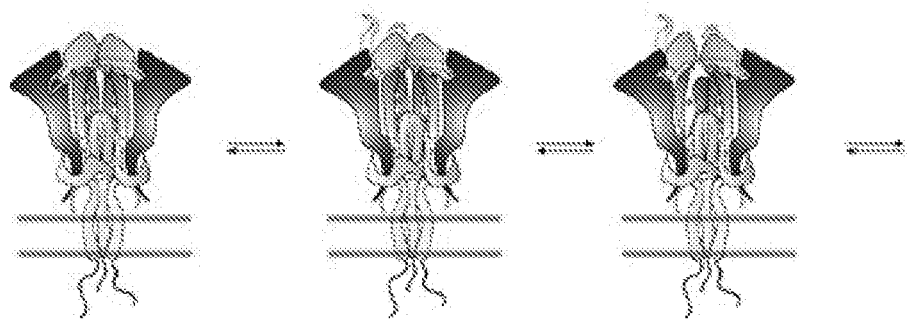

(E)

1- Pre-triggered state[38].

2- CD4 engagement induces rearrangement in 20-21 triggering V1/V2 instability[23] leading to V3 exposure[27, 39].

3- Rearrangement in layer-2 allowing release of gp41 W571 via V1/V2 rearrangement[24] [this study].

Layer-1, Layer-2, V1/V2, V3, gp41,

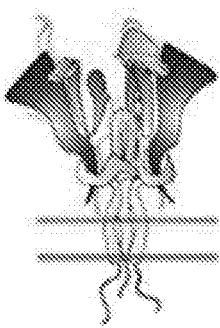 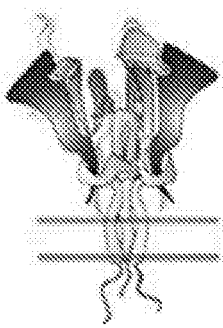 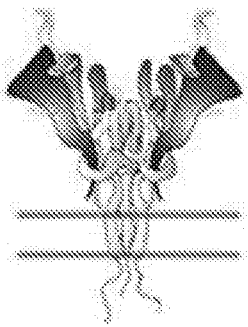

4- Release of layer-1 allowing gp120 rotation away from the internal gp41 3-helix bundle [this study].

5- Single protomer open, layer-1 rearranged intermediate yielding an asymmetric intermediate[34].

6- Final open state[20, 38].

B20-B21, gp120 inner/outer domains

Figure 6E

| Mutation | Mutations |
|---|---|
| F1 | V68I, S115V, A204L, V208L, V255W, N377L, M426W, M434W, H66S |
| F2 | V68I, S115V, A204L, V208L, V255W, H66S |
| F3 | V68I, A204V, V208L, V255L, H66S |
| F4 | V68I, S115V, V208L, V255L, H66S |
| F5 | V68I, S115V, A204L, V208L, V255W, N377L, H66S |
| F6 | V68I, S115V, A204L, V208L, V255L, W69L |
| F7 | V68I, S115V, A204L, V208L, V255L, W69V |
| F8 | V68I, S115V, A204L, V255L, V208L, W69A |
| F9 | V68I, S115V, A204L, V208L, V255W, N377L, M426W, H66S |
| F10 | V68I, S115V, A204L, V208L, V255W, N377L, M434W, H66S |
| F11 | V68I, S115V, A204V, V208L, V255L, H72P, H66S |
| F12 | V68I, S115V, V208L, V255L, H66K |
| F13 | V68I, S115V, A204L, V208L, V255W, N377L, M426W, M434W |
| F14 | V68I, A204V, V208L, V255L |
| F15 | V68I, A204L, V208L, V255W, N377L |
| Vt1 | Y177F, T320L, D180A, Q422L, Y435F, Q203M, E381L, R298M, N302L, N300L |
| Vt2 | Y177F, T320L, D180A, Q422L, Y435F, Q203M, N302L, N300L |
| Vt3 | Y177F, T320L, D180A, Q422L, Y435F, Q203M, R298M, N302L, N300L |
| Vt4 | Y177F, T320L, D180A, Q422L, Y435F, Q203M, E381L, N302L, N300L |
| Vt5 | T320L, D180A, Q422L, Q203M, E381L, R298M, N302L, N300L |
| Vt6 | T320L, D180A, Q422L, Q203M, N302L, N300L |
| Vt7* | I201C, A433C, L154M, N300M, N302M, T320L |
| Vt8 | T320M, Q422M, Q203M, N302L, N300L |
| Vt9 | T320M, Q422M, Q203M, N302L, N300L, S174V |

Figure 15

| CD4 Binding* | $k_a$ (M$^{-1}$s$^{-1}$) | $k_d$ (s$^{-1}$) | $K_d$ (nM) |
|---|---|---|---|
| BG505 WT | 1.12E+04 ± 5.77E+03 | 6.10E-04 ± 9.50E-05 | 67.9 ± 26.4 |
| BG505 F14 | 1.72E+04 ± 4.75E+03 | 1.13E-03 ± 1.00E-04 | 73.0 ± 26.2 |
| BG505 Vt8 | 9.44E+03 ± 6.65E+02 | 7.81E-04 ± 6.40E-05 | 83.9 ± 12.6 |
| BG505 F14/Vt8 | 2.92E+04 ± 5.35E+03 | 4.52E-04 ± 7.40E-05 | 15.6 ± 0.4 |

* Values reported as the average of two replicate measures ± one standard deviation

Figure 16

|  | BG505 WT | BG505 F14 | BG505 Vt8 | BG505 F14/Vt8 |
|---|---|---|---|---|
| PGT145 | 64.2 | 76.52 | 68.04 | 80.2 |
| PGT151 | 26.9 | 23.34 | 24.04 | 24.04 |
| VRC01 | 611.7 | 565.7 | 268.9 | 313.7 |
| PG9 | 444 | 45.9 | 335 | 336.8 |
| VRC26 | 67.6 | 50.23 | 60.4 | 50.6 |
| PGT121 | 222.3 | 218.6 | 260.3 | 262 |

* Values reported from fit to average the average value of two experiments

Figure 17

|  | BG505 F14 SOSIP | BG505 F14/Vt8 SOSIP |
|---|---|---|
| *Data Collection* | | |
| Microscope | FEI Titan Krios | FEI Titan Krios |
| Voltage (kV) | 300 | 300 |
| Electron dose ($e^-/Å^2$) | 42 | 42 |
| Detector | Falcon 3 | Falcon 3 |
| Pixel Size (Å) | 1.08 | 1.08 |
| Defocus Range (μm) | ~1.5-3 | ~1.5-3 |
| Magnification | 75000 | 75000 |
| *Reconstruction* | | |
| Software | cisTEM | cisTEM |
| Particles | 77632 | 84378 |
| Symmetry | C3 | C3 |
| Box size (pix) | 320 | 320 |
| Resolution (Å) (FSC0.143)* | 3.0 | 2.9 |
| *Refinement (Phenix)* | | |
| Protein residues | 999 | 1472 |
| Chimera CC | 0.77 | 0.63 |
| R.m.s. deviations | | |
|   Bond lengths (Å) | 0.01 | 0.01 |
|   Bond angles (°) | 1.06 | 1.24 |
| *Validation* | | |
| Molprobity score | 1.71 | 1.87 |
| Clash score | 4.4 | 6.0 |
| Favored rotamers (%) | 99.4 | 97.2 |
| Ramachandran | | |
|   Favored regions (%) | 91.6 | 90.3 |
|   Disallowed regions (%) | 0.41 | 0.6 |

Figure 18

|  | Control | BG505 | BG505 DS | BG505 F14/Vt8 | BG505 F14 | BG505 Vt8 |
|---|---|---|---|---|---|---|
| N6 | 0.3 ± 0.2 | 45.3 ± 8.1 | 41.0 ± 5.8 | 40.3 ± 3.7 | 53.9 ± 12.0 | 44.4 ± 5.0 |
| CH01 | 0.2 ± 0.1 | 32.8 ± 2.6 | 20.8 ± 9.7 | 22.1 ± 11.9 | 37.7 ± 12.4 | 30.2 ± 3.0 |
| PGT125 | 0.2 ± 0.1 | 47.1 ± 6.6 | 38.2 ± 9.1 | 37.9 ± 5.2 | 54.7 ± 10.1 | 43.2 ± 10.5 |
| PGT145 | 0.3 ± 0.2 | 46.0 ± 4.6 | 35.4 ± 3.0 | 34.8 ± 2.6 | 48.8 ± 11.9 | 38.2 ± 4.5 |
| 17B | 0.3 ± 0.1 | 9.0 ± 3.6 | 0.6 ± 0.2 | 1.2 ± 0.9 | 2.7 ± 1.0 | 0.8 ± 0.5 |
| 19B | 0.2 ± 0.2 | 17.1 ± 8.2 | 16.8 ± 1.7 | 8.0 ± 4.8 | 23.5 ± 8.4 | 8.0 ± 5.4 |
| 17B + sCD4 | 0.2 ± 0.1 | 25.9 ± 7.1 | 1.3 ± 0.2 | 0.7 ± 0.3 | 3.7 ± 1.2 | 0.9 ± 0.5 |
| 19B + sCD4 | 0.2 ± 0.1 | 25.3 ± 8.9 | 16.9 ± 8.3 | 9.0 ± 5.5 | 23.6 ± 8.0 | 9.0 ± 6.4 |
| 17B + CD4Ig | 0.2 ± 0.1 | 32.9 ± 6.5 | 0.9 ± 0.3 | 0.8 ± 0.6 | 8.2 ± 0.8 | 9.5 ± 1.1 |
| 19B + CD4Ig | 0.3 ± 0.2 | 38.3 ± 8.2 | 15.0 ± 7.1 | 9.5 ± 5.6 | 27.0 ± 7.1 | 21.8 ± 5.5 |

* Values reported as the average of three experiments with standard deviations

Figure 19

|  | Control | BG505 | BG505 DS | BG505 F14/Vt8 | BG505 F14 | BG505 Vt8 |
|---|---|---|---|---|---|---|
| N6 | 39.9 ± 14.1 | 457.3 ± 137.9 | 338.0 ± 72.6 | 341.3 ± 43.2 | 568.0 ± 152.6 | 378.3 ± 73.1 |
| 17B | 34.1 ± 11.5 | 103.4 ± 38.6 | 49.2 ± 24.2 | 51.6 ± 28.0 | 60.0 ± 29.0 | 51.0 ± 25.0 |
| 19B | 33.1 ± 11.5 | 211.3 ± 73.2 | 198.3 ± 67.9 | 109.3 ± 39.0 | 265.0 ± 84.2 | 103.8 ± 45.4 |
| 17B + sCD4 | 33.7 ± 11.1 | 244.7 ± 65.0 | 51.6 ± 27.1 | 48.8 ± 24.1 | 67.8 ± 34.0 | 48.4 ± 23.4 |
| 19B + sCD4 | 33.5 ± 11.4 | 306.7 ± 83.0 | 194.0 ± 63.0 | 115.2 ± 37.7 | 255.0 ± 88.4 | 114.8 ± 53.6 |
| 17B + CD4Ig | 42.5 ± 25.1 | 400.0 ± 115.2 | 50.2 ± 23.9 | 50.3 ± 28.4 | 102.4 ± 28.9 | 90.8 ± 29.1 |
| 19B + CD4Ig | 35.5 ± 13.1 | 531.3 ± 134.1 | 176.3 ± 62.7 | 119.5 ± 45.9 | 269.7 ± 63.2 | 190.7 ± 43.1 |

* Values reported as the average of three experiments with standard deviations

Figure 20

| gp160 | BG505 WT | BG505 WT + 12xCD4 | BG505 F14/Vt8 | BG505 F14/Vt8 + 12xCD4 |
|---|---|---|---|---|
| State 1 | 46 ± 7 | 20 ± 8 | 49 ± 9 | 43 ± 7 |
| State 2 | 26 ± 8 | 30 ± 11 | 20 ± 9 | 22 ± 11 |
| State 3 | 28 ± 10 | 50 ± 13 | 31 ± 12 | 35 ± 12 |

Figure 21

| BG505 WT SOSIP Immunized Rabbits (R41) | ID50 (dilution) in TZM-bl Cells[1] | | | |
|---|---|---|---|---|
| Animal # | MLV | SF162.LS | MW965.26 | BG505/T332N |
| 1 | <20 | 164 | 295 | 1402 |
| 2 | <20 | 88 | 223 | 3646 |
| 3 | <20 | 66 | 339 | 116 |
| 4 | <20 | 63 | 220 | 101 |

Figure 38

| BG505 F14 SOSIP Immunized Rabbits (R47) | ID50 (dilution) in TZM-bl Cells[1] | | | |
|---|---|---|---|---|
| Animal # | MLV | SF162.LS | MW965.26 | BG505/T332N |
| 1 | <20 | 34 | 81 | 975 |
| 2 | <20 | 2 | 28 | 512 |
| 3 | <20 | 227 | 316 | 1087 |
| 4 | <20 | 331 | 407 | 213 |

Figure 39

| BG505 F14/Vt8 SOSIP Immunized Rabbits (R48) | ID50 (dilution) in TZM-bl Cells[1] | |
|---|---|---|
| Animal # | MLV | BG505/T332N |
| 1 | <20 | 1428 |
| 2 | <20 | 716 |
| 3 | <20 | 742 |
| 4 | <20 | <20 |
| 5 | <20 | <20 |

Figure 40

>CH0848.D0949.10.17_N133D_N138T.ch.SOSIP.Vt8
*MPMGSLQPLATLYLLGMLVASVLA*AENLWVTVYYGVPVWKEAKTTLFCASDARAYEKEVHNVWATHACVPTDP
SPQELVLGNVTENFNMWKNDMVDQMHEDIISLWDQSLKPCVKLTPLCVTLICSDATVKTGTVEEMKNCSFNTTT
EIRDKEKKEYALFYKPDIVPLSETNNTSEYRLINCNTSAVTMACPKVTFEPIPIHYCAPAGYAILKCNDETFNGTGPCS
NVSTVQCTHGIRPVVSTQLLLNGSLAEKEIVIRSENLTNNAKIIIVHLHTPVEIVCTRPLNLTRKSVRIGPGQTFYAMG
DIIGDIKQAHCNISEEKWNDTLQKVGIELQKHFPNKTIKYNQSAGGDMEITTHSFNCGGEFFYCNTSNLFNGTYNG
TYISTNSSANSTSTITLQCRIKMIINMWQGVGRAMYAPPIAGNITCRSNITGLLLTRDGGTNSNETETFRPAGGDMR
DNWRSELYKYKVVKIEPLGVAPTRCKRRVVGRRRRRAVGIGAVFLGFLGAAGSTMGAASMTLTVQARNLLSGIV
QQQSNLLRAPEAQQHLLKLTVWGIKQLQARVLAVERYLRDQQLLGIWGCSGKLICCTNVPWNSSWSNRNLSEIW
DNMTWLQWDKEISNYTQIIYGLLEESQNQQEKNEQDLLALD** (SEQ ID NO: 20)

Figure 41A

>CH0848.D0949.10.17_N133D_N138T.ch.SOSIP.Vt8
GTCGACGCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGCGCCTCCGATGCCAGAGCCTACGAGAAGAGGTGCACAACGTCTGGGCCACACACGCCTGTGT
GCCTACCGATCCATCTCCTCAAGAGCTGGTGCTGGGCAACGTGACCGAGAACTTCAACATGTGGAAGAACGA
CATGGTGGACCAGATGCACGAGGACATCATCAGCCTGTGGGACCAGAGCCTGAAGCCTTGCGTGAAGCTGAC
CCCTCTGTGCGTGACCCTGATCTGTTCTGACGCCACCGTGAAAACCGGCACCGTGGAAGAGATGAAGAACTGC
AGCTTCAACACCACCACCGAGATCCGGGACAAAGAGAAGAAAGAGTACGCCCTGTTCTACAAGCCCGACATC
GTGCCCCTGAGCGAGACAAACAACACCAGCGAGTACCGGCTGATCAACTGCAACACAAGCGCCGTGACCATG
GCCTGTCCTAAAGTGACCTTCGAGCCCATTCCTATCCACTACTGTGCCCCTGCCGGCTACGCCATCCTGAAGTG
CAACGACGAGACATTCAACGGCACAGGCCCCTGCAGCAATGTGTCCACCGTGCAGTGTACCCACGGCATCAG
ACCAGTGGTGTCTACCCAGCTGCTGCTGAATGGAAGCCTGGCCGAGAAAGAAATCGTGATCAGAAGCGAGAA
CCTGACCAACAACGCCAAGATCATCATTGTGCATCTGCACACCCCTGTGGAAATCGTGTGCACCCGGCCTCTG
AATCTGACCAGAAAGAGCGTGCGGATCGGCCCTGGCCAGACCTTTTATGCCATGGGCGACATCATCGGCGAT
ATCAAGCAGGCCCACTGCAACATCAGCGAGGAAAAGTGGAACGACACCCTGCAGAAAGTGGGCATCGAGCT
GCAGAAGCACTTCCCCAACAAGACCATCAAGTACAACCAGAGCGCTGGCGGCGACATGGAAATCACCACACA
CAGCTTCAATTGTGGCGGCGAGTTCTTCTACTGCAATACCAGCAACCTGTTCAACGGGACCTACAATGGCACCT
ACATCAGCACCAACAGCAGCGCCAACTCCACCAGCACCATCACTCTGCAGTGCCGGATCAAGATGATCATTAA
CATGTGGCAAGGCGTCGGCAGGGCTATGTACGCCCCTCCTATCGCCGGCAACATCACCTGTCGGAGCAATATC
ACAGGCCTGCTGCTCACCAGAGATGGCGGCACCAATAGCAACGAGACAGAAACCTTCAGACCTGCCGGCGGA
GACATGAGAGACAATTGGAGAAGCGAGCTGTACAAGTACAAGGTGGTCAAGATCGAGCCCCTGGGCGTCGC
ACCTACACGGTGCAAGAGAAGAGTCGTGGGCCGTCGTAGAAGGCGGAGAGCCGTTGGAATTGGCGCCGTGT
TCCTGGGCTTTCTGGGAGCCGCTGGATCTACAATGGGCGCTGCCAGCATGACCCTGACAGTGCAGGCTAGAA
ATCTGCTGAGCGGCATCGTGCAGCAGCAGAGCAATCTGCTCAGAGCCCCTGAGGCTCAGCAGCACCTCCTGA
AACTGACAGTGTGGGGCATCAAGCAGCTGCAGGCAAGAGTGCTGGCAGTGGAAAGATACCTGCGGGACCAG
CAGCTCCTCGGAATCTGGGGATGTAGCGGCAAGCTGATCTGCTGCACCAACGTGCCCTGGAACAGCTCCTGGT
CCAACCGGAATCTGTCCGAGATCTGGGATAACATGACCTGGCTGCAGTGGGACAAAGAAATCAGCAACTACA
CCCAGATCATCTACGGCCTGCTGGAAGAGAGCCAGAACCAGCAAGAGAAAAACGAGCAGGACCTGCTGGCC
CTGGACTGATAAGGATCC (SEQ ID NO: 21)

Figure 41B

>CH0848.D0949.10.17_N133D_N138T.SOSIP.Vt8

*MPMGSLQPLATLYLLGMLVASVLA*AENLWVTVYYGVPVWKEAKTTLFCASDARAYEKEVHNVWATHACVPTDP
SPQELVLGNVTENFNMWKNDMVDQMHEDIISLWDQSLKPCVKLTPLCVTLICSDATVKTGTVEEMKNCSFNTTT
EIRDKEKKEYALFYKPDIVPLSETNNTSEYRLINCNTSAVTMACPKVTFEPIPIHYCAPAGYAILKCNDETFNGTGPCS
NVSTVQCTHGIRPVVSTQLLLNGSLAEKEIVIRSENLTNNAKIIIVHLHTPVEIVCTRPLNLTRKSVRIGPGQTFYAMG
DIIGDIKQAHCNISEEKWNDTLQKVGIELQKHFPNKTIKYNQSAGGDMEITTHSFNCGGEFFYCNTSNLFNGTYNG
TYISTNSSANSTSTITLQCRIKMIINMWQGVGRAMYAPPIAGNITCRSNITGLLLTRDGGTNSNETETFRPAGGDMR
DNWRSELYKYKVVEIQPLGIAPTGAKRRVVERRRRRRAAGLGALFLGFLGAAGSTMGAASITLTVQARQLLSGIVQ
QQSNLLRAPEAQQHMLQLTVWGIKQLQARVLALERYLKDQQLLGMWGCSGKLICCTNVPWNTSWSNKSETDI
WDNMTWMQWEREISNYTETIYKLLEDSQNQQERNEQDLLALD** (SEQ ID NO: 22)

Figure 41C

>CH0848.D0949.10.17_N133D_N138T.SOSIP.Vt8
GTCGACGCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGCGCCTCCGATGCCAGAGCCTACGAGAAAGAGGTGCACAACGTCTGGGCCACACACGCCTGTGT
GCCTACCGATCCATCTCCTCAAGAGCTGGTGCTGGGCAACGTGACCGAGAACTTCAACATGTGGAAGAACGA
CATGGTGGACCAGATGCACGAGGACATCATCAGCCTGTGGGACCAGAGCCTGAAGCCTTGCGTGAAGCTGAC
CCCTCTGTGCGTGACCCTGATCTGTTCTGACGCCACCGTGAAAACCGGCACCGTGGAAGAGATGAAGAACTGC
AGCTTCAACACCACCACCGAGATCCGGGACAAAGAGAAGAAAGAGTACGCCCTGTTCTACAAGCCCGACATC
GTGCCCCTGAGCGAGACAAACAACACCAGCGAGTACCGGCTGATCAACTGCAACACAAGCGCCGTGACCATG
GCCTGTCCTAAAGTGACCTTCGAGCCCATTCCTATCCACTACTGTGCCCCTGCCGGCTACGCCATCCTGAAGTG
CAACGACGAGACATTCAACGGCACAGGCCCCTGCAGCAATGTGTCCACCGTGCAGTGTACCCACGGCATCAG
ACCAGTGGTGTCTACCCAGCTGCTGCTGAATGGAAGCCTGGCCGAGAAAGAAATCGTGATCAGAAGCGAGAA
CCTGACCAACAACGCCAAGATCATCATTGTGCATCTGCACACCCCTGTGGAAATCGTGTGCACCCGGCCTCTG
AATCTGACCAGAAAGAGCGTGCGGATCGGCCCTGGCCAGACCTTTTATGCCATGGGCGACATCATCGGCGAT
ATCAAGCAGGCCCACTGCAACATCAGCGAGGAAAAGTGGAACGACACCCTGCAGAAAGTGGGCATCGAGCT
GCAGAAGCACTTCCCCAACAAGACCATCAAGTACAACCAGAGCGCTGGCGGCGACATGGAAATCACCACACA
CAGCTTCAATTGTGGCGGCGAGTTCTTCTACTGCAATACCAGCAACCTGTTCAACGGGACCTACAATGGCACCT
ACATCAGCACCAACAGCAGCGCCAACTCCACCAGCACCATCACTCTGCAGTGCCGGATCAAGATGATCATTAA
CATGTGGCAAGGCGTCGGCAGGGCTATGTACGCCCCTCCTATCGCCGGCAACATCACCTGTCGGAGCAATATC
ACAGGCCTGCTGCTCACCAGAGATGGCGGCACCAATAGCAACGAGACAGAAACCTTCAGACCTGCCGGCGGA
GACATGAGAGACAATTGGAGAAGCGAGCTGTACAAGTACAAGGTCGTGGAAATCCAGCCACTGGGAATCGC
CCCAACCGGCGCTAAGAGAAGAGTGGTGGAACGGCGAAGAAGGCGGAGAGCTGCTGGACTGGGTGCTCTGT
TCCTGGGCTTTCTTGGAGCCGCCGGATCTACAATGGGAGCCGCCTCTATCACCCTGACCGTGCAGGCTAGACA
GCTGCTGAGCGGAATTGTGCAGCAGCAGAGCAACCTGCTGAGAGCCCCTGAAGCACAGCAGCACATGCTGCA
GCTGACAGTGTGGGGCATCAAACAGCTGCAGGCCAGAGTGCTGGCCCTGGAAAGATACCTGAAGGATCAGC
AGCTCCTCGGCATGTGGGGCTGTTCTGGCAAGCTGATCTGCTGCACCAACGTGCCCTGGAACACCTCCTGGTC
CAACAAGAGCGAAACCGACATCTGGGACAACATGACCTGGATGCAGTGGGAGAGAGAGATCAGCAACTACA
CCGAGACAATCTACAAGCTGCTCGAGGACAGCCAGAACCAGCAAGAGAGAAACGAGCAGGACCTGCTGGCT
CTGGACTGATGAGGATCC (SEQ ID NO: 23)

Figure 41D

>CH0848.D0949.10.17_N133D_N138T.ch.SOSIP.F14

*MPMGSLQPLATLYLLGMLVASVLA*AENLWVTVYYGVPVWKEAKTTLFCASDARAYEKEVHNIWATHACVPTDPS
PQELVLGNVTENFNMWKNDMVDQMHEDIISLWDQSLKPCVKLTPLCVTLICSDATVKTGTVEEMKNCSFNTTTEI
RDKEKKEYALFYKPDIVPLSETNNTSEYRLINCNTSAVTQVCPKLTFEPIPIHYCAPAGYAILKCNDETFNGTGPCSNVS
TVQCTHGIRPVLSTQLLLNGSLAEKEIVIRSENLTNNAKIIIVHLHTPVEIVCTRPNNNTRKSVRIGPGQTFYATGDIIG
DIKQAHCNISEEKWNDTLQKVGIELQKHFPNKTIKYNQSAGGDMEITTHSFNCGGEFFYCNTSNLFNGTYNGTYIST
NSSANSTSTITLQCRIKQIINMWQGVGRAMYAPPIAGNITCRSNITGLLLTRDGGTNSNETETFRPAGGDMRDNW
RSELYKYKVVKIEPLGVAPTRCKRRVVGRRRRRRAVGIGAVFLGFLGAAGSTMGAASMTLTVQARNLLSGIVQQQS
NLLRAPEAQQHLLKLTVWGIKQLQARVLAVERYLRDQQLLGIWGCSGKLICCTNVPWNSSWSNRNLSEIWDNMT
WLQWDKEISNYTQIIYGLLEESQNQQEKNEQDLLALD** (SEQ ID NO: 24)

Figure 41E

>CH0848.D0949.10.17_N133D_N138T.ch.SOSIP.F14

GTCGACGCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGCGCCTCCGATGCCAGAGCCTACGAGAAAGAGGTGCACAACATCTGGGCCACACACGCCTGCGT
GCCAACCGATCCATCTCCTCAAGAACTGGTGCTGGGCAACGTGACCGAGAACTTCAACATGTGGAAGAACGA
CATGGTGGACCAGATGCACGAGGACATCATCAGCCTGTGGGACCAGAGCCTGAAGCCTTGCGTGAAGCTGAC
CCCTCTGTGCGTGACCCTGATCTGTTCTGACGCCACCGTGAAAACCGGCACCGTGGAAGAGATGAAGAACTGC
AGCTTCAACACCACCACCGAGATCCGGGACAAAGAGAAGAAAGAGTACGCCCTGTTCTACAAGCCCGACATC
GTGCCCCTGAGCGAGACAAACAACACCAGCGAGTACCGGCTGATCAACTGCAACACCTCCGCCGTGACACAA
GTGTGCCCCAAGCTGACCTTCGAGCCCATTCCTATCCACTACTGTGCCCCTGCCGGCTACGCCATCCTGAAGTG
CAACGACGAGACATTCAACGGCACAGGCCCCTGCAGCAATGTGTCCACCGTGCAGTGTACCCACGGCATCAG
ACCTGTGCTGAGCACACAGCTGCTGCTGAATGGAAGCCTGGCCGAGAAAGAAATCGTGATCAGAAGCGAGA
ACCTGACCAACAACGCCAAGATCATCATTGTGCATCTGCACACCCCTGTGGAAATCGTGTGCACCCGGCCTAA
CAACAACACCCGGAAGTCTGTGCGGATCGGCCCTGGCCAGACATTCTATGCCACCGGCGATATCATCGGCGAC
ATCAAGCAGGCCCACTGCAACATCAGCGAGGAAAAGTGGAACGACACCCTGCAGAAAGTGGGCATCGAGCT
GCAGAAGCACTTCCCCAACAAGACCATCAAGTACAACCAGAGCGCTGGCGGCGACATGGAAATCACCACACA
CAGCTTCAATTGTGGCGGCGAGTTCTTCTACTGCAATACCAGCAACCTGTTCAACGGGACCTACAATGGCACCT
ACATCAGCACCAACAGCAGCGCCAACTCCACCAGCACCATCACTCTGCAGTGCCGGATCAAGCAGATCATCAA
TATGTGGCAAGGCGTGGGCAGAGCTATGTACGCCCCTCCTATCGCCGGCAACATCACCTGTCGGAGCAATATC
ACAGGCCTGCTGCTCACCAGAGATGGCGGCACCAATAGCAACGAGACAGAAACCTTCAGACCTGCCGGCGGA
GACATGAGAGACAATTGGAGAAGCGAGCTGTACAAGTACAAGGTGGTCAAGATCGAGCCCCTGGGCGTCGC
ACCTACACGGTGCAAGAGAAGAGTCGTGGGACGTAGACGAAGGCGGAGAGCCGTTGGAATCGGAGCCGTGT
TCCTGGGCTTTCTGGGAGCCGCTGGATCTACAATGGGCGCTGCCAGCATGACCCTGACAGTGCAGGCTAGAA
ATCTGCTGAGCGGCATCGTGCAGCAGCAGAGCAATCTGCTCAGAGCCCCTGAGGCTCAGCAGCACCTCCTGA
AACTGACAGTGTGGGGAATCAAGCAGCTGCAGGCCAGAGTGCTGGCAGTGGAAAGATACCTGAGGGACCAG
CAGCTCCTCGGAATCTGGGGCTGTTCTGGCAAGCTGATCTGCTGCACCAACGTGCCCTGGAACAGCAGCTGGT
CCAACCGGAATCTGTCCGAGATCTGGGATAACATGACCTGGCTGCAGTGGGACAAAGAAATCAGCAACTACA
CCCAGATCATCTACGGCCTGCTGGAAGAGAGCCAGAACCAGCAAGAGAAAAACGAGCAGGACCTGCTGGCC
CTGGACTGATAAGGATCC (SEQ ID NO: 25)

Figure 41F

>CH0848.D0949.10.17_N133D_N138T.SOSIP.F14.Vt8

*MPMGSLQPLATLYLLGMLVASVLA*AENLWVTVYYGVPVWKEAKTTLFCASDARAYEKEVHNIWATHACVPTDPS
PQELVLGNVTENFNMWKNDMVDQMHEDIISLWDQSLKPCVKLTPLCVTLICSDATVKTGTVEEMKNCSFNTTTEI
RDKEKKEYALFYKPDIVPLSETNNTSEYRLINCNTSAVTMVCPKLTFEPIPIHYCAPAGYAILKCNDETFNGTGPCSNV
STVQCTHGIRPVLSTQLLLNGSLAEKEIVIRSENLTNNAKIIIVHLHTPVEIVCTRPLNLTRKSVRIGPGQTFYAMGDIIG
DIKQAHCNISEEKWNDTLQKVGIELQKHFPNKTIKYNQSAGGDMEITTHSFNCGGEFFYCNTSNLFNGTYNGTYIST
NSSANSTSTITLQCRIKMIINMWQGVGRAMYAPPIAGNITCRSNITGLLLTRDGGTNSNETETFRPAGGDMRDNW
RSELYKYKVVEIQPLGIAPTGAKRRVVERRRRRRAAGLGALFLGFLGAAGSTMGAASITLTVQARQLLSGIVQQQSN
LLRAPEAQQHMLQLTVWGIKQLQARVLALERYLKDQQLLGMWGCSGKLICCTNVPWNTSWSNKSETDIWDNM
TWMQWEREISNYTETIYKLLEDSQNQQERNEQDLLALD** (SEQ ID NO: 26)

Figure 41G

>CH0848.D0949.10.17_N133D_N138T.SOSIP.F14.Vt8

GTCGACGCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGCGCCTCCGATGCCAGAGCCTACGAGAAGGAGGTGCACAACATCTGGGCCACACACGCCTGCGT
GCCAACCGATCCATCTCCTCAAGAACTGGTGCTGGGCAACGTGACCGAGAACTTCAACATGTGGAAGAACGA
CATGGTGGACCAGATGCACGAGGACATCATCAGCCTGTGGGACCAGAGCCTGAAGCCTTGCGTGAAGCTGAC
CCCTCTGTGCGTGACCCTGATCTGTTCTGACGCCACCGTGAAAACCGGCACCGTGGAAGAGATGAAGAACTGC
AGCTTCAACACCACCACCGAGATCCGGGACAAAGAGAAGAAAGAGTACGCCCTGTTCTACAAGCCCGACATC
GTGCCCCTGAGCGAGACAAACAACACCAGCGAGTACCGGCTGATCAACTGCAACACAAGCGCCGTGACAATG
GTCTGCCCCAAGCTGACCTTCGAGCCCATTCCTATCCACTACTGTGCCCCTGCCGGCTACGCCATCCTGAAGTG
CAACGACGAGACATTCAACGGCACAGGCCCCTGCAGCAATGTGTCCACCGTGCAGTGTACCCACGGCATCAG
ACCTGTGCTGAGCACACAGCTGCTGCTGAATGGAAGCCTGGCCGAGAAGAAATCGTGATCAGAAGCGAGA
ACCTGACCAACAACGCCAAGATCATCATTGTGCATCTGCACACCCCTGTGGAAATCGTGTGCACCCGGCCTCT
GAATCTGACCAGAAAGAGCGTGCGGATCGGCCCTGGCCAGACCTTTTATGCCATGGGCGACATCATCGGCGA
TATCAAGCAGGCCCACTGCAACATCAGCGAGGAAAAGTGGAACGACACCCTGCAGAAAGTGGGCATCGAGCT
GCAGAAGCACTTCCCCAACAAGACCATCAAGTACAACCAGAGCGCTGGCGGCGACATGGAAATCACCACACA
CAGCTTCAATTGTGGCGGCGAGTTCTTCTACTGCAATACCAGCAACCTGTTCAACGGGACCTACAATGGCACCT
ACATCAGCACCAACAGCAGCGCCAACTCCACCAGCACCATCACTCTGCAGTGCCGGATCAAGATGATCATTAA
CATGTGGCAAGGCGTCGGCAGGGCTATGTACGCCCCTCCTATCGCCGGCAACATCACCTGTCGGAGCAATATC
ACAGGCCTGCTGCTCACCAGAGATGGCGGCACCAATAGCAACGAGACAGAAACCTTCAGACCTGCCGGCGGA
GACATGAGAGACAATTGGAGAAGCGAGCTGTACAAGTACAAGGTCGTGGAAATCCAGCCACTGGGAATCGC
CCCAACCGGCGCTAAGAGAAGAGTGGTGGAACGGCGAAGAAGGCGGAGAGCTGCTGGACTGGGTGCTCTGT
TCCTGGGCTTTCTTGGAGCCGCCGGATCTACAATGGGAGCCGCCTCTATCACCCTGACCGTGCAGGCTAGACA
GCTGCTCTCTGGAATCGTGCAGCAGCAGAGCAACCTGCTGAGAGCCCCTGAAGCTCAGCAGCACATGCTGCA
GCTGACAGTGTGGGGCATCAAACAGCTGCAGGCCAGAGTGCTGGCCCTGGAAAGATACCTGAAGGATCAGC
AGCTCCTCGGCATGTGGGGCTGTTCTGGCAAGCTGATCTGCTGCACCAACGTGCCCTGGAACACCTCCTGGTC
CAACAAGAGCGAAACCGACATCTGGGACAACATGACCTGGATGCAGTGGGAGAGAGAGATCAGCAACTACA
CCGAGACAATCTACAAGCTGCTCGAGGACAGCCAGAACCAGCAAGAGAGAAACGAGCAGGACCTGCTGGCT
CTGGACTGATGAGGATCC (SEQ ID NO: 27)

Figure 41H

>CH0848.D0949.10.17_N133D_N138T.SOSIP.F14
*MPMGSLQPLATLYLLGMLVASVLA*AENLWVTVYYGVPVWKEAKTTLFCASDARAYEKEVHNIWATHACVPTDPS
PQELVLGNVTENFNMWKNDMVDQMHEDIISLWDQSLKPCVKLTPLCVTLICSDATVKTGTVEEMKNCSFNTTTEI
RDKEKKEYALFYKPDIVPLSETNNTSEYRLINCNTSAVTQVCPKLTFEPIPIHYCAPAGYAILKCNDETFNGTPCSNVS
TVQCTHGIRPVLSTQLLLNGSLAEKEIVIRSENLTNNAKIIIVHLHTPVEIVCTRPNNNTRKSVRIGPGQTFYATGDIIG
DIKQAHCNISEEKWNDTLQKVGIELQKHFPNKTIKYNQSAGGDMEITTHSFNCGGEFFYCNTSNLFNGTYNGTYIST
NSSANSTSTITLQCRIKQIINMWQGVGRAMYAPPIAGNITCRSNITGLLLTRDGGTNSNETETFRPAGGDMRDNW
RSELYKYKVVEIQPLGIAPTGAKRRVVERRRRRRAAGLGALFLGFLGAAGSTMGAASITLTVQARQLLSGIVQQQSN
LLRAPEAQQHMLQLTVWGIKQLQARVLALERYLKDQQLLGMWGCSGKLICCTNVPWNTSWSNKSETDIWDNM
TWMQWEREISNYTETIYKLLEDSQNQQERNEQDLLALD** (SEQ ID NO: 28)

Figure 4I

>CH0848.D0949.10.17_N133D_N138T.SOSIP.F14
GTCGACGCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGCGCCTCCGATGCCAGAGCCTACGAGAAGAGGTGCACAACATCTGGGCCACACACGCCTGCGT
GCCAACCGATCCATCTCCTCAAGAACTGGTGCTGGGCAACGTGACCGAGAACTTCAACATGTGGAAGAACGA
CATGGTGGACCAGATGCACGAGGACATCATCAGCCTGTGGGACCAGAGCCTGAAGCCTTGCGTGAAGCTGAC
CCCTCTGTGCGTGACCCTGATCTGTTCTGACGCCACCGTGAAAACCGGCACCGTGGAAGAGATGAAGAACTGC
AGCTTCAACACCACCACCGAGATCCGGGACAAAGAGAAGAAAGAGTACGCCCTGTTCTACAAGCCCGACATC
GTGCCCCTGAGCGAGACAAACAACACCAGCGAGTACCGGCTGATCAACTGCAACACCTCCGCCGTGACACAA
GTGTGCCCCAAGCTGACCTTCGAGCCCATTCCTATCCACTACTGTGCCCCTGCCGGCTACGCCATCCTGAAGTG
CAACGACGAGACATTCAACGGCACAGGCCCCTGCAGCAATGTGTCCACCGTGCAGTGTACCCACGGCATCAG
ACCTGTGCTGAGCACACAGCTGCTGCTGAATGGAAGCCTGGCCGAGAAAGAAATCGTGATCAGAAGCGAGA
ACCTGACCAACAACGCCAAGATCATCATTGTGCATCTGCACACCCCTGTGGAAATCGTGTGCACCCGGCCTAA
CAACAACACCCGGAAGTCTGTGCGGATCGGCCCTGGCCAGACATTCTATGCCACCGGCGATATCATCGGCGAC
ATCAAGCAGGCCCACTGCAACATCAGCGAGGAAAAGTGGAACGACACCCTGCAGAAAGTGGGCATCGAGCT
GCAGAAGCACTTCCCCAACAAGACCATCAAGTACAACCAGAGCGCTGGCGGCGACATGGAAATCACCACACA
CAGCTTCAATTGTGGCGGCGAGTTCTTCTACTGCAATACCAGCAACCTGTTCAACGGGACCTACAATGGCACCT
ACATCAGCACCAACAGCAGCGCCAACTCCACCAGCACCATCACTCTGCAGTGCCGGATCAAGCAGATCATCAA
TATGTGGCAAGGCGTGGGCAGAGCTATGTACGCCCCTCCTATCGCCGGCAACATCACCTGTCGGAGCAATATC
ACAGGCCTGCTGCTCACCAGAGATGGCGGCACCAATAGCAACGAGACAGAAACCTTCAGACCTGCCGGCGGA
GACATGAGAGACAATTGGAGAAGCGAGCTGTACAAGTACAAGGTGGTGGAAATCCAGCCACTGGGAATCGC
CCCAACCGGCGCTAAGAGAAGAGTGGTCGAGCGGAGAAGAAGGCGGAGAGCTGCTGGACTGGGTGCCCTG
TTTCTGGGCTTTCTTGGAGCCGCCGGAAGCACAATGGGAGCCGCCTCTATTACCCTGACCGTGCAGGCTAGAC
AGCTGCTCTCTGGAATCGTGCAGCAGCAGAGCAACCTGCTGAGAGCCCCTGAAGCTCAGCAGCACATGCTGC
AGCTGACAGTGTGGGGAATCAAGCAGCTGCAGGCCAGAGTGCTGGCCCTGGAAAGATACCTGAAGGATCAG
CAGCTCCTCGGCATGTGGGGCTGTTCTGGCAAGCTGATCTGCTGCACCAACGTGCCCTGGAACACCTCCTGGT
CCAACAAGAGCGAAACCGACATCTGGGACAACATGACCTGGATGCAGTGGGAGAGAGAGATCAGCAACTAC
ACCGAGACAATCTACAAGCTGCTCGAGGACAGCCAGAACCAGCAAGAGAAACGAGCAGGACCTGCTGGC
TCTGGACTGATGAGGATCC (SEQ ID NO: 29)

Figure 4J

```
                                              1                                                           50
CH0848.D0949.10.17_N133D_N138T.ch.SOSIP   (1) MPMGSLQPLATLYLLGMLVASVLAAENLWVTVYYGVPVWKEAKTTLFCAS
CH0848.D0949.10.17_N133D_N138T.ch.SOSIP.F14 (1) MPMGSLQPLATLYLLGMLVASVLAAENLWVTVYYGVPVWKEAKTTLFCAS
CH0848.D0949.10.17_N133D_N138T.ch.SOSIP.Vt8 (1) MPMGSLQPLATLYLLGMLVASVLAAENLWVTVYYGVPVWKEAKTTLFCAS
                                  Consensus (1) MPMGSLQPLATLYLLGMLVASVLAAENLWVTVYYGVPVWKEAKTTLFCAS 51                                                          100
CH0848.D0949.10.17_N133D_N138T.ch.SOSIP  (51) DARAYEKEVHNVWATHACVPTDPSPQELVLGNVTENFNMWKNDMVDQMHE
CH0848.D0949.10.17_N133D_N138T.ch.SOSIP.F14 (51) DARAYEKEVHNVWATHACVPTDPSPQELVLGNVTENFNMWKNDMVDQMHE
CH0848.D0949.10.17_N133D_N138T.ch.SOSIP.Vt8 (51) DARAYEKEVHNVWATHACVPTDPSPQELVLGNVTENFNMWKNDMVDQMHE
                                  Consensus (51) DARAYEKEVHNVWATHACVPTDPSPQELVLGNVTENFNMWKNDMVDQMHE 101                                                          150
CH0848.D0949.10.17_N133D_N138T.ch.SOSIP (101) DIISLWDQSLKPCVKLTPLCVTLICSDATVKTGTVEEMKNCSFNTTTEIR
CH0848.D0949.10.17_N133D_N138T.ch.SOSIP.F14 (101) DIISLWDQSLKPCVKLTPLCVTLICSDATVKTGTVEEMKNCSFNTTTEIR
CH0848.D0949.10.17_N133D_N138T.ch.SOSIP.Vt8 (101) DIISLWDQSLKPCVKLTPLCVTLICSDATVKTGTVEEMKNCSFNTTTEIR
                                  Consensus (101) DIISLWDQSLKPCVKLTPLCVTLICSDATVKTGTVEEMKNCSFNTTTEIR 151                                                          200
CH0848.D0949.10.17_N133D_N138T.ch.SOSIP (151) DKEKKEYALFYKPDIVPLSETNNTSEYRLINCNTSAVTQACPKVTFEPIP
CH0848.D0949.10.17_N133D_N138T.ch.SOSIP.F14 (151) DKEKKEYALFYKPDIVPLSETNNTSEYRLINCNTSAVTQACPKVTFEPIP
CH0848.D0949.10.17_N133D_N138T.ch.SOSIP.Vt8 (151) DKEKKEYALFYKPDIVPLSETNNTSEYRLINCNTSAVTQACPKVTFEPIP
                                  Consensus (151) DKEKKEYALFYKPDIVPLSETNNTSEYRLINCNTSAVTQACPKVTFEPIP 201                                                          250
CH0848.D0949.10.17_N133D_N138T.ch.SOSIP (201) IHYCAPAGYAILKCNDETFNGTGPCSNVSTVQCTHGIRPVVSTQLLLNGS
CH0848.D0949.10.17_N133D_N138T.ch.SOSIP.F14 (201) IHYCAPAGYAILKCNDETFNGTGPCSNVSTVQCTHGIRPVVSTQLLLNGS
CH0848.D0949.10.17_N133D_N138T.ch.SOSIP.Vt8 (201) IHYCAPAGYAILKCNDETFNGTGPCSNVSTVQCTHGIRPVVSTQLLLNGS
                                  Consensus (201) IHYCAPAGYAILKCNDETFNGTGPCSNVSTVQCTHGIRPVVSTQLLLNGS 251                                                          300
CH0848.D0949.10.17_N133D_N138T.ch.SOSIP (251) LAEKEIVIRSENLTNNAKIIIVHLHTPVEIVCTRPNNNTRKSVRIGPGQT
CH0848.D0949.10.17_N133D_N138T.ch.SOSIP.F14 (251) LAEKEIVIRSENLTNNAKIIIVHLHTPVEIVCTRPNNNTRKSVRIGPGQT
CH0848.D0949.10.17_N133D_N138T.ch.SOSIP.Vt8 (251) LAEKEIVIRSENLTNNAKIIIVHLHTPVEIVCTRPNNNTRKSVRIGPGQT
                                  Consensus (251) LAEKEIVIRSENLTNNAKIIIVHLHTPVEIVCTRPNNNTRKSVRIGPGQT 301                                                          350
``` figure 42

```
CH0848.D0949.10.17_N133D_N138T.ch.SOSIP   (301) FYATGDIIGDIKQAHCNISEEKWNDTLQKVGIELQKHFPNKTIKYNQSAG
CH0848.D0949.10.17_N133D_N138T.ch.SOSIP.F14 (301) FYATGDIIGDIKQAHCNISEEKWNDTLQKVGIELQKHFPNKTIKYNQSAG
CH0848.D0949.10.17_N133D_N138T.ch.SOSIP.Vt8 (301) FYAMGDIIGDIKQAHCNISEEKWNDTLQKVGIELQKHFPNKTIKYNQSAG
                                Consensus   (301) FYATGDIIGDIKQAHCNISEEKWNDTLQKVGIELQKHFPNKTIKYNQSAG
                                                                                                 400

CH0848.D0949.10.17_N133D_N138T.ch.SOSIP   (351) GDMEITTHSFNCGGEFFYCNTSNLFNGTYNGTYISTNSSANSTSTITLQC
CH0848.D0949.10.17_N133D_N138T.ch.SOSIP.F14 (351) GDMEITTHSFNCGGEFFYCNTSNLFNGTYNGTYISTNSSANSTSTITLQC
CH0848.D0949.10.17_N133D_N138T.ch.SOSIP.Vt8 (351) GDMEITTHSFNCGGEFFYCNTSNLFNGTYNGTYISTNSSANSTSTITLQC
                                Consensus   (351) GDMEITTHSFNCGGEFFYCNTSNLFNGTYNGTYISTNSSANSTSTITLQC
                                                                                                 450

CH0848.D0949.10.17_N133D_N138T.ch.SOSIP   (401) RIKQIINMWQGVGRAMYAPPIAGNITCRSNITGLLLTRDGGTNSNETETF
CH0848.D0949.10.17_N133D_N138T.ch.SOSIP.F14 (401) RIKQIINMWQGVGRAMYAPPIAGNITCRSNITGLLLTRDGGTNSNETETF
CH0848.D0949.10.17_N133D_N138T.ch.SOSIP.Vt8 (401) RIKMIINMWQGVGRAMYAPPIAGNITCPSNITGLLLTRDGGTNSNETETF
                                Consensus   (401) RIKQIINMWQGVGRAMYAPPIAGNITCRSNITGLLLTRDGGTNSNETETF
                                                                                                 500

CH0848.D0949.10.17_N133D_N138T.ch.SOSIP   (451) RPAGGDMRDNWRSELYKYKVVKIEPLGVAPTRCKRRVGRRRRRAVGIG
CH0848.D0949.10.17_N133D_N138T.ch.SOSIP.F14 (451) RPAGGDMRDNWRSELYKYKVVKIEPLGVAPTRCKRRVGRRRRRAVGIG
CH0848.D0949.10.17_N133D_N138T.ch.SOSIP.Vt8 (451) RPAGGDMRDNWRSELYKYKVVKIEPLGVAPTRCKRRVGRRRRRAVGIG
                                Consensus   (451) RPAGGDMRDNWRSELYKYKVVKIEPLGVAPTRCKRRVGRRRRRAVGIG
                                                                                                 550

CH0848.D0949.10.17_N133D_N138T.ch.SOSIP   (501) AVFLGFLGAAGSTMGAASMTLTVQARNLLSGIVQQQSNLLRAPEAQQHLL
CH0848.D0949.10.17_N133D_N138T.ch.SOSIP.F14 (501) AVFLGFLGAAGSTMGAASMTLTVQARNLLSGIVQQQSNLLRAPEAQQHLL
CH0848.D0949.10.17_N133D_N138T.ch.SOSIP.Vt8 (501) AVFLGFLGAAGSTMGAASMTLTVQARNLLSGIVQQQSNLLRAPEAQQHLL
                                Consensus   (501) AVFLGFLGAAGSTMGAASMTLTVQARNLLSGIVQQQSNLLRAPEAQQHLL
                                                                                                 600

CH0848.D0949.10.17_N133D_N138T.ch.SOSIP   (551) KLTVWGIKQLQARVLAVERYLRDQQLLGIWGCSGKLICCTNVPWNSSWSN
CH0848.D0949.10.17_N133D_N138T.ch.SOSIP.F14 (551) KLTVWGIKQLQARVLAVERYLRDQQLLGIWGCSGKLICCTNVPWNSSWSN
CH0848.D0949.10.17_N133D_N138T.ch.SOSIP.Vt8 (551) KLTVWGIKQLQARVLAVERYLRDQQLLGIWGCSGKLICCTNVPWNSSWSN
                                Consensus   (551) KLTVWGIKQLQARVLAVERYLRDQQLLGIWGCSGKLICCTNVPWNSSWSN
                                                                                                 650
```

Figure 42 continued

CH0848.D0949.10.17_N133D_N138T.ch.SOSIP (601) RNLSEIWDNMTWLQWDKEISNYTQIIYGLLEESQNQQEKNEQDLLALD--
(SEQ ID NO: 30)
CH0848.D0949.10.17_N133D_N138T.ch.SOSIP.F14 (601) RNLSEIWDNMTWLQWDKEISNYTQIIYGLLEESQNQQEKNEQDLLALD--
(SEQ ID NO: 31)
CH0848.D0949.10.17_N133D_N138T.ch.SOSIP.Vt8 (601) RNLSEIWDNMTWLQWDKEISNYTQIIYGLLEESQNQQEKNEQDLLALD--
(SEQ ID NO: 32)
Consensus (601) RNLSEIWDNMTWLQWDKEISNYTQIIYGLLEESQNQQEKNEQDLLALD (SEQ
ID NO: 33)

figure 42 continued

```
                                                                                              50
CH0848.D0949.10.17_N133D_N138T.SOSIP       (1) MPMGSLQPLATLYLLGMLVASVLAAENLWVTVYYGVPVWKEAKTTLFCAS
CH0848.D0949.10.17_N133D_N138T.SOSIP.F14   (1) MPMGSLQPLATLYLLGMLVASVLAAENLWVTVYYGVPVWKEAKTTLFCAS
CH0848.D0949.10.17_N133D_N138T.SOSIP.F14.Vt8 (1) MPMGSLQPLATLYLLGMLVASVLAAENLWVTVYYGVPVWKEAKTTLFCAS
CH0848.D0949.10.17_N133D_N138T.SOSIP.Vt8   (1) MPMGSLQPLATLYLLGMLVASVLAAENLWVTVYYGVPVWKEAKTTLFCAS
                                 Consensus (1) MPMGSLQPLATLYLLGMLVASVLAAENLWVTVYYGVPVWKEAKTTLFCAS
                                                                                             100
CH0848.D0949.10.17_N133D_N138T.SOSIP      (51) DAPAYEKEVHNVWATHACVPTDPSFQELVLGNVTENFNMWKNDMVDQMHE
CH0848.D0949.10.17_N133D_N138T.SOSIP.F14  (51) DAPAYEKEVHNIWATHACVPTDPSFQELVLGNVTENFNMWKNDMVDQMHE
CH0848.D0949.10.17_N133D_N138T.SOSIP.F14.Vt8 (51) DAPAYEKEVHNIWATHACVPTDPSFQELVLGNVTENFNMWKNDMVDQMHE
CH0848.D0949.10.17_N133D_N138T.SOSIP.Vt8  (51) DAPAYEKEVHNVWATHACVPTDPSFQELVLGNVTENFNMWKNDMVDQMHE
                                 Consensus (51) DARAYEKEVHNIWATHACVPTDPSQELVLGNVTENFNMWKNDMVDQMHE
                                                                                             150
CH0848.D0949.10.17_N133D_N138T.SOSIP     (101) DIISLWDQSLKPCVKLTPLCVTLICSDATVKTGTVEEMKNCSFNTTTEIR
CH0848.D0949.10.17_N133D_N138T.SOSIP.F14 (101) DIISLWDQSLKPCVKLTPLCVTLICSDATVKTGTVEEMKNCSFNTTTEIR
CH0848.D0949.10.17_N133D_N138T.SOSIP.F14.Vt8 (101) DIISLWDQSLKPCVKLTPLCVTLICSDATVKTGTVEEMKNCSFNTTTEIR
CH0848.D0949.10.17_N133D_N138T.SOSIP.Vt8 (101) DIISLWDQSLKPCVKLTPLCVTLICSDATVKTGTVEEMKNCSFNTTTEIR
                                Consensus (101) DIISLWDQSLKPCVKLTPLCVTLICSDATVKTGTVEEMKNCSFNTTTEIR
                                                                                             200
CH0848.D0949.10.17_N133D_N138T.SOSIP     (151) DKEKKEYALFYKPDIVPLSETNNTSEYRLINCNTSAVTQVCPKVTFEPIP
CH0848.D0949.10.17_N133D_N138T.SOSIP.F14 (151) DKEKKEYALFYKPDIVPLSETNNTSEYRLINCNTSAVTQVCPKLTFEPIP
CH0848.D0949.10.17_N133D_N138T.SOSIP.F14.Vt8 (151) DKEKKEYALFYKPDIVPLSETNNTSEYRLINCNTSAVTMVCPKLTFEPIP
CH0848.D0949.10.17_N133D_N138T.SOSIP.Vt8 (151) DKEKKEYALFYKPDIVPLSETNNTSEYRLINCNTSAVTMACPKVTFEPIP
                                Consensus (151) DKEKKEYALFYKPDIVPLSETNNTSEYRLINCNTSAVTQVCPKLTFEPIP
                                                                                             250
CH0848.D0949.10.17_N133D_N138T.SOSIP     (201) IHYCAPAGYAILKCNDETFNGTGPCSNVSTVQCTHGIRPVVSTQLLLNGS
CH0848.D0949.10.17_N133D_N138T.SOSIP.F14 (201) IHYCAPAGYAILKCNDETFNGTGPCSNVSTVQCTHGIRPVLSTQLLLNGS
CH0848.D0949.10.17_N133D_N138T.SOSIP.F14.Vt8 (201) IHYCAPAGYAILKCNDETFNGTGPCSNVSTVQCTHGIRPVLSTQLLLNGS
CH0848.D0949.10.17_N133D_N138T.SOSIP.Vt8 (201) IHYCAPAGYAILKCNDETFNGTGPCSNVSTVQCTHGIRPVVSTQLLLNGS
                                Consensus (201) IHYCAPAGYAILKCNDETFNGTGPCSNVSTVQCTHGIRPVLSTQLLLNGS
                                                                                             300
                                          (251)
```

Figure 43 figure 43 continued

```
CH0848.D0949.10.17_N133D_N138T.SOSIP       (501) ALFLGFLGAAGSTMGAASITLTVQARQLLSGIVQQQSNLLRAPEAQQHML
CH0848.D0949.10.17_N133D_N138T.SOSIP.F14   (501) ALFLGFLGAAGSTMGAASITLTVQARQLLSGIVQQQSNLLRAPEAQQHML
CH0848.D0949.10.17_N133D_N138T.SOSIP.F14.Vt8 (501) ALFLGFLGAAGSTMGAASITLTVQARQLLSGIVQQQSNLLRAPEAQQHML
CH0848.D0949.10.17_N133D_N138T.SOSIP.Vt8   (501) ALFLGFLGAAGSTMGAASITLTVQARQLLSGIVQQQSNLLRAPEAQQHML
                                 Consensus       ALFLGFLGAAGSTMGAASITLTVQARQLLSGIVQQQSNLLRAPEAQQHML
                                                 551                                            600

CH0848.D0949.10.17_N133D_N138T.SOSIP       (551) QLTVWGIKQLQARVLALERYLKDQQLLGIWGCSGKLICCTNVPWNTSWSN
CH0848.D0949.10.17_N133D_N138T.SOSIP.F14   (551) QLTVWGIKQLQARVLALERYLKDQQLLGIWGCSGKLICCTNVPWNTSWSN
CH0848.D0949.10.17_N133D_N138T.SOSIP.F14.Vt8 (551) QLTVWGIKQLQARVLALERYLKDQQLLGIWGCSGKLICCTNVPWNTSWSN
CH0848.D0949.10.17_N133D_N138T.SOSIP.Vt8   (551) QLTVWGIKQLQARVLALERYLKDQQLLGIWGCSGKLICCTNVPWNTSWSN
                                 Consensus       QLTVWGIKQLQARVLALERYLKDQQLLGMWGCSGKLICCTNVPWNTSWSN
                                                 601                                            650

CH0848.D0949.10.17_N133D_N138T.SOSIP       (601) KSETDIWDNMTWMQWEREISNYTETIYKLLEDSQNQQERNEQDLLALD--- (SEQ ID NO: 34)
CH0848.D0949.10.17_N133D_N138T.SOSIP.F14   (601) KSETDIWDNMTWMQWEREISNYTETIYKLLEDSQNQQERNEQDLLALD--- (SEQ ID NO: 35)
CH0848.D0949.10.17_N133D_N138T.SOSIP.F14.Vt8 (601) KSETDIWDNMTWMQWEREISNYTETIYKLLEDSQKQQERNEQDLLALD--- (SEQ ID NO: 36)
CH0848.D0949.10.17_N133D_N138T.SOSIP.Vt8   (601) KSETDIWDNMTWMQWEREISNYTETIYKLLEDSQKQQERNEQDLLALD--- (SEQ ID NO: 37)
                                 Consensus (601) KSETDIWDNMTWMQWEREISNYTETIYKLLEDSQNQQERNEQDLLALD (SEQ ID NO: 38)
```

Figure 43 continued

CH0848.D0949.10.17 N133D N138T.SOSIP.Vt8

650 aa

```
  1 MPMGSIQPLA TLYLLGMLVA SVLAAENLWV TVYYGVPVWK EAKTTLFCAS DARAYEKEVH NIWATHACVP TDPSPQELVL GNVTENFNMW KNDMVDQMHE
101 DIISLWDQSL KPCVKLTPLC VTLICSDATV KTGTVEEMKN CSFNTTTEIR DKEKKEYALF YKPDIVPLSE TNNTSEYRLI NCNTSAVTMV CPKLTFEPIP
201 IHYCAPAGYA ILKCNDETFN GTGPCSNVST VQCTHGIRPV VSTQLLLNGS LAEKEIVIRS ENLTNNAKII IVHLHTFVEI VCTRPLNLTR KSVRIGPGQT
301 FYAMGDIIGD IKQAHCNISE EKWNDTLQKV GIELQKHFPN KTIKYNQSAG GEMEITTHSF NCGGEFFYCN TSNLFNGTYN GTYISTNSSA NSTSTTTLQC
401 RIKMLINMWQ GVGRAMYAPP IAGNITCRSN ITGLLLTRDG GTNSNETETF RPAGGDMRDN WRSELYKYKV VEIQPLGIAP TGAKRRVVER RRRRAAGLG
501 ALFLGFLGAA GSTMGAASIT LTVQARQLLS GIVQQQSNLL RAPEAQQHML QLTVWGIKQL QARVLALERY LKDQQLLGMW GCSGKLICCT NVPWNTSWSN
601 KSETDIWDNM TWMQWEREIS NYTETIYKLL EDSQNQQERN EQDLLALD**          (SEQ ID NO: 39)
```

Sequence confirmation

Figure 44

Translate results
\>HV1301735_N133D_N138T;CH0848.D0949.10.17_N133D_N138T.ch.SOSIP.Vt8
*MPMGSLQPLATLYLLGMLVASVLAA*ENLWVTVYYGVPVWKEAKTTLFCASDARAYE
KEVHNVWATHACVPTDPSPQELVLGNVTENFNMWKNDMVDQMHEDIISLWDQSLKPCVKL
TPLCVTLICSDATVKTGTVEEMKNCSFNTTTEIRDKEKKEYALFYKPDIVPLSETNNTSE
YRLINCNTSAVTMACPKVTFEPIPIHYCAPAGYAILKCNDETFNGTGPCSNVSTVQCTHG
IRPVVSTQLLLNGSLAEKEIVIRSENLTNNAKIIIVHLHTPVEIVCTRPLNLTRKSVRIG
PGQTFYAMGDIIGDIKQAHCNISEEKWNDTLQKVGIELQKHFPNKTIKYNQSAGGDMEIT
THSFNCGGEFFYCNTSNLFNGTYNGTYISTNSSANSTSTITLQCRIKMIINMWQGVGRAM
YAPPIAGNITCRSNITGLLLTRDGGTNSNETETFRPAGGDMRDNWRSELYKYKVVKIEPL
GVAPTRCKRRVVGRRRRRRAVGIGAVFLGFLGAAGSTMGAASMTLTVQARNLLSGIVQQQ
SNLLRAPEAQQHLLKLTVWGIKQLQARVLAVERYLRDQQLLGIWGCSGKLICCTNVPWNS
SWSNRNLSEIWDNMTWLQWDKEISNYTQIIYGLLEESQNQQEKNEQDLLALD** (SEQ ID NO: 40)

Figure 45A

\>HV1301736_N133D_N138T;CH0848.D0949.10.17_N133D_N138T.SOSIP.Vt8
*MPMGSLQPLATLYLLGMLVASVLAA*ENLWVTVYYGVPVWKEAKTTLFCASDARAYE
KEVHNVWATHACVPTDPSPQELVLGNVTENFNMWKNDMVDQMHEDIISLWDQSLKPCVKL
TPLCVTLICSDATVKTGTVEEMKNCSFNTTTEIRDKEKKEYALFYKPDIVPLSETNNTSE
YRLINCNTSAVTMACPKVTFEPIPIHYCAPAGYAILKCNDETFNGTGPCSNVSTVQCTHG
IRPVVSTQLLLNGSLAEKEIVIRSENLTNNAKIIIVHLHTPVEIVCTRPLNLTRKSVRIG
PGQTFYAMGDIIGDIKQAHCNISEEKWNDTLQKVGIELQKHFPNKTIKYNQSAGGDMEIT
THSFNCGGEFFYCNTSNLFNGTYNGTYISTNSSANSTSTITLQCRIKMIINMWQGVGRAM
YAPPIAGNITCRSNITGLLLTRDGGTNSNETETFRPAGGDMRDNWRSELYKYKVVEIQPL
GIAPTGAKRRVVERRRRRRAAGLGALFLGFLGAAGSTMGAASITLTVQARQLLSGIVQQQ
SNLLRAPEAQQHMLQLTVWGIKQLQARVLALERYLKDQQLLGMWGCSGKLICCTNVPWNT
SWSNKSETDIWDNMTWMQWEREISNYTETIYKLLEDSQNQQERNEQDLLALD** (SEQ ID NO: 41)

Figure 45B

\>HV1301737_N133D_N138T;CH0848.D0949.10.17_N133D_N138T.ch.SOSIP.F14
*MPMGSLQPLATLYLLGMLVASVLAA*ENLWVTVYYGVPVWKEAKTTLFCASDARAYE
KEVHNIWATHACVPTDPSPQELVLGNVTENFNMWKNDMVDQMHEDIISLWDQSLKPCVKL
TPLCVTLICSDATVKTGTVEEMKNCSFNTTTEIRDKEKKEYALFYKPDIVPLSETNNTSE
YRLINCNTSAVTQVCPKLTFEPIPIHYCAPAGYAILKCNDETFNGTGPCSNVSTVQCTHG
IRPVLSTQLLLNGSLAEKEIVIRSENLTNNAKIIIVHLHTPVEIVCTRPNNNTRKSVRIG
PGQTFYATGDIIGDIKQAHCNISEEKWNDTLQKVGIELQKHFPNKTIKYNQSAGGDMEIT
THSFNCGGEFFYCNTSNLFNGTYNGTYISTNSSANSTSTITLQCRIKQIINMWQGVGRAM
YAPPIAGNITCRSNITGLLLTRDGGTNSNETETFRPAGGDMRDNWRSELYKYKVVKIEPL
GVAPTRCKRRVVGRRRRRRAVGIGAVFLGFLGAAGSTMGAASMTLTVQARNLLSGIVQQQ
SNLLRAPEAQQHLLKLTVWGIKQLQARVLAVERYLRDQQLLGIWGCSGKLICCTNVPWNS
SWSNRNLSEIWDNMTWLQWDKEISNYTQIIYGLLEESQNQQEKNEQDLLALD** (SEQ ID NO: 42)

Figure 45C

>HV1301738_N133D_N138T;CH0848.D0949.10.17_N133D_N138T.SOSIP.F14.Vt8
*MPMGSLQPLATLYLLGMLVASVLAA*ENLWVTVYYGVPVWKEAKTTLFCASDARAYE
KEVHNIWATHACVPTDPSPQELVLGNVTENFNMWKNDMVDQMHEDIISLWDQSLKPCVKL
TPLCVTLICSDATVKTGTVEEMKNCSFNTTTEIRDKEKKEYALFYKPDIVPLSETNNTSE
YRLINCNTSAVTMVCPKLTFEPIPIHYCAPAGYAILKCNDETFNGTGPCSNVSTVQCTHG
IRPVLSTQLLLNGSLAEKEIVIRSENLTNNAKIIIVHLHTPVEIVCTRPLNLTRKSVRIG
PGQTFYAMGDIIGDIKQAHCNISEEKWNDTLQKVGIELQKHFPNKTIKYNQSAGGDMEIT
THSFNCGGEFFYCNTSNLFNGTYNGTYISTNSSANSTSTITLQCRIKMIINMWQGVGRAM
YAPPIAGNITCRSNITGLLLTRDGGTNSNETETFRPAGGDMRDNWRSELYKYKVVEIQPL
GIAPTGAKRRVVERRRRRAAGLGALFLGFLGAAGSTMGAASITLTVQARQLLSGIVQQQ
SNLLRAPEAQQHMLQLTVWGIKQLQARVLALERYLKDQQLLGMWGCSGKLICCTNVPWNT
SWSNKSETDIWDNMTWMQWEREISNYTETIYKLLEDSQNQQERNEQDLLALD** (SEQ ID NO: 43)

Figure 45D

>HV1301739_N133D_N138T;CH0848.D0949.10.17_N133D_N138T.SOSIP.F14
*MPMGSLQPLATLYLLGMLVASVLAA*ENLWVTVYYGVPVWKEAKTTLFCASDARAYE
KEVHNIWATHACVPTDPSPQELVLGNVTENFNMWKNDMVDQMHEDIISLWDQSLKPCVKL
TPLCVTLICSDATVKTGTVEEMKNCSFNTTTEIRDKEKKEYALFYKPDIVPLSETNNTSE
YRLINCNTSAVTQVCPKLTFEPIPIHYCAPAGYAILKCNDETFNGTGPCSNVSTVQCTHG
IRPVLSTQLLLNGSLAEKEIVIRSENLTNNAKIIIVHLHTPVEIVCTRPNNNTRKSVRIG
PGQTFYATGDIIGDIKQAHCNISEEKWNDTLQKVGIELQKHFPNKTIKYNQSAGGDMEIT
THSFNCGGEFFYCNTSNLFNGTYNGTYISTNSSANSTSTITLQCRIKQIINMWQGVGRAM
YAPPIAGNITCRSNITGLLLTRDGGTNSNETETFRPAGGDMRDNWRSELYKYKVVEIQPL
GIAPTGAKRRVVERRRRRAAGLGALFLGFLGAAGSTMGAASITLTVQARQLLSGIVQQQ
SNLLRAPEAQQHMLQLTVWGIKQLQARVLALERYLKDQQLLGMWGCSGKLICCTNVPWNT
SWSNKSETDIWDNMTWMQWEREISNYTETIYKLLEDSQNQQERNEQDLLALD** (SEQ ID NO: 44)

Figure 45E

>CH848.3.D0949.10.17N133DN138Tchim.SOSIP.Vt8
AENLWVTVYYGVPVWKEAKTTLFCASDARAYEKEVHNVWATHACVPTDPSPQELVLGNVTEN
FNMWKNDMVDQMHEDIISLWDQSLKPCVKLTPLCVTLICS▓ATVK▓GTVEEMKNCSFNTTTE
IRDKEKKEYALFYKPDIVPLSETNNTSEYRLINCNTSAVT▓ACPKVTFEPIPIHYCAPAGYA
ILKCNDETFNGTGPCSNVSTVQCTHGIRPVVSTQLLLNGSLAEKEIVIRSENLTNNAKIIIV
HLHTPVEIVCTRP▓N▓TRKSVRIGPGQTFYA▓GDIIGDIKQAHCNISEEKWNDTLQKVGIEL
QKHFPNKTIKYNQSAGGDMEITTHSFNCGGEFFYCNTSNLFNGTYNGTYISTNSSANSTSTI
TLQCRIK▓IINMWQGVGRAMYAPPIAGNITCRSNITGLLLTRDGGTNSNETETFRPAGGDMR
DNWRSELYKYKVVKIEPLGVAPTRCKRRVVGRRRRRRAVGIGAVFLGFLGAAGSTMGAASMT
LTVQARNLLSGIVQQQSNLLRAPEAQQHLLKLTVWGIKQLQARVLAVERYLRDQQLLGIWGC
SGKLICCTNVPWNSSWSNRNLSEIWDNMTWLQWDKEISNYTQIIYGLLEESQNQQEKNEQDL
LALD* (SEQ ID NO: 45)

Figure 46A

>CH848.3.D0949.10.17N133DN138Tchim.SOSIP.F14
AENLWVTVYYGVPVWKEAKTTLFCASDARAYEKEVHN▓WATHACVPTDPSPQELVLGNVTEN
FNMWKNDMVDQMHEDIISLWDQSLKPCVKLTPLCVTLICS▓ATVK▓GTVEEMKNCSFNTTTE
IRDKEKKEYALFYKPDIVPLSETNNTSEYRLINCNTSAVTQvCPK▓TFEPIPIHYCAPAGYA
ILKCNDETFNGTGPCSNVSTVQCTHGIRPV▓STQLLLNGSLAEKEIVIRSENLTNNAKIIIV
HLHTPVEIVCTRPNNNTRKSVRIGPGQTFYATGDIIGDIKQAHCNISEEKWNDTLQKVGIEL
QKHFPNKTIKYNQSAGGDMEITTHSFNCGGEFFYCNTSNLFNGTYNGTYISTNSSANSTSTI
TLQCRIKQIINMWQGVGRAMYAPPIAGNITCRSNITGLLLTRDGGTNSNETETFRPAGGDMR
DNWRSELYKYKVVKIEPLGVAPTRCKRRVVGRRRRRRAVGIGAVFLGFLGAAGSTMGAASMT
LTVQARNLLSGIVQQQSNLLRAPEAQQHLLKLTVWGIKQLQARVLAVERYLRDQQLLGIWGC
SGKLICCTNVPWNSSWSNRNLSEIWDNMTWLQWDKEISNYTQIIYGLLEESQNQQEKNEQDL
LALD* (SEQ ID NO: 46)

Figure 46B

>CH848.3.D0949.10.17N133DN138Tchim.SOSIP.F14Vt8
AENLWVTVYYGVPVWKEAKTTLFCASDARAYEKEVHN▓WATHACVPTDPSPQELVLGNVTEN
FNMWKNDMVDQMHEDIISLWDQSLKPCVKLTPLCVTLICS▓ATVK▓GTVEEMKNCSFNTTTE
IRDKEKKEYALFYKPDIVPLSETNNTSEYRLINCNTSAVT▓vCPK▓TFEPIPIHYCAPAGYA
ILKCNDETFNGTGPCSNVSTVQCTHGIRPV▓STQLLLNGSLAEKEIVIRSENLTNNAKIIIV
HLHTPVEIVCTRP▓N▓TRKSVRIGPGQTFYA▓GDIIGDIKQAHCNISEEKWNDTLQKVGIEL
QKHFPNKTIKYNQSAGGDMEITTHSFNCGGEFFYCNTSNLFNGTYNGTYISTNSSANSTSTI
TLQCRIK▓IINMWQGVGRAMYAPPIAGNITCRSNITGLLLTRDGGTNSNETETFRPAGGDMR
DNWRSELYKYKVVKIEPLGVAPTRCKRRVVGRRRRRRAVGIGAVFLGFLGAAGSTMGAASMT
LTVQARNLLSGIVQQQSNLLRAPEAQQHLLKLTVWGIKQLQARVLAVERYLRDQQLLGIWGC
SGKLICCTNVPWNSSWSNRNLSEIWDNMTWLQWDKEISNYTQIIYGLLEESQNQQEKNEQDL
LALD* (SEQ ID NO: 47)

Figure 46C

\>CH848.3.D0949.10.17N133DN138Tchim.SOSIP.F14Vt8
gtcgacgccaccatgcctatgggatctctgcagcctctggccacactgtacctgctgggaat
gctggtggcttctgtgctggccgccgagaatctgtgggtcacagtgtactatggcgtgcccg
tgtggaaagaggccaagaccacactgttctgcgcctccgatgccagagcctacgagaaagag
gtgcacaacatctgggccacacacgcctgcgtgccaaccgatccatctcctcaagaactggt
gctgggcaacgtgaccgagaacttcaacatgtggaagaacgacatggtggaccagatgcacg
aggacatcatcagcctgtgggaccagagcctgaagccttgcgtgaagctgacccctctgtgc
gtgaccctgatctgttctgacgccaccgtgaaaaccggcaccgtggaagagatgaagaactg
cagcttcaacaccaccaccgagatccgggacaaagagaagaaagagtacgccctgttctaca
agcccgacatcgtgcccctgagcgagacaaacaacaccagcgagtaccggctgatcaactgc
aacacaagcgccgtgacaatggtctgccccaagctgaccttcgagcccattcctatccacta
ctgtgccctgccggctacgccatcctgaagtgcaacgacgagacattcaacggcacaggcc
cctgcagcaatgtgtccaccgtgcagtgtacccacggcatcagacctgtgctgagcacacag
ctgctgctgaatggaagcctggccgagaaagaaatcgtgatcagaagcgagaacctgaccaa
caacgccaagatcatcattgtgcatctgcacacccctgtggaaatcgtgtgcacccggcctc
tgaatctgaccagaaagagcgtgcggatcggccctggccagaccttttatgccatgggcgac
atcatcggcgatatcaagcaggccactgcaacatcagcgaggaaaagtggaacgacaccct
gcagaaagtgggcatcgagctgcagaagcacttccccaacaagaccatcaagtacaaccaga
gcgctggcggcgacatggaaatcaccacacacagcttcaattgtggcggcgagttcttctac
tgcaataccagcaacctgttcaacgggacctacaatggcacctacatcagcaccaacagcag
cgccaactccaccagcaccatcactctgcagtgccggatcaagatgatcattaacatgtggc
aaggcgtcggcagggctatgtacgcccctcctatcgccggcaacatcacctgtcggagcaat
atcacaggcctgctgctcaccagagatggcggcaccaatagcaacgagacagaaaccttcag
acctgccggcggagacatgagagacaattggagaagcgagctgtacaagtacaaggtggtca
agatcgagcccctgggcgtcgcacctacacggtgcaagagaagagtcgtgggccgtcgtaga
aggcggagagccgttggaattggcgccgtgttcctgggctttctgggagccgctggatctac
aatgggcgctgccagcatgaccctgacagtgcaggctagaaatctgctgagcggcatcgtgc
agcagcagagcaatctgctcagagcccctgaggctcagcagcacctcctgaaactgacagtg
tggggcatcaagcagctgcaggcaagagtgctggcagtggaaagatacctgcgggaccagca
gctcctcggaatctggggatgtagcggcaagctgatctgctgcaccaacgtgccctggaaca
gcagctggtccaaccggaatctgtccgagatctgggataacatgacctggctgcagtgggac
aaagaaatcagcaactacacccagatcatctacggcctgctggaagagccagaaccagca
agagaaaaacgagcaggacctgctggccctggactgaggatcc (SEQ ID NO: 48)

Figure 46D

\>CH0505M5G458Ychim.6R.SOSIP.664
AENLWVTVYYGVPVWKEAKTTLFCASDAKAYEKEVHNVWATHACVPTDPNPQEMVLKNVTEN
FNMWKNDMVDQMHEDVISLWDQSLKPCVKLTPLCVTLNCTNATASNSSIIEGMKNCSFNITT
ELRDKREKKNALFYKLDIVQLDGNSSQYRLINCNTSVITQACPKVSFDPIPIHYCAPAGYAI
LKCNNKTFTGTGPCNNVSTVQCTHGIKPVVSTQLLLNGSLAEGEIIIRSENITKNVKTIIVH
LNESVKIECTRPNNKTRTSIRIGPGQAFYATGQVIGDIREAYCNINESKWNETLQRVSKKLK
EYFPHKNITFQPSSGGDLEITTHSFNCGGEFFYCNTSSLFNRTYMANSTDMANSTETNSTRT
ITIHCRIKQIINMWQEVGRAMYAPPIAGNITCISNITGLLLTRDGKNNTETFRPGGGNMKD
NWRSELYKYKVVKIEPLGVAPTRCKRRVVGRRRRRAVGIGAVFLGFLGAAGSTMGAASMTL
TVQARNLLSGIVQQQSNLLRAPEAQQHLLKLTVWGIKQLQARVLAVERYLRDQQLLGIWGCS
GKLICCTNVPWNSSWSNRNLSEIWDNMTWLQWDKEISNYTQIIYGLLEESQNQQEKNEQDLL
ALD* (SEQ ID NO: 49)

Figure 47A

\>CH0505M5G458Ychim.6R.SOSIP.Vt8
AENLWVTVYYGVPVWKEAKTTLFCASDAKAYEKEVHNVWATHACVPTDPNPQEMVLKNVTEN
FNMWKNDMVDQMHEDVISLWDQSLKPCVKLTPLCVTLNCTNATASNSSIIEGMKNCSFNITT
ELRDKREKKNALFYKLDIVQLDGNSSQYRLINCNTSVITNACPKVSFDPIPIHYCAPAGYAI
LKCNNKTFTGTGPCNNVSTVQCTHGIKPVVSTQLLLNGSLAEGEIIIRSENITKNVKTIIVH
LNESVKIECTRPINITRTSIRIGPGQAFYANGQVIGDIREAYCNINESKWNETLQRVSKKLK
EYFPHKNITFQPSSGGDLEITTHSFNCGGEFFYCNTSSLFNRTYMANSTDMANSTETNSTRT
ITIHCRIKNIINMWQEVGRAMYAPPIAGNITCISNITGLLLTRDGKNNTETFRPGGGNMKD
NWRSELYKYKVVKIEPLGVAPTRCKRRVVGRRRRRAVGIGAVFLGFLGAAGSTMGAASMTL
TVQARNLLSGIVQQQSNLLRAPEAQQHLLKLTVWGIKQLQARVLAVERYLRDQQLLGIWGCS
GKLICCTNVPWNSSWSNRNLSEIWDNMTWLQWDKEISNYTQIIYGLLEESQNQQEKNEQDLL
ALD* (SEQ ID NO: 50)

Figure 47B

\>CH0505M5G458Ychim.6R.SOSIP.F14
AENLWVTVYYGVPVWKEAKTTLFCASDAKAYEKEVHNIWATHACVPTDPNPQEMVLKNVTEN
FNMWKNDMVDQMHEDVISLWDQSLKPCVKLTPLCVTLNCTNATASNSSIIEGMKNCSFNITT
ELRDKREKKNALFYKLDIVQLDGNSSQYRLINCNTSVITQVCPKISFDPIPIHYCAPAGYAI
LKCNNKTFTGTGPCNNVSTVQCTHGIKPVISTQLLLNGSLAEGEIIIRSENITKNVKTIIVH
LNESVKIECTRPNNKTRTSIRIGPGQAFYATGQVIGDIREAYCNINESKWNETLQRVSKKLK
EYFPHKNITFQPSSGGDLEITTHSFNCGGEFFYCNTSSLFNRTYMANSTDMANSTETNSTRT
ITIHCRIKQIINMWQEVGRAMYAPPIAGNITCISNITGLLLTRDGKNNTETFRPGGGNMKD
NWRSELYKYKVVKIEPLGVAPTRCKRRVVGRRRRRAVGIGAVFLGFLGAAGSTMGAASMTL
TVQARNLLSGIVQQQSNLLRAPEAQQHLLKLTVWGIKQLQARVLAVERYLRDQQLLGIWGCS
GKLICCTNVPWNSSWSNRNLSEIWDNMTWLQWDKEISNYTQIIYGLLEESQNQQEKNEQDLL
ALD* (SEQ ID NO: 51)

Figure 47C

>CH0505M5G458Ychim.6R.SOSIP.F14Vt8

AENLWVTVYYGVPVWKEAKTTLFCASDAKAYEKEVHNiWATHACVPTDPNPQEMVLKNVTEN
FNMWKNDMVDQMHEDVISLWDQSLKPCVKLTPLCVTLNCTNATASNSSIIEGMKNCSFNITT
ELRDKREKKNALFYKLDIVQLDGNSSQYRLINCNTSVITmvCPKlSFDPIPIHYCAPAGYAI
LKCNNKTFTGTGPCNNVSTVQCTHGIKPVlSTQLLLNGSLAEGEIIIRSENITKNVKTIIVH
LNESVKIECTRPlNlTRTSIRIGPGQAFYAmGQVIGDIREAYCNINESKWNETLQRVSKKLK
EYFPHKNITFQPSSGGDLEITTHSFNCGGEFFYCNTSSLFNRTYMANSTDMANSTETNSTRT
ITIHCRIKmIINMWQEVGRAMYAPPIAGNITCISNITGLLLTRDYGKNNTETFRPGGGNMKD
NWRSELYKYKVVKIEPLGVAPTRCKRRVVGRRRRRRAVGIGAVFLGFLGAAGSTMGAASMTL
TVQARNLLSGIVQQQSNLLRAPEAQQHLLKLTVWGIKQLQARVLAVERYLRDQQLLGIWGCS
GKLICCTNVPWNSSWSNRNLSEIWDNMTWLQWDKEISNYTQIIYGLLEESQNQQEKNEQDLL
ALD* (SEQ ID NO: 52)

Figure 47D

For figures 48-51: Underline = F14; Bold = Vt8; *Italic* = other mutation
For figures 48-50: Highlighted positions are NOT the original amino acids!
*Signal sequence*

>BG505gp160T332N_F14_VT8
*MRVMGIQRNCQHLFRWGTMILGMIICSA*AENLWVTVYYGVPVWKDAETTLFCASDAKAYETEKHN<u>I</u>WAT
HACVPTDPNPQEIHLENVTEEFNMWKNNMVEQMHTDIISLWDQSLKPCVKLTPLCVTLQCTNVTNNITDD
MRGELKNCSFNMTTELRDKKQKVYSLFYRLDVVQINENQGNRSNNSNKEYRLINCNTSAITM<u>V</u>CPK<u>L</u>SFE
PIPIHYCAPAGFAILKCKDKKFNGTGPCPSVSTVQCTHGIKPV<u>L</u>STQLLLNGSLAEEEVMIRSENITNNA
KNILVQFNTPVQINCTRP<u>LN</u>LTRKSIRIGPGQAFYAMGDIIGDIRQAHC*N*VSKATWNETLGKVVKQLRKH
FGNNTIIRFANSSGGDLEVTTHSFNCGGEFFYCNTSGLFNSTWISNTSVQGSNSTGSNDSITLPCRIKMI
INMWQRIGQAMYAPPIQGVIRCVSNITGLILTRDGGSTNSTTETFRPGGGDMRDNWRSELYKYKVVKIEP
LGVAPTRAKRRVVGREKRAVGIGAVFLGFLGAAGSTMGAASMTLTVQARNLLSGIVQQQSNLLRAIEAQQ
HLLKLTVWGIKQLQARVLAVERYLRDQQLLGIWGCSGKLICTTNVPWNSSWSNRNLSEIWDNMTWLQWDK
EISNYTQIIYGLLEESQNQQEKNEQDLLALDKWASLWNWFDISNWLWYIKIFIMIVGGLIGLRIVFAVLS
VIHRVRQGYSPLSFQTHTPNPRGLDRPERIEEEDGEQDRGRSTRLVSGFLALAWDDLRSLCLFCYHRLRD
FILIAARIVELLGHSSLKGLRLGWEGLKYLWNLLAYWGRELKISAINLFDTIAIAVAEWTDRVIEIGQRL
CRAFLHIPRRIRQGLERALL** (SEQ ID NO: 53)

Figure 48

>CH505.M5gp160_G458Y_F14_VT8
*MRVMGIQRNYPQWINSMLGFWMLMICN*GMWVTVYYGVPVWKEAKTTLFCASDAKAYEKEVHN<u>I</u>WATHACVPTDP
NPQEMVLKNVTENFNMWKNDMVDQMHEDVISLWDQSLKPCVKLTPLCVTLNCTNATASNSSIIEGMKNCSFNITT
ELRDKREKKNALFYKLDIVQLDGNSSQYRLINCNTSVITM<u>V</u>CPK<u>L</u>SFDPIPIHYCAPAGYAILKCNNKTFTGTGP
CNNVSTVQCTHGIKPV<u>L</u>STQLLLNGSLAEGEIIIRSENITKNVKTIIVHLNESVKIECTRP<u>LN</u>LTRTSIRIGPGQ
AFYAMGQVIGDIREAYCNINESKWNETLQRVSKKLKEYFPHKNITFQPSSGGDLEITTHSFNCGGEFFYCNTSSL
FNRTYMANSTDMANSTETNSTRTITIHCRIKMIINMWQEVGRAMYAPPIAGNITCISNITGLLLTRD*T*GKNNTET
FRPGGGNMKDNWRSELYKYKVVEVKPLGVAPTNARRRVVEREKRAVGMGAVFLGFLGAAGSTMGAASITLTVQAR
QLLSGIVQQQSNLLKAIEAQQHMLKLTVWGIKQLQARVLALERYLKDQQLLGMWGCSGKLICTTNVYWNSSWSNK
TYGDIWDNMTWMQWEREISNYTEIIYELLEESQNQQEKNEQDLLALDRWNSLWNWFNITNWLWYIKIFIMIVGGL
IGLRIIFAVLSLVNRVRQGYSPLSLQTLIPSPRGPDRPGGIEEEGGEQDRNRSTRLVSGFLALVWDDLRSLCLFI
YHRLRDFILIAARAGELLGRSSLKGLRRGWEALKYLGSLVQYWGLELKRSAISLLDTLAIAVGEGTDRILEFVLG
ICRAIRNIPTRIRQGFETALL** (SEQ ID NO: 54)

Figure 49

>CH0848.d949.10.17N133DN138Tgp160_F14_VT8
*MGILKNYPQWIWGILGFWMLMICN*KGKLWVTVYYGVPVWKEAKTTLFCASDARAYEKEVHN<u>I</u>WATHACVPTDP
SPQELVLGNVTENFNMWKNDMVDQMHEDIISLWDQSLKPCVKLTPLCVTLICS*D*ATVK*T*GTVEEMKNCSFNTTTE
IRDKEKKEYALFYKPDIVPLSETNNTSEYRLINCNTSAVTM<u>V</u>CPK<u>L</u>TFEPIPIHYCAPAGYAILKCNDETFNGTG
PCSNVSTVQCTHGIRPV<u>L</u>STQLLLNGSLAEKEIVIRSENLTNNAKIIIVHLHTPVEIVCTRP<u>LN</u>LTRKSVRIGPG
QTFYAMGDIIGDIKQAHCNISEEKWNDTLQKVGIELQKHFPNKTIKYNQSAGGDMEITTHSFNCGGEFFYCNTSN
LFNGTYNGTYISTNSSANSTSTITLQCRIKMIINMWQGVGRAMYAPPIAGNITCRSNITGLLLTRDGGTNSNETE
TFRPAGGDMRDNWRSELYKYKVVEIQPLGIAPTGAKRRVVEREKRAAGLGALFLGFLGAAGSTMGAASITLTVQA
RQLLSGIVQQQSNLLRAIEAQQHMLQLTVWGIKQLQARVLALERYLKDQQLLGMWGCSGKLICTTNVPWNTSWSN
KSETDIWDNMTWMQWEREISNYTETIYKLLEDSQNQQERNEQDLLALDSWNSLWNWFSITKWLWYIKIFIMIVGG
LIGLRIVFAVLSIVNRVRQGYSPLSLQTLTPNPREPDRLRGIEEEGGEQDRDRSIRLVSGFLPIVWDDLRSLCLF
SYHRLRDFLLLAARVVELLGRSSLRGLQRGWEVLKYLGSLVQYWGLELKKSAISLFDTLAIAVAEGTDRIIELIQ
GFCRAIRNIPTRIRQGFEASLL* (SEQ ID NO: 55)

Figure 50

For Figure 51: Highlighted positions are the original amino acids!

>BG505gp140SOSIPT332N
*MPMGSLQPLATLYLLGMLVASVLAAENLWVTVYYGVPVWKDAETTLFCASDAKAYETEKHNVWATHACVPTDPNP
QEIHLENVTEEFNMWKNNMVEQMHTDIISLWDQSLKPCVKLTPLCVTLQCTNVTNNITDDMRGELKNCSFNMTTE
LRDKKQKVYSLFYRLDVVQINENQGNRSNNSNKEYRLINCNTSAITQACPKVSFEPIPIHYCAPAGFAILKCKDK
KFNGTGPCPSVSTVQCTHGIKPVVSTQLLLNGSLAEEEVMIRSENITNNAKNILVQFNTPVQINCTRPNNNTRKS
IRIGPGQAFYATGDIIGDIRQAHCNVSKATWNETLGKVVKQLRKHFGNNTIIRFANSSGGDLEVTTHSFNCGGEF
FYCNTSGLFNSTWISNTSVQGSNSTGSNDSITLPCRIKQIINMWQRIGQAMYAPPIQGVIRCVSNITGLILTRDG
GSTNSTTETFRPGGGDMRDNWRSELYKYKVVKIEPLGVAPTRCKRRVVGRRRRRRAVGIGAVFLGFLGAAGSTMG
AASMTLTVQARNLLSGIVQQQSNLLRAPEAQQHLLKLTVWGIKQLQARVLAVERYLRDQQLLGIWGCSGKLICCT
NVPWNSSWSNRNLSEIWDNMTWLQWDKEISNYTQIIYGLLEESQNQQEKNEQDLLALD*   (SEQ ID NO: 56)*

Figure 51

>HV1301509;CH0848.3.d1305.10.19gp160 (natural env)
MRVTGILRNYPQWWIWGILGFWMLMTCNGEGNLWVTVYYGVPVWKEAKTTLFCASDAKAY
KKEVHNVWATHACVPTDPSPQELFLENVTENFNMWKNDMVDQMHEDIISLWDQSLKPCVK
LTPLCVTLICSTATVNNRAVDEMKNCSFNTTTEIRDKKKKEYALFYRSDVVPLDETNNTS
EYRLINCNTSAVTQACPKVTFEPIPIHYCAPAGYAILKCNDETFNGTGPCSNVSTVQCTH
GIRPVVSTQLLLNGSLAEKEIVIRSENLTNNAKIIIVHLHTPVEIVCTRPGHNTRKSVRI
GPGQTFYATGDIIGDIRQAHCNINESKWNETLQKVGIELQKHFPNKTIKYNQSAGGDMEI
TTHSFNCGGEFFYCNTSKLFNSTYNGTYISTNSTNSTSYITLQCRIKQIINMWQGVGRAM
YAPPIAGNITCRSNITGLLLTRDGGINNVSNETETFRPAGGDMRDNWRSELYKYKVVEVQ
PLGIAPTGAKRRVVEREKRAAGLGALFLGFLGAAGSTMGAASITLTVQARQLLSGIVQQQ
SNLLRAIEAQQHMLQLTVWGIKQLQARVLALERYLKDQQLLGMWGCSGKLICTTNVPWNT
SWSNKSEMDIWNNMTWMQWEREISNYTETIYMLLEDSQRQQERNEKDLLALDSWNSLWNW
FNITNWLWYIKIFIMIVGGLIGLRIVFAVLSIVNRVRQGYSPLSLQTLTPNPREPDRLRG
IEEEGGEQDRDRSIRLVSGFLPIVWDDLRSLCLFSYHRLRDFLLAARVVELLGHSSLRG
LQRGWEVLKYLGSLVQYWGLELKRSAISLFDTLAIAVAEGTDRIIELIQGFCRAIRNIPT
RIRQGFEASLL**   (SEQ ID NO: 57)

Figure 52

One embodiment of 19CV3 envelope design is:
>HV1301580;CH848.3.D1305.10.19_D949V3.DS.SOSIP (19CV3)
MGSLQPLATLYLLGMLVASVLAAENLWVTVYYGVPVWKEAKTTLFCASDAKAYKKEVHNV
WATHACVPTDPSPQELFLENVTENFNMWKNDMVDQMHEDIISLWDQSLKPCVKLTPLCVT
LICSTATVNNRAVDEMKNCSFNTTTEIRDKKKKEYALFYRSDVVPLDETNNTSEYRLINC
NTSACTQACPKVTFEPIPIHYCAPAGYAILKCNDETFNGTGPCSNVSTVQCTHGIRPVVS
TQLLLNGSLAEKEIVIRSENLTNNAKIIIVHLHTPVEIVCTRPNNNTRKSVRIGPGQTFY
ATGDIIGDIKQAHCNISEEKWNETLQKVGIELQKHFPNKTIKYNQSAGGDMEITTHSFNC
GGEFFYCNTSKLFNSTYNGTYISTNSTNSTSYITLQCRIKQIINMWQGVGRCMYAPPIAG
NITCRSNITGLLLTRDGGINNVSNETETFRPAGGDMRDNWRSELYKYKVVKIEPLGVAPT
RCKRRVVGRRRRRRAVGIGAVFLGFLGAAGSTMGAASMTLTVQARNLLSGIVQQQSNLLR
APEAQQHLLKLTVWGIKQLQARVLAVERYLRDQQLLGIWGCSGKLICCTNVPWNSSWSNR
NLSEIWDNMTWLQWDKEISNYTQIIYGLLEESQNQQEKNEQDLLALD**   (SEQ ID NO: 58)

Figure 53

| HV1301731_F14 | BG505T332NCD5ss_F14gp160 |
| --- | --- |
| HV1301731_Vt8 | BG505T332NCD5ss_Vt8gp160 |
| HV1301731_F14Vt8 | BG505T332NCD5ss_F14Vt8gp160 |
| HV1301581_F14 | CH0848.d949.10.17N133DN138Tgp160_F14 |
| HV1301581_VT8 | CH0848.d949.10.17N133DN138Tgp160_VT8 |
| HV1301581_F14VT8 | CH0848.d949.10.17N133DN138Tgp160_F14VT8 |

```
>HV1301731_F14,BG505T332NCD5ss_F14gp160
AAGCTTGTCGACGCCACCATGCCTATGGGAAGCCTGCAACCTCTGGCCACACTGTACCTGCTGGGAAT
GCTGGTGGCTTCTGTGCTGGCCGCCGAGAATCTGTGGGTCACAGTGTACTATGGCGTGCCCGTGTGGA
AGGACGCCGAGACAACACTGTTTTGTGCCAGCGACGCCAAGGCCTACGAGACAGAGAAGCACAACATC
TGGGCCACTCACGCCTGCGTGCCAACCGATCCTAATCCTCAAGAGATCCACCTGGAAAACGTGACCGA
GGAATTCAACATGTGGAAGAACAACATGGTCGAGCAGATGCACACCGACATCATCAGCCTGTGGGACC
AGAGCCTGAAGCCTTGCGTGAAGCTGACCCCTCTGTGTGTGACCCTGCAGTGCACCAACGTGACCAAC
AACATCACCGACGACATGCGGGGCGAGCTGAAGAACTGCAGCTTCAACATGACCACCGAGCTGCGGGA
CAAGAAACAGAAGGTGTACAGCCTGTTCTACCGGCTGGACGTGGTGCAGATCAACGAGAACCAGGGCA
ACAGAAGCAACAACAGCAACAAAGAGTACCGGCTGATCAACTGCAACACCAGCGCCATCACTCAGGCC
TGTCCTAAGGTGTCCTTCGAGCCCATTCCTATCCACTACTGTGCCCCTGCCGGCTTCGCCATCCTGAA
GTGCAAGGACAAGAAGTTCAACGGCACAGGCCCCTGTCCTTCCGTGTCTACCGTGCAGTGTACCCACG
GCATCAAGCCCGTGCTGTCTACACAGCTGCTGCTGAATGGCAGCCTGGCCGAAGAGGAAGTGATGATC
AGAAGCGAGAACATCACCAACAACGCCAAGAACATCCTGGTCCAGTTCAACACCCCTGTGCAGATTAA
CTGTACCCGGCCTAACAACAACACCCGGAAGTCCATCAGAATCGGCCCAGGCCAGGCCTTTTATGCCA
CCGGCGATATCATCGGCGACATCAGACAGGCCCACTGCAACGTGTCCAAGGCCACATGGAATGAGACA
CTGGGCAAAGTGGTCAAGCAGCTGCGGAAGCACTTCGGCAACAATACCATCATCAGATTCGCCAACAG
CTCTGGCGGCGACCTGGAAGTGACCACACACAGCTTTAACTGTGGCGGCGAGTTCTTCTACTGCAATA
CCTCCGGCCTGTTCAACAGCACCTGGATCAGCAACACAAGCGTGCAGGGCAGCAATAGCACCGGCAGC
AACGACAGCATCACCCTGCCTTGCCGGATCAAGCAGATCATCAATATGTGGCAGCGGATCGGACAGGC
TATGTACGCCCCTCCTATTCAGGGCGTGATCAGATGCGTGTCCAATATCACCGGCCTGATCCTGACCA
GAGATGGCGGCAGCACCAACTCCACCACCGAGACTTTTAGACCCGGCGGAGGCGACATGAGAGACAAT
TGGAGAAGCGAGCTGTACAAGTACAAGGTGGTCAAGATCGAGCCCCTGGGCGTCGCACCTACCAGAGC
CAAGAGAAGAGTCGTGGGCCGCGAGAAGAGAGCCGTTGGAATTGGAGCCGTGTTCCTGGGCTTTCTGG
GAGCCGCTGGATCTACAATGGGCGCTGCCAGCATGACACTGACCGTGCAGGCTAGAAATCTGCTGAGC
GGCATCGTGCAGCAGCAGAGCAATCTGCTGCGGGCCATTGAAGCCCAGCAGCATCTGCTGAAACTGAC
AGTGTGGGGCATCAAACAGCTGCAGGCCAGAGTGCTGGCTGTGGAAAGATACCTGAGGGACCAGCAGC
TCCTCGGCATCTGGGGATGTTCTGGCAAGCTGATCTGTACCACCAATGTGCCCTGGAACAGCAGCTGG
TCCAACCGGAATCTGAGCGAGATCTGGGACAATATGACCTGGCTGCAGTGGGACAAAGAGATCTCCAA
CTACACCCAGATCATCTACGGCCTGCTGGAAGAGTCCCAGAACCAGCAAGAGAAAAACGAGCAGGACC
TGCTGGCCCTGGATAAGTGGGCTAGCCTGTGGAATTGGTTCGACATCAGCAATTGGCTGTGGTACATC
AAGATCTTCATCATGATCGTCGGCGGACTGATCGGCCTGAGAATCGTGTTTGCCGTGCTGAGCGTGAT
CCACAGAGTGCGGCAGGGATATAGCCCTCTGAGCTTCCAGACACACACCCCTAATCCTAGAGGCCTGG
ACAGACCCGAGCGGATCGAAGAAGAGGACGGCGAACAGGACAGAGGCAGAAGCACCAGACTGGTTTCC
GGCTTCCTGGCTCTGGCTTGGACGATCTGAGAAGCCTGTGCCTGTTCTGCTACCACCGGCTGAGAGA
CTTTATCCTGATTGCCGCCAGGATCGTGGAACTGCTGGACACAGCTCTCTGAAGGGCCTGAGACTCG
GATGGGAGGGCCTGAAGTATCTGTGGAACCTGCTCGCCTACTGGGGAAGAGAGCTGAAAATCTCCGCC
ATCAACCTGTTCGACACAATCGCCATTGCCGTGGCCGAGTGGACCGACAGAGTGATCGAGATTGGCCA
GAGACTGTGCCGGGCCTTCCTGCACATCCCTCGGAGAATTAGACAGGGCCTCGAACGGGCCCTGCTGT
GATAAGGATCCTCTAGA (SEQ ID NO: 59)
```

Figure 54

>HV1301731_Vt8,BG505T332NCD5ss_Vt8gp160
AAGCTTGTCGACGCCACCATGCCTATGGGAAGCCTGCAACCTCTGGCCACACTGTACCTGCTGGGAAT
GCTGGTGGCTTCTGTGCTGGCCGCCGAGAATCTGTGGGTCACAGTGTACTATGGCGTGCCCGTGTGGA
AGGACGCCGAGACAACACTGTTTTGTGCCAGCGACGCCAAGGCCTACGAGACAGAGAAGCACAACGTG
TGGGCCACTCACGCCTGCGTGCCAACCGATCCTAATCCTCAAGAGATCCACCTGGAAAACGTGACCGA
GGAATTCAACATGTGGAAGAACAACATGGTCGAGCAGATGCACACCGACATCATCAGCCTGTGGGACC
AGAGCCTGAAGCCTTGCGTGAAGCTGACCCCTCTGTGTGTGACCCTGCAGTGCACCAACGTGACCAAC
AACATCACCGACGACATGCGGGGCGAGCTGAAGAACTGCAGCTTCAACATGACCACCGAGCTGCGGGA
CAAGAAACAGAAGGTGTACAGCCTGTTCTACCGGCTGGACGTGGTGCAGATCAACGAGAACCAGGGCA
ACAGAAGCAACAACAGCAACAAAGAGTACCGGCTGATCAACTGCAACACCAGCGCCATCACTATGGCC
TGTCCTAAGGTGTCCTTCGAGCCCATTCCTATCCACTACTGTGCCCCTGCCGGCTTCGCCATCCTGAA
GTGCAAGGACAAGAAGTTCAACGGCACAGGCCCCTGTCCTTCCGTGTCTACCGTGCAGTGTACCCACG
GCATCAAGCCCGTGGTGTCTACACAGCTGCTGCTGAATGGCAGCCTGGCCGAAGAGGAAGTGATGATC
AGAAGCGAGAACATCACCAACAACGCCAAGAACATCCTGGTCCAGTTCAACACCCCTGTGCAGATTAA
CTGTACCCGGCCTCTGAACCTGACCGGAAGTCCATCAGAATCGGCCCAGGCCAGGCCTTTTATGCCA
TGGGCGATATCATCGGCGACATCAGACAGGCCCACTGCAACGTGTCCAAGGCCACATGGAATGAGACA
CTGGGCAAAGTGGTCAAGCAGCTGCGGAAGCACTTCGGCAACAATACCATCATCAGATTCGCCAACAG
CTCTGGCGGCGACCTGGAAGTGACCACACACAGCTTTAACTGTGGCGGCGAGTTCTTCTACTGCAATA
CCTCCGGCCTGTTCAACAGCACCTGGATCAGCAACACAAGCGTGCAGGGCAGCAATAGCACCGGCAGC
AACGACAGCATCACCCTGCCTTGCCGGATCAAGAGATCATCAATATGTGGCAGCGGATCGGACAGGC
TATGTACGCCCCTCCTATTCAGGGCGTGATCAGATGCGTGTCCAATATCACCGGCCTGATCCTGACCA
GAGATGGCGGCAGCACCAACTCCACCACCGAGACTTTTAGACCCGGCGGAGGCGACATGAGAGACAAT
TGGAGAAGCGAGCTGTACAAGTACAAGGTGGTCAAGATCGAGCCCCTGGGCGTCGCACCTACCAGAGC
CAAGAGAAGAGTCGTGGGCCGCGAGAAGAGAGCCGTTGGAATTGGAGCCGTGTTCCTGGGCTTTCTGG
GAGCCGCTGGATCTACAATGGGCGCTGCCAGCATGACACTGACCGTGCAGGCTAGAAATCTGCTGAGC
GGCATCGTGCAGCAGCAGAGCAATCTGCTGCGGGCCATTGAAGCCCAGCAGCATCTGCTGAAACTGAC
AGTGTGGGGCATCAAACAGCTGCAGGCCAGAGTGCTGGCTGTGGAAAGATACCTGAGGGACCAGCAGC
TCCTCGGCATCTGGGGATGTTCTGGCAAGCTGATCTGTACCACCAATGTGCCCTGGAACAGCAGCTGG
TCCAACCGGAATCTGAGCGAGATCTGGGACAATATGACCTGGCTGCAGTGGGACAAAGAGATCTCCAA
CTACACCCAGATCATCTACGGCCTGCTGGAAGAGTCCCAGAACCAGCAAGAGAAAAACGAGCAGGACC
TGCTGGCCCTGGATAAGTGGGCTAGCCTGTGGAATTGGTTCGACATCAGCAATTGGCTGTGGTACATC
AAGATCTTCATCATGATCGTCGGCGGACTGATCGGCCTGAGAATCGTGTTTGCCGTGCTGAGCGTGAT
CCACAGAGTGCGGCAGGGATATAGCCCTCTGAGCTTCCAGACACACACCCCTAATCCTAGAGGCCTGG
ACAGACCCGAGCGGATCGAAGAAGAGGACGGCGAACAGGACAGAGGCAGAAGCACCAGACTGGTTTCC
GGCTTCCTGGCTCTGGCTTGGGACGATCTGAGAAGCCTGTGCCTGTTCTGCTACCACCGGCTGAGAGA
CTTTATCCTGATTGCCGCCAGGATCGTGGAACTGCTGGGACACAGCTCTCTGAAGGGCCTGAGACTCG
GATGGGAGGGCCTGAAGTATCTGTGGAACCTGCTCGCCTACTGGGGAAGAGAGCTGAAAATCTCCGCC
ATCAACCTGTTCGACACAATCGCCATTGCCGTGGCCGAGTGGACCGACAGAGTGATCGAGATTGGCCA
GAGACTGTGCCGGGCCTTCCTGCACATCCCTCGGAGAATTAGACAGGGCCTCGAACGGGCCCTGCTGT
GATAAGGATCCTCTAGA (SEQ ID NO: 60)

>HV1301731_F14Vt8,BG505T332NCD5ss_F14Vt8gp160
AAGCTTGTCGACGCCACCATGCCTATGGGAAGCCTGCAACCTCTGGCCACACTGTACCTGCTGGGAAT
GCTGGTGGCTTCTGTGCTGGCCGCCGAGAATCTGTGGGTCACAGTGTACTATGGCGTGCCCGTGTGGA
AGGACGCCGAGACAACACTGTTTTGTGCCAGCGACGCCAAGGCCTACGAGACAGAGAAGCACAACT
TGGGCCACTCACGCCTGCGTGCCAACCGATCCTAATCCTCAAGAGATCCACCTGGAAAACGTGACCGA
GGAATTCAACATGTGGAAGAACAACATGGTCGAGCAGATGCACACCGACATCATCAGCCTGTGGGACC
AGAGCCTGAAGCCTTGCGTGAAGCTGACCCCTCTGTGTGTGACCCTGCAGTGCACCAACGTGACCAAC
AACATCACCGACGACATGCGGGGCGAGCTGAAGAACTGCAGCTTCAACATGACCACCGAGCTGCGGGA
CAAGAAACAGAAGGTGTACAGCCTGTTCTACCGGCTGGACGTGGTGCAGATCAACGAGAACCAGGGCA
ACAGAAGCAACAACAGCAACAAAGAGTACCGGCTGATCAACTGCAACACCAGCGCCATCACTATGG
TGTCCTAAGTGTCCTTCGAGCCCATTCCTATCCACTACTGTGCCCCTGCCGGCTTCGCCATCCTGAA

Figure 54 continued

GTGCAAGGACAAGAAGTTCAACGGCACAGGCCCCTGTCCTTCCGTGTCTACCGTGCAGTGTACCCACG
GCATCAAGCCCGTGCTGTCTACACAGCTGCTGCTGAATGGCAGCCTGGCCGAAGAGGAAGTGATGATC
AGAAGCGAGAACATCACCAACAACGCCAAGAACATCCTGGTCCAGTTCAACACCCCTGTGCAGATTAA
CTGTACCCGGCCTCTGAACCTGACCCGGAAGTCCATCAGAATCGGCCCAGGCCAGGCCTTTTATGCCA
TGGGCGATATCATCGGCGACATCAGACAGGCCCACTGCAACGTGTCCAAGGCCACATGGAATGAGACA
CTGGGCAAAGTGGTCAAGCAGCTGCGGAAGCACTTCGGCAACAATACCATCATCAGATTCGCCAACAG
CTCTGGCGGCGACCTGGAAGTGACCACACACAGCTTTAACTGTGGCGGCGAGTTCTTCTACTGCAATA
CCTCCGGCCTGTTCAACAGCACCTGGATCAGCAACACAAGCGTGCAGGGCAGCAATAGCACCGGCAGC
AACGACAGCATCACCCTGCCTTGCCGGATCAAGAGGATCATCAATATGTGGCAGCGGATCGGACAGGC
TATGTACGCCCCTCCTATTCAGGGCGTGATCAGATGCGTGTCCAATATCACCGGCCTGATCCTGACCA
GAGATGGCGGCAGCACCAACTCCACCACCGAGACTTTTAGACCCGGCGGAGGCGACATGAGAGACAAT
TGGAGAAGCGAGCTGTACAAGTACAAGGTGGTCAAGATCGAGCCCCTGGGCGTCGCACCTACCAGAGC
CAAGAGAAGAGTCGTGGGCCGCGAGAAGAGAGCCGTTGGAATTGGAGCCGTGTTCCTGGGCTTTCTGG
GAGCCGCTGGATCTACAATGGGCGCTGCCAGCATGACACTGACCGTGCAGGCTAGAAATCTGCTGAGC
GGCATCGTGCAGCAGCAGAGCAATCTGCTGCGGGCCATTGAAGCCCAGCAGCATCTGCTGAAACTGAC
AGTGTGGGGCATCAAACAGCTGCAGGCCAGAGTGCTGGCTGTGGAAAGATACCTGAGGGACCAGCAGC
TCCTCGGCATCTGGGGATGTTCTGGCAAGCTGATCTGTACCACCAATGTGCCCTGGAACAGCAGCTGG
TCCAACCGGAATCTGAGCGAGATCTGGGACAATATGACCTGGCTGCAGTGGGACAAAGAGATCTCCAA
CTACACCCAGATCATCTACGGCCTGCTGGAAGAGTCCCAGAACCAGCAAGAGAAAAACGAGCAGGACC
TGCTGGCCCTGGATAAGTGGGCTAGCCTGTGGAATTGGTTCGACATCAGCAATTGGCTGTGGTACATC
AAGATCTTCATCATGATCGTCGGCGGACTGATCGGCCTGAGAATCGTGTTTGCCGTGCTGAGCGTGAT
CCACAGAGTGCGGCAGGGATATAGCCCTCTGAGCTTCCAGACACACACCCCTAATCCTAGAGGCCTGG
ACAGACCCGAGCGGATCGAAGAAGAGGACGGCGAACAGGACAGAGGCAGAAGCACCAGACTGGTTTCC
GGCTTCCTGGCTCTGGCTTGGGACGATCTGAGAAGCCTGTGCCTGTTCTGCTACCACCGGCTGAGAGA
CTTTATCCTGATTGCCGCCAGGATCGTGGAACTGCTGGGACACAGCTCTCTGAAGGGCCTGAGACTCG
GATGGGAGGGCCTGAAGTATCTGTGGAACCTGCTCGCCTACTGGGGAAGAGAGCTGAAAATCTCCGCC
ATCAACCTGTTCGACACAATCGCCATTGCCGTGGCCGAGTGGACCGACAGAGTGATCGAGATTGGCCA
GAGACTGTGCCGGGCCTTCCTGCACATCCCTCGGAGAATTAGACAGGGCCTCGAACGGGCCCTGCTGT
GATAAGGATCCTCTAGA (SEQ ID NO: 61)

>HV1301581_F14,CH0848.d949.10.17N133DN138Tgp160_F14
AAGCTTGTCGACGCCACCATGGGATCTCTGCAGCCTCTGGCCACACTGTACCTGCTGGGAATGCTGGT
GGCTAGCGTGCTGGCCAAGGGAAAGCTGTGGGTCACAGTGTACTACGGCGTGCCCGTGTGGAAAGAGG
CCAAGACCACACTGTTCTGCGCCTCCGATGCCAGAGCCTACGAGAAAGAGGTGCACAACATCTGGGCC
ACACACGCCTGTGTGCCTACCGATCCATCTCCTCAAGAGCTGGTGCTGGGCAACGTGACCGAGAACTT
CAACATGTGGAAGAACGACATGGTGGACCAGATGCACGAGGACATCATCAGCCTGTGGGACCAGAGCC
TGAAGCCTTGCGTGAAGCTGACCCCTCTGTGCGTGACCCTGATCTGTTCTGACGCCACCGTGAAAACC
GGCACCGTGGAAGAGATGAAGAACTGCAGCTTCAACACCACCACCGAGATCCGGGACAAAGAGAAGAA
AGAGTACGCCCTGTTCTACAAGCCCGACATCGTGCCCCTGAGCGAGACAAACAACACCAGCGAGTACC
GGCTGATCAACTGCAACACCTCCGCCGTGACACAGGTGTGCCCCAAAGTGACCTTCGAGCCCATTCCT
ATCCACTACTGTGCCCCTGCCGGCTACGCCATCCTGAAGTGCAACGACGAGACATTCAACGGCACAGG
CCCCTGCAGCAATGTGTCCACCGTGCAGTGTACCCACGGCATCAGACCAGTGGTGTCTACCCAGCTGC
TGCTGAATGGAAGCCTGGCCGAGAAGAAATCGTGATCAGAAGCGAGAACCTGACCAACAACGCCAAG
ATCATCATTGTGCATCTGCACACCCCTGTGGAAATCGTGTGCACCCGGCCTAACAACAACACCCGGAA
GTCTGTGCGGATCGGCCCTGGCCAGACATTCTATGCCACCGGCGATATCATCGGCGACATCAAGCAGG
CCCACTGCAACATCAGCGAGGAAAAGTGGAACGACACCCTGCAGAAAGTGGGCATCGAGCTGCAGAAG
CACTTCCCCAACAAGACCATCAAGTACAACCAGAGCGCTGGCGGCGACATGGAAATCACCACACACAG
CTTCAATTGTGGCGGCGAGTTCTTCTACTGCAATACCAGCAACCTGTTCAACGGGACCTACAATGGCA
CCTACATCAGCACCAACAGCAGCGCCAACTCCACCAGCACCATCACTCTGCAGTGCCGGATCAAGCAG
ATCATCAATATGTGGCAAGGCGTGGGCAGAGCTATGTACGCCCCTCCTATCGCCGGCAACATCACCTG
TCGGAGCAATATCACAGGCCTGCTGCTCACCAGAGATGGCGGCACCAATAGCAACGAGACAGAAACCT
TCAGACCTGCCGGCGGAGACATGAGAGACAATTGGAGAAGCGAGCTGTACAAGTACAAGGTGGTGGAA

*Figure 54 continued*

ATCCAGCCACTGGGAATCGCCCCAACCGGCGCTAAGAGAAGAGTGGTGGAACGCGAGAAAAGAGCCGC
TGGACTGGGAGCCCTGTTCCTGGGATTTCTTGGAGCCGCCGGAAGCACAATGGGAGCCGCCTCTATTA
CCCTGACCGTGCAGGCTAGACAGCTGCTGAGCGGAATTGTGCAGCAGCAGAGCAACCTGCTGAGAGCC
ATTGAAGCCCAGCAGCACATGCTGCAGCTGACCGTGTGGGGAATCAAACAGCTGCAGGCCAGAGTGCT
GGCCCTGGAAAGATACCTGAAGGACCAGCAGCTCCTCGGCATGTGGGCTGTTCTGGCAAGCTGATCT
GCACCACCAACGTGCCCTGGAACACCTCCTGGTCCAACAAGAGCGAAACCGACATCTGGGACAACATG
ACCTGGATGCAGTGGGAGAGAGAGATCAGCAACTACACCGAGACAATCTACAAGCTGCTCGAGGACAG
CCAGAACCAGCAAGAGAGAAACGAGCAGGACCTGCTGGCTCTGGACAGCTGGAATAGCCTGTGGAACT
GGTTCAGCATCACCAAGTGGCTGTGGTACATCAAGATCTTCATCATGATCGTCGGCGGCCTGATCGGC
CTGAGAATCGTGTTTGCCGTGCTGAGCATCGTGAACAGAGTGCGGCAGGGATACAGCCCACTGAGCCT
GCAAACCCTGACACCTAATCCTAGAGAGCCCGACCGGCTGAGAGGCATCGAAGAAGAAGGCGGCGAGC
AGGATCGGGACAGATCCATCAGACTGGTGTCCGGCTTCCTGCCTATCGTGTGGGACGATCTGAGAAGC
CTGTGCCTGTTCAGCTACCACCGGCTGCGGGATTTTCTGCTGCTTGCCGCCAGAGTGGTTGAACTGCT
GGGCAGATCTAGCCTGAGGGGCCTGCAAAGAGGCTGGGAAGTCCTGAAGTACCTGGGCAGCCTGGTGC
AGTATTGGGGCCTCGAGCTGAAAAAGAGCGCCATTAGCCTGTTCGATACCCTGGCCATTGCTGTGGCC
GAGGGCACCGATAGAATCATTGAGCTGATCCAGGGCTTCTGCCGGGCCATCAGAAACATCCCCACCAG
AATCAGACAGGGCTTCGAGGCCAGCCTGCTGTGATAAGGATCC<u>TCTAGA</u> (SEQ ID NO: 62)

>HV1301581_VT8,CH0848.d949.10.17N133DN138Tgp160_VT8
AAGCTTGTCGACGCCACCATGGGATCTCTGCAGCCTCTGGCCACACTGTACCTGCTGGGAATGCTGGT
GGCTAGCGTGCTGGCCAAGGGAAAGCTGTGGGTCACAGTGTACTACGGCGTGCCCGTGTGGAAAGAGG
CCAAGACCACACTGTTCTGCGCCTCCGATGCCAGAGCCTACGAGAAAGAGGTGCACAACGTCTGGGCC
ACACACGCCTGTGTGCCTACCGATCCATCTCCTCAAGAGCTGGTGCTGGGCAACGTGACCGAGAACTT
CAACATGTGGAAGAACGACATGGTGGACCAGATGCACGAGGACATCATCAGCCTGTGGGACCAGAGCC
TGAAGCCTTGCGTGAAGCTGACCCCTCTGTGCGTGACCCTGATCTGTTCTGACGCCACCGTGAAAACC
GGCACCGTGGAAGAGATGAAGAACTGCAGCTTCAACACCACCACCGAGATCCGGGACAAAGAGAAGAA
AGAGTACGCCCTGTTCTACAAGCCCGACATCGTGCCCCTGAGCGAGACAAACAACACCAGCGAGTACC
GGCTGATCAACTGCAACACCTCCGCCGTGACAATGGCTTGCCCCAAAGTGACCTTCGAGCCCATTCCT
ATCCACTACTGTGCCCCTGCCGGCTACGCCATCCTGAAGTGCAACGACGAGACATTCAACGGCACAGG
CCCCTGCAGCAATGTGTCCACCGTGCAGTGTACCCACGGCATCAGACCAGTGGTGTCTACCCAGCTGC
TGCTGAATGGAAGCCTGGCCGAGAAGAAATCGTGATCAGAAGCGAGAACCTGACCAACAACGCCAAG
ATCATCATTGTGCATCTGCACACCCCTGTGGAAATCGTGTGCACCCGGCCTCTGAAC▓▓▓ACCCGGAA
GTCTGTGCGGATCGGCCCTGGCCAGACATTCTATGCCA▓▓GGCGATATCATCGGCGACATCAAGCAGG
CCCACTGCAACATCAGCGAGGAAAGTGGAACGACACCCTGCAGAAAGTGGGCATCGAGCTGCAGAAG
CACTTCCCCAACAAGACCATCAAGTACAACCAGAGCGCTGGCGGCGACATGGAAATCACCACACACAG
CTTCAATTGTGGCGGCGAGTTCTTCTACTGCAATACCAGCAACCTGTTCAACGGGACCTACAATGGCA
CCTACATCAGCACCAACAGCAGCGCCAACTCCACCAGCACCATCACTCTGCAGTGCCGGATCAAGATG
ATCATCAATATGTGGCAAGGCGTGGGCAGAGCTATGTACGCCCCTCCATCGCCGGCAACATCACCTG
TCGGAGCAATATCACAGGCCTGCTGCTCACCAGAGATGGCGGCACCAATAGCAACGAGACAGAAACCT
TCAGACCTGCCGGCGGAGACATGAGAGACAATTGGAGAAGCGAGCTGTACAAGTACAAGGTGGTGGAA
ATCCAGCCACTGGGAATCGCCCCAACCGGCGCTAAGAGAAGAGTGGTGGAACGCGAGAAAAGAGCCGC
TGGACTGGGAGCCCTGTTCCTGGGATTTCTTGGAGCCGCCGGAAGCACAATGGGAGCCGCCTCTATTA
CCCTGACCGTGCAGGCTAGACAGCTGCTGAGCGGAATTGTGCAGCAGCAGAGCAACCTGCTGAGAGCC
ATTGAAGCCCAGCAGCACATGCTGCAGCTGACCGTGTGGGGAATCAAACAGCTGCAGGCCAGAGTGCT
GGCCCTGGAAAGATACCTGAAGGACCAGCAGCTCCTCGGCATGTGGGCTGTTCTGGCAAGCTGATCT
GCACCACCAACGTGCCCTGGAACACCTCCTGGTCCAACAAGAGCGAAACCGACATCTGGGACAACATG
ACCTGGATGCAGTGGGAGAGAGAGATCAGCAACTACACCGAGACAATCTACAAGCTGCTCGAGGACAG
CCAGAACCAGCAAGAGAGAAACGAGCAGGACCTGCTGGCTCTGGACAGCTGGAATAGCCTGTGGAACT
GGTTCAGCATCACCAAGTGGCTGTGGTACATCAAGATCTTCATCATGATCGTCGGCGGCCTGATCGGC
CTGAGAATCGTGTTTGCCGTGCTGAGCATCGTGAACAGAGTGCGGCAGGGATACAGCCCACTGAGCCT
GCAAACCCTGACACCTAATCCTAGAGAGCCCGACCGGCTGAGAGGCATCGAAGAAGAAGGCGGCGAGC
AGGATCGGGACAGATCCATCAGACTGGTGTCCGGCTTCCTGCCTATCGTGTGGGACGATCTGAGAAGC

Figure 54 continued

CTGTGCCTGTTCAGCTACCACCGGCTGCGGGATTTTCTGCTGCTTGCCGCCAGAGTGGTTGAACTGCT
GGGCAGATCTAGCCTGAGGGGCCTGCAAAGAGGCTGGGAAGTCCTGAAGTACCTGGGCAGCCTGGTGC
AGTATTGGGGCCTCGAGCTGAAAAAGAGCGCCATTAGCCTGTTCGATACCCTGGCCATTGCTGTGGCC
GAGGGCACCGATAGAATCATTGAGCTGATCCAGGGCTTCTGCCGGGCCATCAGAAACATCCCCACCAG
AATCAGACAGGGCTTCGAGGCCAGCCTGCTGTGATAAGGATCCTCTAGA (SEQ ID NO: 63)

>HV1301581_F14VT8,CH0848.d949.10.17N133DN138Tgp160_F14VT8
AAGCTTGTCGACGCCACCATGGGATCTCTGCAGCCTCTGGCCACACTGTACCTGCTGGGAATGCTGGT
GGCTAGCGTGCTGGCCAAGGGAAAGCTGTGGGTCACAGTGTACTACGGCGTGCCCGTGTGGAAAGAGG
CCAAGACCACACTGTTCTGCGCCTCCGATGCCAGAGCCTACGAGAAGAGGTGCACAAC TCTGGGCC
ACACACGCCTGTGTGCCTACCGATCCATCTCCTCAAGAGCTGGTGCTGGGCAACGTGACCGAGAACTT
CAACATGTGGAAGAACGACATGGTGGACCAGATGCACGAGGACATCATCAGCCTGTGGGACCAGAGCC
TGAAGCCTTGCGTGAAGCTGACCCCTCTGTGCGTGACCCTGATCTGTTCTGACGCCACCGTGAAAACC
GGCACCGTGGAAGAGATGAAGAACTGCAGCTTCAACACCACCACCGAGATCCGGGACAAAGAGAAGAA
AGAGTACGCCCTGTTCTACAAGCCCGACATCGTGCCCCTGAGCGAGACAAACAACACCAGCGAGTACC
GGCTGATCAACTGCAACACCTCCGCCGTGACAATGG C TGCCCAAA TGACCTTCGAGCCCATTCCT
ATCCACTACTGTGCCCCTGCCGGCTACGCCATCCTGAAGTGCAACGACGAGACATTCAACGGCACAGG
CCCCTGCAGCAATGTGTCCACCGTGCAGTGTACCCACGGCATCAGACCAGTG TGTCTACCCAGCTGC
TGCTGAATGGAAGCCTGGCCGAGAAAGAAATCGTGATCAGAAGCGAGAACCTGACCAACAACGCCAAG
ATCATCATTGTGCATCTGCACACCCCTGTGGAAATCGTGTGCACCGGCCTCTGAAC  ACCCGGAA
GTCTGTGCGGATCGGCCCTGGCCAGACATTCTATGCCA GGCGATATCATCGGCGACATCAAGCAGG
CCCACTGCAACATCAGCGAGGAAAAGTGGAACGACACCCTGCAGAAAGTGGGCATCGAGCTGCAGAAG
CACTTCCCCAACAAGACCATCAAGTACAACCAGAGCGCTGGCGGCGACATGGAAATCACCACACACAG
CTTCAATTGTGGCGGCGAGTTCTTCTACTGCAATACCAGCAACCTGTTCAACGGGACCTACAATGGCA
CCTACATCAGCACCAACAGCAGCGCCAACTCCACCAGCACCATCACTCTGCAGTGCCGGATCAAGATG
ATCATCAATATGTGGCAAGGCGTGGGCAGAGCTATGTACGCCCCTCCTATCGCCGGCAACATCACCTG
TCGGAGCAATATCACAGGCCTGCTGCTCACCAGAGATGGCGGCACCAATAGCAACGAGACAGAAACCT
TCAGACCTGCCGGCGGAGACATGAGAGACAATTGGAGAAGCGAGCTGTACAAGTACAAGGTGGTGGAA
ATCCAGCCACTGGGAATCGCCCCAACCGGCGCTAAGAGAAGAGTGGTGGAACGCGAGAAAAGAGCCGC
TGGACTGGGAGCCCTGTTCCTGGGATTTCTTGGAGCCGCCGGAAGCACAATGGGAGCCGCCTCTATTA
CCCTGACCGTGCAGGCTAGACAGCTGCTGAGCGGAATTGTGCAGCAGCAGAGCAACCTGCTGAGAGCC
ATTGAAGCCCAGCAGCACATGCTGCAGCTGACCGTGTGGGGAATCAAACAGCTGCAGGCCAGAGTGCT
GGCCCTGGAAAGATACCTGAAGGACCAGCAGCTCCTCGGCATGTGGGGCTGTTCTGGCAAGCTGATCT
GCACCACCAACGTGCCCTGGAACACCTCCTGGTCCAACAAGAGCGAAACCGACATCTGGGACAACATG
ACCTGGATGCAGTGGGAGAGAGAGATCAGCAACTACACCGAGACAATCTACAAGCTGCTCGAGGACAG
CCAGAACCAGCAAGAGAGAAACGAGCAGGACCTGCTGGCTCTGGACAGCTGGAATAGCCTGTGGAACT
GGTTCAGCATCACCAAGTGGCTGTGGTACATCAAGATCTTCATCATGATCGTCGGCGGCCTGATCGGC
CTGAGAATCGTGTTTGCCGTGCTGAGCATCGTGAACAGAGTGCGGCAGGGATACAGCCCACTGAGCCT
GCAAACCCTGACACCTAATCCTAGAGAGCCCGACCGGCTGAGAGGCATCGAAGAAGAAGGCGGCGAGC
AGGATCGGGACAGATCCATCAGACTGGTGTCCGGCTTCCTGCCTATCGTGTGGGACGATCTGAGAAGC
CTGTGCCTGTTCAGCTACCACCGGCTGCGGGATTTTCTGCTGCTTGCCGCCAGAGTGGTTGAACTGCT
GGGCAGATCTAGCCTGAGGGGCCTGCAAAGAGGCTGGGAAGTCCTGAAGTACCTGGGCAGCCTGGTGC
AGTATTGGGGCCTCGAGCTGAAAAAGAGCGCCATTAGCCTGTTCGATACCCTGGCCATTGCTGTGGCC
GAGGGCACCGATAGAATCATTGAGCTGATCCAGGGCTTCTGCCGGGCCATCAGAAACATCCCCACCAG
AATCAGACAGGGCTTCGAGGCCAGCCTGCTGTGATAAGGATCCTCTAGA (SEQ ID NO: 64)

Figure 54 continued ary="US 12,138,304 B2"

SEQUENCE LISTING

<160> NUMBER OF SEQ ID NOS: 64

<210> SEQ ID NO 1
<211> LENGTH: 4
<212> TYPE: PRT
<213> ORGANISM: Unknown
<220> FEATURE:
<223> OTHER INFORMATION: Description of Unknown:
    cleavage site sequence

<400> SEQUENCE: 1

Arg Glu Lys Arg
1

<210> SEQ ID NO 2
<211> LENGTH: 9
<212> TYPE: PRT

-continued

```
<213> ORGANISM: Unknown
<220> FEATURE:
<223> OTHER INFORMATION: Description of Unknown:
      cleavage site sequence

<400> SEQUENCE: 2

Arg Arg Val Val Glu Arg Glu Lys Arg
1               5

<210> SEQ ID NO 3
<211> LENGTH: 9
<212> TYPE: PRT
<213> ORGANISM: Unknown
<220> FEATURE:
<223> OTHER INFORMATION: Description of Unknown:
      cleavage site sequence

<400> SEQUENCE: 3

Glu Arg Val Val Glu Arg Glu Lys Glu
1               5

<210> SEQ ID NO 4
<211> LENGTH: 4
<212> TYPE: PRT
<213> ORGANISM: Unknown
<220> FEATURE:
<223> OTHER INFORMATION: Description of Unknown:
      cleavage site sequence

<400> SEQUENCE: 4

Ser Glu Lys Ser
1

<210> SEQ ID NO 5
<211> LENGTH: 79
<212> TYPE: PRT
<213> ORGANISM: Unknown
<220> FEATURE:
<223> OTHER INFORMATION: Description of Unknown:
      envelope sequence

<400> SEQUENCE: 5

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu
65                  70                  75

<210> SEQ ID NO 6
<211> LENGTH: 24
<212> TYPE: PRT
<213> ORGANISM: Homo sapiens

<400> SEQUENCE: 6

Met Pro Met Gly Ser Leu Gln Pro Leu Ala Thr Leu Tyr Leu Leu Gly
1               5                   10                  15

Met Leu Val Ala Ser Val Leu Ala
            20
```

```
<210> SEQ ID NO 7
<211> LENGTH: 5
<212> TYPE: PRT
<213> ORGANISM: Unknown
<220> FEATURE:
<223> OTHER INFORMATION: Description of Unknown:
      recognition motif sequence
<220> FEATURE:
<221> NAME/KEY: MOD_RES
<222> LOCATION: (3)..(3)
<223> OTHER INFORMATION: Any amino acid

<400> SEQUENCE: 7

Leu Pro Xaa Thr Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Gly Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gln Gln Gln Leu Gly
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asp Ser Leu Asp Met Leu Glu Trp Ser Leu Met
1               5                   10

<210> SEQ ID NO 11
<211> LENGTH: 75
<212> TYPE: PRT
<213> ORGANISM: Human immunodeficiency virus 1

<400> SEQUENCE: 11

Glu Thr Thr Leu Phe Cys Ala Ser Asp Ala Lys Ala Tyr Glu Thr Glu
1               5                   10                  15

Lys His Asn Val Trp Ala Thr His Ala Cys Val Pro Thr Asp Pro Asn
            20                  25                  30

Pro Gln Glu Ile His Leu Glu Asn Val Thr Glu Glu Phe Asn Met Trp
        35                  40                  45

Lys Asn Asn Met Val Glu Gln Met His Thr Asp Ile Ile Ser Leu Trp
    50                  55                  60
```

```
Asp Gln Ser Leu Lys Pro Cys Val Lys Leu Thr
65                  70                  75
```

<210> SEQ ID NO 12
<211> LENGTH: 126
<212> TYPE: PRT
<213> ORGANISM: Human immunodeficiency virus 1

<400> SEQUENCE: 12

```
Thr Ser Ala Ile Thr Gln Ala Cys Pro Lys Val Ser Phe Glu Pro Ile
1               5                   10                  15

Pro Ile His Tyr Cys Ala Pro Ala Gly Phe Ala Ile Leu Lys Cys Lys
            20                  25                  30

Asp Lys Lys Phe Asn Gly Thr Gly Pro Cys Pro Ser Val Ser Thr Val
        35                  40                  45

Gln Cys Thr His Gly Ile Lys Pro Val Val Ser Thr Gln Leu Leu Leu
    50                  55                  60

Asn Gly Ser Leu Ala Glu Glu Val Met Ile Arg Ser Glu Asn Ile
65                  70                  75                  80

Thr Asn Asn Ala Lys Asn Ile Leu Val Gln Phe Asn Thr Pro Val Gln
                85                  90                  95

Ile Asn Cys Thr Arg Pro Asn Asn Asn Thr Arg Lys Ser Ile Arg Ile
            100                 105                 110

Gly Pro Gly Gln Ala Phe Tyr Ala Thr Gly Asp Ile Ile Gly
        115                 120                 125
```

<210> SEQ ID NO 13
<211> LENGTH: 47
<212> TYPE: PRT
<213> ORGANISM: Human immunodeficiency virus 1

<400> SEQUENCE: 13

```
Gly Glu Phe Phe Tyr Cys Asn Thr Ser Gly Leu Phe Asn Ser Thr Trp
1               5                   10                  15

Ile Ser Asn Thr Ser Val Gln Gly Ser Asn Ser Thr Gly Ser Asn Asp
            20                  25                  30

Ser Ile Thr Leu Pro Cys Arg Ile Lys Gln Ile Ile Asn Met Trp
        35                  40                  45
```

<210> SEQ ID NO 14
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Glu Thr Thr Leu Phe Cys Ala Ser Asp Ala Lys Ala Tyr Glu Thr Glu
1               5                   10                  15

Lys His Asn Ile Trp Ala Thr His Ala Cys Val Pro Thr Asp Pro Asn
            20                  25                  30

Pro Gln Glu Ile His Leu Glu Asn Val Thr Glu Glu Phe Asn Met Trp
        35                  40                  45

Lys Asn Asn Met Val Glu Gln Met His Thr Asp Ile Ile Ser Leu Trp
    50                  55                  60

Asp Gln Ser Leu Lys Pro Cys Val Lys Leu Thr
65                  70                  75
```

<210> SEQ ID NO 15
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Thr Ser Ala Ile Thr Gln Val Cys Pro Lys Leu Ser Phe Glu Pro Ile
1               5                   10                  15

Pro Ile His Tyr Cys Ala Pro Ala Gly Phe Ala Ile Leu Lys Cys Lys
            20                  25                  30

Asp Lys Lys Phe Asn Gly Thr Gly Pro Cys Pro Ser Val Ser Thr Val
        35                  40                  45

Gln Cys Thr His Gly Ile Lys Pro Val Leu Ser Thr Gln Leu Leu Leu
    50                  55                  60

Asn Gly Ser Leu Ala Glu Glu Val Met Ile Arg Ser Glu Asn Ile
65                  70                  75                  80

Thr Asn Asn Ala Lys Asn Ile Leu Val Gln Phe Asn Thr Pro Val Gln
                85                  90                  95

Ile Asn Cys Thr Arg Pro Asn Asn Thr Arg Lys Ser Ile Arg Ile
            100                 105                 110

Gly Pro Gly Gln Ala Phe Tyr Ala Thr Gly Asp Ile Ile Gly
        115                 120                 125

<210> SEQ ID NO 16
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Gly Glu Phe Phe Tyr Cys Asn Thr Ser Gly Leu Phe Asn Ser Thr Trp
1               5                   10                  15

Ile Ser Asn Thr Ser Val Gln Gly Ser Asn Ser Thr Gly Ser Asn Asp
            20                  25                  30

Ser Ile Thr Leu Pro Cys Arg Ile Lys Gln Ile Ile Asn Met Trp
        35                  40                  45

<210> SEQ ID NO 17
<211> LENGTH: 75
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Glu Thr Thr Leu Phe Cys Ala Ser Asp Ala Lys Ala Tyr Glu Thr Glu
1               5                   10                  15

Lys His Asn Ile Trp Ala Thr His Ala Cys Val Pro Thr Asp Pro Asn
            20                  25                  30

Pro Gln Glu Ile His Leu Glu Asn Val Thr Glu Glu Phe Asn Met Trp
        35                  40                  45

Lys Asn Asn Met Val Glu Gln Met His Thr Asp Ile Ile Ser Leu Trp
    50                  55                  60

Asp Gln Ser Leu Lys Pro Cys Val Lys Leu Thr
65                  70                  75

```
<210> SEQ ID NO 18
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Thr Ser Ala Ile Thr Met Val Cys Pro Lys Leu Ser Phe Glu Pro Ile
1               5                   10                  15

Pro Ile His Tyr Cys Ala Pro Ala Gly Phe Ala Ile Leu Lys Cys Lys
            20                  25                  30

Asp Lys Lys Phe Asn Gly Thr Gly Pro Cys Pro Ser Val Ser Thr Val
        35                  40                  45

Gln Cys Thr His Gly Ile Lys Pro Val Leu Ser Thr Gln Leu Leu Leu
    50                  55                  60

Asn Gly Ser Leu Ala Glu Glu Val Met Ile Arg Ser Glu Asn Ile
65                  70                  75                  80

Thr Asn Asn Ala Lys Asn Ile Leu Val Gln Phe Asn Thr Pro Val Gln
                85                  90                  95

Ile Asn Cys Thr Arg Pro Leu Asn Leu Thr Arg Lys Ser Ile Arg Ile
            100                 105                 110

Gly Pro Gly Gln Ala Phe Tyr Ala Met Gly Asp Ile Ile Gly
        115                 120                 125

<210> SEQ ID NO 19
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Glu Phe Phe Tyr Cys Asn Thr Ser Gly Leu Phe Asn Ser Thr Trp
1               5                   10                  15

Ile Ser Asn Thr Ser Val Gln Gly Ser Asn Ser Thr Gly Ser Asn Asp
            20                  25                  30

Ser Ile Thr Leu Pro Cys Arg Ile Lys Met Ile Ile Asn Met Trp
        35                  40                  45

<210> SEQ ID NO 20
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Arg Ala Tyr Glu Lys Glu Val His Asn Val Trp Ala
    50                  55                  60
```

```
Thr His Ala Cys Val Pro Thr Asp Pro Ser Pro Gln Glu Leu Val Leu
 65                  70                  75                  80

Gly Asn Val Thr Glu Asn Phe Asn Met Trp Lys Asn Asp Met Val Asp
                 85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
            115                 120                 125

Thr Val Lys Thr Gly Thr Val Glu Glu Met Lys Asn Cys Ser Phe Asn
130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Ala Cys Pro
            180                 185                 190

Lys Val Thr Phe Glu Pro Ile Pro Ile His Tyr Cys Ala Pro Ala Gly
            195                 200                 205

Tyr Ala Ile Leu Lys Cys Asn Asp Glu Thr Phe Asn Gly Thr Gly Pro
210                 215                 220

Cys Ser Asn Val Ser Thr Val Gln Cys Thr His Gly Ile Arg Pro Val
225                 230                 235                 240

Val Ser Thr Gln Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Leu Asn Leu
            275                 280                 285

Thr Arg Lys Ser Val Arg Ile Gly Pro Gly Gln Thr Phe Tyr Ala Met
            290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
            325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Met Ile Ile Asn Met Trp Gln Gly Val Gly Arg Ala Met
            405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
            450                 455                 460

Leu Tyr Lys Tyr Lys Val Val Lys Ile Glu Pro Leu Gly Val Ala Pro
465                 470                 475                 480

Thr Arg Cys Lys Arg Arg Val Val Gly Arg Arg Arg Arg Arg Arg Ala
```

|  | 485 |  |  | 490 |  |  | 495 |  |
|---|---|---|---|---|---|---|---|---|

Val Gly Ile Gly Ala Val Phe Leu Gly Phe Leu Gly Ala Ala Gly Ser
           500                      505                      510

Thr Met Gly Ala Ala Ser Met Thr Leu Thr Val Gln Ala Arg Asn Leu
           515                      520                      525

Leu Ser Gly Ile Val Gln Gln Gln Ser Asn Leu Leu Arg Ala Pro Glu
           530                      535                      540

Ala Gln Gln His Leu Leu Lys Leu Thr Val Trp Gly Ile Lys Gln Leu
545                      550                      555                      560

Gln Ala Arg Val Leu Ala Val Glu Arg Tyr Leu Arg Asp Gln Gln Leu
           565                      570                      575

Leu Gly Ile Trp Gly Cys Ser Gly Lys Leu Ile Cys Cys Thr Asn Val
           580                      585                      590

Pro Trp Asn Ser Ser Trp Ser Asn Arg Asn Leu Ser Glu Ile Trp Asp
           595                      600                      605

Asn Met Thr Trp Leu Gln Trp Asp Lys Glu Ile Ser Asn Tyr Thr Gln
           610                      615                      620

Ile Ile Tyr Gly Leu Leu Glu Glu Ser Gln Asn Gln Gln Glu Lys Asn
625                      630                      635                      640

Glu Gln Asp Leu Leu Ala Leu Asp
           645

```
<210> SEQ ID NO 21
<211> LENGTH: 1968
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga agaggccaaa gaccacactg ttctgcgcct ccgatgccag agcctacgag     180
aaagaggtgc acaacgtctg gccacacacg gcctgtgtgc ctaccgatcc atctcctcaa     240
gagctggtgc tgggcaacgt gaccgagaac ttcaacatgt ggaagaacga catggtggac     300
cagatgcacg aggacatcat cagcctgtgg gaccagagcc tgaagccttg cgtgaagctg     360
acccctctgt gcgtgaccct gatctgttct gacgccaccg tgaaaaccgg caccgtggaa     420
gagatgaaga actgcagctt caacaccacc accgagatcc gggacaaaga agagaaagag     480
tacgccctgt tctacaagcc cgacatcgtg cccctgagcg agacaaacaa caccagcgag     540
taccggctga tcaactgcaa cacaagcgcc gtgaccatgg cctgtcctaa agtgaccttc     600
gagcccattc ctatccacta ctgtgcccct gccggctacg ccatcctgaa gtgcaacgac     660
gagacattca cggcacaggc ccctgcagca aatgtgtcca ccgtgcagtg tacccacggc     720
atcagaccag tggtgtctac ccagctgctg ctgaatggaa gcctggccga aagaaatc      780 gtgatcagaa gcgagaacct gaccaacaac gccaagatca tcattgtgca tctgcacacc     840
cctgtggaaa tcgtgtgcac ccggcctctg aatctgacca gaagagcgt gcggatcggc     900 cctggccaga cctttatgc catgggcgac atcatcggcg atatcaagca ggcccactgc     960
aacatcagcg aggaaaagtg aacgacacc ctgcagaaag tgggcatcga gctgcagaag    1020
cacttcccca caagaccat caagtacaac cagagcgctg gcggcgacat ggaaatcacc    1080
```

```
acacacagct tcaattgtgg cggcgagttc ttctactgca ataccagcaa cctgttcaac  1140
gggacctaca atggcaccta catcagcacc aacagcagcg ccaactccac cagcaccatc  1200
actctgcagt gccggatcaa gatgatcatt aacatgtggc aaggcgtcgg cagggctatg  1260
tacgcccctc ctatcgccgg caacatcacc tgtcggagca atatcacagg cctgctgctc  1320
accagagatg gcggcaccaa tagcaacgag acagaaacct tcagacctgc cggcggagac  1380
atgagagaca attggagaag cgagctgtac aagtacaagg tggtcaagat cgagcccctg  1440
ggcgtcgcac ctacacggtg caagagaaga gtcgtgggcc gtcgtagaag gcggagagcc  1500
gttggaattg cgccgtgtt cctgggcttt ctgggagccg ctggatctac aatgggcgct  1560
gccagcatga ccctgacagt gcaggctaga atctgctga gcggcatcgt gcagcagcag  1620
agcaatctgc tcagagcccc tgaggctcag cagcacctcc tgaaactgac agtgtgggc  1680
atcaagcagc tgcaggcaag agtgctggca gtggaaagat acctgcggga ccagcagctc  1740
ctcggaatct ggggatgtag cggcaagctg atctgctgca ccaacgtgcc ctggaacagc  1800
tcctggtcca accggaatct gtccgagatc tgggataaca tgacctggct gcagtgggac  1860
aaagaaatca gcaactacac ccagatcatc tacggcctgc tggaagagag ccagaaccag  1920
caagagaaaa acgagcagga cctgctggcc ctggactgat aaggatcc  1968
```

<210> SEQ ID NO 22
<211> LENGTH: 648
<212> TYPE: PRT
<213> ORGANISM: Artificial Sequence
<220> FEATURE:
<223> OTHER INFORMATION: Description of Artificial Sequence: Synthetic
     polypeptide <400> SEQUENCE: 22

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Arg Ala Tyr Glu Lys Glu Val His Asn Val Trp Ala
    50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
    130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Ala Cys Pro
            180                 185                 190

Lys Val Thr Phe Glu Pro Ile Pro Ile His Tyr Cys Ala Pro Ala Gly
        195                 200                 205
```

-continued

Tyr Ala Ile Leu Lys Cys Asn Asp Glu Thr Phe Asn Gly Thr Gly Pro
        210                 215                 220
Cys Ser Asn Val Ser Thr Val Gln Cys Thr His Gly Ile Arg Pro Val
225                 230                 235                 240
Val Ser Thr Gln Leu Leu Leu Asn Gly Ser Leu Ala Glu Lys Glu Ile
                245                 250                 255
Val Ile Arg Ser Glu Asn Leu Thr Asn Asn Ala Lys Ile Ile Ile Val
            260                 265                 270
His Leu His Thr Pro Val Glu Ile Val Cys Thr Arg Pro Leu Asn Leu
        275                 280                 285
Thr Arg Lys Ser Val Arg Ile Gly Pro Gly Gln Thr Phe Tyr Ala Met
290                 295                 300
Gly Asp Ile Ile Gly Asp Ile Lys Gln Ala His Cys Asn Ile Ser Glu
305                 310                 315                 320
Glu Lys Trp Asn Asp Thr Leu Gln Lys Val Gly Ile Glu Leu Gln Lys
                325                 330                 335
His Phe Pro Asn Lys Thr Ile Lys Tyr Asn Gln Ser Ala Gly Gly Asp
            340                 345                 350
Met Glu Ile Thr Thr His Ser Phe Asn Cys Gly Gly Glu Phe Phe Tyr
        355                 360                 365
Cys Asn Thr Ser Asn Leu Phe Asn Gly Thr Tyr Asn Gly Thr Tyr Ile
370                 375                 380
Ser Thr Asn Ser Ser Ala Asn Ser Thr Ser Thr Ile Thr Leu Gln Cys
385                 390                 395                 400
Arg Ile Lys Met Ile Ile Asn Met Trp Gln Gly Val Gly Arg Ala Met
                405                 410                 415
Tyr Ala Pro Pro Ile Ala Gly Asn Ile Thr Cys Arg Ser Asn Ile Thr
            420                 425                 430
Gly Leu Leu Leu Thr Arg Asp Gly Gly Thr Asn Ser Asn Glu Thr Glu
        435                 440                 445
Thr Phe Arg Pro Ala Gly Gly Asp Met Arg Asp Asn Trp Arg Ser Glu
450                 455                 460
Leu Tyr Lys Tyr Lys Val Val Glu Ile Gln Pro Leu Gly Ile Ala Pro
465                 470                 475                 480
Thr Gly Ala Lys Arg Arg Val Val Glu Arg Arg Arg Arg Arg Arg Ala
                485                 490                 495
Ala Gly Leu Gly Ala Leu Phe Leu Gly Phe Leu Gly Ala Ala Gly Ser
            500                 505                 510
Thr Met Gly Ala Ala Ser Ile Thr Leu Thr Val Gln Ala Arg Gln Leu
        515                 520                 525
Leu Ser Gly Ile Val Gln Gln Gln Ser Asn Leu Leu Arg Ala Pro Glu
530                 535                 540
Ala Gln Gln His Met Leu Gln Leu Thr Val Trp Gly Ile Lys Gln Leu
545                 550                 555                 560
Gln Ala Arg Val Leu Ala Leu Glu Arg Tyr Leu Lys Asp Gln Gln Leu
                565                 570                 575
Leu Gly Met Trp Gly Cys Ser Gly Lys Leu Ile Cys Cys Thr Asn Val
            580                 585                 590
Pro Trp Asn Thr Ser Trp Ser Asn Lys Ser Glu Thr Asp Ile Trp Asp
        595                 600                 605
Asn Met Thr Trp Met Gln Trp Glu Arg Glu Ile Ser Asn Tyr Thr Glu
610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
            645

<210> SEQ ID NO 23
<211> LENGTH: 1968
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga agaggccaa gaccacactg ttctgcgcct ccgatgccag agcctacgag      180
aaagaggtgc acaacgtctg gccacacac gcctgtgtgc ctaccgatcc atctcctcaa      240
gagctggtgc tgggcaacgt gaccgagaac ttcaacatgt ggaagaacga catggtggac     300
cagatgcacg aggacatcat cagcctgtgg gaccagagcc tgaagccttg cgtgaagctg     360
accectctgt gcgtgaccct gatctgttct gacgccaccg tgaaaaccgg caccgtggaa     420
gagatgaaga actgcagctt caacaccacc accgagatcc gggacaaaga agaaaagag     480
tacgccctgt tctacaagcc cgacatcgtg cccctgagcg agacaaacaa caccagcgag     540
taccggctga tcaactgcaa cacaagcgcc gtgaccatgg cctgtcctaa agtgaccttc     600
gagcccattc ctatccacta ctgtgcccct gccggctacg ccatcctgaa gtgcaacgac     660
gagacattca cggcacaggg cccctgcagc aatgtgtcca ccgtgcagtg tacccacggc     720
atcagaccag tggtgtctac ccagctgctg ctgaatggaa gcctggccga aaagaaatc     780
gtgatcagaa gcgagaacct gaccaacaac gccaagatca tcattgtgca tctgcacacc     840
cctgtggaaa tcgtgtgcac ccggcctctg aatctgacca gaaagagcgt gcggatcggc     900
cctggccaga ccttttatgc catgggcgac atcatcggcg atatcaagca ggcccactgc     960
aacatcagcg aggaaaagtg gaacgacacc ctgcagaaag tgggcatcga gctgcagaag    1020
cacttccca caagaccat caagtacaac cagagcgctg cggcgacat ggaaatcacc       1080
acacacagct tcaattgtgg cggcgagttc ttctactgca ataccagcaa cctgttcaac    1140
gggacctaca tggcaccta tcagcaccc aacagcagcg ccaactccac cagcaccatc      1200
actctgcagt gccggatcaa gatgatcatt aacatgtggc aaggcgtcgg cagggctatg    1260
tacgcccctc ctatcgccgg caacatcacc tgtcggagca atatcacagg cctgctgctc    1320
accagagatg gcggcaccaa tagcaacgag acagaaacct tcagacctgc cggcggagac    1380
atgagagaca attggagaag cgagctgtac aagtacaagg tcgtggaaat ccagccactg    1440
ggaatcgccc caaccggcgc taagagaaga gtggtggaac ggcgaagaag gcggagagct    1500
gctggactgg gtgctctgtt cctgggcttt cttggagccg ccggatctac aatgggagcc    1560
gcctctatca ccctgaccgt gcaggctaga cagctgctga gcggaattgt gcagcagcag    1620
agcaacctgc tgagagcccc tgaagcacag cagcacatgc tgcagctgac agtgtggggc    1680
atcaaacagc tgcaggccag agtgctggcc ctgaaagat acctgaagga tcagcagctc    1740
ctcggcatgt ggggctgttc tggcaagctg atctgctgca ccaacgtgcc ctggaacacc    1800
tcctggtcca caagagcga aaccgacatc tgggacaaca tgacctggat gcagtgggag    1860
```

```
agagagatca gcaactacac cgagacaatc tacaagctgc tcgaggacag ccagaaccag    1920
caagagagaa acgagcagga cctgctggct ctggactgat gaggatcc                 1968
```

<210> SEQ ID NO 24
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Ile Trp Ala
        50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Gln Val Cys Pro
            180                 185                 190

Lys Leu Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
    210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Asn Asn Asn
        275                 280                 285

Thr Arg Lys Ser Val Arg Ile Gly Pro Gly Gln Thr Phe Tyr Ala Thr
    290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
```

340             345                 350
Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
            405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
            450                 455                 460

Leu Tyr Lys Tyr Lys Val Val Lys Ile Glu Pro Leu Gly Val Ala Pro
465                 470                 475                 480

Thr Arg Cys Lys Arg Arg Val Val Gly Arg Arg Arg Arg Arg Arg Ala
            485                 490                 495

Val Gly Ile Gly Ala Val Phe Leu Gly Phe Leu Gly Ala Ala Gly Ser
            500                 505                 510

Thr Met Gly Ala Ala Ser Met Thr Leu Thr Val Gln Ala Arg Asn Leu
            515                 520                 525

Leu Ser Gly Ile Val Gln Gln Gln Ser Asn Leu Leu Arg Ala Pro Glu
            530                 535                 540

Ala Gln Gln His Leu Leu Lys Leu Thr Val Trp Gly Ile Lys Gln Leu
545                 550                 555                 560

Gln Ala Arg Val Leu Ala Val Glu Arg Tyr Leu Arg Asp Gln Gln Leu
            565                 570                 575

Leu Gly Ile Trp Gly Cys Ser Gly Lys Leu Ile Cys Cys Thr Asn Val
            580                 585                 590

Pro Trp Asn Ser Ser Trp Ser Asn Arg Asn Leu Ser Glu Ile Trp Asp
            595                 600                 605

Asn Met Thr Trp Leu Gln Trp Asp Lys Glu Ile Ser Asn Tyr Thr Gln
            610                 615                 620

Ile Ile Tyr Gly Leu Leu Glu Glu Ser Gln Asn Gln Gln Glu Lys Asn
625                 630                 635                 640

Glu Gln Asp Leu Leu Ala Leu Asp
            645

<210> SEQ ID NO 25
<211> LENGTH: 1968
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 25
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga agaggccaa gaccacactg ttctgcgcct ccgatgccag agcctacgag      180
aaagaggtgc acaacatctg gccacacac gcctgcgtgc aaccgatcc atctcctcaa      240 gaactggtgc tgggcaacgt gaccgagaac ttcaacatgt ggaagaacga catggtggac     300

-continued

```
cagatgcacg aggacatcat cagcctgtgg gaccagagcc tgaagccttg cgtgaagctg    360
acccctctgt gcgtgaccct gatctgttct gacgccaccg tgaaaaccgg caccgtggaa    420
gagatgaaga actgcagctt caacaccacc accgagatcc gggacaaaga gaagaaagag    480
tacgccctgt tctacaagcc cgacatcgtg cccctgagcg agacaaacaa caccagcgag    540
taccggctga tcaactgcaa cacctccgcc gtgacacaag tgtgccccaa gctgaccttc    600
gagcccattc ctatccacta ctgtgcccct gccggctacg ccatcctgaa gtgcaacgac    660
gagacattca acggcacagg cccctgcagc aatgtgtcca ccgtgcagtg tacccacggc    720
atcagacctg tgctgagcac acagctgctg ctgaatggaa gcctggccga aaagaaatc    780 gtgatcagaa gcgagaacct gaccaacaac gccaagatca tcattgtgca tctgcacacc    840
cctgtggaaa tcgtgtgcac ccggcctaac aacaacaccc ggaagtctgt gcggatcggc    900
cctggccaga cattctatgc caccggcgat atcatcggcg acatcaagca ggcccactgc    960
aacatcagcg aggaaaagtg gaacgacacc ctgcagaaag tgggcatcga gctgcagaag   1020
cacttcccca caagaccat caagtacaac cagagcgctg gcggcgacat ggaaatcacc    1080
acacacagct tcaattgtgg cggcgagttc ttctactgca ataccagcaa cctgttcaac    1140
gggacctaca atggcaccta catcagcacc aacagcagcg ccaactccac cagcaccatc    1200
actctgcagt gccggatcaa gcagatcatc aatatgtggc aaggcgtggg cagagctatg    1260
tacgcccctc ctatcgccgg caacatcacc tgtcggagca atatcacagg cctgctgctc    1320
accagagatg gcggcaccaa tagcaacgag acagaaacct tcagacctgc cggcggagac    1380
atgagagaca attggagaag cgagctgtac aagtacaagg tggtcaagat cgagcccctg    1440
ggcgtcgcac ctacacggtg caagagaaga gtcgtgggac gtagacgaag gcggagagcc    1500
gttggaatcg gagccgtgtt cctgggcttt ctgggagccg ctggatctac aatgggcgct    1560
gccagcatga ccctgacagt gcaggctaga aatctgctga gcggcatcgt gcagcagcag   1620
agcaatctgc tcagagcccc tgaggctcag cagcacctcc tgaaactgac agtgtgggga    1680
atcaagcagc tgcaggccag agtgctggca gtggaaagat acctgaggga ccagcagctc    1740
ctcggaatct ggggctgttc tggcaagctg atctgctgca ccaacgtgcc ctggaacagc    1800
agctggtcca accggaatct gtccgagatc tgggataaca tgacctggct gcagtgggac    1860
aaagaaatca gcaactacac ccagatcatc tacgcctgc tggaagagag ccagaaccag    1920
caagagaaaa acgagcagga cctgctggcc ctggactgat aaggatcc                1968
```

<210> SEQ ID NO 26
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Ile Trp Ala
        50                  55                  60
```

-continued

```
Thr His Ala Cys Val Pro Thr Asp Pro Ser Pro Gln Glu Leu Val Leu
 65                  70                  75                  80

Gly Asn Val Thr Glu Asn Phe Asn Met Trp Lys Asn Asp Met Val Asp
                 85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Val Cys Pro
            180                 185                 190

Lys Leu Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Leu Asn Leu
        275                 280                 285

Thr Arg Lys Ser Val Arg Ile Gly Pro Gly Gln Thr Phe Tyr Ala Met
290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
        355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Met Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
        435                 440                 445

Thr Phe Arg Pro Ala Gly Gly Asp Met Arg Asp Asn Trp Arg Ser Glu
450                 455                 460

Leu Tyr Lys Tyr Lys Val Val Glu Ile Gln Pro Leu Gly Ile Ala Pro
465                 470                 475                 480
```

```
Thr Gly Ala Lys Arg Arg Val Val Glu Arg Arg Arg Arg Arg Ala
            485                 490                 495
Ala Gly Leu Gly Ala Leu Phe Leu Gly Phe Leu Gly Ala Ala Gly Ser
        500                 505                 510
Thr Met Gly Ala Ala Ser Ile Thr Leu Thr Val Gln Ala Arg Gln Leu
        515                 520                 525
Leu Ser Gly Ile Val Gln Gln Gln Ser Asn Leu Leu Arg Ala Pro Glu
        530                 535                 540
Ala Gln Gln His Met Leu Gln Leu Thr Val Trp Gly Ile Lys Gln Leu
545                 550                 555                 560
Gln Ala Arg Val Leu Ala Leu Glu Arg Tyr Leu Lys Asp Gln Gln Leu
                565                 570                 575
Leu Gly Met Trp Gly Cys Ser Gly Lys Leu Ile Cys Cys Thr Asn Val
            580                 585                 590
Pro Trp Asn Thr Ser Trp Ser Asn Lys Ser Glu Thr Asp Ile Trp Asp
            595                 600                 605
Asn Met Thr Trp Met Gln Trp Glu Arg Glu Ile Ser Asn Tyr Thr Glu
        610                 615                 620
Thr Ile Tyr Lys Leu Leu Glu Asp Ser Gln Asn Gln Gln Glu Arg Asn
625                 630                 635                 640
Glu Gln Asp Leu Leu Ala Leu Asp
            645
```

<210> SEQ ID NO 27
<211> LENGTH: 1968
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gtcgacgcca ccatgcctat gggatctctg cagcctctgg ccacactgta cctgctggga    60
atgctggtgg cttctgtgct ggccgccgag aatctgtggg tcacagtgta ctatggcgtg   120
cccgtgtgga agaggccaag accacactgt tctgcgcct ccgatgccag agcctacgag    180
aaagaggtgc acaacatctg gccacacac gcctgcgtgc aaccgatcc atctcctcaa     240
gaactggtgc tgggcaacgt gaccgagaac ttcaacatgt ggaagaacga catggtggac   300
cagatgcacg aggacatcat cagcctgtgg gaccagagcc tgaagccttg cgtgaagctg   360
acccctctgt gcgtgaccct gatctgttct gacgccaccg tgaaaaccgg caccgtggaa   420
gagatgaaga actgcagctt caacaccacc accgagatcc gggacaaaga gaagaaagag   480
tacgccctgt tctacaagcc cgacatcgtg cccctgagcg agacaaacaa caccagcgag   540
taccggctga tcaactgcaa cacaagcgcc gtgacaatgg tctgccccaa gctgaccttc   600
gagcccattc ctatccacta ctgtgcccct gccggctacg ccatcctgaa gtgcaacgac   660
gagacattca acggcacagg ccctgcagc aatgtgtcca ccgtgcagtg tacccacggc   720
atcagacctg tgctgagcac acagctgctg ctgaatggaa gcctggccga aagaaatc    780
gtgatcagaa gcgagaacct gaccaacaac gccaagatca tcattgtgca ctgcacacc    840
cctgtggaaa tcgtgtgcac ccggcctctg aatctgacca aaagagcgt gcggatcggc    900
cctggccaga cctttttatgc catgggcgac atcatcggcg atatcaagca ggcccactgc   960
aacatcagcg aggaaaagtg aacgacacc ctgcagaaag tgggcatcga gctgcagaag   1020
cacttcccca caagaccat caagtacaac cagagcgctg gcggcgacat ggaaatcacc   1080
```

```
acacacagct tcaattgtgg cggcgagttc ttctactgca ataccagcaa cctgttcaac   1140
gggacctaca atggcaccta catcagcacc aacagcagcg ccaactccac cagcaccatc   1200
actctgcagt gccggatcaa gatgatcatt aacatgtggc aaggcgtcgg cagggctatg   1260 tacgccctc ctatcgccgg caacatcacc tgtcggagca atatcacagg cctgctgctc    1320
accagagatg gcggcaccaa tagcaacgag acagaaacct tcagacctgc cggcggagac   1380
atgagagaca attggagaag cgagctgtac aagtacaagg tcgtggaaat ccagccactg   1440
ggaatcgccc caaccggcgc taagagaaga gtggtggaac ggcgaagaag cggagagct    1500 gctggactgg gtgctctgtt cctgggcttt cttggagccg ccggatctac aatgggagcc   1560
gcctctatca ccctgaccgt gcaggctaga cagctgctct ctggaatcgt gcagcagcag   1620
agcaacctgc tgagagcccc tgaagctcag cagcacatgc tgcagctgac agtgtgggc    1680 atcaaacagc tgcaggccag agtgctggcc ctggaaagat acctgaagga tcagcagctc   1740
ctcggcatgt ggggctgttc tggcaagctg atctgctgca ccaacgtgcc ctggaacacc   1800
tcctggtcca acaagagcga aaccgacatc tgggacaaca tgacctggat gcagtgggag   1860
agagagatca gcaactacac cgagacaatc tacaagctgc tcgaggacag ccagaaccag   1920
caagagagaa acgagcagga cctgctggct ctggactgat gaggatcc               1968
```

<210> SEQ ID NO 28
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Ile Trp Ala
        50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
    130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Gln Val Cys Pro
            180                 185                 190

Lys Leu Thr Phe Glu Pro Ile Pro Ile His Tyr Cys Ala Pro Ala Gly
```

-continued

```
            195                 200                 205
Tyr Ala Ile Leu Lys Cys Asn Asp Glu Thr Phe Asn Gly Thr Gly Pro
        210                 215                 220

Cys Ser Asn Val Ser Thr Val Gln Cys Thr His Gly Ile Arg Pro Val
225                 230                 235                 240

Leu Ser Thr Gln Leu Leu Asn Gly Ser Leu Ala Glu Lys Glu Ile
                245                 250                 255

Val Ile Arg Ser Glu Asn Leu Thr Asn Asn Ala Lys Ile Ile Val
            260                 265                 270

His Leu His Thr Pro Val Glu Ile Val Cys Thr Arg Pro Asn Asn Asn
        275                 280                 285

Thr Arg Lys Ser Val Arg Ile Gly Pro Gly Gln Thr Phe Tyr Ala Thr
        290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
        355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
        435                 440                 445

Thr Phe Arg Pro Ala Gly Gly Asp Met Arg Asp Asn Trp Arg Ser Glu
        450                 455                 460

Leu Tyr Lys Tyr Lys Val Val Glu Ile Gln Pro Leu Gly Ile Ala Pro
465                 470                 475                 480

Thr Gly Ala Lys Arg Arg Val Val Glu Arg Arg Arg Arg Arg Ala
                485                 490                 495

Ala Gly Leu Gly Ala Leu Phe Leu Gly Phe Leu Gly Ala Ala Gly Ser
            500                 505                 510

Thr Met Gly Ala Ala Ser Ile Thr Leu Thr Val Gln Ala Arg Gln Leu
        515                 520                 525

Leu Ser Gly Ile Val Gln Gln Ser Asn Leu Leu Arg Ala Pro Glu
        530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
                565                 570                 575

Leu Gly Met Trp Gly Cys Ser Gly Lys Leu Ile Cys Cys Thr Asn Val
            580                 585                 590

Pro Trp Asn Thr Ser Trp Ser Asn Lys Ser Glu Thr Asp Ile Trp Asp
        595                 600                 605

Asn Met Thr Trp Met Gln Trp Glu Arg Glu Ile Ser Asn Tyr Thr Glu
        610                 615                 620
```

Thr Ile Tyr Lys Leu Leu Glu Asp Ser Gln Asn Gln Gln Glu Arg Asn
625                 630                 635                 640

Glu Gln Asp Leu Leu Ala Leu Asp
            645

<210> SEQ ID NO 29
<211> LENGTH: 1968
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga agaggccaa gaccacactg ttctgcgcct ccgatgccag agcctacgag      180
aaagaggtgc acaacatctg gccacacac gcctgcgtgc aaccgatcc atctcctcaa      240 gaactggtgc tgggcaacgt gaccgagaac ttcaacatgt ggaagaacga catggtggac    300
cagatgcacg aggacatcat cagcctgtgg gaccagagcc tgaagccttg cgtgaagctg    360 accectctgt gcgtgaccct gatctgttct gacgccaccg tgaaaaccgg caccgtggaa    420
gagatgaaga actgcagctt caacaccacc accgagatcc gggacaaaga agaaaagag    480 tacgccctgt tctacaagcc cgacatcgtg cccctgagcg agacaaacaa caccagcgag    540
taccggctga tcaactgcaa cacctccgcc gtgacacaag tgtgcccaa gctgaccttc    600 gagcccattc ctatccacta ctgtgccct gccggctacg ccatcctgaa gtgcaacgac    660
gagacattca cggcacaggg ccctgcagc aatgtgtcca ccgtgcagtg tacccacggc    720
atcagacctg tgctgagcac acagctgctg ctgaatggaa gcctggccga aagaaatc    780 gtgatcagaa gcgagaacct gaccaacaac gccaagatca tcattgtgca tctgcacacc    840
cctgtggaaa tcgtgtgcac ccggcctaac aacaacaccc ggaagtctgt gcggatcggc    900
cctggccaga cattctatgc caccggcgat atcatcggcg acatcaagca ggcccactgc    960
aacatcagcg aggaaaagtg aacgacacc ctgcagaaag tgggcatcga gctgcagaag   1020
cacttcccca caagaccat caagtacaac cagagcgctg cggcgacat ggaaatcacc    1080 acacacagct tcaattgtgg cggcgagttc ttctactgca taccagcaa cctgttcaac    1140 gggacctaca tggcacccta catcagcacc aacagcagcg ccaactccac cagcaccatc    1200
actctgcagt gccggatcaa gcagatcatc aatatgtggc aaggcgtggg cagagctatg    1260
tacgcccctc ctatcgccgg caacatcacc tgtcggagca atatcacagg cctgctgctc    1320
accagagatg gcggcaccaa tagcaacgag acagaaacct tcagacctgc cggcggagac    1380
atgagagaca attggagaag cgagctgtac aagtacaagg tggtggaaat ccagccactg    1440
ggaatcgccc caaccggcgc taagagaaga gtggtcgagc ggagaagaag gcggagagct    1500
gctggactgg gtgccctgtt tctgggcttt cttggagccg ccggaagcac aatgggagcc    1560
gcctctatta ccctgaccgt gcaggctaga cagctgctct ctggaatcgt gcagcagcag    1620
agcaacctgc tgagagcccc tgaagctcag cagcacatgc tgcagctgac agtgtgggga    1680
atcaagcagc tgcaggccag agtgctggcc ctgaaagat acctgaagga tcagcagctc    1740
ctcggcatgt ggggctgttc tggcaagctg atctgctgca ccaacgtgcc ctggaacacc    1800
tcctggtcca acaagagcga aaccgacatc tgggacaaca tgacctggat gcagtgggag    1860

```
agagagatca gcaactacac cgagacaatc tacaagctgc tcgaggacag ccagaaccag   1920
caagagagaa acgagcagga cctgctggct ctggactgat gaggatcc                1968
```

<210> SEQ ID NO 30  
<211> LENGTH: 648  
<212> TYPE: PRT  
<213> ORGANISM: Artificial Sequence  
<220> FEATURE:  
<223> OTHER INFORMATION: Description of Artificial Sequence: Synthetic
      polypeptide

<400> SEQUENCE: 30

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Val Trp Ala
        50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Gln Ala Cys Pro
            180                 185                 190

Lys Val Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
210                 215                 220

Cys Ser Asn Val Ser Thr Val Gln Cys Thr His Gly Ile Arg Pro Val
225                 230                 235                 240

Val Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Asn Asn Asn
        275                 280                 285

Thr Arg Lys Ser Val Arg Ile Gly Pro Gly Gln Thr Phe Tyr Ala Thr
290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335
```

His Phe Pro Asn Lys Thr Ile Lys Tyr Asn Gln Ser Ala Gly Gly Asp
                340                 345                 350

Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
        435                 440                 445

Thr Phe Arg Pro Ala Gly Gly Asp Met Arg Asp Asn Trp Arg Ser Glu
    450                 455                 460

Leu Tyr Lys Tyr Lys Val Val Lys Ile Glu Pro Leu Gly Val Ala Pro
465                 470                 475                 480

Thr Arg Cys Lys Arg Arg Val Val Gly Arg Arg Arg Arg Arg Arg Ala
                485                 490                 495

Val Gly Ile Gly Ala Val Phe Leu Gly Phe Leu Gly Ala Ala Gly Ser
            500                 505                 510

Thr Met Gly Ala Ala Ser Met Thr Leu Thr Val Gln Ala Arg Asn Leu
        515                 520                 525

Leu Ser Gly Ile Val Gln Gln Gln Ser Asn Leu Leu Arg Ala Pro Glu
    530                 535                 540

Ala Gln Gln His Leu Leu Lys Leu Thr Val Trp Gly Ile Lys Gln Leu
545                 550                 555                 560

Gln Ala Arg Val Leu Ala Val Glu Arg Tyr Leu Arg Asp Gln Gln Leu
                565                 570                 575

Leu Gly Ile Trp Gly Cys Ser Gly Lys Leu Ile Cys Cys Thr Asn Val
            580                 585                 590

Pro Trp Asn Ser Ser Trp Ser Asn Arg Asn Leu Ser Glu Ile Trp Asp
        595                 600                 605

Asn Met Thr Trp Leu Gln Trp Asp Lys Glu Ile Ser Asn Tyr Thr Gln
    610                 615                 620

Ile Ile Tyr Gly Leu Leu Glu Glu Ser Gln Asn Gln Gln Glu Lys Asn
625                 630                 635                 640

Glu Gln Asp Leu Leu Ala Leu Asp
                645

<210> SEQ ID NO 31
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

```
Ala Ser Asp Ala Arg Ala Tyr Glu Lys Glu Val His Asn Ile Trp Ala
    50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
                100                 105                 110

Cys Val Lys Leu Thr Pro Leu Cys Val Thr Leu Ile Cys Ser Asp Ala
            115                 120                 125

Thr Val Lys Thr Gly Thr Val Glu Glu Met Lys Asn Cys Ser Phe Asn
    130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Gln Val Cys Pro
                180                 185                 190

Lys Leu Thr Phe Glu Pro Ile Pro Ile His Tyr Cys Ala Pro Ala Gly
            195                 200                 205

Tyr Ala Ile Leu Lys Cys Asn Asp Glu Thr Phe Asn Gly Thr Gly Pro
    210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
                260                 265                 270

His Leu His Thr Pro Val Glu Ile Val Cys Thr Arg Pro Asn Asn Asn
            275                 280                 285

Thr Arg Lys Ser Val Arg Ile Gly Pro Gly Gln Thr Phe Tyr Ala Thr
    290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
                340                 345                 350

Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
    370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
                420                 425                 430

Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
    450                 455                 460
```

Leu Tyr Lys Tyr Lys Val Lys Ile Glu Pro Leu Gly Val Ala Pro
465                 470                 475                 480

Thr Arg Cys Lys Arg Arg Val Val Gly Arg Arg Arg Arg Arg Ala
            485                 490                 495

Val Gly Ile Gly Ala Val Phe Leu Gly Phe Leu Gly Ala Ala Gly
            500                 505                 510

Ser Thr Met Gly Ala Ala Ser Met Thr Leu Thr Val Gln Ala Arg
        515                 520                 525

Asn Leu Leu Ser Gly Ile Val Gln Gln Gln Ser Asn Leu Leu Arg
    530                 535                 540

Ala Pro Glu Ala Gln Gln His Leu Leu Lys Leu Thr Val Trp Gly
545                 550                 555                 560

Ile Lys Gln Leu Gln Ala Arg Val Leu Ala Val Glu Arg Tyr Leu
                565                 570                 575

Arg Asp Gln Gln Leu Leu Gly Ile Trp Gly Cys Ser Gly Lys Leu
                580                 585                 590

Ile Cys Cys Thr Asn Val Pro Trp Asn Ser Ser Trp Ser Asn Arg
                595                 600                 605

Asn Leu Ser Glu Ile Trp Asp Asn Met Thr Trp Leu Gln Trp Asp
                610                 615                 620

Lys Glu Ile Ser Asn Tyr Thr Gln Ile Ile Tyr Gly Leu Leu Glu
625                 630                 635                 640

Glu Ser Gln Asn Gln Gln Glu Lys Asn Glu Gln Asp Leu Leu Ala
                645

Leu Asp
    645

<210> SEQ ID NO 32
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Pro Met Gly Ser Leu Gln Pro Leu Ala Thr Leu Tyr Leu Leu
1               5                   10                  15

Gly Met Leu Val Ala Ser Val Leu Ala Ala Glu Asn Leu Trp Val
                20                  25                  30

Thr Val Tyr Tyr Gly Val Pro Val Trp Lys Glu Ala Lys Thr Thr
                35                  40                  45

Leu Phe Cys Ala Ser Asp Ala Arg Ala Tyr Glu Lys Glu Val His
            50                  55                  60

Asn Val Trp Ala Thr His Ala Cys Val Pro Thr Asp Pro Ser Pro
65                  70                  75                  80

Gln Glu Leu Val Leu Gly Asn Val Thr Glu Asn Phe Asn Met Trp
                85                  90                  95

Lys Asn Asp Met Val Asp Gln Met His Glu Asp Ile Ile Ser Leu
                100                 105                 110

Trp Asp Gln Ser Leu Lys Pro Cys Val Lys Leu Thr Pro Leu Cys
            115                 120                 125

Val Thr Leu Ile Cys Ser Asp Ala Thr Val Lys Thr Gly Thr Val
            130                 135                 140

Glu Glu Met Lys Asn Cys Ser Phe Asn Thr Thr Thr Glu Ile Arg
145                 150                 155                 160

Asp Lys Glu Lys Lys Glu Tyr Ala Leu Phe Tyr Lys Pro Asp Ile
                165                 170                 175

```
Tyr Arg Leu Ile Asn Cys Asn Thr Ser Ala Val Thr Met Ala Cys Pro
                180                 185                 190

Lys Val Thr Phe Glu Pro Ile Pro Ile His Tyr Cys Ala Pro Ala Gly
            195                 200                 205

Tyr Ala Ile Leu Lys Cys Asn Asp Glu Thr Phe Asn Gly Thr Gly Pro
        210                 215                 220

Cys Ser Asn Val Ser Thr Val Gln Cys Thr His Gly Ile Arg Pro Val
225                 230                 235                 240

Val Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
                260                 265                 270

His Leu His Thr Pro Val Glu Ile Val Cys Thr Arg Pro Leu Asn Leu
                275                 280                 285

Thr Arg Lys Ser Val Arg Ile Gly Pro Gly Gln Thr Phe Tyr Ala Met
            290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
                340                 345                 350

Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
            370                 375                 380

Ser Thr Asn Ser Ser Ala Asn Ser Thr Ser Thr Ile Thr Leu Gln Cys
385                 390                 395                 400

Arg Ile Lys Met Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
                420                 425                 430

Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
            450                 455                 460

Leu Tyr Lys Tyr Lys Val Val Lys Ile Glu Pro Leu Gly Val Ala Pro
465                 470                 475                 480

Thr Arg Cys Lys Arg Val Val Gly Arg Arg Arg Arg Arg Ala
                485                 490                 495

Val Gly Ile Gly Ala Val Phe Leu Gly Phe Leu Gly Ala Ala Gly Ser
            500                 505                 510

Thr Met Gly Ala Ala Ser Met Thr Leu Thr Val Gln Ala Arg Asn Leu
            515                 520                 525

Leu Ser Gly Ile Val Gln Gln Gln Ser Asn Leu Leu Arg Ala Pro Glu
            530                 535                 540

Ala Gln Gln His Leu Leu Lys Leu Thr Val Trp Gly Ile Lys Gln Leu
545                 550                 555                 560

Gln Ala Arg Val Leu Ala Val Glu Arg Tyr Leu Arg Asp Gln Gln Leu
                565                 570                 575

Leu Gly Ile Trp Gly Cys Ser Gly Lys Leu Ile Cys Cys Thr Asn Val
            580                 585                 590
```

```
Pro Trp Asn Ser Ser Trp Ser Asn Arg Asn Leu Ser Glu Ile Trp Asp
            595                 600                 605

Asn Met Thr Trp Leu Gln Trp Asp Lys Glu Ile Ser Asn Tyr Thr Gln
    610                 615                 620

Ile Ile Tyr Gly Leu Leu Glu Glu Ser Gln Asn Gln Gln Lys Asn
625                 630                 635                 640

Glu Gln Asp Leu Leu Ala Leu Asp
                645

<210> SEQ ID NO 33
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Arg Ala Tyr Glu Lys Glu Val His Asn Val Trp Ala
    50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
    130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Gln Ala Cys Pro
            180                 185                 190

Lys Val Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
    210                 215                 220

Cys Ser Asn Val Ser Thr Val Gln Cys Thr His Gly Ile Arg Pro Val
225                 230                 235                 240

Val Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Asn Asn Asn
        275                 280                 285

Thr Arg Lys Ser Val Arg Ile Gly Pro Gly Gln Thr Phe Tyr Ala Thr
    290                 295                 300
```

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
            325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
            405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
450                 455                 460

Leu Tyr Lys Tyr Lys Val Val Lys Ile Glu Pro Leu Gly Val Ala Pro
465                 470                 475                 480

Thr Arg Cys Lys Arg Arg Val Val Gly Arg Arg Arg Arg Arg Arg Ala
            485                 490                 495

Val Gly Ile Gly Ala Val Phe Leu Gly Phe Leu Gly Ala Ala Gly Ser
            500                 505                 510

Thr Met Gly Ala Ala Ser Met Thr Leu Thr Val Gln Ala Arg Asn Leu
            515                 520                 525

Leu Ser Gly Ile Val Gln Gln Gln Ser Asn Leu Leu Arg Ala Pro Glu
530                 535                 540

Ala Gln Gln His Leu Leu Lys Leu Thr Val Trp Gly Ile Lys Gln Leu
545                 550                 555                 560

Gln Ala Arg Val Leu Ala Val Glu Arg Tyr Leu Arg Asp Gln Gln Leu
            565                 570                 575

Leu Gly Ile Trp Gly Cys Ser Gly Lys Leu Ile Cys Cys Thr Asn Val
            580                 585                 590

Pro Trp Asn Ser Ser Trp Ser Asn Arg Asn Leu Ser Glu Ile Trp Asp
            595                 600                 605

Asn Met Thr Trp Leu Gln Trp Asp Lys Glu Ile Ser Asn Tyr Thr Gln
            610                 615                 620

Ile Ile Tyr Gly Leu Leu Glu Glu Ser Gln Asn Gln Gln Glu Lys Asn
625                 630                 635                 640

Glu Gln Asp Leu Leu Ala Leu Asp
            645

<210> SEQ ID NO 34
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Pro Met Gly Ser Leu Gln Pro Leu Ala Thr Leu Tyr Leu Leu Gly

-continued

```
1               5                   10                  15
Met Leu Val Ala Ser Val Leu Ala Ala Glu Asn Leu Trp Val Thr Val
            20                  25                  30
Tyr Tyr Gly Val Pro Val Trp Lys Glu Ala Lys Thr Thr Leu Phe Cys
            35                  40                  45
Ala Ser Asp Ala Arg Ala Tyr Glu Lys Glu Val His Asn Val Trp Ala
50                      55                  60
Thr His Ala Cys Val Pro Thr Asp Pro Ser Pro Gln Glu Leu Val Leu
65                  70                  75                  80
Gly Asn Val Thr Glu Asn Phe Asn Met Trp Lys Asn Asp Met Val Asp
                85                  90                  95
Gln Met His Glu Asp Ile Ile Ser Leu Trp Asp Gln Ser Leu Lys Pro
            100                 105                 110
Cys Val Lys Leu Thr Pro Leu Cys Val Thr Leu Ile Cys Ser Asp Ala
            115                 120                 125
Thr Val Lys Thr Gly Thr Val Glu Glu Met Lys Asn Cys Ser Phe Asn
            130                 135                 140
Thr Thr Thr Glu Ile Arg Asp Lys Glu Lys Lys Glu Tyr Ala Leu Phe
145                 150                 155                 160
Tyr Lys Pro Asp Ile Val Pro Leu Ser Glu Thr Asn Asn Thr Ser Glu
                165                 170                 175
Tyr Arg Leu Ile Asn Cys Asn Thr Ser Ala Val Thr Gln Ala Cys Pro
            180                 185                 190
Lys Val Thr Phe Glu Pro Ile Pro Ile His Tyr Cys Ala Pro Ala Gly
            195                 200                 205
Tyr Ala Ile Leu Lys Cys Asn Asp Glu Thr Phe Asn Gly Thr Gly Pro
210                 215                 220
Cys Ser Asn Val Ser Thr Val Gln Cys Thr His Gly Ile Arg Pro Val
225                 230                 235                 240
Val Ser Thr Gln Leu Leu Leu Asn Gly Ser Leu Ala Glu Lys Glu Ile
            245                 250                 255
Val Ile Arg Ser Glu Asn Leu Thr Asn Asn Ala Lys Ile Ile Ile Val
            260                 265                 270
His Leu His Thr Pro Val Glu Ile Val Cys Thr Arg Pro Asn Asn Asn
            275                 280                 285
Thr Arg Lys Ser Val Arg Ile Gly Pro Gly Gln Thr Phe Tyr Ala Thr
            290                 295                 300
Gly Asp Ile Ile Gly Asp Ile Lys Gln Ala His Cys Asn Ile Ser Glu
305                 310                 315                 320
Glu Lys Trp Asn Asp Thr Leu Gln Lys Val Gly Ile Glu Leu Gln Lys
                325                 330                 335
His Phe Pro Asn Lys Thr Ile Lys Tyr Asn Gln Ser Ala Gly Gly Asp
            340                 345                 350
Met Glu Ile Thr Thr His Ser Phe Asn Cys Gly Gly Glu Phe Phe Tyr
            355                 360                 365
Cys Asn Thr Ser Asn Leu Phe Asn Gly Thr Tyr Asn Gly Thr Tyr Ile
            370                 375                 380
Ser Thr Asn Ser Ser Ala Asn Ser Thr Ser Thr Ile Thr Leu Gln Cys
385                 390                 395                 400
Arg Ile Lys Gln Ile Ile Asn Met Trp Gln Gly Val Gly Arg Ala Met
                405                 410                 415
Tyr Ala Pro Pro Ile Ala Gly Asn Ile Thr Cys Arg Ser Asn Ile Thr
            420                 425                 430
```

```
Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
450                 455                 460

Leu Tyr Lys Tyr Lys Val Val Glu Ile Gln Pro Leu Gly Ile Ala Pro
465                 470                 475                 480

Thr Gly Ala Lys Arg Arg Val Val Glu Arg Arg Arg Arg Arg Arg Ala
            485                 490                 495

Ala Gly Leu Gly Ala Leu Phe Leu Gly Phe Leu Gly Ala Ala Gly Ser
            500                 505                 510

Thr Met Gly Ala Ala Ser Ile Thr Leu Thr Val Gln Ala Arg Gln Leu
            515                 520                 525

Leu Ser Gly Ile Val Gln Gln Gln Ser Asn Leu Leu Arg Ala Pro Glu
            530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
                565                 570                 575

Leu Gly Met Trp Gly Cys Ser Gly Lys Leu Ile Cys Cys Thr Asn Val
            580                 585                 590

Pro Trp Asn Thr Ser Trp Ser Asn Lys Ser Glu Thr Asp Ile Trp Asp
            595                 600                 605

Asn Met Thr Trp Met Gln Trp Glu Arg Glu Ile Ser Asn Tyr Thr Glu
            610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
                645

<210> SEQ ID NO 35
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Ile Trp Ala
50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
                100                 105                 110

Cys Val Lys Leu Thr Pro Leu Cys Val Thr Leu Ile Cys Ser Asp Ala
            115                 120                 125

Thr Val Lys Thr Gly Thr Val Glu Glu Met Lys Asn Cys Ser Phe Asn
```

```
                    130             135                 140
Thr Thr Thr Glu Ile Arg Asp Lys Glu Lys Glu Tyr Ala Leu Phe
145                 150                 155                 160

Tyr Lys Pro Asp Ile Val Pro Leu Ser Glu Thr Asn Thr Ser Glu
                165                 170                 175

Tyr Arg Leu Ile Asn Cys Asn Thr Ser Ala Val Thr Gln Val Cys Pro
                180                 185                 190

Lys Leu Thr Phe Glu Pro Ile Pro Ile His Tyr Cys Ala Pro Ala Gly
                195                 200                 205

Tyr Ala Ile Leu Lys Cys Asn Asp Glu Thr Phe Asn Gly Thr Gly Pro
                210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
                260                 265                 270

His Leu His Thr Pro Val Glu Ile Val Cys Thr Arg Pro Asn Asn Asn
                275                 280                 285

Thr Arg Lys Ser Val Arg Ile Gly Pro Gly Gln Thr Phe Tyr Ala Thr
290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
                340                 345                 350

Met Glu Ile Thr Thr His Ser Phe Asn Cys Gly Gly Glu Phe Phe Tyr
                355                 360                 365

Cys Asn Thr Ser Asn Leu Phe Asn Gly Thr Tyr Asn Gly Thr Tyr Ile
                370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
                420                 425                 430

Gly Leu Leu Leu Thr Arg Asp Gly Gly Thr Asn Ser Asn Glu Thr Glu
                435                 440                 445

Thr Phe Arg Pro Ala Gly Gly Asp Met Arg Asp Asn Trp Arg Ser Glu
450                 455                 460

Leu Tyr Lys Tyr Lys Val Val Glu Ile Gln Pro Leu Gly Ile Ala Pro
465                 470                 475                 480

Thr Gly Ala Lys Arg Arg Val Val Glu Arg Arg Arg Arg Arg Arg Ala
                485                 490                 495

Ala Gly Leu Gly Ala Leu Phe Leu Gly Phe Leu Gly Ala Ala Gly Ser
                500                 505                 510

Thr Met Gly Ala Ala Ser Ile Thr Leu Thr Val Gln Ala Arg Gln Leu
                515                 520                 525

Leu Ser Gly Ile Val Gln Gln Ser Asn Leu Leu Arg Ala Pro Glu
                530                 535                 540

Ala Gln Gln His Met Leu Gln Leu Thr Val Trp Gly Ile Lys Gln Leu
545                 550                 555                 560
```

```
Gln Ala Arg Val Leu Ala Leu Glu Arg Tyr Leu Lys Asp Gln Gln Leu
            565                 570                 575

Leu Gly Met Trp Gly Cys Ser Gly Lys Leu Ile Cys Cys Thr Asn Val
        580                 585                 590

Pro Trp Asn Thr Ser Trp Ser Asn Lys Ser Glu Thr Asp Ile Trp Asp
            595                 600                 605

Asn Met Thr Trp Met Gln Trp Glu Arg Glu Ile Ser Asn Tyr Thr Glu
        610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
            645

<210> SEQ ID NO 36
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Arg Ala Tyr Glu Lys Glu Val His Asn Ile Trp Ala
    50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
            85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
    130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
            165                 170                 175

Tyr Arg Leu Ile Asn Cys Asn Thr Ser Ala Val Thr Met Val Cys Pro
        180                 185                 190

Lys Leu Thr Phe Glu Pro Ile Pro Ile His Tyr Cys Ala Pro Ala Gly
    195                 200                 205

Tyr Ala Ile Leu Lys Cys Asn Asp Glu Thr Phe Asn Gly Thr Gly Pro
    210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
            245                 250                 255

Val Ile Arg Ser Glu Asn Leu Thr Asn Asn Ala Lys Ile Ile Val
```

|     |     |     |     |     | 260 |     |     |     | 265 |     |     |     |     | 270 |     |
| --- | --- | --- | --- | --- | --- | --- | --- | --- | --- | --- | --- | --- | --- | --- | --- |
His Leu His Thr Pro Val Glu Ile Val Cys Thr Arg Pro Leu Asn Leu
            275                    280                    285

Thr Arg Lys Ser Val Arg Ile Gly Pro Gly Gln Thr Phe Tyr Ala Met
290                   295                    300

Gly Asp Ile Ile Gly Asp Ile Lys Gln Ala His Cys Asn Ile Ser Glu
305                   310                    315                    320

Glu Lys Trp Asn Asp Thr Leu Gln Lys Val Gly Ile Glu Leu Gln Lys
            325                    330                    335

His Phe Pro Asn Lys Thr Ile Lys Tyr Asn Gln Ser Ala Gly Gly Asp
            340                    345                    350

Met Glu Ile Thr Thr His Ser Phe Asn Cys Gly Gly Glu Phe Phe Tyr
            355                    360                    365

Cys Asn Thr Ser Asn Leu Phe Asn Gly Thr Tyr Asn Gly Thr Tyr Ile
            370                    375                    380

Ser Thr Asn Ser Ser Ala Asn Ser Thr Ser Thr Ile Thr Leu Gln Cys
385                   390                    395                    400

Arg Ile Lys Met Ile Ile Asn Met Trp Gln Gly Val Gly Arg Ala Met
            405                    410                    415

Tyr Ala Pro Pro Ile Ala Gly Asn Ile Thr Cys Arg Ser Asn Ile Thr
            420                    425                    430

Gly Leu Leu Leu Thr Arg Asp Gly Gly Thr Asn Ser Asn Glu Thr Glu
            435                    440                    445

Thr Phe Arg Pro Ala Gly Gly Asp Met Arg Asp Asn Trp Arg Ser Glu
450                   455                    460

Leu Tyr Lys Tyr Lys Val Val Glu Ile Gln Pro Leu Gly Ile Ala Pro
465                   470                    475                    480

Thr Gly Ala Lys Arg Arg Val Val Glu Arg Arg Arg Arg Arg Arg Ala
            485                    490                    495

Ala Gly Leu Gly Ala Leu Phe Leu Gly Phe Leu Gly Ala Ala Gly Ser
            500                    505                    510

Thr Met Gly Ala Ala Ser Ile Thr Leu Thr Val Gln Ala Arg Gln Leu
            515                    520                    525

Leu Ser Gly Ile Val Gln Gln Gln Ser Asn Leu Leu Arg Ala Pro Glu
            530                    535                    540

Ala Gln Gln His Met Leu Gln Leu Thr Val Trp Gly Ile Lys Gln Leu
545                   550                    555                    560

Gln Ala Arg Val Leu Ala Leu Glu Arg Tyr Leu Lys Asp Gln Gln Leu
            565                    570                    575

Leu Gly Met Trp Gly Cys Ser Gly Lys Leu Ile Cys Cys Thr Asn Val
            580                    585                    590

Pro Trp Asn Thr Ser Trp Ser Asn Lys Ser Glu Thr Asp Ile Trp Asp
            595                    600                    605

Asn Met Thr Trp Met Gln Trp Glu Arg Glu Ile Ser Asn Tyr Thr Glu
            610                    615                    620

Thr Ile Tyr Lys Leu Leu Glu Asp Ser Gln Asn Gln Gln Glu Arg Asn
625                   630                    635                    640

Glu Gln Asp Leu Leu Ala Leu Asp
            645

<210> SEQ ID NO 37
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Arg Ala Tyr Glu Lys Glu Val His Asn Val Trp Ala
50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Ala Cys Pro
            180                 185                 190

Lys Val Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
210                 215                 220

Cys Ser Asn Val Ser Thr Val Gln Cys Thr His Gly Ile Arg Pro Val
225                 230                 235                 240

Val Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Leu Asn Leu
        275                 280                 285

Thr Arg Lys Ser Val Arg Ile Gly Pro Gly Gln Thr Phe Tyr Ala Met
290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
        355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
```

```
385                 390                 395                 400
Arg Ile Lys Met Ile Ile Asn Met Trp Gln Gly Val Gly Arg Ala Met
            405                 410                 415
Tyr Ala Pro Pro Ile Ala Gly Asn Ile Thr Cys Arg Ser Asn Ile Thr
        420                 425                 430
Gly Leu Leu Leu Thr Arg Asp Gly Thr Asn Ser Asn Glu Thr Glu
        435                 440                 445
Thr Phe Arg Pro Ala Gly Gly Asp Met Arg Asp Asn Trp Arg Ser Glu
    450                 455                 460
Leu Tyr Lys Tyr Lys Val Val Glu Ile Gln Pro Leu Gly Ile Ala Pro
465                 470                 475                 480
Thr Gly Ala Lys Arg Arg Val Val Glu Arg Arg Arg Arg Ala
                485                 490                 495
Ala Gly Leu Gly Ala Leu Phe Leu Gly Phe Leu Gly Ala Ala Gly Ser
                500                 505                 510
Thr Met Gly Ala Ala Ser Ile Thr Leu Thr Val Gln Ala Arg Gln Leu
            515                 520                 525
Leu Ser Gly Ile Val Gln Gln Gln Ser Asn Leu Leu Arg Ala Pro Glu
        530                 535                 540
Ala Gln Gln His Met Leu Gln Leu Thr Val Trp Gly Ile Lys Gln Leu
545                 550                 555                 560
Gln Ala Arg Val Leu Ala Leu Glu Arg Tyr Leu Lys Asp Gln Gln Leu
                565                 570                 575
Leu Gly Met Trp Gly Cys Ser Gly Lys Leu Ile Cys Cys Thr Asn Val
            580                 585                 590
Pro Trp Asn Thr Ser Trp Ser Asn Lys Ser Glu Thr Asp Ile Trp Asp
        595                 600                 605
Asn Met Thr Trp Met Gln Trp Glu Arg Glu Ile Ser Asn Tyr Thr Glu
    610                 615                 620
Thr Ile Tyr Lys Leu Leu Glu Asp Ser Gln Asn Gln Gln Glu Arg Asn
625                 630                 635                 640
Glu Gln Asp Leu Leu Ala Leu Asp
                645

<210> SEQ ID NO 38
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Pro Met Gly Ser Leu Gln Pro Leu Ala Thr Leu Tyr Leu Leu Gly
1               5                   10                  15
Met Leu Val Ala Ser Val Leu Ala Ala Glu Asn Leu Trp Val Thr Val
            20                  25                  30
Tyr Tyr Gly Val Pro Val Trp Lys Glu Ala Lys Thr Thr Leu Phe Cys
        35                  40                  45
Ala Ser Asp Ala Arg Ala Tyr Glu Lys Glu Val His Asn Ile Trp Ala
    50                  55                  60
Thr His Ala Cys Val Pro Thr Asp Pro Ser Pro Gln Glu Leu Val Leu
65                  70                  75                  80
Gly Asn Val Thr Glu Asn Phe Asn Met Trp Lys Asn Asp Met Val Asp
                85                  90                  95
```

```
Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
        130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Gln Val Cys Pro
            180                 185                 190

Lys Leu Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
        210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Asn Asn Asn
        275                 280                 285

Thr Arg Lys Ser Val Arg Ile Gly Pro Gly Gln Thr Phe Tyr Ala Thr
        290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
        355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
        435                 440                 445

Thr Phe Arg Pro Ala Gly Gly Asp Met Arg Asp Asn Trp Arg Ser Glu
        450                 455                 460

Leu Tyr Lys Tyr Lys Val Val Glu Ile Gln Pro Leu Gly Ile Ala Pro
465                 470                 475                 480

Thr Gly Ala Lys Arg Arg Val Val Glu Arg Arg Arg Arg Arg Arg Ala
                485                 490                 495

Ala Gly Leu Gly Ala Leu Phe Leu Gly Phe Leu Gly Ala Ala Gly Ser
            500                 505                 510

Thr Met Gly Ala Ala Ser Ile Thr Leu Thr Val Gln Ala Arg Gln Leu
```

```
                515                 520                 525
Leu Ser Gly Ile Val Gln Gln Gln Ser Asn Leu Leu Arg Ala Pro Glu
    530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
                565                 570                 575

Leu Gly Met Trp Gly Cys Ser Gly Lys Leu Ile Cys Cys Thr Asn Val
            580                 585                 590

Pro Trp Asn Thr Ser Trp Ser Asn Lys Ser Glu Thr Asp Ile Trp Asp
                595                 600                 605

Asn Met Thr Trp Met Gln Trp Glu Arg Glu Ile Ser Asn Tyr Thr Glu
            610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
                645
```

<210> SEQ ID NO 39
<211> LENGTH: 648
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 39

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Arg Ala Tyr Glu Lys Glu Val His Asn Ile Trp Ala
    50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
    130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Val Cys Pro
            180                 185                 190

Lys Leu Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
    210                 215                 220
```

```
Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
            245                 250                 255

Val Ile Arg Ser Glu Asn Leu Thr Asn Asn Ala Lys Ile Ile Ile Val
        260                 265                 270

His Leu His Thr Pro Val Glu Ile Val Cys Thr Arg Pro Leu Asn Leu
    275                 280                 285

Thr Arg Lys Ser Val Arg Ile Gly Pro Gly Gln Thr Phe Tyr Ala Met
290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
                340                 345                 350

Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Met Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
                420                 425                 430

Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
            450                 455                 460

Leu Tyr Lys Tyr Lys Val Val Glu Ile Gln Pro Leu Gly Ile Ala Pro
465                 470                 475                 480

Thr Gly Ala Lys Arg Arg Val Val Glu Arg Arg Arg Arg Arg Arg Ala
                485                 490                 495

Ala Gly Leu Gly Ala Leu Phe Leu Gly Phe Leu Gly Ala Ala Gly Ser
            500                 505                 510

Thr Met Gly Ala Ala Ser Ile Thr Leu Thr Val Gln Ala Arg Gln Leu
            515                 520                 525

Leu Ser Gly Ile Val Gln Gln Gln Ser Asn Leu Leu Arg Ala Pro Glu
            530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
                565                 570                 575

Leu Gly Met Trp Gly Cys Ser Gly Lys Leu Ile Cys Cys Thr Asn Val
            580                 585                 590

Pro Trp Asn Thr Ser Trp Ser Asn Lys Ser Glu Thr Asp Ile Trp Asp
            595                 600                 605

Asn Met Thr Trp Met Gln Trp Glu Arg Glu Ile Ser Asn Tyr Thr Glu
            610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
```

<210> SEQ ID NO 40
<211> LENGTH: 648
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Arg Ala Tyr Glu Lys Glu Val His Asn Val Trp Ala
    50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
    130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Ala Cys Pro
            180                 185                 190

Lys Val Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
    210                 215                 220

Cys Ser Asn Val Ser Thr Val Gln Cys Thr His Gly Ile Arg Pro Val
225                 230                 235                 240

Val Ser Thr Gln Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Leu Asn Leu
        275                 280                 285

Thr Arg Lys Ser Val Arg Ile Gly Pro Gly Gln Thr Phe Tyr Ala Met
    290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350
```

Met Glu Ile Thr Thr His Ser Phe Asn Cys Gly Glu Phe Phe Tyr
            355                 360                 365

Cys Asn Thr Ser Asn Leu Phe Asn Gly Thr Tyr Asn Gly Thr Tyr Ile
    370                 375                 380

Ser Thr Asn Ser Ser Ala Asn Ser Thr Ser Thr Ile Thr Leu Gln Cys
385                 390                 395                 400

Arg Ile Lys Met Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
            435                 440                 445

Thr Phe Arg Pro Ala Gly Gly Asp Met Arg Asp Asn Trp Arg Ser Glu
    450                 455                 460

Leu Tyr Lys Tyr Lys Val Val Lys Ile Glu Pro Leu Gly Val Ala Pro
465                 470                 475                 480

Thr Arg Cys Lys Arg Arg Val Val Gly Arg Arg Arg Arg Arg Ala
                485                 490                 495

Val Gly Ile Gly Ala Val Phe Leu Gly Phe Leu Gly Ala Ala Gly Ser
            500                 505                 510

Thr Met Gly Ala Ala Ser Met Thr Leu Thr Val Gln Ala Arg Asn Leu
            515                 520                 525

Leu Ser Gly Ile Val Gln Gln Gln Ser Asn Leu Leu Arg Ala Pro Glu
            530                 535                 540

Ala Gln Gln His Leu Leu Lys Leu Thr Val Trp Gly Ile Lys Gln Leu
545                 550                 555                 560

Gln Ala Arg Val Leu Ala Val Glu Arg Tyr Leu Arg Asp Gln Gln Leu
                565                 570                 575

Leu Gly Ile Trp Gly Cys Ser Gly Lys Leu Ile Cys Cys Thr Asn Val
            580                 585                 590

Pro Trp Asn Ser Ser Trp Ser Asn Arg Asn Leu Ser Glu Ile Trp Asp
            595                 600                 605

Asn Met Thr Trp Leu Gln Trp Asp Lys Glu Ile Ser Asn Tyr Thr Gln
            610                 615                 620

Ile Ile Tyr Gly Leu Leu Glu Glu Ser Gln Asn Gln Gln Lys Asn
625                 630                 635                 640

Glu Gln Asp Leu Leu Ala Leu Asp
                645

<210> SEQ ID NO 41
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Val Trp Ala
50                  55                  60

```
Thr His Ala Cys Val Pro Thr Asp Pro Ser Pro Gln Glu Leu Val Leu
 65                  70                  75                  80

Gly Asn Val Thr Glu Asn Phe Asn Met Trp Lys Asn Asp Met Val Asp
                 85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Ala Cys Pro
            180                 185                 190

Lys Val Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
210                 215                 220

Cys Ser Asn Val Ser Thr Val Gln Cys Thr His Gly Ile Arg Pro Val
225                 230                 235                 240

Val Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Leu Asn Leu
        275                 280                 285

Thr Arg Lys Ser Val Arg Ile Gly Pro Gly Gln Thr Phe Tyr Ala Met
290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
        355                 360                 365

Cys Asn Thr Ser Asn Leu Phe Asn Gly Thr Tyr Asn Gly Thr Tyr Ile
370                 375                 380

Ser Thr Asn Ser Ser Ala Asn Ser Thr Ser Thr Ile Thr Leu Gln Cys
385                 390                 395                 400

Arg Ile Lys Met Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
        435                 440                 445

Thr Phe Arg Pro Ala Gly Gly Asp Met Arg Asp Asn Trp Arg Ser Glu
450                 455                 460

Leu Tyr Lys Tyr Lys Val Val Glu Ile Gln Pro Leu Gly Ile Ala Pro
465                 470                 475                 480
```

```
Thr Gly Ala Lys Arg Val Val Glu Arg Arg Arg Arg Ala
              485                 490                 495

Ala Gly Leu Gly Ala Leu Phe Leu Gly Phe Leu Gly Ala Ala Gly Ser
              500                 505                 510

Thr Met Gly Ala Ala Ser Ile Thr Leu Thr Val Gln Ala Arg Gln Leu
              515                 520                 525

Leu Ser Gly Ile Val Gln Gln Gln Ser Asn Leu Leu Arg Ala Pro Glu
              530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
              565                 570                 575

Leu Gly Met Trp Gly Cys Ser Gly Lys Leu Ile Cys Cys Thr Asn Val
              580                 585                 590

Pro Trp Asn Thr Ser Trp Ser Asn Lys Ser Glu Thr Asp Ile Trp Asp
              595                 600                 605

Asn Met Thr Trp Met Gln Trp Glu Arg Glu Ile Ser Asn Tyr Thr Glu
              610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
              645

<210> SEQ ID NO 42
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
              20                  25                  30

Tyr Tyr Gly Val Pro Val Trp Lys Glu Ala Lys Thr Thr Leu Phe Cys
              35                  40                  45

Ala Ser Asp Ala Arg Ala Tyr Glu Lys Glu Val His Asn Ile Trp Ala
          50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
              85                  90                  95

Gln Met His Glu Asp Ile Ile Ser Leu Trp Asp Gln Ser Leu Lys Pro
              100                 105                 110

Cys Val Lys Leu Thr Pro Leu Cys Val Thr Leu Ile Cys Ser Asp Ala
              115                 120                 125

Thr Val Lys Thr Gly Thr Val Glu Glu Met Lys Asn Cys Ser Phe Asn
              130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
              165                 170                 175

Tyr Arg Leu Ile Asn Cys Asn Thr Ser Ala Val Thr Gln Val Cys Pro
              180                 185                 190
```

-continued

```
Lys Leu Thr Phe Glu Pro Ile Pro Ile His Tyr Cys Ala Pro Ala Gly
            195                 200                 205
Tyr Ala Ile Leu Lys Cys Asn Asp Glu Thr Phe Asn Gly Thr Gly Pro
        210                 215                 220
Cys Ser Asn Val Ser Thr Val Gln Cys Thr His Gly Ile Arg Pro Val
225                 230                 235                 240
Leu Ser Thr Gln Leu Leu Asn Gly Ser Leu Ala Glu Lys Glu Ile
                245                 250                 255
Val Ile Arg Ser Glu Asn Leu Thr Asn Asn Ala Lys Ile Ile Ile Val
            260                 265                 270
His Leu His Thr Pro Val Glu Ile Val Cys Thr Arg Pro Asn Asn Asn
        275                 280                 285
Thr Arg Lys Ser Val Arg Ile Gly Pro Gly Gln Thr Phe Tyr Ala Thr
        290                 295                 300
Gly Asp Ile Ile Gly Asp Ile Lys Gln Ala His Cys Asn Ile Ser Glu
305                 310                 315                 320
Glu Lys Trp Asn Asp Thr Leu Gln Lys Val Gly Ile Glu Leu Gln Lys
                325                 330                 335
His Phe Pro Asn Lys Thr Ile Lys Tyr Asn Gln Ser Ala Gly Gly Asp
            340                 345                 350
Met Glu Ile Thr Thr His Ser Phe Asn Cys Gly Gly Glu Phe Phe Tyr
            355                 360                 365
Cys Asn Thr Ser Asn Leu Phe Asn Gly Thr Tyr Asn Gly Thr Tyr Ile
        370                 375                 380
Ser Thr Asn Ser Ser Ala Asn Ser Thr Ser Thr Ile Thr Leu Gln Cys
385                 390                 395                 400
Arg Ile Lys Gln Ile Ile Asn Met Trp Gln Gly Val Gly Arg Ala Met
                405                 410                 415
Tyr Ala Pro Pro Ile Ala Gly Asn Ile Thr Cys Arg Ser Asn Ile Thr
            420                 425                 430
Gly Leu Leu Leu Thr Arg Asp Gly Gly Thr Asn Ser Asn Glu Thr Glu
        435                 440                 445
Thr Phe Arg Pro Ala Gly Gly Asp Met Arg Asp Asn Trp Arg Ser Glu
        450                 455                 460
Leu Tyr Lys Tyr Lys Val Val Lys Ile Glu Pro Leu Gly Val Ala Pro
465                 470                 475                 480
Thr Arg Cys Lys Arg Arg Val Val Gly Arg Arg Arg Arg Arg Arg Ala
                485                 490                 495
Val Gly Ile Gly Ala Val Phe Leu Gly Phe Leu Gly Ala Ala Gly Ser
            500                 505                 510
Thr Met Gly Ala Ala Ser Met Thr Leu Thr Val Gln Ala Arg Asn Leu
        515                 520                 525
Leu Ser Gly Ile Val Gln Gln Gln Ser Asn Leu Leu Arg Ala Pro Glu
        530                 535                 540
Ala Gln Gln His Leu Leu Lys Leu Thr Val Trp Gly Ile Lys Gln Leu
545                 550                 555                 560
Gln Ala Arg Val Leu Ala Val Glu Arg Tyr Leu Arg Asp Gln Gln Leu
                565                 570                 575
Leu Gly Ile Trp Gly Cys Ser Gly Lys Leu Ile Cys Cys Thr Asn Val
            580                 585                 590
Pro Trp Asn Ser Ser Trp Ser Asn Arg Asn Leu Ser Glu Ile Trp Asp
        595                 600                 605
```

```
Asn Met Thr Trp Leu Gln Trp Asp Lys Glu Ile Ser Asn Tyr Thr Gln
    610                 615                 620

Ile Ile Tyr Gly Leu Leu Glu Glu Ser Gln Asn Gln Gln Glu Lys Asn
625                 630                 635                 640

Glu Gln Asp Leu Leu Ala Leu Asp
                645

<210> SEQ ID NO 43
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Ile Trp Ala
    50                  55                  60

Thr His Ala Cys Val Pro Thr Asp Pro Ser Pro Gln Glu Leu Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
        115                 120                 125

Thr Val Lys Thr Gly Thr Val Glu Glu Met Lys Asn Cys Ser Phe Asn
130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Met Val Cys Pro
            180                 185                 190

Lys Leu Thr Phe Glu Pro Ile Pro Ile His Tyr Cys Ala Pro Ala Gly
        195                 200                 205

Tyr Ala Ile Leu Lys Cys Asn Asp Glu Thr Phe Asn Gly Thr Gly Pro
    210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Leu Asn Leu
        275                 280                 285

Thr Arg Lys Ser Val Arg Ile Gly Pro Gly Gln Thr Phe Tyr Ala Met
    290                 295                 300

Gly Asp Ile Ile Gly Asp Ile Lys Gln Ala His Cys Asn Ile Ser Glu
305                 310                 315                 320
```

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
        355                 360                 365

Cys Asn Thr Ser Asn Leu Phe Asn Gly Thr Tyr Asn Gly Thr Tyr Ile
    370                 375                 380

Ser Thr Asn Ser Ser Ala Asn Ser Thr Ser Thr Ile Thr Leu Gln Cys
385                 390                 395                 400

Arg Ile Lys Met Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
        435                 440                 445

Thr Phe Arg Pro Ala Gly Gly Asp Met Arg Asp Asn Trp Arg Ser Glu
    450                 455                 460

Leu Tyr Lys Tyr Lys Val Val Glu Ile Gln Pro Leu Gly Ile Ala Pro
465                 470                 475                 480

Thr Gly Ala Lys Arg Arg Val Val Glu Arg Arg Arg Arg Arg Ala
                485                 490                 495

Ala Gly Leu Gly Ala Leu Phe Leu Gly Phe Leu Gly Ala Ala Gly Ser
            500                 505                 510

Thr Met Gly Ala Ala Ser Ile Thr Leu Thr Val Gln Ala Arg Gln Leu
        515                 520                 525

Leu Ser Gly Ile Val Gln Gln Gln Ser Asn Leu Leu Arg Ala Pro Glu
    530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
                565                 570                 575

Leu Gly Met Trp Gly Cys Ser Gly Lys Leu Ile Cys Cys Thr Asn Val
            580                 585                 590

Pro Trp Asn Thr Ser Trp Ser Asn Lys Ser Glu Thr Asp Ile Trp Asp
        595                 600                 605

Asn Met Thr Trp Met Gln Trp Glu Arg Glu Ile Ser Asn Tyr Thr Glu
    610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
                645

<210> SEQ ID NO 44
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val

```
            20                  25                  30
Tyr Tyr Gly Val Pro Val Trp Lys Glu Ala Lys Thr Thr Leu Phe Cys
            35                  40                  45

Ala Ser Asp Ala Arg Ala Tyr Glu Lys Glu Val His Asn Ile Trp Ala
        50                  55                  60

Thr His Ala Cys Val Pro Thr Asp Pro Ser Pro Gln Glu Leu Val Leu
 65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu Ile Cys Ser Asp Ala
            115                 120                 125

Thr Val Lys Thr Gly Thr Val Glu Glu Met Lys Asn Cys Ser Phe Asn
        130                 135                 140

Thr Thr Thr Glu Ile Arg Asp Lys Glu Lys Lys Glu Tyr Ala Leu Phe
145                 150                 155                 160

Tyr Lys Pro Asp Ile Val Pro Leu Ser Glu Thr Asn Asn Thr Ser Glu
                165                 170                 175

Tyr Arg Leu Ile Asn Cys Asn Thr Ser Ala Val Thr Gln Val Cys Pro
            180                 185                 190

Lys Leu Thr Phe Glu Pro Ile Pro Ile His Tyr Cys Ala Pro Ala Gly
            195                 200                 205

Tyr Ala Ile Leu Lys Cys Asn Asp Glu Thr Phe Asn Gly Thr Gly Pro
        210                 215                 220

Cys Ser Asn Val Ser Thr Val Gln Cys Thr His Gly Ile Arg Pro Val
225                 230                 235                 240

Leu Ser Thr Gln Leu Leu Leu Asn Gly Ser Leu Ala Glu Lys Glu Ile
                245                 250                 255

Val Ile Arg Ser Glu Asn Leu Thr Asn Asn Ala Lys Ile Ile Ile Val
            260                 265                 270

His Leu His Thr Pro Val Glu Ile Val Cys Thr Arg Pro Asn Asn Asn
            275                 280                 285

Thr Arg Lys Ser Val Arg Ile Gly Pro Gly Gln Thr Phe Tyr Ala Thr
        290                 295                 300

Gly Asp Ile Ile Gly Asp Ile Lys Gln Ala His Cys Asn Ile Ser Glu
305                 310                 315                 320

Glu Lys Trp Asn Asp Thr Leu Gln Lys Val Gly Ile Glu Leu Gln Lys
                325                 330                 335

His Phe Pro Asn Lys Thr Ile Lys Tyr Asn Gln Ser Ala Gly Gly Asp
            340                 345                 350

Met Glu Ile Thr Thr His Ser Phe Asn Cys Gly Gly Glu Phe Phe Tyr
            355                 360                 365

Cys Asn Thr Ser Asn Leu Phe Asn Gly Thr Tyr Asn Gly Thr Tyr Ile
        370                 375                 380

Ser Thr Asn Ser Ser Ala Asn Ser Thr Ser Thr Ile Thr Leu Gln Cys
385                 390                 395                 400

Arg Ile Lys Gln Ile Ile Asn Met Trp Gln Gly Val Gly Arg Ala Met
                405                 410                 415

Tyr Ala Pro Pro Ile Ala Gly Asn Ile Thr Cys Arg Ser Asn Ile Thr
            420                 425                 430

Gly Leu Leu Leu Thr Arg Asp Gly Gly Thr Asn Ser Asn Glu Thr Glu
            435                 440                 445
```

Thr Phe Arg Pro Ala Gly Gly Asp Met Arg Asp Asn Trp Arg Ser Glu
        450                 455                 460

Leu Tyr Lys Tyr Lys Val Val Glu Ile Gln Pro Leu Gly Ile Ala Pro
465                 470                 475                 480

Thr Gly Ala Lys Arg Arg Val Val Glu Arg Arg Arg Arg Arg Arg Ala
                485                 490                 495

Ala Gly Leu Gly Ala Leu Phe Leu Gly Phe Leu Gly Ala Ala Gly Ser
                500                 505                 510

Thr Met Gly Ala Ala Ser Ile Thr Leu Thr Val Gln Ala Arg Gln Leu
                515                 520                 525

Leu Ser Gly Ile Val Gln Gln Gln Ser Asn Leu Leu Arg Ala Pro Glu
530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
                565                 570                 575

Leu Gly Met Trp Gly Cys Ser Gly Lys Leu Ile Cys Cys Thr Asn Val
                580                 585                 590

Pro Trp Asn Thr Ser Trp Ser Asn Lys Ser Glu Thr Asp Ile Trp Asp
                595                 600                 605

Asn Met Thr Trp Met Gln Trp Glu Arg Glu Ile Ser Asn Tyr Thr Glu
610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp
                645

<210> SEQ ID NO 45
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Glu Asn Leu Trp Val Thr Val Tyr Tyr Gly Val Pro Val Trp Lys
1               5                   10                  15

Glu Ala Lys Thr Thr Leu Phe Cys Ala Ser Asp Ala Arg Ala Tyr Glu
                20                  25                  30

Lys Glu Val His Asn Val Trp Ala Thr His Ala Cys Val Pro Thr Asp
                35                  40                  45

Pro Ser Pro Gln Glu Leu Val Leu Gly Asn Val Thr Glu Asn Phe Asn
        50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Ile Cys Ser Asp Ala Thr Val Lys Thr Gly Thr Val Glu
                100                 105                 110

Glu Met Lys Asn Cys Ser Phe Asn Thr Thr Thr Glu Ile Arg Asp Lys
                115                 120                 125

Glu Lys Lys Glu Tyr Ala Leu Phe Tyr Lys Pro Asp Ile Val Pro Leu
        130                 135                 140

Ser Glu Thr Asn Asn Thr Ser Glu Tyr Arg Leu Ile Asn Cys Asn Thr

-continued

```
            145                 150                 155                 160
        Ser Ala Val Thr Met Ala Cys Pro Lys Val Thr Phe Glu Pro Ile Pro
                            165                 170                 175
        Ile His Tyr Cys Ala Pro Ala Gly Tyr Ala Ile Leu Lys Cys Asn Asp
                            180                 185                 190
        Glu Thr Phe Asn Gly Thr Gly Pro Cys Ser Asn Val Ser Thr Val Gln
                            195                 200                 205
        Cys Thr His Gly Ile Arg Pro Val Val Ser Thr Gln Leu Leu Leu Asn
                210                 215                 220
        Gly Ser Leu Ala Glu Lys Glu Ile Val Ile Arg Ser Glu Asn Leu Thr
        225                 230                 235                 240
        Asn Asn Ala Lys Ile Ile Ile Val His Leu His Thr Pro Val Glu Ile
                            245                 250                 255
        Val Cys Thr Arg Pro Leu Asn Leu Thr Arg Lys Ser Val Arg Ile Gly
                            260                 265                 270
        Pro Gly Gln Thr Phe Tyr Ala Met Gly Asp Ile Ile Gly Asp Ile Lys
                            275                 280                 285
        Gln Ala His Cys Asn Ile Ser Glu Glu Lys Trp Asn Asp Thr Leu Gln
                            290                 295                 300
        Lys Val Gly Ile Glu Leu Gln Lys His Phe Pro Asn Lys Thr Ile Lys
        305                 310                 315                 320
        Tyr Asn Gln Ser Ala Gly Gly Asp Met Glu Ile Thr Thr His Ser Phe
                            325                 330                 335
        Asn Cys Gly Gly Glu Phe Phe Tyr Cys Asn Thr Ser Asn Leu Phe Asn
                            340                 345                 350
        Gly Thr Tyr Asn Gly Thr Tyr Ile Ser Thr Asn Ser Ser Ala Asn Ser
                            355                 360                 365
        Thr Ser Thr Ile Thr Leu Gln Cys Arg Ile Lys Met Ile Ile Asn Met
                            370                 375                 380
        Trp Gln Gly Val Gly Arg Ala Met Tyr Ala Pro Pro Ile Ala Gly Asn
        385                 390                 395                 400
        Ile Thr Cys Arg Ser Asn Ile Thr Gly Leu Leu Leu Thr Arg Asp Gly
                            405                 410                 415
        Gly Thr Asn Ser Asn Glu Thr Glu Thr Phe Arg Pro Ala Gly Gly Asp
                            420                 425                 430
        Met Arg Asp Asn Trp Arg Ser Glu Leu Tyr Lys Tyr Lys Val Val Lys
                            435                 440                 445
        Ile Glu Pro Leu Gly Val Ala Pro Thr Arg Cys Lys Arg Arg Val Val
                450                 455                 460
        Gly Arg Arg Arg Arg Arg Ala Val Gly Ile Gly Ala Val Phe Leu
        465                 470                 475                 480
        Gly Phe Leu Gly Ala Ala Gly Ser Thr Met Gly Ala Ala Ser Met Thr
                            485                 490                 495
        Leu Thr Val Gln Ala Arg Asn Leu Leu Ser Gly Ile Val Gln Gln Gln
                            500                 505                 510
        Ser Asn Leu Leu Arg Ala Pro Glu Ala Gln Gln His Leu Leu Lys Leu
                            515                 520                 525
        Thr Val Trp Gly Ile Lys Gln Leu Gln Ala Arg Val Leu Ala Val Glu
                            530                 535                 540
        Arg Tyr Leu Arg Asp Gln Gln Leu Leu Gly Ile Trp Gly Cys Ser Gly
        545                 550                 555                 560
        Lys Leu Ile Cys Cys Thr Asn Val Pro Trp Asn Ser Ser Trp Ser Asn
                            565                 570                 575
```

Arg Asn Leu Ser Glu Ile Trp Asp Asn Met Thr Trp Leu Gln Trp Asp
            580                 585                 590

Lys Glu Ile Ser Asn Tyr Thr Gln Ile Ile Tyr Gly Leu Glu Glu
        595                 600                 605

Ser Gln Asn Gln Gln Lys Asn Glu Gln Asp Leu Leu Ala Leu Asp
    610                 615                 620

<210> SEQ ID NO 46
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Glu Asn Leu Trp Val Thr Val Tyr Tyr Gly Val Pro Val Trp Lys
1               5                   10                  15

Glu Ala Lys Thr Thr Leu Phe Cys Ala Ser Asp Ala Arg Ala Tyr Glu
            20                  25                  30

Lys Glu Val His Asn Ile Trp Ala Thr His Ala Cys Val Pro Thr Asp
        35                  40                  45

Pro Ser Pro Gln Glu Leu Val Leu Gly Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Ile Cys Ser Asp Ala Thr Val Lys Thr Gly Thr Val Glu
            100                 105                 110

Glu Met Lys Asn Cys Ser Phe Asn Thr Thr Thr Glu Ile Arg Asp Lys
        115                 120                 125

Glu Lys Lys Glu Tyr Ala Leu Phe Tyr Lys Pro Asp Ile Val Pro Leu
    130                 135                 140

Ser Glu Thr Asn Thr Ser Glu Tyr Arg Leu Ile Asn Cys Asn Thr
145                 150                 155                 160

Ser Ala Val Thr Gln Val Cys Pro Lys Leu Thr Phe Glu Pro Ile Pro
                165                 170                 175

Ile His Tyr Cys Ala Pro Ala Gly Tyr Ala Ile Leu Lys Cys Asn Asp
            180                 185                 190

Glu Thr Phe Asn Gly Thr Gly Pro Cys Ser Asn Val Ser Thr Val Gln
        195                 200                 205

Cys Thr His Gly Ile Arg Pro Val Leu Ser Thr Gln Leu Leu Leu Asn
    210                 215                 220

Gly Ser Leu Ala Glu Lys Glu Ile Val Ile Arg Ser Glu Asn Leu Thr
225                 230                 235                 240

Asn Asn Ala Lys Ile Ile Val His Leu His Thr Pro Val Glu Ile
                245                 250                 255

Val Cys Thr Arg Pro Asn Asn Asn Thr Arg Lys Ser Val Arg Ile Gly
            260                 265                 270

Pro Gly Gln Thr Phe Tyr Ala Thr Gly Asp Ile Ile Gly Asp Ile Lys
        275                 280                 285

Gln Ala His Cys Asn Ile Ser Glu Glu Lys Trp Asn Asp Thr Leu Gln
    290                 295                 300

Lys Val Gly Ile Glu Leu Gln Lys His Phe Pro Asn Lys Thr Ile Lys

```
            305                 310                 315                 320
Tyr Asn Gln Ser Ala Gly Gly Asp Met Glu Ile Thr Thr His Ser Phe
                    325                 330                 335
Asn Cys Gly Gly Glu Phe Phe Tyr Cys Asn Thr Ser Asn Leu Phe Asn
                    340                 345                 350
Gly Thr Tyr Asn Gly Thr Tyr Ile Ser Thr Asn Ser Ser Ala Asn Ser
                    355                 360                 365
Thr Ser Thr Ile Thr Leu Gln Cys Arg Ile Lys Gln Ile Ile Asn Met
            370                 375                 380
Trp Gln Gly Val Gly Arg Ala Met Tyr Ala Pro Pro Ile Ala Gly Asn
385                 390                 395                 400
Ile Thr Cys Arg Ser Asn Ile Thr Gly Leu Leu Leu Thr Arg Asp Gly
                    405                 410                 415
Gly Thr Asn Ser Asn Glu Thr Glu Thr Phe Arg Pro Gly Gly Gly Asp
                    420                 425                 430
Met Arg Asp Asn Trp Arg Ser Glu Leu Tyr Lys Tyr Lys Val Val Lys
            435                 440                 445
Ile Glu Pro Leu Gly Val Ala Pro Thr Arg Cys Lys Arg Arg Val Val
            450                 455                 460
Gly Arg Arg Arg Arg Arg Ala Val Gly Ile Gly Ala Val Phe Leu
465                 470                 475                 480
Gly Phe Leu Gly Ala Ala Gly Ser Thr Met Gly Ala Ala Ser Met Thr
                    485                 490                 495
Leu Thr Val Gln Ala Arg Asn Leu Leu Ser Gly Ile Val Gln Gln Gln
                    500                 505                 510
Ser Asn Leu Leu Arg Ala Pro Glu Ala Gln Gln His Leu Leu Lys Leu
            515                 520                 525
Thr Val Trp Gly Ile Lys Gln Leu Gln Ala Arg Val Leu Ala Val Glu
            530                 535                 540
Arg Tyr Leu Arg Asp Gln Gln Leu Leu Gly Ile Trp Gly Cys Ser Gly
545                 550                 555                 560
Lys Leu Ile Cys Cys Thr Asn Val Pro Trp Asn Ser Ser Trp Ser Asn
                    565                 570                 575
Arg Asn Leu Ser Glu Ile Trp Asp Asn Met Thr Trp Leu Gln Trp Asp
                    580                 585                 590
Lys Glu Ile Ser Asn Tyr Thr Gln Ile Ile Tyr Gly Leu Leu Glu Glu
            595                 600                 605
Ser Gln Asn Gln Gln Glu Lys Asn Glu Gln Asp Leu Leu Ala Leu Asp
            610                 615                 620

<210> SEQ ID NO 47
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Glu Asn Leu Trp Val Thr Val Tyr Tyr Gly Val Pro Val Trp Lys
1               5                   10                  15
Glu Ala Lys Thr Thr Leu Phe Cys Ala Ser Asp Ala Arg Ala Tyr Glu
                    20                  25                  30
Lys Glu Val His Asn Ile Trp Ala Thr His Ala Cys Val Pro Thr Asp
            35                  40                  45
```

-continued

Pro Ser Pro Gln Glu Leu Val Leu Gly Asn Val Thr Glu Asn Phe Asn
    50              55              60

Met Trp Lys Asn Asp Met Val Asp Gln Met His Glu Asp Ile Ile Ser
65              70              75              80

Leu Trp Asp Gln Ser Leu Lys Pro Cys Val Lys Leu Thr Pro Leu Cys
                85              90              95

Val Thr Leu Ile Cys Ser Asp Ala Thr Val Lys Thr Gly Thr Val Glu
            100             105             110

Glu Met Lys Asn Cys Ser Phe Asn Thr Thr Glu Ile Arg Asp Lys
            115             120             125

Glu Lys Lys Glu Tyr Ala Leu Phe Tyr Lys Pro Asp Ile Val Pro Leu
130             135             140

Ser Glu Thr Asn Asn Thr Ser Glu Tyr Arg Leu Ile Asn Cys Asn Thr
145             150             155             160

Ser Ala Val Thr Met Val Cys Pro Lys Leu Thr Phe Glu Pro Ile Pro
                165             170             175

Ile His Tyr Cys Ala Pro Ala Gly Tyr Ala Ile Leu Lys Cys Asn Asp
            180             185             190

Glu Thr Phe Asn Gly Thr Gly Pro Cys Ser Asn Val Ser Thr Val Gln
            195             200             205

Cys Thr His Gly Ile Arg Pro Val Leu Ser Thr Gln Leu Leu Leu Asn
210             215             220

Gly Ser Leu Ala Glu Lys Glu Ile Val Ile Arg Ser Glu Asn Leu Thr
225             230             235             240

Asn Asn Ala Lys Ile Ile Ile Val His Leu His Thr Pro Val Glu Ile
                245             250             255

Val Cys Thr Arg Pro Leu Asn Leu Thr Arg Lys Ser Val Arg Ile Gly
            260             265             270

Pro Gly Gln Thr Phe Tyr Ala Met Gly Asp Ile Ile Gly Asp Ile Lys
            275             280             285

Gln Ala His Cys Asn Ile Ser Glu Glu Lys Trp Asn Asp Thr Leu Gln
            290             295             300

Lys Val Gly Ile Glu Leu Gln Lys His Phe Pro Asn Lys Thr Ile Lys
305             310             315             320

Tyr Asn Gln Ser Ala Gly Gly Asp Met Glu Ile Thr Thr His Ser Phe
                325             330             335

Asn Cys Gly Gly Glu Phe Phe Tyr Cys Asn Thr Ser Asn Leu Phe Asn
            340             345             350

Gly Thr Tyr Asn Gly Thr Tyr Ile Ser Thr Asn Ser Ser Ala Asn Ser
            355             360             365

Thr Ser Thr Ile Thr Leu Gln Cys Arg Ile Lys Met Ile Ile Asn Met
370             375             380

Trp Gln Gly Val Gly Arg Ala Met Tyr Ala Pro Pro Ile Ala Gly Asn
385             390             395             400

Ile Thr Cys Arg Ser Asn Ile Thr Gly Leu Leu Leu Thr Arg Asp Gly
                405             410             415

Gly Thr Asn Ser Asn Glu Thr Glu Thr Phe Arg Pro Ala Gly Gly Asp
            420             425             430

Met Arg Asp Asn Trp Arg Ser Glu Leu Tyr Lys Tyr Lys Val Val Lys
            435             440             445

Ile Glu Pro Leu Gly Val Ala Pro Thr Arg Cys Lys Arg Arg Val Val
450             455             460

Gly Arg Arg Arg Arg Arg Arg Ala Val Gly Ile Gly Ala Val Phe Leu

```
                465                 470                 475                 480
Gly Phe Leu Gly Ala Ala Gly Ser Thr Met Gly Ala Ala Ser Met Thr
                    485                 490                 495
Leu Thr Val Gln Ala Arg Asn Leu Leu Ser Gly Ile Val Gln Gln Gln
                500                 505                 510
Ser Asn Leu Leu Arg Ala Pro Glu Ala Gln Gln His Leu Leu Lys Leu
            515                 520                 525
Thr Val Trp Gly Ile Lys Gln Leu Gln Ala Arg Val Leu Ala Val Glu
        530                 535                 540
Arg Tyr Leu Arg Asp Gln Gln Leu Leu Gly Ile Trp Gly Cys Ser Gly
545                 550                 555                 560
Lys Leu Ile Cys Cys Thr Asn Val Pro Trp Asn Ser Ser Trp Ser Asn
                565                 570                 575
Arg Asn Leu Ser Glu Ile Trp Asp Asn Met Thr Trp Leu Gln Trp Asp
                580                 585                 590
Lys Glu Ile Ser Asn Tyr Thr Gln Ile Ile Tyr Gly Leu Leu Glu Glu
                595                 600                 605
Ser Gln Asn Gln Gln Glu Lys Asn Glu Gln Asp Leu Leu Ala Leu Asp
        610                 615                 620

<210> SEQ ID NO 48
<211> LENGTH: 1965
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga agaggccaa gaccacactg ttctgcgcct ccgatgccag agcctacgag     180
aaagaggtgc acaacatctg gccacacac gcctgcgtgc aaccgatcc atctcctcaa     240
gaactggtgc tgggcaacgt gaccgagaac ttcaacatgt ggaagaacga catggtggac     300
cagatgcacg aggacatcat cagcctgtgg gaccagagcc tgaagccttg cgtgaagctg     360
acccctctgt gcgtgaccct gatctgttct gacgccaccg tgaaaaccgg caccgtggaa     420
gagatgaaga actgcagctt caacaccacc accgagatcc gggacaaaga agagaaagag     480
tacgccctgt tctacaagcc cgacatcgtg cccctgagcg agacaaacaa caccagcgag     540
taccggctga tcaactgcaa cacaagcgcc gtgacaatgg tctgccccaa gctgaccttc     600
gagcccattc ctatccacta ctgtgcccct gccggctacg ccatcctgaa gtgcaacgac     660
gagacattca acggcacagg ccctgcagc aatgtgtcca ccgtgcagtg tacccacggc     720
atcagacctg tgctgagcac acagctgctg ctgaatggaa gcctggccga aaagaaatc     780
gtgatcagaa gcgagaacct gaccaacaac gccaagatca tcattgtgca tctgcacacc     840
cctgtggaaa tcgtgtgcac ccggcctctg aatctgacca gaaagagcgt gcggatcggc     900
cctggccaga ccttttatgc catgggcgac atcatcggcg atatcaagca ggcccactgc     960
aacatcagcg aggaaaagtg aacgacacc ctgcagaaag tgggcatcga gctgcagaag    1020
cacttcccca caagaccat caagtacaac cagagcgctg gcggcgacat ggaaatcacc    1080
acacacagct tcaattgtgg cggcgagttc ttctactgca ataccagcaa cctgttcaac    1140
gggacctaca tggcaccta catcagcacc aacagcagcg ccaactccac cagcaccatc    1200
```

```
actctgcagt gccggatcaa gatgatcatt aacatgtggc aaggcgtcgg cagggctatg    1260
tacgcccctc ctatcgccgg caacatcacc tgtcggagca atatcacagg cctgctgctc    1320
accagagatg gcggcaccaa tagcaacgag acagaaacct tcagacctgc cggcggagac    1380
atgagagaca attggagaag cgagctgtac aagtacaagg tggtcaagat cgagcccctg    1440
ggcgtcgcac ctacacggtg caagagaaga gtcgtgggcc gtcgtagaag cggagagcc     1500 gttggaattg gcgccgtgtt cctgggcttt ctgggagccg ctggatctac aatgggcgct    1560
gccagcatga ccctgacagt gcaggctaga aatctgctga gcggcatcgt gcagcagcag    1620
agcaatctgc tcagagcccc tgaggctcag cagcacctcc tgaaactgac agtgtggggc    1680
atcaagcagc tgcaggcaag agtgctggca gtggaaagat acctgcggga ccagcagctc    1740
ctcggaatct ggggatgtag cggcaagctg atctgctgca ccaacgtgcc ctggaacagc    1800
agctggtcca accggaatct gtccgagatc tgggataaca tgacctggct gcagtgggac    1860
aaagaaatca gcaactacac ccagatcatc tacggcctgc tggaagagag ccagaaccag    1920
caagagaaaa acgagcagga cctgctggcc ctggactgag gatcc                    1965
```

<210> SEQ ID NO 49
<211> LENGTH: 623
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Ala Glu Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
        35                  40                  45

Pro Asn Pro Gln Glu Met Val Leu Lys Asn Val Thr Glu Asn Phe Asn
    50                  55                  60

Met Trp Lys Asn Asp Met Val Asp Gln Met His Glu Asp Val Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asn Ala Thr Ala Ser Asn Ser Ser Ile Ile
            100                 105                 110

Glu Gly Met Lys Asn Cys Ser Phe Asn Ile Thr Thr Glu Leu Arg Asp
        115                 120                 125

Lys Arg Glu Lys Lys Asn Ala Leu Phe Tyr Lys Leu Asp Ile Val Gln
    130                 135                 140

Leu Asp Gly Asn Ser Ser Gln Tyr Arg Leu Ile Asn Cys Asn Thr Ser
145                 150                 155                 160

Val Ile Thr Gln Ala Cys Pro Lys Val Ser Phe Asp Pro Ile Pro Ile
                165                 170                 175

His Tyr Cys Ala Pro Ala Gly Tyr Ala Ile Leu Lys Cys Asn Asn Lys
            180                 185                 190

Thr Phe Thr Gly Thr Gly Pro Cys Asn Asn Val Ser Thr Val Gln Cys
        195                 200                 205

Thr His Gly Ile Lys Pro Val Val Ser Thr Gln Leu Leu Leu Asn Gly
    210                 215                 220
```

```
Ser Leu Ala Glu Gly Glu Ile Ile Arg Ser Asn Ile Thr Lys
225                 230                 235                 240

Asn Val Lys Thr Ile Val His Leu Asn Glu Ser Val Lys Ile Glu
            245                 250                 255

Cys Thr Arg Pro Asn Asn Lys Thr Arg Thr Ser Ile Arg Ile Gly Pro
                260                 265                 270

Gly Gln Ala Phe Tyr Ala Thr Gly Gln Val Ile Gly Asp Ile Arg Glu
            275                 280                 285

Ala Tyr Cys Asn Ile Asn Glu Ser Lys Trp Asn Glu Thr Leu Gln Arg
            290                 295                 300

Val Ser Lys Lys Leu Lys Glu Tyr Phe Pro His Lys Asn Ile Thr Phe
305                 310                 315                 320

Gln Pro Ser Ser Gly Gly Asp Leu Glu Ile Thr Thr His Ser Phe Asn
                325                 330                 335

Cys Gly Gly Glu Phe Phe Tyr Cys Asn Thr Ser Ser Leu Phe Asn Arg
            340                 345                 350

Thr Tyr Met Ala Asn Ser Thr Asp Met Ala Asn Ser Thr Glu Thr Asn
            355                 360                 365

Ser Thr Arg Thr Ile Thr Ile His Cys Arg Ile Lys Gln Ile Ile Asn
370                 375                 380

Met Trp Gln Glu Val Gly Arg Ala Met Tyr Ala Pro Pro Ile Ala Gly
385                 390                 395                 400

Asn Ile Thr Cys Ile Ser Asn Ile Thr Gly Leu Leu Leu Thr Arg Asp
                405                 410                 415

Tyr Gly Lys Asn Asn Thr Glu Thr Phe Arg Pro Gly Gly Gly Asn Met
            420                 425                 430

Lys Asp Asn Trp Arg Ser Glu Leu Tyr Lys Tyr Lys Val Val Lys Ile
            435                 440                 445

Glu Pro Leu Gly Val Ala Pro Thr Arg Cys Lys Arg Arg Val Val Gly
            450                 455                 460

Arg Arg Arg Arg Arg Arg Ala Val Gly Ile Gly Ala Val Phe Leu Gly
465                 470                 475                 480

Phe Leu Gly Ala Ala Gly Ser Thr Met Gly Ala Ala Ser Met Thr Leu
                485                 490                 495

Thr Val Gln Ala Arg Asn Leu Leu Ser Gly Ile Val Gln Gln Gln Ser
            500                 505                 510

Asn Leu Leu Arg Ala Pro Glu Ala Gln Gln His Leu Leu Lys Leu Thr
            515                 520                 525

Val Trp Gly Ile Lys Gln Leu Gln Ala Arg Val Leu Ala Val Glu Arg
530                 535                 540

Tyr Leu Arg Asp Gln Gln Leu Leu Gly Ile Trp Gly Cys Ser Gly Lys
545                 550                 555                 560

Leu Ile Cys Cys Thr Asn Val Pro Trp Asn Ser Ser Trp Ser Asn Arg
                565                 570                 575

Asn Leu Ser Glu Ile Trp Asp Asn Met Thr Trp Leu Gln Trp Asp Lys
            580                 585                 590

Glu Ile Ser Asn Tyr Thr Gln Ile Ile Tyr Gly Leu Leu Glu Glu Ser
            595                 600                 605

Gln Asn Gln Gln Glu Lys Asn Glu Gln Asp Leu Leu Ala Leu Asp
            610                 615                 620

<210> SEQ ID NO 50
<211> LENGTH: 623
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Glu Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
                20                  25                  30

Lys Glu Val His Asn Val Trp Ala Thr His Ala Cys Val Pro Thr Asp
            35                  40                  45

Pro Asn Pro Gln Glu Met Val Leu Lys Asn Val Thr Glu Asn Phe Asn
        50                  55                  60

Met Trp Lys Asn Asp Met Val Asp Gln Met His Glu Asp Val Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asn Ala Thr Ala Ser Asn Ser Ser Ile Ile
                100                 105                 110

Glu Gly Met Lys Asn Cys Ser Phe Asn Ile Thr Thr Glu Leu Arg Asp
            115                 120                 125

Lys Arg Glu Lys Lys Asn Ala Leu Phe Tyr Lys Leu Asp Ile Val Gln
130                 135                 140

Leu Asp Gly Asn Ser Ser Gln Tyr Arg Leu Ile Asn Cys Asn Thr Ser
145                 150                 155                 160

Val Ile Thr Met Ala Cys Pro Lys Val Ser Phe Asp Pro Ile Pro Ile
                165                 170                 175

His Tyr Cys Ala Pro Ala Gly Tyr Ala Ile Leu Lys Cys Asn Asn Lys
            180                 185                 190

Thr Phe Thr Gly Thr Gly Pro Cys Asn Asn Val Ser Thr Val Gln Cys
        195                 200                 205

Thr His Gly Ile Lys Pro Val Val Ser Thr Gln Leu Leu Leu Asn Gly
    210                 215                 220

Ser Leu Ala Glu Gly Glu Ile Ile Ile Arg Ser Glu Asn Ile Thr Lys
225                 230                 235                 240

Asn Val Lys Thr Ile Ile Val His Leu Asn Glu Ser Val Lys Ile Glu
                245                 250                 255

Cys Thr Arg Pro Leu Asn Leu Thr Arg Thr Ser Ile Arg Ile Gly Pro
            260                 265                 270

Gly Gln Ala Phe Tyr Ala Met Gly Gln Val Ile Gly Asp Ile Arg Glu
        275                 280                 285

Ala Tyr Cys Asn Ile Asn Glu Ser Lys Trp Asn Glu Thr Leu Gln Arg
    290                 295                 300

Val Ser Lys Lys Leu Lys Glu Tyr Phe Pro His Lys Asn Ile Thr Phe
305                 310                 315                 320

Gln Pro Ser Ser Gly Gly Asp Leu Glu Ile Thr Thr His Ser Phe Asn
                325                 330                 335

Cys Gly Gly Glu Phe Phe Tyr Cys Asn Thr Ser Ser Leu Phe Asn Arg
            340                 345                 350

Thr Tyr Met Ala Asn Ser Thr Asp Met Ala Asn Ser Thr Glu Thr Asn
        355                 360                 365

Ser Thr Arg Thr Ile Thr Ile His Cys Arg Ile Lys Met Ile Ile Asn
    370                 375                 380
```

```
Met Trp Gln Glu Val Gly Arg Ala Met Tyr Ala Pro Pro Ile Ala Gly
385                 390                 395                 400

Asn Ile Thr Cys Ile Ser Asn Ile Thr Gly Leu Leu Leu Thr Arg Asp
            405                 410                 415

Tyr Gly Lys Asn Asn Thr Glu Thr Phe Arg Pro Gly Gly Gly Asn Met
        420                 425                 430

Lys Asp Asn Trp Arg Ser Glu Leu Tyr Lys Tyr Lys Val Val Lys Ile
            435                 440                 445

Glu Pro Leu Gly Val Ala Pro Thr Arg Cys Lys Arg Arg Val Val Gly
        450                 455                 460

Arg Arg Arg Arg Arg Ala Val Gly Ile Gly Ala Val Phe Leu Gly
465                 470                 475                 480

Phe Leu Gly Ala Ala Gly Ser Thr Met Gly Ala Ala Ser Met Thr Leu
            485                 490                 495

Thr Val Gln Ala Arg Asn Leu Leu Ser Gly Ile Val Gln Gln Gln Ser
        500                 505                 510

Asn Leu Leu Arg Ala Pro Glu Ala Gln Gln His Leu Leu Lys Leu Thr
        515                 520                 525

Val Trp Gly Ile Lys Gln Leu Gln Ala Arg Val Leu Ala Val Glu Arg
        530                 535                 540

Tyr Leu Arg Asp Gln Gln Leu Leu Gly Ile Trp Gly Cys Ser Gly Lys
545                 550                 555                 560

Leu Ile Cys Cys Thr Asn Val Pro Trp Asn Ser Ser Trp Ser Asn Arg
            565                 570                 575

Asn Leu Ser Glu Ile Trp Asp Asn Met Thr Trp Leu Gln Trp Asp Lys
        580                 585                 590

Glu Ile Ser Asn Tyr Thr Gln Ile Ile Tyr Gly Leu Leu Glu Glu Ser
        595                 600                 605

Gln Asn Gln Gln Glu Lys Asn Glu Gln Asp Leu Leu Ala Leu Asp
    610                 615                 620

<210> SEQ ID NO 51
<211> LENGTH: 623
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Glu Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Lys Glu Val His Asn Ile Trp Ala Thr His Ala Cys Val Pro Thr Asp
        35                  40                  45

Pro Asn Pro Gln Glu Met Val Leu Lys Asn Val Thr Glu Asn Phe Asn
    50                  55                  60

Met Trp Lys Asn Asp Met Val Asp Gln Met His Glu Asp Val Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asn Ala Thr Ala Ser Asn Ser Ser Ile Ile
            100                 105                 110

Glu Gly Met Lys Asn Cys Ser Phe Asn Ile Thr Thr Glu Leu Arg Asp
```

```
              115                 120                 125
Lys Arg Glu Lys Lys Asn Ala Leu Phe Tyr Lys Leu Asp Ile Val Gln
130                 135                 140

Leu Asp Gly Asn Ser Ser Gln Tyr Arg Leu Ile Asn Cys Asn Thr Ser
145                 150                 155                 160

Val Ile Thr Gln Val Cys Pro Lys Leu Ser Phe Asp Pro Ile Pro Ile
                165                 170                 175

His Tyr Cys Ala Pro Ala Gly Tyr Ala Ile Leu Lys Cys Asn Asn Lys
                180                 185                 190

Thr Phe Thr Gly Thr Gly Pro Cys Asn Asn Val Ser Thr Val Gln Cys
                195                 200                 205

Thr His Gly Ile Lys Pro Val Leu Ser Thr Gln Leu Leu Leu Asn Gly
                210                 215                 220

Ser Leu Ala Glu Gly Glu Ile Ile Ile Arg Ser Glu Asn Ile Thr Lys
225                 230                 235                 240

Asn Val Lys Thr Ile Ile Val His Leu Asn Glu Ser Val Lys Ile Glu
                245                 250                 255

Cys Thr Arg Pro Asn Asn Lys Thr Arg Thr Ser Ile Arg Ile Gly Pro
                260                 265                 270

Gly Gln Ala Phe Tyr Ala Thr Gly Gln Val Ile Gly Asp Ile Arg Glu
                275                 280                 285

Ala Tyr Cys Asn Ile Asn Glu Ser Lys Trp Asn Glu Thr Leu Gln Arg
290                 295                 300

Val Ser Lys Lys Leu Lys Glu Tyr Phe Pro His Lys Asn Ile Thr Phe
305                 310                 315                 320

Gln Pro Ser Ser Gly Gly Asp Leu Glu Ile Thr Thr His Ser Phe Asn
                325                 330                 335

Cys Gly Gly Glu Phe Phe Tyr Cys Asn Thr Ser Ser Leu Phe Asn Arg
                340                 345                 350

Thr Tyr Met Ala Asn Ser Thr Asp Met Ala Asn Ser Thr Glu Thr Asn
                355                 360                 365

Ser Thr Arg Thr Ile Thr Ile His Cys Arg Ile Lys Gln Ile Ile Asn
                370                 375                 380

Met Trp Gln Glu Val Gly Arg Ala Met Tyr Ala Pro Pro Ile Ala Gly
385                 390                 395                 400

Asn Ile Thr Cys Ile Ser Asn Ile Thr Gly Leu Leu Leu Thr Arg Asp
                405                 410                 415

Tyr Gly Lys Asn Asn Thr Glu Thr Phe Arg Pro Gly Gly Gly Asn Met
                420                 425                 430

Lys Asp Asn Trp Arg Ser Glu Leu Tyr Lys Tyr Lys Val Val Lys Ile
                435                 440                 445

Glu Pro Leu Gly Val Ala Pro Thr Arg Cys Lys Arg Arg Val Val Gly
                450                 455                 460

Arg Arg Arg Arg Arg Arg Ala Val Gly Ile Gly Ala Val Phe Leu Gly
465                 470                 475                 480

Phe Leu Gly Ala Ala Gly Ser Thr Met Gly Ala Ala Ser Met Thr Leu
                485                 490                 495

Thr Val Gln Ala Arg Asn Leu Leu Ser Gly Ile Val Gln Gln Gln Ser
                500                 505                 510

Asn Leu Leu Arg Ala Pro Glu Ala Gln Gln His Leu Leu Lys Leu Thr
                515                 520                 525

Val Trp Gly Ile Lys Gln Leu Gln Ala Arg Val Leu Ala Val Glu Arg
530                 535                 540
```

Tyr Leu Arg Asp Gln Gln Leu Leu Gly Ile Trp Gly Cys Ser Gly Lys
545                 550                 555                 560

Leu Ile Cys Cys Thr Asn Val Pro Trp Asn Ser Ser Trp Ser Asn Arg
            565                 570                 575

Asn Leu Ser Glu Ile Trp Asp Asn Met Thr Trp Leu Gln Trp Asp Lys
            580                 585                 590

Glu Ile Ser Asn Tyr Thr Gln Ile Ile Tyr Gly Leu Leu Glu Glu Ser
            595                 600                 605

Gln Asn Gln Gln Glu Lys Asn Glu Gln Asp Leu Leu Ala Leu Asp
610                 615                 620

<210> SEQ ID NO 52
<211> LENGTH: 623
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Glu Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Lys Glu Val His Asn Ile Trp Ala Thr His Ala Cys Val Pro Thr Asp
            35                  40                  45

Pro Asn Pro Gln Glu Met Val Leu Lys Asn Val Thr Glu Asn Phe Asn
50                  55                  60

Met Trp Lys Asn Asp Met Val Asp Gln Met His Glu Asp Val Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asn Ala Thr Ala Ser Asn Ser Ser Ile Ile
                100                 105                 110

Glu Gly Met Lys Asn Cys Ser Phe Asn Ile Thr Thr Glu Leu Arg Asp
            115                 120                 125

Lys Arg Glu Lys Lys Asn Ala Leu Phe Tyr Lys Leu Asp Ile Val Gln
130                 135                 140

Leu Asp Gly Asn Ser Ser Gln Tyr Arg Leu Ile Asn Cys Asn Thr Ser
145                 150                 155                 160

Val Ile Thr Met Val Cys Pro Lys Leu Ser Phe Asp Pro Ile Pro Ile
                165                 170                 175

His Tyr Cys Ala Pro Ala Gly Tyr Ala Ile Leu Lys Cys Asn Asn Lys
            180                 185                 190

Thr Phe Thr Gly Thr Gly Pro Cys Asn Asn Val Ser Thr Val Gln Cys
            195                 200                 205

Thr His Gly Ile Lys Pro Val Leu Ser Thr Gln Leu Leu Leu Asn Gly
        210                 215                 220

Ser Leu Ala Glu Gly Glu Ile Ile Ile Arg Ser Glu Asn Ile Thr Lys
225                 230                 235                 240

Asn Val Lys Thr Ile Ile Val His Leu Asn Glu Ser Val Lys Ile Glu
                245                 250                 255

Cys Thr Arg Pro Leu Asn Leu Thr Arg Thr Ser Ile Arg Ile Gly Pro
            260                 265                 270

Gly Gln Ala Phe Tyr Ala Met Gly Gln Val Ile Gly Asp Ile Arg Glu

```
                        275                 280                 285
Ala Tyr Cys Asn Ile Asn Glu Ser Lys Trp Asn Glu Thr Leu Gln Arg
            290                 295                 300

Val Ser Lys Lys Leu Lys Glu Tyr Phe Pro His Lys Asn Ile Thr Phe
305                 310                 315                 320

Gln Pro Ser Ser Gly Asp Leu Glu Ile Thr Thr His Ser Phe Asn
                325                 330                 335

Cys Gly Gly Glu Phe Phe Tyr Cys Asn Thr Ser Ser Leu Phe Asn Arg
            340                 345                 350

Thr Tyr Met Ala Asn Ser Thr Asp Met Ala Asn Ser Thr Glu Thr Asn
                355                 360                 365

Ser Thr Arg Thr Ile Thr Ile His Cys Arg Ile Lys Met Ile Ile Asn
            370                 375                 380

Met Trp Gln Glu Val Gly Arg Ala Met Tyr Ala Pro Pro Ile Ala Gly
385                 390                 395                 400

Asn Ile Thr Cys Ile Ser Asn Ile Thr Gly Leu Leu Leu Thr Arg Asp
                405                 410                 415

Tyr Gly Lys Asn Asn Thr Glu Thr Phe Arg Pro Gly Gly Gly Asn Met
            420                 425                 430

Lys Asp Asn Trp Arg Ser Glu Leu Tyr Lys Tyr Lys Val Val Lys Ile
                435                 440                 445

Glu Pro Leu Gly Val Ala Pro Thr Arg Cys Lys Arg Arg Val Val Gly
450                 455                 460

Arg Arg Arg Arg Arg Ala Val Gly Ile Gly Ala Val Phe Leu Gly
465                 470                 475                 480

Phe Leu Gly Ala Ala Gly Ser Thr Met Gly Ala Ala Ser Met Thr Leu
                485                 490                 495

Thr Val Gln Ala Arg Asn Leu Leu Ser Gly Ile Val Gln Gln Ser
                500                 505                 510

Asn Leu Leu Arg Ala Pro Glu Ala Gln Gln His Leu Leu Lys Leu Thr
            515                 520                 525

Val Trp Gly Ile Lys Gln Leu Gln Ala Arg Val Leu Ala Val Glu Arg
530                 535                 540

Tyr Leu Arg Asp Gln Gln Leu Leu Gly Ile Trp Gly Cys Ser Gly Lys
545                 550                 555                 560

Leu Ile Cys Cys Thr Asn Val Pro Trp Asn Ser Ser Trp Ser Asn Arg
                565                 570                 575

Asn Leu Ser Glu Ile Trp Asp Asn Met Thr Trp Leu Gln Trp Asp Lys
            580                 585                 590

Glu Ile Ser Asn Tyr Thr Gln Ile Ile Tyr Gly Leu Leu Glu Glu Ser
            595                 600                 605

Gln Asn Gln Gln Glu Lys Asn Glu Gln Asp Leu Leu Ala Leu Asp
            610                 615                 620

<210> SEQ ID NO 53
<211> LENGTH: 860
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Arg Val Met Gly Ile Gln Arg Asn Cys Gln His Leu Phe Arg Trp
1               5                   10                  15
```

Gly Thr Met Ile Leu Gly Met Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Ile Trp Ala Thr His Ala Cys Val Pro Thr Asp Pro Asn Pro
65                  70                  75                  80

Gln Glu Ile His Leu Glu Asn Val Thr Glu Phe Asn Met Trp Lys
            85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
            115                 120                 125

Gln Cys Thr Asn Val Thr Asn Asn Ile Thr Asp Asp Met Arg Gly Glu
            130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
            165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Met Val Cys Pro Lys Leu Ser
            195                 200                 205

Phe Glu Pro Ile Pro Ile His Tyr Cys Ala Pro Ala Gly Phe Ala Ile
            210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Leu Ser Thr
            245                 250                 255

Gln Leu Leu Leu Asn Gly Ser Leu Ala Glu Glu Val Met Ile Arg
            260                 265                 270

Ser Glu Asn Ile Thr Asn Asn Ala Lys Asn Ile Leu Val Gln Phe Asn
            275                 280                 285

Thr Pro Val Gln Ile Asn Cys Thr Arg Pro Leu Asn Leu Thr Arg Lys
            290                 295                 300

Ser Ile Arg Ile Gly Pro Gly Gln Ala Phe Tyr Ala Met Gly Asp Ile
305                 310                 315                 320

Ile Gly Asp Ile Arg Gln Ala His Cys Asn Val Ser Lys Ala Thr Trp
            325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
            355                 360                 365

Val Thr Thr His Ser Phe Asn Cys Gly Gly Glu Phe Phe Tyr Cys Asn
            370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
            405                 410                 415

Ile Lys Met Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly

```
                    435                 440                 445
Leu Ile Leu Thr Arg Asp Gly Gly Ser Thr Asn Ser Thr Glu Thr
450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Arg Ala Lys Arg Val Val Gly Arg Glu Lys Arg Ala Val Gly Ile
                500                 505                 510

Gly Ala Val Phe Leu Gly Phe Leu Gly Ala Ala Gly Ser Thr Met Gly
                515                 520                 525

Ala Ala Ser Met Thr Leu Thr Val Gln Ala Arg Asn Leu Leu Ser Gly
530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
                580                 585                 590

Trp Gly Cys Ser Gly Lys Leu Ile Cys Thr Thr Asn Val Pro Trp Asn
                595                 600                 605

Ser Ser Trp Ser Asn Arg Asn Leu Ser Glu Ile Trp Asp Asn Met Thr
610                 615                 620

Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Glu Lys Asn Glu Gln Asp
                645                 650                 655

Leu Leu Ala Leu Asp Lys Trp Ala Ser Leu Trp Asn Trp Phe Asp Ile
                660                 665                 670

Ser Asn Trp Leu Trp Tyr Ile Lys Ile Phe Ile Met Ile Val Gly Gly
                675                 680                 685

Leu Ile Gly Leu Arg Ile Val Phe Ala Val Leu Ser Val Ile His Arg
690                 695                 700

Val Arg Gln Gly Tyr Ser Pro Leu Ser Phe Gln Thr His Thr Pro Asn
705                 710                 715                 720

Pro Arg Gly Leu Asp Arg Pro Glu Arg Ile Glu Glu Asp Gly Glu
                725                 730                 735

Gln Asp Arg Gly Arg Ser Thr Arg Leu Val Ser Gly Phe Leu Ala Leu
                740                 745                 750

Ala Trp Asp Asp Leu Arg Ser Leu Cys Leu Phe Cys Tyr His Arg Leu
                755                 760                 765

Arg Asp Phe Ile Leu Ile Ala Ala Arg Ile Val Glu Leu Leu Gly His
770                 775                 780

Ser Ser Leu Lys Gly Leu Arg Leu Gly Trp Glu Gly Leu Lys Tyr Leu
785                 790                 795                 800

Trp Asn Leu Leu Ala Tyr Trp Gly Arg Glu Leu Lys Ile Ser Ala Ile
                805                 810                 815

Asn Leu Phe Asp Thr Ile Ala Ile Ala Val Ala Glu Trp Thr Asp Arg
                820                 825                 830

Val Ile Glu Ile Gly Gln Arg Leu Cys Arg Ala Phe Leu His Ile Pro
                835                 840                 845

Arg Arg Ile Arg Gln Gly Leu Glu Arg Ala Leu Leu
850                 855                 860
```

```
<210> SEQ ID NO 54
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
                20                  25                  30

Thr Val Tyr Tyr Gly Val Pro Val Trp Lys Glu Ala Lys Thr Thr Leu
            35                  40                  45

Phe Cys Ala Ser Asp Ala Lys Ala Tyr Glu Lys Glu Val His Asn Ile
        50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
                100                 105                 110

Lys Pro Cys Val Lys Leu Thr Pro Leu Cys Val Thr Leu Asn Cys Thr
            115                 120                 125

Asn Ala Thr Ala Ser Asn Ser Ser Ile Ile Glu Gly Met Lys Asn Cys
        130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Met Val Cys
                180                 185                 190

Pro Lys Leu Ser Phe Asp Pro Ile Pro Ile His Tyr Cys Ala Pro Ala
            195                 200                 205

Gly Tyr Ala Ile Leu Lys Cys Asn Asn Lys Thr Phe Thr Gly Thr Gly
        210                 215                 220

Pro Cys Asn Asn Val Ser Thr Val Gln Cys Thr His Gly Ile Lys Pro
225                 230                 235                 240

Val Leu Ser Thr Gln Leu Leu Leu Asn Gly Ser Leu Ala Glu Gly Glu
                245                 250                 255

Ile Ile Ile Arg Ser Glu Asn Ile Thr Lys Asn Val Lys Thr Ile Ile
                260                 265                 270

Val His Leu Asn Glu Ser Val Lys Ile Glu Cys Thr Arg Pro Leu Asn
            275                 280                 285

Leu Thr Arg Thr Ser Ile Arg Ile Gly Pro Gly Gln Ala Phe Tyr Ala
        290                 295                 300

Met Gly Gln Val Ile Gly Asp Ile Arg Glu Ala Tyr Cys Asn Ile Asn
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
                340                 345                 350

Asp Leu Glu Ile Thr Thr His Ser Phe Asn Cys Gly Gly Glu Phe Phe
```

```
                355                 360                 365
Tyr Cys Asn Thr Ser Ser Leu Phe Asn Arg Thr Tyr Met Ala Asn Ser
370                 375                 380

Thr Asp Met Ala Asn Ser Thr Glu Thr Asn Ser Thr Arg Thr Ile Thr
385                 390                 395                 400

Ile His Cys Arg Ile Lys Met Ile Ile Asn Met Trp Gln Glu Val Gly
                405                 410                 415

Arg Ala Met Tyr Ala Pro Pro Ile Ala Gly Asn Ile Thr Cys Ile Ser
                420                 425                 430

Asn Ile Thr Gly Leu Leu Leu Thr Arg Asp Tyr Gly Lys Asn Asn Thr
                435                 440                 445

Glu Thr Phe Arg Pro Gly Gly Gly Asn Met Lys Asp Asn Trp Arg Ser
                450                 455                 460

Glu Leu Tyr Lys Tyr Lys Val Val Glu Val Lys Pro Leu Gly Val Ala
465                 470                 475                 480

Pro Thr Asn Ala Arg Arg Arg Val Val Glu Arg Glu Lys Arg Ala Val
                485                 490                 495

Gly Met Gly Ala Val Phe Leu Gly Phe Leu Gly Ala Ala Gly Ser Thr
                500                 505                 510

Met Gly Ala Ala Ser Ile Thr Leu Thr Val Gln Ala Arg Gln Leu Leu
                515                 520                 525

Ser Gly Ile Val Gln Gln Gln Ser Asn Leu Leu Lys Ala Ile Glu Ala
530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
                565                 570                 575

Gly Met Trp Gly Cys Ser Gly Lys Leu Ile Cys Thr Thr Asn Val Tyr
                580                 585                 590

Trp Asn Ser Ser Trp Ser Asn Lys Thr Tyr Gly Asp Ile Trp Asp Asn
                595                 600                 605

Met Thr Trp Met Gln Trp Glu Arg Glu Ile Ser Asn Tyr Thr Glu Ile
                610                 615                 620

Ile Tyr Glu Leu Leu Glu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                645                 650                 655

Asn Ile Thr Asn Trp Leu Trp Tyr Ile Lys Ile Phe Ile Met Ile Val
                660                 665                 670

Gly Gly Leu Ile Gly Leu Arg Ile Ile Phe Ala Val Leu Ser Leu Val
                675                 680                 685

Asn Arg Val Arg Gln Gly Tyr Ser Pro Leu Ser Leu Gln Thr Leu Ile
                690                 695                 700

Pro Ser Pro Arg Gly Pro Asp Arg Pro Gly Ile Glu Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
                740                 745                 750

Arg Leu Arg Asp Phe Ile Leu Ile Ala Ala Arg Ala Gly Glu Leu Leu
                755                 760                 765

Gly Arg Ser Ser Leu Lys Gly Leu Arg Arg Gly Trp Glu Ala Leu Lys
770                 775                 780
```

-continued

```
Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
            820                 825                 830

Ile Pro Thr Arg Ile Arg Gln Gly Phe Glu Thr Ala Leu Leu
        835                 840                 845

<210> SEQ ID NO 55
<211> LENGTH: 847
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Ile Leu Lys Asn Tyr Pro Gln Trp Trp Ile Trp Gly Ile Leu
1               5                   10                  15

Gly Phe Trp Met Leu Met Ile Cys Asn Gly Lys Gly Lys Leu Trp Val
                20                  25                  30

Thr Val Tyr Tyr Gly Val Pro Val Trp Lys Glu Ala Lys Thr Thr Leu
            35                  40                  45

Phe Cys Ala Ser Asp Ala Arg Ala Tyr Glu Lys Glu Val His Asn Ile
        50                  55                  60

Trp Ala Thr His Ala Cys Val Pro Thr Asp Pro Ser Pro Gln Glu Leu
65                  70                  75                  80

Val Leu Gly Asn Val Thr Glu Asn Phe Asn Met Trp Lys Asn Asp Met
                85                  90                  95

Val Asp Gln Met His Glu Asp Ile Ile Ser Leu Trp Asp Gln Ser Leu
            100                 105                 110

Lys Pro Cys Val Lys Leu Thr Pro Leu Cys Val Thr Leu Ile Cys Ser
        115                 120                 125

Asp Ala Thr Val Lys Thr Gly Thr Val Glu Glu Met Lys Asn Cys Ser
130                 135                 140

Phe Asn Thr Thr Thr Glu Ile Arg Asp Lys Glu Lys Lys Glu Tyr Ala
145                 150                 155                 160

Leu Phe Tyr Lys Pro Asp Ile Val Pro Leu Ser Glu Thr Asn Asn Thr
                165                 170                 175

Ser Glu Tyr Arg Leu Ile Asn Cys Asn Thr Ser Ala Val Thr Met Val
            180                 185                 190

Cys Pro Lys Leu Thr Phe Glu Pro Ile Pro Ile His Tyr Cys Ala Pro
        195                 200                 205

Ala Gly Tyr Ala Ile Leu Lys Cys Asn Asp Glu Thr Phe Asn Gly Thr
    210                 215                 220

Gly Pro Cys Ser Asn Val Ser Thr Val Gln Cys Thr His Gly Ile Arg
225                 230                 235                 240

Pro Val Leu Ser Thr Gln Leu Leu Asn Gly Ser Leu Ala Glu Lys
                245                 250                 255

Glu Ile Val Ile Arg Ser Glu Asn Leu Thr Asn Asn Ala Lys Ile Ile
            260                 265                 270

Ile Val His Leu His Thr Pro Val Glu Ile Val Cys Thr Arg Pro Leu
        275                 280                 285

Asn Leu Thr Arg Lys Ser Val Arg Ile Gly Pro Gly Gln Thr Phe Tyr
```

-continued

```
            290                 295                 300
Ala Met Gly Asp Ile Ile Gly Asp Ile Lys Gln Ala His Cys Asn Ile
305                 310                 315                 320

Ser Glu Glu Lys Trp Asn Asp Thr Leu Gln Lys Val Gly Ile Glu Leu
                325                 330                 335

Gln Lys His Phe Pro Asn Lys Thr Ile Lys Tyr Asn Gln Ser Ala Gly
                340                 345                 350

Gly Asp Met Glu Ile Thr Thr His Ser Phe Asn Cys Gly Gly Glu Phe
            355                 360                 365

Phe Tyr Cys Asn Thr Ser Asn Leu Phe Asn Gly Thr Tyr Asn Gly Thr
        370                 375                 380

Tyr Ile Ser Thr Asn Ser Ser Ala Asn Ser Thr Ser Thr Ile Thr Leu
385                 390                 395                 400

Gln Cys Arg Ile Lys Met Ile Ile Asn Met Trp Gln Gly Val Gly Arg
                405                 410                 415

Ala Met Tyr Ala Pro Pro Ile Ala Gly Asn Ile Thr Cys Arg Ser Asn
                420                 425                 430

Ile Thr Gly Leu Leu Leu Thr Arg Asp Gly Gly Thr Asn Ser Asn Glu
            435                 440                 445

Thr Glu Thr Phe Arg Pro Ala Gly Gly Asp Met Arg Asp Asn Trp Arg
        450                 455                 460

Ser Glu Leu Tyr Lys Tyr Lys Val Val Glu Ile Gln Pro Leu Gly Ile
465                 470                 475                 480

Ala Pro Thr Gly Ala Lys Arg Arg Val Val Glu Arg Glu Lys Arg Ala
                485                 490                 495

Ala Gly Leu Gly Ala Leu Phe Leu Gly Phe Leu Gly Ala Ala Gly Ser
                500                 505                 510

Thr Met Gly Ala Ala Ser Ile Thr Leu Thr Val Gln Ala Arg Gln Leu
            515                 520                 525

Leu Ser Gly Ile Val Gln Gln Gln Ser Asn Leu Leu Arg Ala Ile Glu
530                 535                 540

Ala Gln Gln His Met Leu Gln Leu Thr Val Trp Gly Ile Lys Gln Leu
545                 550                 555                 560

Gln Ala Arg Val Leu Ala Leu Glu Arg Tyr Leu Lys Asp Gln Gln Leu
                565                 570                 575

Leu Gly Met Trp Gly Cys Ser Gly Lys Leu Ile Cys Thr Thr Asn Val
            580                 585                 590

Pro Trp Asn Thr Ser Trp Ser Asn Lys Ser Glu Thr Asp Ile Trp Asp
            595                 600                 605

Asn Met Thr Trp Met Gln Trp Glu Arg Glu Ile Ser Asn Tyr Thr Glu
610                 615                 620

Thr Ile Tyr Lys Leu Leu Glu Asp Ser Gln Asn Gln Gln Glu Arg Asn
625                 630                 635                 640

Glu Gln Asp Leu Leu Ala Leu Asp Ser Trp Asn Ser Leu Trp Asn Trp
                645                 650                 655

Phe Ser Ile Thr Lys Trp Leu Trp Tyr Ile Lys Ile Phe Ile Met Ile
            660                 665                 670

Val Gly Gly Leu Ile Gly Leu Arg Ile Val Phe Ala Val Leu Ser Ile
            675                 680                 685

Val Asn Arg Val Arg Gln Gly Tyr Ser Pro Leu Ser Leu Gln Thr Leu
            690                 695                 700

Thr Pro Asn Pro Arg Glu Pro Asp Arg Leu Arg Gly Ile Glu Glu Glu
705                 710                 715                 720
```

```
Gly Gly Glu Gln Asp Arg Asp Arg Ser Ile Arg Leu Val Ser Gly Phe
                725                 730                 735

Leu Pro Ile Val Trp Asp Asp Leu Arg Ser Leu Cys Leu Phe Ser Tyr
            740                 745                 750

His Arg Leu Arg Asp Phe Leu Leu Ala Ala Arg Val Val Glu Leu
        755                 760                 765

Leu Gly Arg Ser Ser Leu Arg Gly Leu Gln Arg Gly Trp Glu Val Leu
    770                 775                 780

Lys Tyr Leu Gly Ser Leu Val Gln Tyr Trp Gly Leu Glu Leu Lys Lys
785                 790                 795                 800

Ser Ala Ile Ser Leu Phe Asp Thr Leu Ala Ile Ala Val Ala Glu Gly
                805                 810                 815

Thr Asp Arg Ile Ile Glu Leu Ile Gln Gly Phe Cys Arg Ala Ile Arg
                820                 825                 830

Asn Ile Pro Thr Arg Ile Arg Gln Gly Phe Glu Ala Ser Leu Leu
            835                 840                 845

<210> SEQ ID NO 56
<211> LENGTH: 658
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
```

-continued

```
                225                 230                 235                 240
        Cys Thr His Gly Ile Lys Pro Val Val Ser Thr Gln Leu Leu Leu Asn
                        245                 250                 255
        Gly Ser Leu Ala Glu Glu Val Met Ile Arg Ser Glu Asn Ile Thr
                        260                 265                 270
        Asn Asn Ala Lys Asn Ile Leu Val Gln Phe Asn Thr Pro Val Gln Ile
                        275                 280                 285
        Asn Cys Thr Arg Pro Asn Asn Asn Thr Arg Lys Ser Ile Arg Ile Gly
                290                 295                 300
        Pro Gly Gln Ala Phe Tyr Ala Thr Gly Asp Ile Ile Gly Asp Ile Arg
        305                 310                 315                 320
        Gln Ala His Cys Asn Val Ser Lys Ala Thr Trp Asn Glu Thr Leu Gly
                        325                 330                 335
        Lys Val Val Lys Gln Leu Arg Lys His Phe Gly Asn Asn Thr Ile Ile
                        340                 345                 350
        Arg Phe Ala Asn Ser Ser Gly Gly Asp Leu Glu Val Thr Thr His Ser
                        355                 360                 365
        Phe Asn Cys Gly Gly Glu Phe Phe Tyr Cys Asn Thr Ser Gly Leu Phe
                        370                 375                 380
        Asn Ser Thr Trp Ile Ser Asn Thr Ser Val Gln Gly Ser Asn Ser Thr
        385                 390                 395                 400
        Gly Ser Asn Asp Ser Ile Thr Leu Pro Cys Arg Ile Lys Gln Ile Ile
                        405                 410                 415
        Asn Met Trp Gln Arg Ile Gly Gln Ala Met Tyr Ala Pro Pro Ile Gln
                        420                 425                 430
        Gly Val Ile Arg Cys Val Ser Asn Ile Thr Gly Leu Ile Leu Thr Arg
                        435                 440                 445
        Asp Gly Gly Ser Thr Asn Ser Thr Thr Glu Thr Phe Arg Pro Gly Gly
                        450                 455                 460
        Gly Asp Met Arg Asp Asn Trp Arg Ser Glu Leu Tyr Lys Tyr Lys Val
        465                 470                 475                 480
        Val Lys Ile Glu Pro Leu Gly Val Ala Pro Thr Arg Cys Lys Arg Arg
                        485                 490                 495
        Val Val Gly Arg Arg Arg Arg Arg Ala Val Gly Ile Gly Ala Val
                        500                 505                 510
        Phe Leu Gly Phe Leu Gly Ala Ala Gly Ser Thr Met Gly Ala Ala Ser
                        515                 520                 525
        Met Thr Leu Thr Val Gln Ala Arg Asn Leu Leu Ser Gly Ile Val Gln
                        530                 535                 540
        Gln Gln Ser Asn Leu Leu Arg Ala Pro Glu Ala Gln Gln His Leu Leu
        545                 550                 555                 560
        Lys Leu Thr Val Trp Gly Ile Lys Gln Leu Gln Ala Arg Val Leu Ala
                        565                 570                 575
        Val Glu Arg Tyr Leu Arg Asp Gln Gln Leu Leu Gly Ile Trp Gly Cys
                        580                 585                 590
        Ser Gly Lys Leu Ile Cys Cys Thr Asn Val Pro Trp Asn Ser Ser Trp
                        595                 600                 605
        Ser Asn Arg Asn Leu Ser Glu Ile Trp Asp Asn Met Thr Trp Leu Gln
                        610                 615                 620
        Trp Asp Lys Glu Ile Ser Asn Tyr Thr Gln Ile Ile Tyr Gly Leu Leu
        625                 630                 635                 640
        Glu Glu Ser Gln Asn Gln Gln Glu Lys Asn Glu Gln Asp Leu Leu Ala
                        645                 650                 655
```

Leu Asp

<210> SEQ ID NO 57
<211> LENGTH: 851
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Arg Val Thr Gly Ile Leu Arg Asn Tyr Pro Gln Trp Trp Ile Trp
1               5                   10                  15

Gly Ile Leu Gly Phe Trp Met Leu Met Thr Cys Asn Gly Glu Gly Asn
                20                  25                  30

Leu Trp Val Thr Val Tyr Tyr Gly Val Pro Val Trp Lys Glu Ala Lys
            35                  40                  45

Thr Thr Leu Phe Cys Ala Ser Asp Ala Lys Ala Tyr Lys Lys Glu Val
50                  55                  60

His Asn Val Trp Ala Thr His Ala Cys Val Pro Thr Asp Pro Ser Pro
65                  70                  75                  80

Gln Glu Leu Phe Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Ile Cys Ser Thr Ala Thr Val Asn Asn Arg Ala Val Asp Glu Met Lys
130                 135                 140

Asn Cys Ser Phe Asn Thr Thr Thr Glu Ile Arg Asp Lys Lys Lys Lys
145                 150                 155                 160

Glu Tyr Ala Leu Phe Tyr Arg Ser Asp Val Val Pro Leu Asp Glu Thr
                165                 170                 175

Asn Asn Thr Ser Glu Tyr Arg Leu Ile Asn Cys Asn Thr Ser Ala Val
            180                 185                 190

Thr Gln Ala Cys Pro Lys Val Thr Phe Glu Pro Ile Pro Ile His Tyr
        195                 200                 205

Cys Ala Pro Ala Gly Tyr Ala Ile Leu Lys Cys Asn Asp Glu Thr Phe
210                 215                 220

Asn Gly Thr Gly Pro Cys Ser Asn Val Ser Thr Val Gln Cys Thr His
225                 230                 235                 240

Gly Ile Arg Pro Val Val Ser Thr Gln Leu Leu Leu Asn Gly Ser Leu
                245                 250                 255

Ala Glu Lys Glu Ile Val Ile Arg Ser Glu Asn Leu Thr Asn Asn Ala
            260                 265                 270

Lys Ile Ile Ile Val His Leu His Thr Pro Val Glu Ile Val Cys Thr
        275                 280                 285

Arg Pro Gly His Asn Thr Arg Lys Ser Val Arg Ile Gly Pro Gly Gln
290                 295                 300

Thr Phe Tyr Ala Thr Gly Asp Ile Ile Gly Asp Ile Arg Gln Ala His
305                 310                 315                 320

Cys Asn Ile Asn Glu Ser Lys Trp Asn Glu Thr Leu Gln Lys Val Gly
                325                 330                 335

Ile Glu Leu Gln Lys His Phe Pro Asn Lys Thr Ile Lys Tyr Asn Gln
            340                 345                 350
```

```
Ser Ala Gly Gly Asp Met Glu Ile Thr Thr His Ser Phe Asn Cys Gly
        355                 360                 365
Gly Glu Phe Phe Tyr Cys Asn Thr Ser Lys Leu Phe Asn Ser Thr Tyr
        370                 375                 380
Asn Gly Thr Tyr Ile Ser Thr Asn Ser Thr Asn Ser Thr Ser Tyr Ile
385                 390                 395                 400
Thr Leu Gln Cys Arg Ile Lys Gln Ile Ile Asn Met Trp Gln Gly Val
                405                 410                 415
Gly Arg Ala Met Tyr Ala Pro Pro Ile Ala Gly Asn Ile Thr Cys Arg
                420                 425                 430
Ser Asn Ile Thr Gly Leu Leu Leu Thr Arg Asp Gly Gly Ile Asn Asn
                435                 440                 445
Val Ser Asn Glu Thr Glu Thr Phe Arg Pro Ala Gly Gly Asp Met Arg
                450                 455                 460
Asp Asn Trp Arg Ser Glu Leu Tyr Lys Tyr Lys Val Val Glu Val Gln
465                 470                 475                 480
Pro Leu Gly Ile Ala Pro Thr Gly Ala Lys Arg Val Val Glu Arg
                    485                 490                 495
Glu Lys Arg Ala Ala Gly Leu Gly Ala Leu Phe Leu Gly Phe Leu Gly
                500                 505                 510
Ala Ala Gly Ser Thr Met Gly Ala Ala Ser Ile Thr Leu Thr Val Gln
                515                 520                 525
Ala Arg Gln Leu Leu Ser Gly Ile Val Gln Gln Ser Asn Leu Leu
                530                 535                 540
Arg Ala Ile Glu Ala Gln Gln His Met Leu Gln Leu Thr Val Trp Gly
545                 550                 555                 560
Ile Lys Gln Leu Gln Ala Arg Val Leu Ala Leu Glu Arg Tyr Leu Lys
                565                 570                 575
Asp Gln Gln Leu Leu Gly Met Trp Gly Cys Ser Gly Lys Leu Ile Cys
                580                 585                 590
Thr Thr Asn Val Pro Trp Asn Thr Ser Trp Ser Asn Lys Ser Glu Met
                595                 600                 605
Asp Ile Trp Asn Asn Met Thr Trp Met Gln Trp Glu Arg Glu Ile Ser
                610                 615                 620
Asn Tyr Thr Glu Thr Ile Tyr Met Leu Leu Glu Asp Ser Gln Arg Gln
625                 630                 635                 640
Gln Glu Arg Asn Glu Lys Asp Leu Leu Ala Leu Asp Ser Trp Asn Ser
                645                 650                 655
Leu Trp Asn Trp Phe Asn Ile Thr Asn Trp Leu Trp Tyr Ile Lys Ile
                660                 665                 670
Phe Ile Met Ile Val Gly Gly Leu Ile Gly Leu Arg Ile Val Phe Ala
                675                 680                 685
Val Leu Ser Ile Val Asn Arg Val Arg Gln Gly Tyr Ser Pro Leu Ser
                690                 695                 700
Leu Gln Thr Leu Thr Pro Asn Pro Arg Glu Pro Asp Arg Leu Arg Gly
705                 710                 715                 720
Ile Glu Glu Glu Gly Gly Glu Gln Asp Arg Asp Arg Ser Ile Arg Leu
                725                 730                 735
Val Ser Gly Phe Leu Pro Ile Val Trp Asp Asp Leu Arg Ser Leu Cys
                740                 745                 750
Leu Phe Ser Tyr His Arg Leu Arg Asp Phe Leu Leu Leu Ala Ala Arg
                755                 760                 765
```

```
Val Val Glu Leu Leu Gly His Ser Ser Leu Arg Gly Leu Gln Arg Gly
770                 775                 780

Trp Glu Val Leu Lys Tyr Leu Gly Ser Leu Val Gln Tyr Trp Gly Leu
785                 790                 795                 800

Glu Leu Lys Arg Ser Ala Ile Ser Leu Phe Asp Thr Leu Ala Ile Ala
                805                 810                 815

Val Ala Glu Gly Thr Asp Arg Ile Ile Glu Leu Ile Gln Gly Phe Cys
                820                 825                 830

Arg Ala Ile Arg Asn Ile Pro Thr Arg Ile Arg Gln Gly Phe Glu Ala
                835                 840                 845

Ser Leu Leu
    850

<210> SEQ ID NO 58
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Gly Ser Leu Gln Pro Leu Ala Thr Leu Tyr Leu Leu Gly Met Leu
1               5                   10                  15

Val Ala Ser Val Leu Ala Ala Glu Asn Leu Trp Val Thr Val Tyr Tyr
                20                  25                  30

Gly Val Pro Val Trp Lys Glu Ala Lys Thr Thr Leu Phe Cys Ala Ser
            35                  40                  45

Asp Ala Lys Ala Tyr Lys Lys Glu Val His Asn Val Trp Ala Thr His
    50                  55                  60

Ala Cys Val Pro Thr Asp Pro Ser Pro Gln Glu Leu Phe Leu Glu Asn
65                  70                  75                  80

Val Thr Glu Asn Phe Asn Met Trp Lys Asn Asp Met Val Asp Gln Met
                85                  90                  95

His Glu Asp Ile Ile Ser Leu Trp Asp Gln Ser Leu Lys Pro Cys Val
                100                 105                 110

Lys Leu Thr Pro Leu Cys Val Thr Leu Ile Cys Ser Thr Ala Thr Val
            115                 120                 125

Asn Asn Arg Ala Val Asp Glu Met Lys Asn Cys Ser Phe Asn Thr Thr
    130                 135                 140

Thr Glu Ile Arg Asp Lys Lys Lys Glu Tyr Ala Leu Phe Tyr Arg
145                 150                 155                 160

Ser Asp Val Val Pro Leu Asp Glu Thr Asn Asn Thr Ser Glu Tyr Arg
                165                 170                 175

Leu Ile Asn Cys Asn Thr Ser Ala Cys Thr Gln Ala Cys Pro Lys Val
                180                 185                 190

Thr Phe Glu Pro Ile Pro Ile His Tyr Cys Ala Pro Ala Gly Tyr Ala
            195                 200                 205

Ile Leu Lys Cys Asn Asp Glu Thr Phe Asn Gly Thr Gly Pro Cys Ser
    210                 215                 220

Asn Val Ser Thr Val Gln Cys Thr His Gly Ile Arg Pro Val Val Ser
225                 230                 235                 240

Thr Gln Leu Leu Leu Asn Gly Ser Leu Ala Glu Lys Glu Ile Val Ile
                245                 250                 255

Arg Ser Glu Asn Leu Thr Asn Asn Ala Lys Ile Ile Ile Val His Leu
                260                 265                 270
```

```
His Thr Pro Val Glu Ile Val Cys Thr Arg Pro Asn Asn Asn Thr Arg
        275                 280                 285

Lys Ser Val Arg Ile Gly Pro Gly Gln Thr Phe Tyr Ala Thr Gly Asp
        290                 295                 300

Ile Ile Gly Asp Ile Lys Gln Ala His Cys Asn Ile Ser Glu Glu Lys
305                 310                 315                 320

Trp Asn Glu Thr Leu Gln Lys Val Gly Ile Glu Leu Gln Lys His Phe
                325                 330                 335

Pro Asn Lys Thr Ile Lys Tyr Asn Gln Ser Ala Gly Gly Asp Met Glu
                340                 345                 350

Ile Thr Thr His Ser Phe Asn Cys Gly Gly Glu Phe Phe Tyr Cys Asn
                355                 360                 365

Thr Ser Lys Leu Phe Asn Ser Thr Tyr Asn Gly Thr Tyr Ile Ser Thr
        370                 375                 380

Asn Ser Thr Asn Ser Thr Ser Tyr Ile Thr Leu Gln Cys Arg Ile Lys
385                 390                 395                 400

Gln Ile Ile Asn Met Trp Gln Gly Val Gly Arg Cys Met Tyr Ala Pro
                405                 410                 415

Pro Ile Ala Gly Asn Ile Thr Cys Arg Ser Asn Ile Thr Gly Leu Leu
                420                 425                 430

Leu Thr Arg Asp Gly Gly Ile Asn Asn Val Ser Asn Glu Thr Glu Thr
        435                 440                 445

Phe Arg Pro Ala Gly Gly Asp Met Arg Asp Asn Trp Arg Ser Glu Leu
        450                 455                 460

Tyr Lys Tyr Lys Val Val Lys Ile Glu Pro Leu Gly Val Ala Pro Thr
465                 470                 475                 480

Arg Cys Lys Arg Arg Val Val Gly Arg Arg Arg Arg Arg Ala Val
                485                 490                 495

Gly Ile Gly Ala Val Phe Leu Gly Phe Leu Gly Ala Ala Gly Ser Thr
                500                 505                 510

Met Gly Ala Ala Ser Met Thr Leu Thr Val Gln Ala Arg Asn Leu Leu
        515                 520                 525

Ser Gly Ile Val Gln Gln Gln Ser Asn Leu Leu Arg Ala Pro Glu Ala
        530                 535                 540

Gln Gln His Leu Leu Lys Leu Thr Val Trp Gly Ile Lys Gln Leu Gln
545                 550                 555                 560

Ala Arg Val Leu Ala Val Glu Arg Tyr Leu Arg Asp Gln Gln Leu Leu
                565                 570                 575

Gly Ile Trp Gly Cys Ser Gly Lys Leu Ile Cys Cys Thr Asn Val Pro
                580                 585                 590

Trp Asn Ser Ser Trp Ser Asn Arg Asn Leu Ser Glu Ile Trp Asp Asn
                595                 600                 605

Met Thr Trp Leu Gln Trp Asp Lys Glu Ile Ser Asn Tyr Thr Gln Ile
        610                 615                 620

Ile Tyr Gly Leu Leu Glu Glu Ser Gln Asn Gln Glu Lys Asn Glu
625                 630                 635                 640

Gln Asp Leu Leu Ala Leu Asp
                645

<210> SEQ ID NO 59
<211> LENGTH: 2601
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 59

```
aagcttgtcg acgccaccat gcctatggga agcctgcaac ctctggccac actgtacctg      60
ctgggaatgc tggtggcttc tgtgctggcc gccgagaatc tgtgggtcac agtgtactat     120
ggcgtgcccg tgtggaagga cgccgagaca acactgtttt gtgccagcga cgccaaggcc     180
tacgagacag agaagcacaa catctgggcc actcacgcct gcgtgccaac cgatcctaat     240
cctcaagaga tccacctgga aaacgtgacc gaggaattca acatgtggaa gaacaacatg     300
gtcgagcaga tgcacaccga catcatcagc ctgtgggacc agagcctgaa gccttgcgtg     360
aagctgaccc ctctgtgtgt gaccctgcag tgcaccaacg tgaccaacaa catcaccgac     420
gacatgcggg gcgagctgaa gaactgcagc ttcaacatga ccaccgagct gcgggacaag     480
aaacagaagg tgtacagcct gttctaccgg ctggacgtgg tgcagatcaa cgagaaccag     540
ggcaacagaa gcaacaacag caacaaagag taccggctga tcaactgcaa caccagcgcc     600
atcactcagg tgtgtcctaa gctgtccttc gagcccattc ctatccacta ctgtgcccct     660
gccggcttcg ccatcctgaa gtgcaaggac aagaagttca cggcacagg ccctgtcct      720
tccgtgtcta ccgtgcagtg tacccacggc atcaagcccg tgctgtctac acagctgctg     780
ctgaatggca gcctggccga gaggaagtg atgatcagaa gcgagaacat caccaacaac     840
gccaagaaca tcctggtcca gttcaacacc cctgtgcaga ttaactgtac ccggcctaac     900
aacaacaccc cggaagtccat cagaatcggc ccaggccagg cctttatgc caccggcgat     960
atcatcggcg acatcagaca ggcccactgc aacgtgtcca aggccacatg gaatgagaca    1020
ctgggcaaag tggtcaagca gctgcggaag cacttcggca acaataccat catcagattc    1080
gccaacagct ctggcggcga cctggaagtg accacacaca gctttaactg tggcggcgag    1140
ttcttctact gcaataccct cggcctgttc aacagcacct ggatcagcaa cacaagcgtg    1200
cagggcagca atagcaccgg cagcaacgac agcatcaccc tgccttgccg gatcaagcag    1260
atcatcaata tgtggcagcg gatcggacag gctatgtacg cccctcctat tcagggcgtg    1320
atcagatgcg tgtccaatat caccggcctg atcctgacca gagatggcgg cagcaccaac    1380
tccaccaccg agacttttag acccggcgga ggcgacatga gagacaattg gagaagcgag    1440
ctgtacaagt acaaggtggt caagatcgag cccctgggcg tcgcacctac agagccaag    1500
agaagagtcg tgggccgcga gaagagagcc gttggaattg gagccgtgtt cctgggcttt    1560
ctgggagccc ctggatctac aatgggcgct gccagcatga cactgaccgt gcaggctaga    1620
aatctgctga gcggcatcgt gcagcagcag agcaatctgc tgcgggccat gaagcccag     1680
cagcatctgc tgaaactgac agtgtgggc atcaaacagc tgcaggccag agtgctggct    1740
gtggaaagat acctgaggga ccagcagctc ctcggcatct ggggatgttc tggcaagctg    1800
atctgtacca ccaatgtgcc ctggaacagc agctggtcca accggaatct gagcgagatc    1860
tgggacaata tgacctggct gcagtgggac aaagagatct ccaactacac ccagatcatc    1920
tacggcctgc tggaagagtc ccagaaccag caagagaaaa acgagcagga cctgctggcc    1980
ctgataagt gggctagcct gtggaattgg ttcgacatca gcaattggct gtggtacatc    2040
aagatcttca tcatgatcgt cggcggactg atcggcctga atcgtgtt tgccgtgctg    2100
agcgtgatcc acagagtgcg gcagggatat agccctctga gcttccagac acacacccct    2160
aatcctagag gcctggacag acccgagcgg atcgaagaag aggacggcga acaggacaga    2220
```

```
ggcagaagca ccagactggt ttccggcttc ctggctctgg cttgggacga tctgagaagc   2280
ctgtgcctgt tctgctacca ccggctgaga gactttatcc tgattgccgc caggatcgtg   2340
gaactgctgg acacagctc tctgaagggc ctgagactcg gatgggaggg cctgaagtat    2400
ctgtggaacc tgctcgccta ctggggaaga gagctgaaaa tctccgccat caacctgttc   2460
gacacaatcg ccattgccgt ggccgagtgg accgacagag tgatcgagat tggccagaga   2520
ctgtgccggg ccttcctgca catccctcgg agaattagac agggcctcga acgggccctg   2580
ctgtgataag gatcctctag a                                             2601
```

<210> SEQ ID NO 60
<211> LENGTH: 2601
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
aagcttgtcg acgccaccat gcctatggga agcctgcaac ctctggccac actgtacctg    60
ctgggaatgc tggtggcttc tgtgctggcc gccgagaatc tgtgggtcac agtgtactat   120
ggcgtgcccg tgtggaagga cgccgagaca acactgtttt gtgccagcga cgccaaggcc   180
tacgagacag agaagcacaa cgtgtgggcc actcacgcct gcgtgccaac cgatcctaat   240
cctcaagaga tccacctgga aaacgtgacc gaggaattca acatgtggaa gaacaacatg   300
gtcgagcaga tgcacaccga catcatcagc ctgtgggacc agagcctgaa gccttgcgtg   360
aagctgaccc ctctgtgtgt gaccctgcag tgcaccaacg tgaccaacaa catcaccgac   420
gacatgcggg gcgagctgaa gaactgcagc ttcaacatga ccaccgagct gcgggacaag   480
aaacagaagg tgtacagcct gttctaccgg ctggacgtgg tgcagatcaa cgagaaccag   540
ggcaacagaa gcaacaacag caacaaagag taccggctga tcaactgcaa caccagcgcc   600
atcactatgg cctgtcctaa ggtgtccttc gagcccattc ctatccacta ctgtgcccct   660
gccggcttcg ccatcctgaa gtgcaaggac aagaagttca acggcacagg ccctgtgcct   720
tccgtgtcta ccgtgcagtg tacccacggc atcaagcccg tggtgtctac acagctgctg   780
ctgaatggca gcctggccga agaggaagtg atgatcagaa gcgagaacat caccaacaac   840
gccaagaaca tcctggtcca gttcaacacc ctgtgcagat taactgtac ccggcctctg     900 aacctgaccc ggaagtccat cagaatcggc ccaggccagg ccttttatgc catgggcgat   960
atcatcggcg acatcagaca ggcccactgc aacgtgtcca ggccacatg gaatgagaca   1020 ctgggcaaag tggtcaagca gctgcggaag cacttcggca acataccat catcagattc   1080 gccaacagct ctggcggcga cctggaagtg accacacaca gctttaactg tggcggcgag   1140
ttcttctact gcaataccctc cggcctgttc aacagcacct ggatcagcaa cacaagcgtg   1200
cagggcagca atagcaccgg cagcaacgac agcatcaccc tgccttgccg gatcaagatg   1260
atcatcaata tgtggcagcg gatcggacag gctatgtacg cccctcctat tcagggcgtg   1320
atcagatgcg tgtccaatat caccggcctg atcctgacca gagatggcgg cagcaccaac   1380
tccaccaccg agacttttag acccggcgga ggcgacatga gagacaattg gagaagcgag   1440
ctgtacaagt acaaggtggt caagatcgag cccctgggcg tcgcacctac cagagccaag   1500
agaagagtcg tgggccgcga agagagacc gttggaattg gagccgtgtt cctgggcttt   1560
ctgggagccg ctggatctac aatgggcgct gccagcatga cactgaccgt gcaggctaga   1620
```

| | | | | |
|---|---|---|---|---|
| aatctgctga | gcggcatcgt | gcagcagcag | agcaatctgc | tgcgggccat tgaagcccag | 1680 |
| cagcatctgc | tgaaactgac | agtgtggggc | atcaaacagc | tgcaggccag agtgctggct | 1740 |
| gtggaaagat | acctgaggga | ccagcagctc | ctcggcatct | ggggatgttc tggcaagctg | 1800 |
| atctgtacca | ccaatgtgcc | ctggaacagc | agctggtcca | accggaatct gagcgagatc | 1860 |
| tgggacaata | tgacctggct | gcagtgggac | aaagagatct | ccaactacac ccagatcatc | 1920 |
| tacggcctgc | tggaagagtc | ccagaaccag | caagagaaaa | acgagcagga cctgctggcc | 1980 |
| ctggataagt | gggctagcct | gtggaattgg | ttcgacatca | gcaattggct gtggtacatc | 2040 |
| aagatcttca | tcatgatcgt | cggcggactg | atcggcctga | gaatcgtgtt tgccgtgctg | 2100 |
| agcgtgatcc | acagagtgcg | gcagggatat | agccctctga | gcttccagac acacacccct | 2160 |
| aatcctagag | gcctggacag | acccgagcgg | atcgaagaag | aggacggcga acaggacaga | 2220 |
| ggcagaagca | ccagactggt | tccggcttc | ctggctctgg | cttgggacga tctgagaagc | 2280 |
| ctgtgcctgt | tctgctacca | ccggctgaga | gactttatcc | tgattgccgc caggatcgtg | 2340 |
| gaactgctgg | gacacagctc | tctgaaggc | ctgagactcg | gatgggaggg cctgaagtat | 2400 |
| ctgtggaacc | tgctcgccta | ctggggaaga | gagctgaaaa | tctccgccat caacctgttc | 2460 |
| gacacaatcg | ccattgccgt | ggccgagtgg | accgacagag | tgatcgagat tggccagaga | 2520 |
| ctgtgccggg | ccttcctgca | catccctcgg | agaattagac | agggcctcga acgggccctg | 2580 |
| ctgtgataag | gatcctctag a | | | | 2601 |

<210> SEQ ID NO 61
<211> LENGTH: 2601
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

| | | | | |
|---|---|---|---|---|
| aagcttgtcg | acgccaccat | gcctatggga | agcctgcaac | ctctggccac actgtacctg | 60 |
| ctggaatgc | tggtggcttc | tgtgctggcc | gccgagaatc | tgtgggtcac agtgtactat | 120 |
| ggcgtgcccg | tgtggaagga | cgccgagaca | acactgtttt | gtgccagcga cgccaaggcc | 180 |
| tacgagacag | agaagcacaa | catctgggcc | actcacgcct | gcgtgccaac cgatcctaat | 240 |
| cctcaagaga | tccacctgga | aaacgtgacc | gaggaattca | acatgtggaa gaacaacatg | 300 |
| gtcgagcaga | tgcacaccga | catcatcagc | ctgtgggacc | agagcctgaa gccttgcgtg | 360 |
| aagctgaccc | ctctgtgtgt | gaccctgcag | tgcaccaacg | tgaccaacaa catcaccgac | 420 |
| gacatgcggg | gcgagctgaa | gaactgcagc | ttcaacatga | ccaccgagct gcgggacaag | 480 |
| aaacagaagg | tgtacagcct | gttctaccgg | ctggacgtgg | tgcagatcaa cgagaaccag | 540 |
| ggcaacagaa | gcaacaacag | caacaaagag | taccggctga | tcaactgcaa caccagcgcc | 600 |
| atcactatgg | tgtgtcctaa | gctgtccttc | gagcccattc | ctatccacta ctgtgccct | 660 |
| gccggcttcg | ccatcctgaa | gtgcaaggac | aagaagttca | acggcacagg ccctgtcct | 720 |
| tccgtgtcta | ccgtgcagtg | tacccacggc | atcaagcccg | tgctgtctac acagctgctg | 780 |
| ctgaatggca | gcctggccga | agaggaagtg | atgatcagaa | gcgagaacat caccaacaac | 840 |
| gccaagaaca | tcctggtcca | gttcaacacc | cctgtgcaga | ttaactgtac ccggcctctg | 900 |
| aacctgaccc | ggaagtccat | cagaatcggc | ccaggccagg | ccttttatgc catgggcgat | 960 |
| atcatcggcg | acatcagaca | ggcccactgc | aacgtgtcca | aggccacatg gaatgagaca | 1020 |

| | |
|---|---|
| ctgggcaaag tggtcaagca gctgcggaag cacttcggca acaataccat catcagattc | 1080 |
| gccaacagct ctggcggcga cctggaagtg accacacaca gctttaactg tggcggcgag | 1140 |
| ttcttctact gcaataccct cggcctgttc aacagcacct ggatcagcaa cacaagcgtg | 1200 |
| cagggcagca atagcaccgg cagcaacgac agcatcaccc tgccttgccg gatcaagatg | 1260 |
| atcatcaata tgtggcagcg gatcggacag gctatgtacg cccctcctat tcagggcgtg | 1320 |
| atcagatgcg tgtccaatat caccggcctg atcctgacca gagatggcgg cagcaccaac | 1380 |
| tccaccaccg agactttag acccggcgga ggcgacatga gagacaattg gagaagcgag | 1440 |
| ctgtacaagt acaaggtggt caagatcgag cccctgggcg tcgcacctac cagagccaag | 1500 |
| agaagagtcg tgggccgcga agagagcc gttggaattg agccgtgtt cctgggcttt | 1560 |
| ctgggagccg ctggatctac aatgggcgct gccagcatga cactgaccgt gcaggctaga | 1620 |
| aatctgctga gcggcatcgt gcagcagcag agcaatctgc tgcgggccat tgaagcccag | 1680 |
| cagcatctgc tgaaactgac agtgtggggc atcaaacagc tgcaggccag agtgctggct | 1740 |
| gtggaaagat acctgaggga ccagcagctc ctcggcatct ggggatgttc tggcaagctg | 1800 |
| atctgtacca ccaatgtgcc ctggaacagc agctggtcca accggaatct gagcgagatc | 1860 |
| tgggacaata tgacctggct gcagtgggac aaagagatct ccaactacac ccagatcatc | 1920 |
| tacggcctgc tggaagagtc ccagaaccag aagagaaaa acgagcagga cctgctggcc | 1980 |
| ctggataagt gggctagcct gtggaattgg ttcgacatca gcaattggct gtggtacatc | 2040 |
| aagatcttca tcatgatcgt cggcggactg atcggcctga aatcgtgtt tgccgtgctg | 2100 |
| agcgtgatcc acagagtgcg gcagggatat agccctctga gcttccagac acacccccct | 2160 |
| aatcctagag gcctggacag acccgagcgg atcgaagaag aggacggcga acaggacaga | 2220 |
| ggcagaagca ccagactggt ttccggcttc ctggctctgg cttgggacga tctgagaagc | 2280 |
| ctgtgcctgt tctgctacca ccggctgaga gactttatcc tgattgccgc caggatcgtg | 2340 |
| gaactgctgg acacagctc tctgaagggc ctgagactcg gatgggaggg cctgaagtat | 2400 |
| ctgtggaacc tgctcgccta ctggggaaga gagctgaaaa tctccgccat caacctgttc | 2460 |
| gacacaatcg ccattgccgt ggccgagtgg accgacagag tgatcgagat tggccagaga | 2520 |
| ctgtgccggg ccttcctgca catccctcgg agaattagac agggcctcga acgggccctg | 2580 |
| ctgtgataag gatcctctag a | 2601 |

<210> SEQ ID NO 62
<211> LENGTH: 2565
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62

| | |
|---|---|
| aagcttgtcg acgccaccat gggatctctg cagcctctgg ccacactgta cctgctggga | 60 |
| atgctggtgg ctagcgtgct ggccaaggga aagctgtggg tcacagtgta ctacggcgtg | 120 |
| cccgtgtgga aagaggccaa gaccacactg ttctgcgcct ccgatgccag agcctacgag | 180 |
| aaagaggtgc acaacatctg ggccacacac gcctgtgtgc ctaccgatcc atctcctcaa | 240 |
| gagctggtgc tgggcaacgt gaccgagaac ttcaacatgt ggaagaacga catggtggac | 300 |
| cagatgcacg aggacatcat cagcctgtgg gaccagagcc tgaagccttg cgtgaagctg | 360 |
| acccctctgt gcgtgaccct gatctgttct gacgccaccg tgaaaaccgg caccgtggaa | 420 |

```
gagatgaaga actgcagctt caacaccacc accgagatcc gggacaaaga gaagaaagag    480
tacgccctgt tctacaagcc cgacatcgtg cccctgagcg agacaaacaa caccagcgag    540
taccggctga tcaactgcaa cacctccgcc gtgacacagg tgtgcccaa  actgaccttc    600
gagcccattc ctatccacta ctgtgcccct gccggctacg ccatcctgaa gtgcaacgac    660
gagacattca acggcacagg cccctgcagc aatgtgtcca ccgtgcagtg tacccacggc    720
atcagaccag tgctgtctac ccagctgctg ctgaatggaa gcctggccga gaaagaaatc    780
gtgatcagaa gcgagaacct gaccaacaac gccaagatca tcattgtgca tctgcacacc    840
cctgtggaaa tcgtgtgcac ccggcctaac aacaaccccc ggaagtctgt gcggatcggc    900
cctggccaga cattctatgc caccggcgat atcatcggcg acatcaagca ggcccactgc    960
aacatcagcg aggaaaagtg gaacgacacc ctgcagaaag tgggcatcga gctgcagaag   1020
cacttcccca caagaccat  caagtacaac cagagcgctg gcggcgacat ggaaatcacc   1080
acacacagct tcaattgtgg cggcgagttc ttctactgca ataccagcaa cctgttcaac   1140
gggacctaca atggcaccta catcagcacc aacagcagcc caactccac  cagcaccatc   1200
actctgcagt gccggatcaa gcagatcatc aatatgtggc aaggcgtggg cagagctatg   1260
tacgcccctc ctatcgccgg caacatcacc tgtcggagca atatcacagg cctgctgctc   1320
accagagatg gcggcaccaa tagcaacgag acagaaacct tcagacctgc cggcggagac   1380
atgagagaca attggagaag cgagctgtac aagtacaagg tggtggaaat ccagccactg   1440
ggaatcgccc caaccggcgc taagagaaga gtggtggaac gcgagaaaag agccgctgga   1500
ctgggagccc tgttcctggg atttcttgga gccgccggaa gcacaatggg agccgcctct   1560
attaccctga ccgtgcaggc tagacagctg ctgagcggaa ttgtgcagca gcagagcaac   1620
ctgctgagag ccattgaagc ccagcagcac atgctgcagc tgaccgtgtg gggaatcaaa   1680
cagctgcagg ccagagtgct ggccctggaa agatacctga aggaccagca gctcctcggc   1740
atgtggggct gttctggcaa gctgatctgc accaccaacg tgccctggaa cacctcctgg   1800
tccaacaaga gcgaaaccga catctgggac aacatgacct ggatgcagtg ggagagagag   1860
atcagcaact acaccgagac aatctacaag ctgctcgagg acagccagaa ccagcaagag   1920
agaaacgagc aggacctgct ggctctggac agctggaata gcctgtggaa ctggttcagc   1980
atcaccaagt ggctgtggta tcatcaagatc ttcatcatga tcgtcggcgg cctgatcggc   2040
ctgagaatcg tgtttgccgt gctgagcatc gtgaacagag tgcggcaggg atacagccca   2100
ctgagcctgc aaaccctgac acctaatcct agagagcccg accggctgag aggcatcgaa   2160
gaagaaggcg gcgagcagga tcgggacaga tccatcagac tggtgtccgg cttcctgcct   2220
atcgtgtggg acgatctgag aagcctgtgc ctgttcagct accaccggct gcgggatttt   2280
ctgctgcttg ccgccagagt ggttgaactg ctgggcagat ctagcctgag gggcctgcaa   2340
agaggctggg aagtcctgaa gtacctgggc agcctggtgc agtattgggg cctcgagctg   2400
aaaaagagcg ccattagcct gttcgatacc ctggccattg ctgtggccga gggcaccgat   2460
agaatcattg agctgatcca gggcttctgc cgggccatca gaaacatccc caccagaatc   2520
agacagggct tcgaggccag cctgctgtga taaggatcct ctaga              2565
```

<210> SEQ ID NO 63
<211> LENGTH: 2565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

| | | | | | |
|---|---|---|---|---|---|
| aagcttgtcg | acgccaccat | gggatctctg | cagcctctgg | ccacactgta | cctgctggga | 60 |
| atgctggtgg | ctagcgtgct | ggccaaggga | aagctgtggg | tcacagtgta | ctacggcgtg | 120 |
| cccgtgtgga | aagaggccaa | gaccacactg | ttctgcgcct | ccgatgccag | agcctacgag | 180 |
| aaagaggtgc | acaacgtctg | gccacacac | gcctgtgtgc | ctaccgatcc | atctcctcaa | 240 |
| gagctggtgc | tgggcaacgt | gaccgagaac | ttcaacatgt | ggaagaacga | catggtggac | 300 |
| cagatgcacg | aggacatcat | cagcctgtgg | gaccagagcc | tgaagccttg | cgtgaagctg | 360 |
| accctctgt | gcgtgaccct | gatctgttct | gacgccaccg | tgaaaaccgg | caccgtggaa | 420 |
| gagatgaaga | actgcagctt | caacaccacc | accgagatcc | gggacaaaga | gaagaaagag | 480 |
| tacgccctgt | tctacaagcc | cgacatcgtg | cccctgagcg | agacaaacaa | caccagcgag | 540 |
| taccggctga | tcaactgcaa | cacctccgcc | gtgacaatgg | cttgcccaa | agtgaccttc | 600 |
| gagcccattc | ctatccacta | ctgtgcccct | gccggctacg | ccatcctgaa | gtgcaacgac | 660 |
| gagacattca | acggcacagg | cccctgcagc | aatgtgtcca | ccgtgcagtg | tacccacggc | 720 |
| atcagaccag | tggtgtctac | ccagctgctg | ctgaatggaa | gcctggccga | gaagaaatc | 780 |
| gtgatcagaa | gcgagaacct | gaccaacaac | gccaagatca | tcattgtgca | tctgcacacc | 840 |
| cctgtggaaa | tcgtgtgcac | ccggcctctg | aacctgaccc | cggaagtctgt | gcggatcggc | 900 |
| cctggccaga | cattctatgc | catgggcgat | atcatcggcg | acatcaagca | ggcccactgc | 960 |
| aacatcagcg | aggaaaagtg | gaacgacacc | ctgcagaaag | tgggcatcga | gctgcagaag | 1020 |
| cacttcccca | caagaccat | caagtacaac | cagagcgctg | gcggcgacat | ggaaatcacc | 1080 |
| acacacagct | tcaattgtgg | cggcgagttc | ttctactgca | ataccagcaa | cctgttcaac | 1140 |
| gggacctaca | atggcaccta | catcagcacc | aacagcagcg | ccaactccac | cagcaccatc | 1200 |
| actctgcagt | gccggatcaa | gatgatcatc | aatatgtggc | aaggcgtggg | cagagctatg | 1260 |
| tacgccccctc | ctatcgccgg | caacatcacc | tgtcggagca | atatcacagg | cctgctgctc | 1320 |
| accagagatg | gcggcaccaa | tagcaacgag | acagaaacct | tcagacctgc | cggcggagac | 1380 |
| atgagagaca | attggagaag | cgagctgtac | aagtacaagg | tggtggaaat | ccagccactg | 1440 |
| ggaatcgccc | caaccggcgc | taagagaaga | gtggtggaac | gcgagaaaag | agccgctgga | 1500 |
| ctgggagccc | tgttcctggg | atttcttgga | gccgccggaa | gcacaatggg | agccgcctct | 1560 |
| attaccctga | ccgtgcaggc | tagacagctg | ctgagcggaa | ttgtgcagca | gcagagcaac | 1620 |
| ctgctgagag | ccattgaagc | ccagcagcac | atgctgcagc | tgaccgtgtg | gggaatcaaa | 1680 |
| cagctgcagg | ccagagtgct | ggcccctgaa | agatacctga | aggaccagca | gctcctcggc | 1740 |
| atgtggggct | gttctggcaa | gctgatctgc | accaccaacg | tgccctggaa | cacctcctgg | 1800 |
| tccaacaaga | gcgaaaccga | catctgggac | aacatgacct | ggatgcagtg | ggagagagag | 1860 |
| atcagcaact | acaccgagac | aatctacaag | ctgctcgagg | acagccagaa | ccagcaagag | 1920 |
| agaaacgagc | aggacctgct | ggctctggac | agctggaata | gcctgtggaa | ctggttcagc | 1980 |
| atcaccaagt | ggctgtggta | catcaagatc | ttcatcatga | tcgtcggcgg | cctgatcggc | 2040 |
| ctgagaatcg | tgtttgccgt | gctgagcatc | gtgaacagag | tgcggcaggg | atacagccca | 2100 |
| ctgagcctgc | aaaccctgac | acctaatcct | agagagcccg | accggctgag | aggcatcgaa | 2160 |
| gaagaaggcg | gcgagcagga | tcgggacaga | tccatcgac | tggtgtccgg | cttcctgcct | 2220 |
| atcgtgtggg | acgatctgag | aagcctgtgc | ctgttcagct | accaccggct | gcgggatttt | 2280 |

```
ctgctgcttg ccgccagagt ggttgaactg ctgggcagat ctagcctgag gggcctgcaa    2340
agaggctggg aagtcctgaa gtacctgggc agcctggtgc agtattgggg cctcgagctg    2400
aaaaagagcg ccattagcct gttcgatacc ctggccattg ctgtggccga gggcaccgat    2460
agaatcattg agctgatcca gggcttctgc cgggccatca gaaacatccc caccagaatc    2520
agacagggct tcgaggccag cctgctgtga taaggatcct ctaga                   2565
```

<210> SEQ ID NO 64
<211> LENGTH: 2565
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
aagcttgtcg acgccaccat gggatctctg cagcctctgg ccacactgta cctgctggga     60
atgctggtgg ctagcgtgct ggccaaggga agctgtgggt cacagtgta ctacggcgtg     120 cccgtgtgga agaggccaa gaccacactg ttctgcgcct ccgatgccag agcctacgag     180
aaagaggtgc acaacatctg gccacacac gcctgtgtgc ctaccgatcc atctcctcaa     240
gagctggtgc tgggcaacgt gaccgagaac ttcaacatgt ggaagaacga catggtggac    300
cagatgcacg aggacatcat cagcctgtgg gaccagagcc tgaagccttg cgtgaagctg    360 accccctctgt gcgtgaccct gatctgttct gacgccaccg tgaaaaccgg caccgtggaa    420
gagatgaaga actgcagctt caacaccacc accgagatcc gggacaaaga gaagaaagag    480
tacgccctgt tctacaagcc cgacatcgtg cccctgagcg agacaaacaa caccagcgag    540
taccggctga tcaactgcaa cacctccgcc gtgacaatgg tgtgcccaa actgaccttc    600 gagcccattc ctatccacta ctgtgcccct gccggctacg ccatcctgaa gtgcaacgac    660
gagacattca cggcacagg cccctgcagc aatgtgtcca ccgtgcagtg tacccacggc    720
atcagaccag tgctgtctac ccagctgctg ctgaatggaa gcctggccga aaagaaatc    780 gtgatcagaa gcgagaacct gaccaacaac gccaagatca tcattgtgca tctgcacacc    840
cctgtggaaa tcgtgtgcac ccggcctctg aacctgaccc ggaagtctgt gcggatcggc    900
cctggccaga cattctatgc catgggcgat atcatcggcg acatcaagca ggcccactgc    960
aacatcagcg aggaaaagtg gaacgacacc ctgcagaaag tgggcatcga gctgcagaag    1020 cacttccccca caagaccat caagtacaac cagagcgctg cggcgacat ggaaatcacc    1080 acacacagct tcaattgtgg cggcgagttc ttctactgca ataccagcaa cctgttcaac    1140
gggacctaca tggcacccta catcagcacc aacagcagcg ccaactccac cagcaccatc    1200
actctgcagt gccggatcaa gatgatcatc aatatgtggc aaggcgtggg cagagctatg    1260
tacgcccctc ctatcgccgg caacatcacc gtcggagca atatcacagg cctgctgctc    1320
accagagatg gcggcaccaa tagcaacgag acagaaacct tcagacctgc cggcggagac    1380
atgagagaca attggagaag cgagctgtac aagtacaagg tggtggaaat ccagccactg    1440
ggaatcgccc caaccggcgc taagagaga gtggtggaac gcgagaaag agccgctgga    1500 ctgggagccc tgttcctggg atttcttgga gccgccggaa gcacaatggg agccgcctct    1560 attacccctga ccgtgcaggc tagacagctg ctgagcggaa ttgtgcagca gcagagcaac    1620
ctgctgagag ccattgaagc ccagcagcac atgctgcagc tgaccgtgtg gggaatcaaa    1680
cagctgcagg ccagagtgct ggccctggaa agatacctga aggaccagca gctcctcggc    1740
```

-continued

```
atgtggggct gttctggcaa gctgatctgc accaccaacg tgccctggaa cacctcctgg    1800
tccaacaaga gcgaaaccga catctgggac aacatgacct ggatgcagtg ggagagagag    1860
atcagcaact acaccgagac aatctacaag ctgctcgagg acagccagaa ccagcaagag    1920
agaaacgagc aggacctgct ggctctggac agctggaata gcctgtggaa ctggttcagc    1980
atcaccaagt ggctgtggta catcaagatc ttcatcatga tcgtcggcgg cctgatcggc    2040
ctgagaatcg tgtttgccgt gctgagcatc gtgaacagag tgcggcaggg atacagccca    2100
ctgagcctgc aaaccctgac acctaatcct agagagcccg accggctgag aggcatcgaa    2160
gaagaaggcg gcgagcagga tcgggacaga tccatcagac tggtgtccgg cttcctgcct    2220
atcgtgtggg acgatctgag aagcctgtgc ctgttcagct accaccggct gcgggatttt    2280
ctgctgcttg ccgccagagt ggttgaactg ctgggcagat ctagcctgag gggcctgcaa    2340
agaggctggg aagtcctgaa gtacctgggc agcctggtgc agtattgggg cctcgagctg    2400
aaaaagagcg ccattagcct gttcgatacc ctggccattg ctgtggccga gggcaccgat    2460
agaatcattg agctgatcca gggcttctgc cgggccatca gaaacatccc caccagaatc    2520
agacagggct tcgaggccag cctgctgtga taaggatcct ctaga                    2565
```

HIV-1 ENVELOPE STABILIZING MUTATIONS

This application is a U.S. National Stage application under 35 U.S.C. § 371 of International Patent Applications No. PCT/US2019/049662, filed on Sep. 5, 2019, which claims the benefit and priority of U.S. Application Ser. No. 62/739,727 filed Oct. 1, 2018. The contents of these applications are incorporated herein by reference in their entirety.

This invention was made with government support under Center for HIV/AIDS Vaccine Immunology-Immunogen Design grant UM1-AI100645 from the NIH, NIAID, Division of AIDS. The government has certain rights in the invention.

SEQUENCE LISTING

The instant application contains a Sequence Listing which has been submitted electronically in ASCII format and is hereby incorporated by reference in its entirety. Said ASCII copy, created on Oct. 28, 2019, is named 1234300_00324WO1_SL.txt and is 240,556 bytes in size.

TECHNICAL FIELD

The present technology relates in general, to a composition suitable for use in inducing anti-HIV-1 antibodies, and, in particular, to immunogenic compositions comprising envelope proteins and nucleic acids to induce cross-reactive neutralizing antibodies and increase their breadth of coverage. The technology also relates to methods of inducing such broadly neutralizing anti-HIV-1 antibodies using such compositions.

BACKGROUND

The development of a safe and effective HIV-1 vaccine is one of the highest priorities of the scientific community working on the HIV-1 epidemic. While anti-retroviral treatment (ART) has dramatically prolonged the lives of HIV-1 infected patients, ART is not routinely available in developing countries.

SUMMARY OF THE INVENTION

In certain aspects the technology provides envelopes designs comprising mutations which stabilize the envelope trimer. In certain embodiments, the stabilized trimer displays antigenic profile similar to the antigenic profile of a BMS-626529 bound trimer. In certain embodiments, the envelopes could comprise additional trimer stabilizing mutations, including but not limited to various SOSIP mutations.

In certain aspects the technology provides SOSIP and membrane bound mutant Envs that display antigenic profiles matching those of the BMS-626529 bound trimer. The BMS compound is known to stabilize state 1 of the virus bound Env and to prevent CD4 induced exposure of non-neutralizing epitopes. The relevant regions in or near the BMS compound's binding site include the β20-β21 loop, a site of CD4 contact playing an important role in CD4 triggering, and the layer-1 and layer-2 elements of gp120, which are involved in gp120 association with gp41. Layer-1 and layer-2 are known to play a role in mediating Env transitions.

In certain aspects the envelopes are designed by a three-pronged approach toward replicating the BMS compound's effect on the envelope trimer via mutation (specific amino acid changes). Specifically, we introduced space filling mutations in the BMS binding site, layer-1 and layer-2 blocking mutations, in addition to V3 locking mutations via increasing V1/V2 to V3 hydrophobic contacts. We began our screen and characterization in the BG505 SOSIP as this allows for a detailed evaluation of the mutation effects on specific sites. Our screening ultimately identified stabilizing residues in layers 1 and 2, in V1/V2, and in V3.

In certain embodiments, the locations of the mutations are depicted here on gp120 and labeled as F14, for layer-1 and layer-2 locking mutations, in the lime green and purple regions, and Vt8, for V1/V2 to V3 coupling mutations, in the green and red regions. See e.g. FIG. 1, FIG. 15. In non-limiting embodiments, inventive envelopes comprise F14 mutations (See e.g. FIG. 15), Vt8 mutations (See e.g. FIG. 15), or the combination F14/Ft8. In non-limiting embodiments, envelopes carrying these mutations are stable, as these mutations prevented CD4-induced transitions of the HIV-1 Env.

In certain embodiments, the stabilized envelopes have improved antigenic, and/or immunogenic properties.

In certain aspects the technology provides a recombinant HIV-1 envelope comprising a set of mutations selected from sets F1-F14, Vt1-Vt8 mutations in Ex. 1, FIG. 15, or any combination or subcombination within a set. In non-limiting embodiments, the envelopes could be designed to multimerize. Non-limiting embodiments of multimers include nano-particles based on ferritin. In certain embodiments, ferritin could be fused to the envelope or attached via a sortase reaction.

In certain embodiments, the envelope is a protomer, and the three protomers form a trimer stabilized by the presence of the mutations. In certain embodiments, the trimer could be soluble (e.g. but not limited to a SOSIP trimer) or membrane bound.

In certain embodiments, any envelope, including but not limited to BG505, CONs, JRFL, CH505 T/F, w.53. M5, M5G458mut, M11, CH848 10.17 DT, 19CV3 could be designed to carry mutations as described.

In certain embodiments, the envelopes could comprise additional stabilizing mutations, including but not limited to various SOSIP mutations.

In certain embodiments, the stabilized trimer displays an antigenic profile similar to the antigenic profile of a BMS-626529 bound trimer.

In certain embodiments, the envelope can be any of the recombinant proteins listed in Table 1, FIGS. 41-54. In certain embodiments, a nucleic acid encodes any of the recombinant envelopes of the technology, e.g. as listed in Table 1, FIGS. 41-54. In certain embodiments the envelopes are membrane bound gp160 envelope.

In certain embodiments, the envelope is provided as an immunogenic composition comprising any one of the envelopes of the technology and a carrier. In certain embodiments, the immunogenic composition further comprises an adjuvant.

In certain embodiments, the technology is a method of inducing an immune response in a subject comprising administering an immunogenic composition comprising any one of the stabilized envelopes of the technology. In certain embodiments, the composition is administered as a prime and/or a boost. In certain embodiments, the composition comprises nanoparticles.

In certain embodiments, the technology is a composition comprising a plurality of nanoparticles comprising a plurality of the envelopes/trimers of the technology. In non-limiting embodiments, the envelopes/trimers of the technology are multimeric when comprised in a nano-particle. In certain embodiments, the nanoparticle size is suitable for a delivery in a pharmaceutical composition. In non-liming embodiments the nanoparticles are ferritin based nanoparticles.

In certain embodiments, the technology provides compositions and methods for induction of immune response, for example cross-reactive (broadly) neutralizing (bn) Ab induction. In certain embodiments, the methods use compositions comprising newly designed HIV-1 immunogens which bind to precursors, and/or UCAs of different HIV-1 bnAbs. In certain embodiments, these are UCAs of V1V2 glycan and V3 glycan antibodies.

In certain aspects the technology provides a recombinant HIV-1 envelope comprising a set of mutations selected from sets F1-F14, sets Vt1-Vt8 mutations in FIG. 15, any combination of sets from F1-F14 and Vt1-Vt8, or subcombination of mutations within a set.

In certain embodiments the set of mutations is F14 (FIG. 15).

In certain embodiments the set of mutations is Vt8 (FIG. 15).

In certain embodiments the combination of sets of mutations is F14 and Vt8 (FIG. 15).

In certain aspects the technology provides a recombinant HIV-1 envelope, wherein the envelope is a protomer, and wherein three protomers form a trimer stabilized by the presence of the mutations. In certain embodiments, the trimer could comprise additional stabilizing mutations, including but not limited to various SOSIP mutations.

In certain embodiments the envelope is BG505, CONs, JRFL, CH505 T/F, w.53., CH505 M5, CH505 M5G458mut, CH505 M11, CH848 10.17 DT, or 19CV3. Any envelope could be modified to comprise the amino acid changes described.

In certain embodiments the envelope comprises additional stabilizing mutations.

In certain embodiments the envelope form stabilized trimers which display antigenic profile similar to the antigenic profile of a BMS-626529 bound trimer.

In certain aspects the technology provides a nucleic acid encoding any of the recombinant HIV-1 envelopes of the preceding claims.

In certain embodiments the nucleic acid encodes a recombinant HIV-1 envelope which is membrane bound gp160 envelope.

In certain aspects the technology provides an immunogenic composition comprising the recombinant HIV-1 envelope of any one of the preceding claims and a carrier.

In certain embodiments the immunogenic compositions further comprise an adjuvant.

In certain embodiments the immunogenic compositions comprise a recombinant HIV-1 envelope in a nanoparticle.

In certain aspects the technology provides an immunogenic composition comprising a nucleic acid encoding a recombinant HIV-1 envelope of the technology and a carrier.

In certain aspects the immunogenic compositions comprising a nucleic acid further comprise an adjuvant.

In certain aspects the technology provides methods of inducing an immune response in a subject comprising administering inventive envelopes, nucleic acid or immunogenic compositions. In certain embodiments the methods further comprise administering an adjuvant.

BRIEF DESCRIPTION OF THE DRAWINGS

FIGS. 1A-1F. Disrupting HIV-1 Env allostery to block CD4-induced conformational changes. FIG. 1A shows the HIV-1 Env SOSIP structure. Protomer to the left colored according to regions of allosteric control with BMS-626529 are represented as black spheres. Protomer to the right in matte color scheme depicts the location of Vt-series mutations (cyan spheres) and F-series mutations (blue spheres). BMS-626529 is depicted in stick representation. FIG. 1B shows the set of Vt8 residues. FIG. 1C shows the set of F14 mutations. Residue sidechains are represented as sticks with Cα atoms represented as cyan spheres. FIG. 1D shows the sequence alignment of BG505 WT (SEQ ID NOS 11-13 and 11-13, respectively, in order of appearance), F14 (SEQ ID NOS 14-16 and 14-16, respectively, in order of appearance), and F14/Vt8 (SEQ ID NOS 17-19 and 17-19, respectively, in order of appearance) with F14 mutations highlighted in blue and Vt8 mutations highlighted in cyan. Layers 1 and 2, the V1/V2 region, and β20-β21 are highlighted using the same color scheme as in FIG. 1A. FIG. 1E shows the binding antigenicity of BG505 SOSIP.664 and mutants. (left) Heatmap of bnAb binding responses, CD4 binding, and CD4 triggering. Values for CD4 binding and CD4 triggering are normalized to WT. (middle) Surface representation of a closed state SOSIP (PDB ID 5CEZ) and (right) an open state structure (PDB ID 5VN3). Colors identify antibody binding locations. FIG. 1F shows the sequences correspond to the aligned sequences in FIG. 1D. F14 and Vt8 mutations are in bolded.

FIG. 3A shows refined cryo-EM map of BG505 F14 SOSIP (gp120 in blue and gp41 in orange) bound to VRC01 (purple). FIG. 3B shows refined cryo-EM map of BG505 F14/Vt8 SOSIP (gp120 in blue and gp41 in orange) bound to VRC03 (red) and 10-1074 (green). FIG. 3C shows alignment of BG505 F14 SOSIP gp140 and BG505 F14/Vt8 SOSIP gp140. RMSD is for the alignment of gp120 and gp41 together. FIG. 3D shows cryo-EM map of the BG505 F14/Vt8 construct with fitted coordinates depicting the F14 mutation sites. FIG. 3E shows alignment of the BG505 F14/Vt8 SOSIP gp120 with the BG505 WT SOSIP gp120 showing the relative positions of the F14 mutations. FIG. 3F shows cryo-EM map of the BG505 F14/Vt8 construct with fitted coordinates depicting the Vt8 mutations. FIG. 3G shows alignment of the BG505 F14/Vt8 SOSIP gp120 with the BG505 WT SOSIP gp120 showing the relative positions of the Vt8 mutation sites. FIGS. 3H and 3I show transparent cryo-EM maps with ribbon representations of refined coordinates for BG505 F14 and F14/Vt8 SOSIPs (gp120 in blue and gp41 in orange) identifying gp41 HR1 helical extension. FIG. 3J shows alignment of gp41 three-helix bundle helix (residues 571-596) of BG505 F14 and F14/Vt8 SOSIPs (light orange and orange, respectively), an open state BG505 SOSIP (PDB ID 5VN3; green), and a closed state BG505 SOSIP (PDB ID 5CEZ; blue) identifying the extension of the gp41 HR1.

FIG. 4A (top) shows side view of VRC01 bound BG505 F14 SOSIP highlighting the location of interior conformational change. (bottom) Cryo-EM map (mesh) depicting position of gp41 residues K567 and W571. FIG. 4B (top) shows VRC01 bound BG505 F14 SOSIP apex facing trimer orientation highlighting the location of interior conformational change. (bottom) Cryo-EM map (mesh) depicting the apparent histidine triad. FIG. 4C shows side view of histidine triad relative to gp120. FIG. 4D shows top down view of histidine triad relative to gp120. FIGS. 4E & 4F show comparison between the BG505 F14/Vt8 and WT SOSIP layer-1/2 and gp41 HR1 conformations.

FIG. 5A shows alignment of closed (PDB ID 5CEZ), partially open (Open$_p$; PDB IDs 6CM3 and 6EDU), and open (PDB IDs 5VN3 and 5VN8) gp41 residues 597 to 664. FIG. 5B shows closed (PDB ID 5CEZ), partially open (PDB IDs 6CM3), and open (PDB IDs 5VN3) gp120 relative orientations from alignment of gp41 residues 597 to 664. (inset, left) Relative gp120 orientations from the gp41 597 to 664 residue alignment depicting the location of the K46/K490 hinge-point. FIG. 5C shows cartoon representations of gp120 (light blue), gp120 V1/V2 region (green), and gp41 (yellow) in the closed, partially open, and open states. Letters indicate location of centroids with arrows depicting vectors between centroids. The reduced size of the V1/V2 region in the partially open state represents rearrangement in this region while the green outline of V1/V2 in the open state indicates complete dissociation and disorder. FIG. 5D shows a graph depicting the gp41 W571-W596, W596-K46/K490 centroid, and K46/K490-gp120 centroid vector dihedral (x-axis) vs. W571-W596, W596-K46/K490 centroid, and K46/K490-gp120 centroid vector dihedral using the W596-K46/K490 centroid vector to W571-W596 projection. The BG505 F14 and F14/Vt8 structures are shown as green circles, with the closed state SOSIPs shown as blue dots, the PGT151 bound trimer domains shown as red Xs, the single CD4 bound domains as yellow Xs, and the open and partially open structures shown as orange triangles. The dashed line represents a linear fitting of the closed state SOSIP structure dihedrals. FIG. 5E shows principal components analysis of centroid vectors with principal component one and two eigenvalues plotted for each closed state SOSIP analyzed. Points are colored according to k-means clusters (k=3). FIG. 5F (left) shows alignment of the BG505 F14/Vt8 coordinates with the vFP7.04 bound BG505 DS SOSIP cryo-EM map (EMD-7621). (right) Alignment of the BG505 F14/Vt8 coordinates with the PDB ID 5CEZ map. W571 (sticks) aligns with density corresponding to 5CEZ V570 coordinates.

FIGS. 6A-6E show F14/Vt8 mutations stabilize native, membrane-bound Env. FIG. 6A shows the percentage of cells positive for binding of bnAbs N6, CH01, PGT125, and PGT145 to 293F cell surface expressed BG505, BG505 DS, and BG505 F14/Vt8 trimers. FIG. 6B shows a chart of the percentage of positive cells from each independent triggering experiment colored according to the first (red), second (green) and third (blue) experiments with BG505 represented as squares, BG505 DS represented as upward oriented triangles, and BG505 F14/Vt8 represented as downward oriented triangles. FIG. 6C shows single molecular FRET distribution for BG505 WT (dashed cyan line) and F14/Vt8 (solid blue line) virus Env. FIG. 6D shows single molecular FRET distribution for BG505 WT (dashed pink line) and F14/Vt8 (solid red line) virus Env in the presence of dodecameric CD4. FIG. 6E shows a mechanism for transition between a closed state trimer to an open state trimer.

FIG. 7A (left) shows a closed state SOSIP gp140 protomer (PDB ID 5CEZ) identifying key structural elements. (right) Elements of the closed state allosteric network including 20-21 (yellow), layer-1/2 (lime green/purple), V1/2/3 (green/red) and tryptophans 69, 112 and 427. FIG. 7B (left) shows an open state SOSIP gp140 protomer (PDB ID 5VN3) identifying key structural elements. (right) Elements of the open state allosteric network including 20-21 (yellow), layer-1/2 (lime green/purple), V1/2/3 (green/red) and tryptophans 69, 112 and 427.

FIG. 8A shows transfection cell supernatant BLI heatmap for F-series, Vt-series, WT SOSIP, WT gp120, BMS-626529 bound BG505 SOSIP, and controls binding to PGT145, 19B, 17B, and VRC01. Results plotted as mean response (nm) from triplicate transfection supernatant screening. FIG. 8B (chart) shows representative size exclusion chromatogram from the BG505 F14 SOSIP purification post PGT145 affinity column purification. (inset) Representative non-reducing SDS-PAGE gel for the BG505 SOSIP.664 mutants. Lanes 1-3 include protein marker, Ferritin, and Thyroglobulin, respectively. Lane 4 contains the SOSIP trimer. FIG. 8C shows negative-stain EM two-dimensional class averages for purified BG505 WT, F14, Vt8, and F14/Vt8 SOSIPs.

FIG. 9A (left) show dose response curves for binding of VRC01, PGT121m PG9, PGT145, PGT151, and VRC26 to the BG505 WT, F14, Vt8, and F14/Vt8 SOSIPs. Results plotted as mean response (nm) from duplicate experiments (mean standard error is within plotted points). Lines represent one-site specific fitting of BLI binding data in Prism. The envelopes are BG505 WT, F14, Vt8, and F14/Vt8 SOSIP. FIG. 9B shows representative SPR titrations for BG505 WT, F14, Vt8, and F14/Vt8 SOSIP binding to CD4-Ig. FIG. 9C shows representative CD4 triggering results for BG505 WT (red), F14 (orange), Vt8 (Vt8), and F14/Vt8 (blue) SOSIP. Responses are normalized to BG505 WT SOSIP.

FIGS. 10A and 10F show representative micrographs showing particles selected for refinement from BG505-F14-SOSIP (FIG. 10A), and BG505-F14/Vt8-SOSIP (FIG. 10F) datasets. FIGS. 10B and 10G show distribution of cisTEM score values assigned to particles extracted from datasets BG505-F14-SOSIP (FIG. 10B), and BG505-F14/Vt8-SOSIP (FIG. 10G). FIGS. 10C and 10H show cryo-EM map (solid) with superimposed shape mask (transparent) used during 3D refinement for BG505-F14-SOSIP (FIG. 10C), and BG505-F14/Vt8-SOSIP (FIG. 10H) datasets. FIGS. 10D and 10I show Fourier Shell Correlation curves between half-maps showing estimated resolution according to the 0.143-cutoff criteria (dashed line) for BG505-F14-SOSIP (FIG. 10D) and BG505-F14/Vt8-SOSIP (FIG. 10I) reconstructions. FIGS. 10E and 10J show local map resolution determined using RELION-3.0 for reconstructions of BG505-F14-SOSIP (FIG. 10E) and BG505-F14/Vt8-SOSIP (FIG. 10J).

FIG. 11A shows Cryo-EM map of the BG505 F14 construct with fitted coordinates depicting the F14 mutation sites. FIG. 11B shows alignment of the BG505 F14 SOSIP gp120 with the BG505 WT SOSIP (PDB ID 5CEZ) gp120 showing the relative positions of the F14 mutations. FIG. 11C shows Cryo-EM map (mesh) depicting H66, H72, and H565. FIG. 11D shows Cryo-EM map (mesh) depicting position of gp41 residues K567 and W571.

FIG. 12A show alignment of the BG505 F14/Vt8 coordinates with the vFP20.01 bound BG505 DS SOSIP cryo-EM map (EMD-7459). FIG. 12B shows alignment of the BG505 F14/Vt8 coordinates with the vFP16.02 bound BG505 DS SOSIP cryo-EM map (EMD-7460). FIG. 12C shows alignment of the BG505 F14/Vt8 coordinates with the vFP1.01 bound BG505 DS SOSIP cryo-EM map (EMD-7622).

FIG. 14A shows percentage of cells positive for binding of bnAbs N6, CH01, PGT125, and PGT145 to 293F cell surface expressed gp160 BG505, BG505 F14/Vt8, BG505 F14, and BG505 Vt8 trimers. FIG. 14B shows MFI data for binding of N6 to gp160 BG505, BG505 DS, and BG505 F14/Vt8 trimers. FIG. 14C shows MFI data for binding of N6 to gp160 BG505, BG505 F14/Vt8, BG505 F14, and BG505 Vt8 trimers. FIG. 14D shows percentage of cells positive for binding of non-bnAbs 17B and 19B to 293F cell surface expressed BG505, BG505 DS, and BG505 F14/Vt8 trimers in the presence and absence of sCD4 or CD4-Ig. FIG. 14E shows MFI data for binding of non-bnAbs 17B and 19B to 293F cell surface expressed BG505, BG505 DS, and BG505 F14/Vt8 trimers in the presence and absence of sCD4 and CD4-Ig. FIG. 14F shows percentage of cells positive for binding of non-bnAbs 17B and 19B to 293F cell surface expressed BG505, BG505 F14/Vt8, BG505 F14, and BG505 Vt8 trimers in the presence and absence of sCD4 or CD4-Ig. FIG. 14G shows MFI data for binding of non-bnAbs 17B and 19B to 293F cell surface expressed BG505, BG505 F14/Vt8, BG505 F14, and BG505 Vt8 trimers in the presence and absence of sCD4 and CD4-Ig.

FIG. 15 shows BG505 SOSIP Env Mutations (HXB2 numbering). * Design DS-SOSIP.4mut from Chuang, G.-Y. et al. Structure-Based Design of a Soluble Prefusion-Closed HIV-1 Env Trimer with Reduced CD4 Affinity and Improved Immunogenicity. Journal of Virology 91, doi:10.1128/JVI.02268-16 (2017).

FIG. 16 shows CD4 Binding Kinetics and Affinities.

FIG. 17 shows bnAb Binding Affinities ($K_d$ [nM]).

FIG. 18 shows Cryo-EM Data Collection and Refinement Statistics.

FIG. 19 shows Cell Surface Expressed Trimer—Percentage of Cells Binding.

FIG. 20 shows Cell Surface Expressed Trimer—MFI.

FIG. 21 shows smFRET Statistics.

FIG. 27A surface plasmon resonance responses for BG505 F14/Vt8 SOSIP trimer interacting with V3 targeting 3074 antibody unliganded (red), in the presence of sCD4 (blue), and in the presence of both sCD4 and the small molecule, open state inhibiting BMS-626529 (green). FIG. 27B shows surface plasmon resonance responses for BG505 F14/Vt8 SOSIP trimer interacting with V3 targeting 447-52D antibody unliganded (red), in the presence of sCD4 (blue), and in the presence of both sCD4 and the small molecule, open state inhibiting BMS-626529 (green). FIG. 27C shows surface plasmon resonance responses for BG505 F14/Vt8 SOSIP trimer interacting with V3 targeting F39F antibody unliganded (red), in the presence of sCD4 (blue), and in the presence of both sCD4 and the small molecule, open state inhibiting BMS-626529 (green).

FIG. 28A show surface plasmon resonance responses for BG505 F14 SOSIP trimer interacting with V3 targeting 3074 antibody unliganded (red), in the presence of sCD4 (blue), and in the presence of both sCD4 and the small molecule, open state inhibiting BMS-626529 (green). FIG. 28B shows surface plasmon resonance responses for BG505 F14 SOSIP trimer interacting with V3 targeting 447-52D antibody unliganded (red), in the presence of sCD4 (blue), and in the presence of both sCD4 and the small molecule, open state inhibiting BMS-626529 (green). FIG. 28C shows surface plasmon resonance responses for BG505 F14 SOSIP trimer interacting with V3 targeting F39F antibody unliganded (red), in the presence of sCD4 (blue), and in the presence of both sCD4 and the small molecule, open state inhibiting BMS-626529 (green).

FIG. 29A shows surface plasmon resonance responses for BG505 Vt8 SOSIP trimer interacting with V3 targeting 3074 antibody unliganded (red), in the presence of sCD4 (blue), and in the presence of both sCD4 and the small molecule, open state inhibiting BMS-626529 (green). FIG.

29B shows surface plasmon resonance responses for BG505 Vt8 SOSIP trimer interacting with V3 targeting 447-52D antibody unliganded (red), in the presence of sCD4 (blue), and in the presence of both sCD4 and the small molecule, open state inhibiting BMS-626529 (green). FIG. 29C shows surface plasmon resonance responses for BG505 Vt8 SOSIP trimer interacting with V3 targeting F39F antibody unliganded (red), in the presence of sCD4 (blue), and in the presence of both sCD4 and the small molecule, open state inhibiting BMS-626529 (green).

FIG. 30A shows surface plasmon resonance responses for BG505 SOSIP trimer interacting with V3 targeting 3074 antibody unliganded (red), in the presence of sCD4 (blue), and in the presence of both sCD4 and the small molecule, open state inhibiting BMS-626529 (green). FIG. 30B shows surface plasmon resonance responses for BG505 SOSIP trimer interacting with V3 targeting 447-52D antibody unliganded (red), in the presence of sCD4 (blue), and in the presence of both sCD4 and the small molecule, open state inhibiting BMS-626529 (green). FIG. 30C shows surface plasmon resonance responses for BG505 SOSIP trimer interacting with V3 targeting F39F antibody unliganded (red), in the presence of sCD4 (blue), and in the presence of both sCD4 and the small molecule, open state inhibiting BMS-626529 (green).

FIG. 31A shows CH848 DT gp160. FIG. 31B shows CH848 F14 DT gp160. FIG. 31C shows CH848 Vt8 DT gp160. FIG. 31D shows CH848 DT F14/Vt8 gp160. The results indicate that, while the CH848 DT gp160 open state is triggered, the stabilized Envs are not.

FIG. 32A shows CH848 DT gp160. FIG. 32B shows CH848 F14 DT gp160. FIG. 32C shows CH848 Vt8 DT gp160. FIG. 32D shows CH848 DT F14/Vt8 gp160. The results indicate that the F14 stabilization most closely recapitulates the WT CH848 DT gp160 Env antigenically.

FIG. 33A shows CH848 DT gp160. FIG. 33B shows CH848 F14 DT gp160. FIG. 33C shows CH848 Vt8 DT gp160. FIG. 33D shows CH848 DT F14/Vt8 gp160. Results indicate that the F14 construct displays an interaction profile consistent with the wild type CH848 DT gp160.

FIG. 36A shows serum neutralization results with standard deviation for BG505 WT and F14 SOSIP immunized rabbits for BG505, SF162.LS, and MW965.26 virus. FIG. 36B shows cartoon representation of the VRC34 blocking experiment. FIG. 36C shows VRC34 serum blocking ELISA results for BG505 WT SOSIP immunized rabbits with SOSIP captured by either PGT151 (red) or PGT145 (blue). FIG. 36D shows VRC34 serum blocking ELISA results for BG505 F14 SOSIP immunized rabbits with SOSIP captured by either PGT151 (red) or PGT145 (blue).

FIG. 38 shows neutralization data from Rabbit study R41.
FIG. 39 shows neutralization data from Rabbit study R47.
FIG. 40 shows neutralization data from Rabbit study R48
FIG. 41A-J show sequences of envelopes of the technology. Italicized amino acids at the N-terminus of the sequence show the signal peptide.

FIG. 42 shows an amino acid sequence alignment of envelopes CH0848.D0949.10.17_N133D_N138T.ch.SOSIP (italicized amino acids at the N-terminus of the sequence show the signal peptide), CH0848.D0949.10.17_N133D_N138T.ch.SOSIP.F14, and CH0848.D0949.10.17_N133D_N138T.ch.SOSIP.Vt8. F14 and Vt8 changes are indicated.

Figure 43:
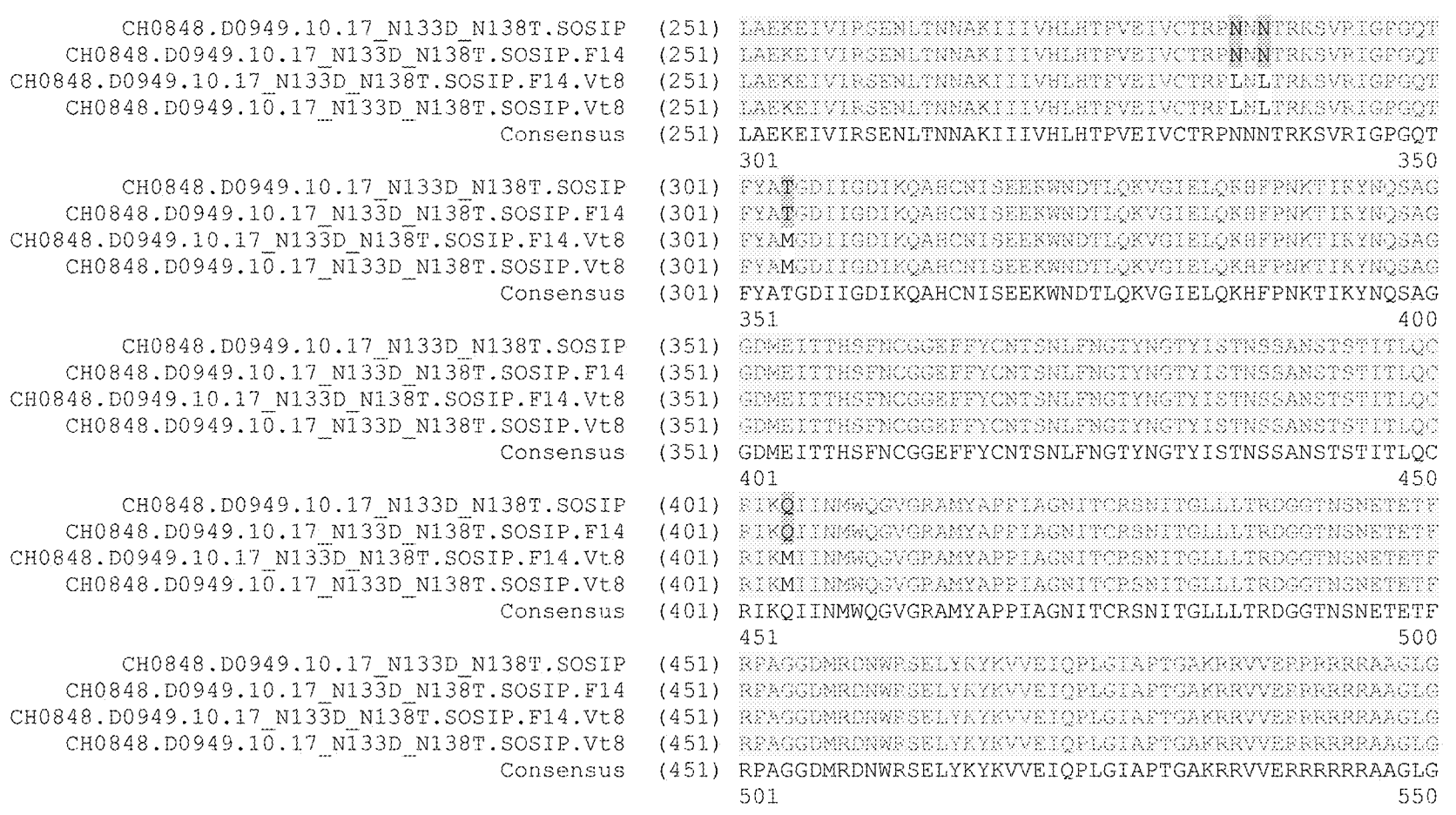

FIG. 43 shows an amino acid sequence alignment of envelopes CH0848.D0949.10.17_N133D_N138T.SOSIP (Italicized amino acids at the N-terminus of the sequence show the signal peptide); CH0848.D0949.10.17_N133D_N138T.SOSIP.F14; CH0848.D0949.10.17_N133D_N138T.SOSIP.F14.Vt8; CH0848.D0949.10.17_N133D_N138T.SOSIP.Vt8. F14 and Vt8 changes are indicated FIG. 44 shows a map of the positions of F14 and Vt8 mutations in the CH0848.D0949.10.17_N133D_N138T.SOSIP sequence.

FIGS. 45A-E show various sequences of envelopes of the technology. Italicized amino acids at the N-terminus of the sequence show the signal peptide.

FIGS. 46A-D show various sequences of envelopes of the technology. Amino acid sequences do not include the signal peptide.

FIGS. 47A-D show various sequences of envelopes of the technology. Amino acid sequences do not include the signal peptide.

FIG. 48 shows BG505gp160T332N_F14_VT8 amino acid sequence. Italicized amino acids at the N-terminus of the sequence show the signal peptide.

FIG. 49 shows amino acid sequence of CH505.M5gp160_G458Y_F14_VT8. Italicized amino acids at the N-terminus of the sequence show the signal peptide.

FIG. 50 shows amino acid sequence of CH0848.d949.10.17N133DN138Tgp160_F14_VT8. Italicized amino acids at the N-terminus of the sequence show the signal peptide.

FIG. 51 shows amino acid sequence of BG505gp140SOSIPT332N. Italicized amino acids at the N-terminus of the sequence show the signal peptide.

FIG. 52 shows amino acid sequence of HV1301509; CH0848.3.d1305.10.19gp160.

FIG. 53 shows amino acid sequence of HV1301580; CH848.3.D1305.10.19_D949V3.DS.SOSIP (19CV3).

FIG. 54 shows non-limiting embodiments of nucleic acid sequences of envelopes of the technology.

DETAILED DESCRIPTION OF THE INVENTION

Figures 1A, 1B, 1C:
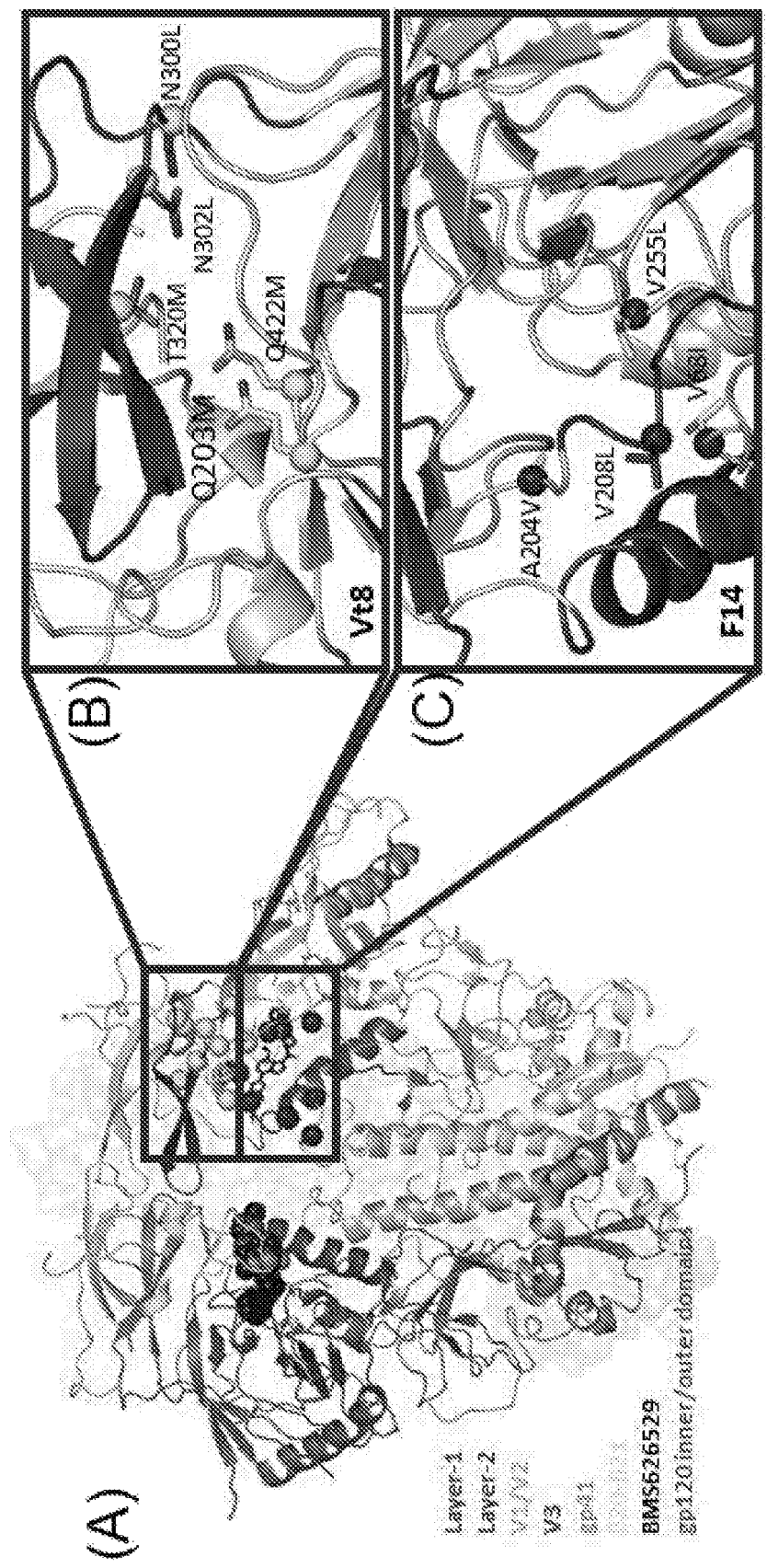

The development of a safe, highly efficacious prophylactic HIV-1 vaccine is of paramount importance for the control and prevention of HIV-1 infection. A major goal of HIV-1 vaccine development is the induction of broadly neutralizing antibodies (bnAbs) (Immunol. Rev. 254: 225-244, 2013). BnAbs are protective in rhesus macaques against SHIV challenge, but as yet, are not induced by current vaccines.

The technology provides methods of using these stabilized envelope immunogens.

In certain aspects, the technology provides compositions for immunizations to induce lineages of broad neutralizing antibodies. In certain embodiments, there is some variance in the immunization regimen; in some embodiments, the selection of HIV-1 envelopes may be grouped in various combinations of primes and boosts, either as nucleic acids, proteins, or combinations thereof. In certain embodiments the compositions are pharmaceutical compositions which are immunogenic. In certain embodiments, the compositions comprise amounts of envelopes which are therapeutic and/or immunogenic.

In one aspect the technology provides a composition for a prime boost immunization regimen comprising any one of the envelopes described herein, or any combination thereof wherein the envelope is a prime or boost immunogen. In certain embodiments the composition for a prime boost immunization regimen comprises one or more envelopes described herein.

In certain embodiments, the compositions contemplate nucleic acid, as DNA and/or RNA, or proteins immunogens either alone or in any combination. In certain embodiments, the methods contemplate genetic, as DNA and/or RNA, immunization either alone or in combination with envelope protein(s).

mRNA

In some embodiments the antigens are nucleic acids, including but not limited to mRNAs which could be modified and/or unmodified. See US Pub 20180028645A1, US Pub 20170369532, US Pub 20090286852, US Pub 20130111615, US Pub 20130197068, US Pub 20130261172, US Pub 20150038558, US Pub 20160032316, US Pub 20170043037, US Pub 20170327842, each content is incorporated by reference in its entirety. mRNAs delivered in LNP formulations have advantages over non-LNPs formulations. See US Pub 20180028645A1.

In certain embodiments the nucleic acid encoding an envelope is operably linked to a promoter inserted an expression vector. In certain aspects the compositions comprise a suitable carrier. In certain aspects the compositions comprise a suitable adjuvant.

In certain embodiments the induced immune response includes induction of antibodies, including but not limited to autologous and/or cross-reactive (broadly) neutralizing antibodies against HIV-1 envelope. Various assays that analyze whether an immunogenic composition induces an immune response, and the type of antibodies induced are known in the art and are also described herein.

In certain aspects the technology provides an expression vector comprising any of the nucleic acid sequences of the technology, wherein the nucleic acid is operably linked to a promoter. In certain aspects the technology provides an expression vector comprising a nucleic acid sequence encoding any of the polypeptides of the technology, wherein the nucleic acid is operably linked to a promoter. In certain embodiments, the nucleic acids are codon optimized for expression in a mammalian cell, in vivo or in vitro. In certain aspects the technology provides nucleic acids comprising any one of the nucleic acid sequences of technology. In certain aspects the technology provides nucleic acids consisting essentially of any one of the nucleic acid sequences of technology. In certain aspects the technology provides nucleic acids consisting of any one of the nucleic acid sequences of technology. In certain embodiments the nucleic acid of the technology, is operably linked to a promoter and is inserted in an expression vector. In certain aspects the technology provides an immunogenic composition comprising the expression vector.

In certain aspects the technology provides a composition comprising at least one of the nucleic acid sequences of the technology. In certain aspects the technology provides a composition comprising any one of the nucleic acid sequences of technology. In certain aspects the technology provides a composition comprising at least one nucleic acid sequence encoding any one of the polypeptides of the technology.

The envelope used in the compositions and methods of the technology can be a gp160, gp150, gp145, gp140, gp120, gp41, N-terminal deletion variants as described herein, cleavage resistant variants as described herein, or codon optimized sequences thereof. In certain embodiments the composition comprises envelopes as trimers. In certain embodiments, envelope proteins are multimerized, for example trimers are attached to a particle such that multiple copies of the trimer are attached and the multimerized envelope is prepared and formulated for immunization in a human. In certain embodiments, the compositions comprise envelopes, including but not limited to trimers as particulate, high-density array on liposomes or other particles, for example but not limited to nanoparticles. In some embodiments, the trimers are in a well ordered, near native like or closed conformation. In some embodiments the trimer compositions comprise a homogenous mix of native like trimers. In some embodiments the trimer compositions comprise at least 85%, 90%, 95% native like trimers.

In certain embodiments the envelope is any of the forms of HIV-1 envelope. In certain embodiments the envelope is gp120, gp140, gp145 (i.e. with a transmembrane), gp150. In certain embodiments, gp140 designed to form a stable trimer and various non-limiting examples of sequences of stable trimers are known. In certain embodiments envelope protomers form a trimer which is not a SOSIP timer. In certain embodiment the trimer is a SOSIP based trimer wherein each protomer comprises additional modifications. In certain embodiments, envelope trimers are recombinantly produced. In certain embodiments, envelope trimers are purified from cellular recombinant fractions by antibody binding and reconstituted in lipid comprising formulations. See for example WO2015/127108 titled "Trimeric HIV-1 envelopes and uses thereof", See also WO/2017151801 each content is herein incorporated by reference in its entirety. In certain embodiments the envelopes of the technology are engineered and comprise non-naturally occurring modifications.

In certain embodiments, the envelope is in a liposome. In certain embodiments the envelope comprises a transmembrane domain with a cytoplasmic tail embedded in a liposome. In certain embodiments, the nucleic acid comprises a nucleic acid sequence which encodes a gp120, gp140, gp145, gp150, gp160.

In certain embodiments, where the nucleic acids are operably linked to a promoter and inserted in a vector, the vector is any suitable vector. Non-limiting examples include VSV, replicating rAdenovirus type 4, MVA, Chimp adenovirus vectors, pox vectors, and the like. In certain embodiments, the nucleic acids are administered in NanoTaxi block polymer nanospheres. In certain embodiments, the composition and methods comprise an adjuvant. Non-limiting examples include, 3M052, AS01 B, AS01 E, gla/SE, alum, Poly I poly C (poly IC), polyIC/long chain (LC) TLR agonists, TLR7/8 and 9 agonists, or a combination of TLR7/8 and TLR9 agonists (see Moody et al. (2014) J. Virol. March 2014 vol. 88 no. 6 3329-3339), or any other adjuvant. Non-limiting examples of TLR7/8 agonist include TLR7/8 ligands, Gardiquimod, Imiquimod and R848 (resiquimod). A non-limiting embodiment of a combination of TLR7/8 and TLR9 agonist comprises R848 and oCpG in STS (see Moody et al. (2014) J. Virol. March 2014 vol. 88 no. 6 3329-3339).

In certain aspects the technology provides a cell comprising a nucleic acid encoding any one of the envelopes of the technology suitable for recombinant expression. In certain aspects, the technology provides a clonally derived population of cells encoding any one of the envelopes of the technology suitable for recombinant expression. In certain aspects, the technology provides a sable pool of cells encoding any one of the envelopes of the technology suitable for recombinant expression.

In certain aspects, the technology provides a recombinant HIV-1 envelope polypeptide as described here, wherein the polypeptide is a non-naturally occurring protomer designed to form an envelope trimer. The technology also provides nucleic acids encoding these recombinant polypeptides. Non-limiting examples of amino acids and nucleic acid of such protomers are shown in FIGS. 41-51.

In certain aspects the technology provides a recombinant trimer comprising three identical protomers of an envelope. In certain aspects the technology provides an immunogenic composition comprising the recombinant trimer and a carrier, wherein the trimer comprises three identical protomers of an HIV-1 envelope as described herein. In certain aspects the technology provides an immunogenic composition comprising nucleic acid encoding these recombinant HIV-1 envelope and a carrier.

Sequences/Clones

Described herein are nucleic and amino acids sequences of HIV-1 envelopes. The sequences for use as immunogens are in any suitable form. In certain embodiments, the described HIV-1 envelope sequences are gp160s. In certain embodiments, the described HIV-1 envelope sequences are gp120s. Other sequences, for example but not limited to stable SOSIP trimer designs, gp145s, gp140s, both cleaved and uncleaved, gp140 Envs with the deletion of the cleavage (C) site, fusion (F) and immunodominant (I) region in gp41—named as gp140ΔCFI (gp140CFI), gp140 Envs with the deletion of only the cleavage (C) site and fusion (F) domain—named as gp140ΔCF (gp140CF), gp140 Envs with the deletion of only the cleavage (C)—named gp140ΔC (gp140C) (See e.g. Liao et al. Virology 2006, 353, 268-282), gp150s, gp41s, which are readily derived from the nucleic acid and amino acid gp160 sequences. In certain embodiments the nucleic acid sequences are codon optimized for optimal expression in a host cell, for example a mammalian cell, a rBCG cell or any other suitable expression system.

An HIV-1 envelope has various structurally defined fragments/forms: gp160; gp140—including cleaved gp140 and uncleaved gp140 (gp140C), gp140CF, or gp140CFI; gp120 and gp41. A skilled artisan appreciates that these fragments/forms are defined not necessarily by their crystal structure, but by their design and bounds within the full length of the gp160 envelope. While the specific consecutive amino acid sequences of envelopes from different strains are different, the bounds and design of these forms are well known and characterized in the art.

For example, it is well known in the art that during its transport to the cell surface, the gp160 polypeptide is processed and proteolytically cleaved to gp120 and gp41 proteins. Cleavages of gp160 to gp120 and gp41 occurs at a conserved cleavage site "REKR (SEQ ID NO: 1)." See Chakrabarti et al. Journal of Virology vol. 76, pp. 5357-5368 (2002) see for example FIG. 1, and Second paragraph in the Introduction on p. 5357; Binley et al. Journal of Virology vol. 76, pp. 2606-2616 (2002) for example at Abstract; Gao et al. Journal of Virology vol. 79, pp. 1154-1163 (2005); Liao et al. Virology vol. 353(2): 268-282 (2006).

The role of the furin cleavage site was well understood both in terms of improving cleave efficiency, see Binley et al. supra, and eliminating cleavage, see Bosch and Pawlita, Virology 64 (5):2337-2344 (1990); Guo et al. Virology 174: 217-224 (1990); McCune et al. Cell 53:55-67 (1988); Liao et al. J Virol. April; 87(8):4185-201 (2013).

Likewise, the design of gp140 envelope forms is also well known in the art, along with the various specific changes which give rise to the gp140C (uncleaved envelope), gp140CF and gp140CFI forms. Envelope gp140 forms are designed by introducing a stop codon within the gp41 sequence. See Chakrabarti et al. at FIG. 1.

Envelope gp140C refers to a gp140 HIV-1 envelope design with a functional deletion of the cleavage (C) site, so that the gp140 envelope is not cleaved at the furin cleavage site. The specification describes cleaved and uncleaved forms, and various furin cleavage site modifications that prevent envelope cleavage are known in the art. In some embodiments of the gp140C form, two of the R residues in and near the furin cleavage site are changed to E, e.g., RRVVEREKR (SEQ ID NO: 2) is changed to ERVVEREKE (SEQ ID NO: 3), and is one example of an uncleaved gp140 form. Another example is the gp140C form which has the REKR (SEQ ID NO: 1) site changed to SEKS (SEQ ID NO: 4). See supra for references.

Envelope gp140CF refers to a gp140 HIV-1 envelope design with a deletion of the cleavage (C) site and fusion (F) region. Envelope gp140CFI refers to a gp140 HIV-1 envelope design with a deletion of the cleavage (C) site, fusion (F) and immunodominant (I) region in gp41. See Chakrabarti et al. Journal of Virology vol. 76, pp. 5357-5368 (2002) see for example FIG. 1, and Second paragraph in the Introduction on p. 5357; Binley et al. Journal of Virology vol. 76, pp. 2606-2616 (2002) for example at Abstract; Gao et al. Journal of Virology vol. 79, pp. 1154-1163 (2005); Liao et al. Virology vol. 353(2): 268-282 (2006).

In certain embodiments, the envelope design in accordance with the present technology involves deletion of residues (e.g., 5-11, 5, 6, 7, 8, 9, 10, or 11 amino acids) at the N-terminus. For delta N-terminal design, amino acid residues ranging from 4 residues or even fewer to 14 residues or even more are deleted. These residues are between the maturation (signal peptide, usually ending with CXX, X can be any amino acid) and "VPVXXXX . . . ". In case of CH505 T/F Env as an example, 8 amino acids (italicized and underlined in the below sequence) were deleted: MRVMGIQRNYPQWWIWSMLGFWMLMIC NGMWVTVYYGVPVWKEAKTTLFCASDA KAYEKEVHNVWATHACVPTDPNPQE . . . (SEQ ID NO: 5) (rest of envelope sequence is indicated as " . . . "). In other embodiments, the delta N-design described for CH505 T/F envelope can be used to make delta N-designs of other CH505 envelopes. In certain embodiments, the technology relates generally to an immunogen, gp160, gp120 or gp140, without an N-terminal Herpes Simplex gD tag substituted for amino acids of the N-terminus of gp120, with an HIV leader sequence (or other leader sequence), and without the original about 4 to about 25, for example 4, 5, 6, 7, 8, 9, 10, 11, 12, 13, 14, 15, 16, 17, 18, 19, 20, 21, 22, 23, 24, 25 amino acids of the N-terminus of the envelope (e.g. gp120). See WO2013/006688, e.g. at pages 10-12, the contents of which publication is hereby incorporated by reference in its entirety.

The general strategy of deletion of N-terminal amino acids of envelopes results in proteins, for example gp120s, expressed in mammalian cells that are primarily monomeric, as opposed to dimeric, and, therefore, solves the production and scalability problem of commercial gp120 Env vaccine production. In other embodiments, the amino acid deletions at the N-terminus result in increased immunogenicity of the envelopes.

In certain aspects, the technology provides composition and methods which use a selection of sequential Envs, as gp120s, gp140s cleaved and uncleaved, gp145s, gp150s and gp160s, stabilized and/or multimerized trimers, as proteins, DNAs, RNAs, or any combination thereof, administered as primes and boosts to elicit immune response. Envs as proteins would be co-administered with nucleic acid vectors containing Envs to amplify antibody induction. In certain embodiments, the compositions and methods include any immunogenic HIV-1 sequences to give the best coverage for T cell help and cytotoxic T cell induction. In certain embodiments, the compositions and methods include mosaic and/or consensus HIV-1 genes to give the best coverage for T cell help and cytotoxic T cell induction. In certain embodiments, the compositions and methods include mosaic group M and/or consensus genes to give the best coverage for T cell help and cytotoxic T cell induction. In some embodiments, the mosaic genes are any suitable gene from the HIV-1 genome. In some embodiments, the mosaic genes are Env genes, Gag genes, Pol genes, Nef genes, or any combination thereof. See e.g. U.S. Pat. No. 7,951,377. In some embodiments the mosaic genes are bivalent mosaics. In some embodiments the mosaic genes are trivalent. In some embodiments, the mosaic genes are administered in a suitable vector with each immunization with Env gene inserts in a suitable vector and/or as a protein. In some embodiments, the mosaic genes, for example as bivalent mosaic Gag group M consensus genes, are administered in a suitable vector, for example but not limited to HSV2, would be administered with each immunization with Env gene inserts in a suitable vector, for example but not limited to HSV-2.

In certain aspects the technology provides compositions and methods of Env genetic immunization either alone or with Env proteins to recreate the swarms of evolved viruses that have led to bnAb induction. Nucleotide-based vaccines offer a flexible vector format to immunize against virtually any protein antigen. Currently, two types of genetic vaccination are available for testing-DNAs and mRNAs.

In certain aspects the technology contemplates using immunogenic compositions wherein immunogens are delivered as DNA. See Graham B S, Enama M E, Nason M C, Gordon I J, Peel S A, et al. (2013) DNA Vaccine Delivered by a Needle-Free Injection Device Improves Potency of Priming for Antibody and CD8+ T-Cell Responses after rAd5 Boost in a Randomized Clinical Trial. PLoS ONE 8(4): e59340, page 9. Various technologies for delivery of nucleic acids, as DNA and/or RNA, so as to elicit immune response, both T-cell and humoral responses, are known in the art and are under developments. In certain embodiments, DNA can be delivered as naked DNA. In certain embodiments, DNA is formulated for delivery by a gene gun. In certain embodiments, DNA is administered by electroporation, or by a needle-free injection technologies, for example but not limited to Biojector® device. In certain embodiments, the DNA is inserted in vectors. The DNA is delivered using a suitable vector for expression in mammalian cells. In certain embodiments the nucleic acids encoding the envelopes are optimized for expression. In certain embodiments DNA is optimized, e.g. codon optimized, for expression. In certain embodiments the nucleic acids are optimized for expression in vectors and/or in mammalian cells. In non-limiting embodiments these are bacterially derived vectors, adenovirus based vectors, rAdenovirus (e.g. Barouch D H, et al. Nature Med. 16: 319-23, 2010), recombinant mycobacteria (e.g. rBCG or *M. smegmatis*) (Yu, J S et al. Clinical Vaccine Immunol. 14: 886-093,2007; ibid 13: 1204-11,2006), and recombinant vaccinia type of vectors (Santra S. Nature Med. 16: 324-8, 2010), for example but not limited to ALVAC, replicating (Kibler K V et al., PLoS One 6: e25674, 2011 nov 9.) and non-replicating (Perreau M et al. J. virology 85: 9854-62, 2011) NYVAC, modified vaccinia Ankara (MVA)), adeno-associated virus, Venezuelan equine encephalitis (VEE) replicons, Herpes Simplex Virus vectors, and other suitable vectors.

In certain aspects the technology contemplates using immunogenic compositions wherein immunogens are delivered as DNA or RNA in suitable formulations. Various technologies which contemplate using DNA or RNA, or may use complexes of nucleic acid molecules and other entities to be used in immunization. In certain embodiments, DNA or RNA is administered as nanoparticles consisting of low dose antigen-encoding DNA formulated with a block copolymer (amphiphilic block copolymer 704). See Cany et al., Journal of Hepatology 2011 vol. 54j 115-121; Amaoty et al., Chapter 17 in Yves Bigot (ed.), Mobile Genetic Elements: Protocols and Genomic Applications, Methods in Molecular Biology, vol. 859, pp 293-305 (2012); Arnaoty et al. (2013) Mol Genet Genomics. 2013 August; 288(7-8): 347-63. Nanocarrier technologies called Nanotaxi® for immunogenic macromolecules (DNA, RNA, Protein) delivery are under development. See for example technologies developed by incellart.

mRNA

In some embodiments the antigens are nucleic acids, including but not limited to mRNAs which could be modified and/or unmodified. See US Pub 20180028645A1, US Pub 20170369532, US Pub 20090286852, US Pub 20130111615, US Pub 20130197068, US Pub 20130261172, US Pub 20150038558, US Pub 20160032316, US Pub 20170043037, US Pub 20170327842, each content is incorporated by reference in its entirety. mRNAs delivered in LNP formulations have advantages over non-LNPs formulations. See US Pub 20180028645A1.

In certain aspects the technology contemplates using immunogenic compositions wherein immunogens are delivered as recombinant proteins. Various methods for production and purification of recombinant proteins, including trimers such as but not limited to SOSIP based trimers, suitable for use in immunization are known in the art. In certain embodiments recombinant proteins are produced in CHO cells.

It is readily understood that the envelope glycoproteins referenced in various examples and figures comprise a signal/leader sequence. It is well known in the art that HIV-1 envelope glycoprotein is a secretory protein with a signal or leader peptide sequence that is removed during processing and recombinant expression (without removal of the signal peptide, the protein is not secreted). See for example Li et al. Control of expression, glycosylation, and secretion of HIV-1 gp120 by homologous and heterologous signal sequences. Virology 204(1):266-78 (1994) ("Li et al. 1994"), at first paragraph, and Li et al. Effects of inefficient cleavage of the signal sequence of HIV-1 gp120 on its association with calnexin, folding, and intracellular transport. PNAS 93:9606-9611 (1996) ("Li et al. 1996"), at 9609. Any suitable signal sequence could be used. In some embodiments the leader sequence is the endogenous leader sequence. Most of the gp120 and gp160 amino acid sequences include the endogenous leader sequence. In other non-limiting examples the leaders sequence is human Tissue Plasminogen Activator (TPA) sequence, human CD5 leader sequence (e.g. MPMGSLQPLATLYLLGMLVASVLA (SEQ ID NO: 6). Most of the chimeric designs include CD5 leader sequence. A skilled artisan appreciates that when used as immunogens, and for example when recombinantly produced, the amino acid sequences of these proteins do not comprise the leader peptide sequences.

The immunogenic envelopes can also be administered as a protein prime and/or boost alone or in combination with a variety of nucleic acid envelope primes (e.g., HIV-1 Envs delivered as DNA expressed in viral or bacterial vectors).

Dosing of proteins and nucleic acids can be readily determined by a skilled artisan. A single dose of nucleic acid can range from a few nanograms (ng) to a few micrograms (µg) or milligram of a single immunogenic nucleic acid. Recombinant protein dose can range from a few µg micrograms to a few hundred micrograms, or milligrams of a single immunogenic polypeptide.

Administration: The compositions can be formulated with appropriate carriers using known techniques to yield compositions suitable for various routes of administration. In certain embodiments the compositions are delivered via intramuscular (IM), via subcutaneous, via intravenous, via nasal, via mucosal routes, or any other suitable route of immunization.

The compositions can be formulated with appropriate carriers and adjuvants using techniques to yield compositions suitable for immunization. The compositions can include an adjuvant, such as, for example but not limited to, alum, poly IC, MF-59 or other squalene-based adjuvant, AS01B, or other liposomal based adjuvant suitable for protein or nucleic acid immunization. In certain embodiments, the adjuvant is GSK AS01E adjuvant containing MPL and QS21. This adjuvant has been shown by GSK to be as potent as the similar adjuvant AS01B but to be less reactogenic using HBsAg as vaccine antigen [Leroux-Roels et al., IABS Conference, April 2013]. In certain embodiments, TLR agonists are used as adjuvants. In other embodiment, adjuvants which break immune tolerance are included in the immunogenic compositions.

In certain embodiments, the compositions and methods comprise any suitable agent or immune modulation which could modulate mechanisms of host immune tolerance and release of the induced antibodies. In non-limiting embodiments modulation includes PD-1 blockade; T regulatory cell depletion; CD40L hyperstimulation; soluble antigen administration, wherein the soluble antigen is designed such that the soluble agent eliminates B cells targeting dominant epitopes, or a combination thereof. In certain embodiments, an immunomodulatory agent is administered in at time and in an amount sufficient for transient modulation of the subject's immune response so as to induce an immune response which comprises broad neutralizing antibodies against HIV-1 envelope. Non-limiting examples of such agents is any one of the agents described herein: e.g. chloroquine (CQ), PTP1B Inhibitor—CAS 765317-72-4—Calbiochem or MSI 1436 clodronate or any other bisphosphonate; a Foxol inhibitor, e.g. 344355|Foxol Inhibitor, AS1842856—Calbiochem; Gleevac, anti-CD25 antibody, anti-CCR4 Ab, an agent which binds to a B cell receptor for a dominant HIV-1 envelope epitope, or any combination thereof. In non-limiting embodiments, the modulation includes administering an anti-CTLA4 antibody, OX-40 agonists, or a combination thereof. Non-limiting examples are of CTLA-1 antibody are ipilimumab and tremelimumab. In certain embodiments, the methods comprise administering a second immunomodulatory agent, wherein the second and first immunomodulatory agents are different.

Multimeric Envelopes

Presentation of antigens as particulates reduces the B cell receptor affinity necessary for signal transduction and expansion (See Baptista et al. EMBO J. 2000 Feb. 15; 19(4): 513-520). Displaying multiple copies of the antigen on a particle provides an avidity effect that can overcome the low affinity between the antigen and B cell receptor. The initial B cell receptor specific for pathogens can be low affinity, which precludes vaccines from being able to stimulate and expand B cells of interest. In particular, very few naïve B cells from which HIV-1 broadly neutralizing antibodies arise can bind to soluble HIV-1 Envelope. Provided are envelopes, including but not limited to trimers as particulate, high-density array on liposomes or other particles, for example but not limited to nanoparticles. See e.g. He et al. Nature Communications 7, Article number: 12041 (2016), doi:10.1038/ncomms12041; Bamrungsap et al. Nanomedicine, 2012, 7 (8), 1253-1271.

To improve the interaction between the naïve B cell receptor and immunogens, envelope designed can be created to wherein the envelope is presented on particles, e.g. but not limited to nanoparticle. In some embodiments, the HIV-1 Envelope trimer could be fused to ferritin. Ferritin protein self assembles into a small nanoparticle with three fold axis of symmetry. At these axis the envelope protein is fused. Therefore the assembly of the three-fold axis also clusters three HIV-1 envelope protomers together to form an envelope trimer. Each ferritin particle has 8 axises which equates to 8 trimers being displayed per particle. See e.g. Sliepen et al. Retrovirology 201512:82, DOI: 10.1186/s12977-015-0210-4; See also FIG. 24H-J.

Another approach to multimerize expression constructs uses *staphylococcus* Sortase A transpeptidase ligation to conjugate inventive envelope trimers to cholesterol. The trimers can then be embedded into liposomes via the conjugated cholesterol. To conjugate the trimer to cholesterol either a C-terminal LPXTG tag (SEQ ID NO: 7) or a N-terminal pentaglycine repeat tag (SEQ ID NO: 8) is added to the CH505 envelope trimer gene. Cholesterol is also synthesized with these two tags. Sortase A is then used to covalently bond the tagged envelope to the cholesterol. The sortase A-tagged trimer protein can also be used to conjugate the trimer to other peptides, proteins, or fluorescent labels. In non-limiting embodiments, the sortase A tagged trimers are conjugated to ferritin to form nanoparticles.

The technology provides design of envelopes and trimer designs wherein the envelope comprises a linker which permits addition of a lipid, such as but not limited to cholesterol, via a Sortase A reaction. See e.g. Tsukiji, S. and Nagamune, T. (2009), Sortase-Mediated Ligation: A Gift from Gram-Positive Bacteria to Protein Engineering. ChemBioChem, 10: 787-798. doi:10.1002/cbic.200800724; Proft, T. Sortase-mediated protein ligation: an emerging biotechnology tool for protein modification and immobilisation. Biotechnol Lett (2010) 32: 1. doi:10.1007/s10529-009-0116-0; Lena Schmohl, Dirk Schwarzer, Sortase-mediated ligations for the site-specific modification of proteins, Current Opinion in Chemical Biology, Volume 22, October 2014, Pages 122-128, ISSN 1367-5931, dx.doi.org/10.1016/j.cbpa.2014.09.020; Tabata et al. Anticancer Res. 2015 August; 35(8):4411-7; Pritz et al. *J. Org. Chem.* 2007, 72, 3909-3912.

The lipid modified envelopes and trimers could be formulated as liposomes. Any suitable liposome composition is contemplated.

Figure 24A:
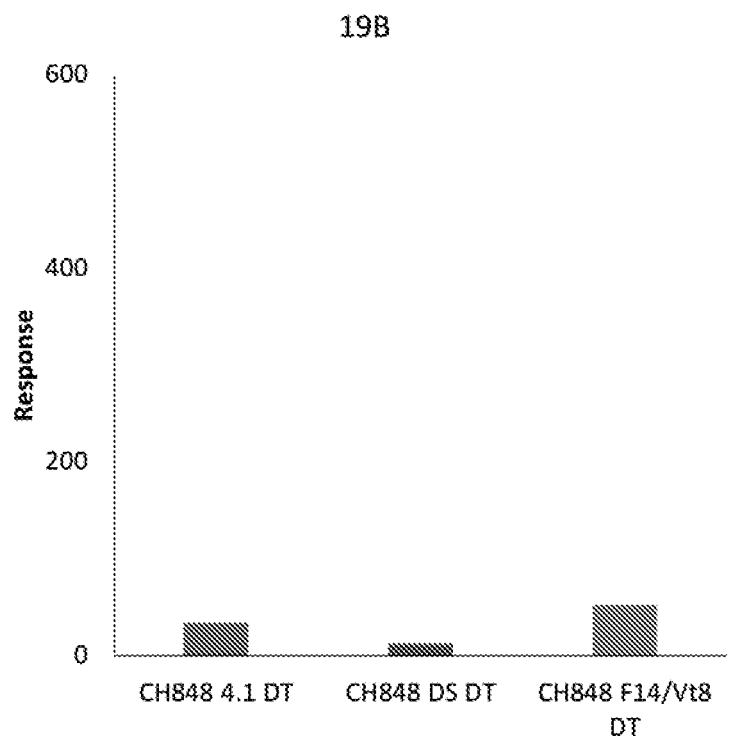
FIG. 24A shows surface plasmon resonance response values for CH848.10.17 DT F14/Vt8 SOSIP, CH848.10.17 DT DS SOSIP and CH848.10.17 DT 4.1 SOSIP trimers comparing the interaction of each with the open state, variable region 3 (V3) targeting 19B antibody.
Figure 24B:
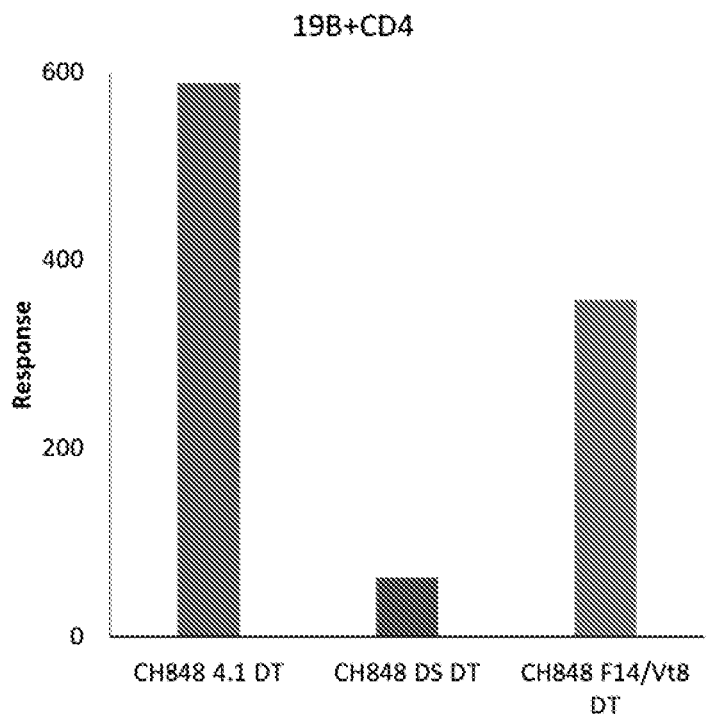
FIG. 24B shows surface plasmon resonance response values for CH848.10.17 DT F14/Vt8 SOSIP, CH848.10.17 DT DS SOSIP and CH848.10.17 DT 4.1 SOSIP trimers in the presence of saturating, open state triggering sCD4 comparing the interaction of each with the open state, variable region 3 (V3) targeting 19B antibody.

Non-limiting embodiments of envelope designs for use in Sortase A reaction are shown in FIG. 24 B-D in WO2017151801, incorporated by reference in its entirety.

Additional sortase linkers could be used so long as their position allows multimerization of the envelopes.

Table 1 shows a summary of sequences. In non-limiting embodiments any of the sequences and designs disclosed in WO2014/042669, WO/2017151801, WO/2017152146 and WO/2018161049, which contents are incorporated by reference their entirety, could comprise additional stabilizing mutations, combinations and/or subsets of mutations described herein.

TABLE 1

| Name | Amino acid or Nucleic | Design | FIG./note |
|---|---|---|---|
| CH0848.D0949.10.17_N133D_N138T | | | |
| >CH0848.D0949.10.17_N133D_N138T.ch.SOSIP.Vt8 | Both | ch.SOSIP.Vt8 | FIG. 41A and 41B FIG. 45A 46A |
| >CH0848.D0949.10.17_N133D_N138T.SOSIP.Vt8 | Both | SOSIP.Vt8 | FIG. 41C and D FIG. 45B |
| >CH0848.D0949.10.17_N133D_N138T.ch.SOSIP.F14 | Both | ch.SOSIP.F14 | FIG. 41E and F FIG. 45C 46B |
| >CH0848.D0949.10.17_N133D_N138T.SOSIP.F14 | both | SOSIP.F14 | FIG. 41I and J FIG. 45E |
| >CH848.3.D0949.10.17N133DN138Tchim.SOSIP.F14Vt8 | aa nt | chim.SOSIP.F14 Vt8 | FIG. 46C FIG. 46D |
| >CH0848.D0949.10.17_N133D_N138T.SOSIP.F14.Vt8 | both | SOSIP.F14.Vt8 | FIG. 41G and H FIG. 45D |
| >CH0848.d949.10.17N133DN138Tgp160_F14_VT8 For additional non-limiting embodiments of CH848 sequences also WO/2017152146 and WO/2018161049 BG505 | aa | gp160_F14_VT8 | FIG. 50 |
| BG505gp160T332N_F14_VT8 | aa | | FIG. 48 |
| >BG505gp140SOSIPT332N 19CV3 | aa | | FIG. 51 |
| HV1301580; CH848.3.D1305.10.19_D949V3.DS.SOSIP (19CV3) CH505 | | | FIG. 53 |
| CH505 sequences (non-limiting embodiments) T/F, M5, M6, M11 and selections disclosed in WO2014/042669 Sequences and selections disclosed in WO2017/151801 G458Mut | | | |
| >CH505.M5gp160_G458Y_F14_VT8 | aa | | 49 |
| >CH0505M5G458Ychim.6R.SOSIP.664 | aa | | 47A (G458Y position is underlined) |
| >CH0505M5G458Ychim.6R.SOSIP.Vt8 | aa | Vt8 | 47B (G458Y position is underlined) |

TABLE 1-continued

| Name | Amino acid or Nucleic | Design | FIG./note |
|---|---|---|---|
| >CH0505M5G458Ychim.6R.SOSIP.F14 | aa | F14 | 47C (G458Y position is underlined) |
| >CH0505M5G458Ychim.6R.SOSIP.F14Vt8 | aa | F14Vt8 | 47D (G458Y position is underlined) |

Any of the designs could be made chimeric (including gp41 from BG505) and/or non-chimeric. Any of the designs described herein could also be designed to exclude SOSIP mutations.

Example 1

Allosteric control of Env conformational states. In order to design a non-covalently stabilized soluble SOSIP and membrane bound Env, we first examined the BMS-626529 stabilization of the Env SOSIP. The BMS-626529 compound prevents transitions from the prefusion closed state to the open state and blocks CD4 interaction, therefore eliminating exposure of non-neutralizing antibody epitope exposure. Further, BMS-626529 is known to stabilize state-1, a major target in Env immunogen design efforts, in the membrane bound Env. We reasoned that an understanding of BMS-626529 stabilization could lead to novel methods by which to stabilize both the soluble SOSIP and membrane bound Envs in a more native, closed state. A recent structure of a BG505 SOSIP in complex with BMS-626529 revealed the compound resides in an induced pocket below the β20-β21 loop between layers 1 & 2 and the V1/V2 apex. The BMS compound likely interrupts β20-β21 loop rearrangements important for allosteric induction of closed to open state transitions. To facilitate rational design based upon these features of the BMS-626529 binding, we aimed to develop a theoretical mechanism for rearrangements in the gp120 allosteric network that allow for CD4 triggering of the Env beginning from the β20-β21 loop. Residues in the β20-β21 loop important for Env triggering were recently identified. In particular, I423 was demonstrated to play an important role along with a previously identified V1/V2 residue, L193, in close proximity. Based upon this information as well as information indicating V3 move independently of V1/V2, we hypothesized that β20-β21 loop rearrangement induces V1/V2 dissociation from the trimer apex, therefore eliminating gp120 apex contacts. Concomitant formation of the bridging sheet would then communicate apex opening to layer-2. Transitions in layer-2 could then disrupt the layer-1 contacts. As layer-1 forms contacts with both layer-2 and the gp41 three-helix bundle, destabilization of layer-1 to layer-2 contacts would in turn destabilize layer-1 to gp41 contacts, thus reducing the barrier for gp120 rotation away from gp41. Together, this mechanism identifies a line of communication between the distant β20-β21 loop and the gp120 to gp41 three-helix bundle interface. Further, this mechanism identifies multiple sites as capable of controlling the Env conformational ensemble.

Design of conformationally stabilized Env constructs. Based upon the BMS-626529 interaction site and the theoretical mechanism for conformational control of the HIV-1 Env, we produced a set of BG505 Env mutations meant to capture the conformational effects of the BMS compound. Specifically, we generated a set of space-filling, hydrophobic mutations in the residues in contact with BMS-626529 in the SOSIP bound crystal structure. In combination with these mutations, mutations were made in layers 1 and 2 in order to prevent transitions in these regions. As V3 exposure occurs independently of V1/V2 exposure, we generated a set of hydrophobic mutations in the V1/V2-V3 interface in order to block V3 exposure. From these large sets of mutations, smaller sets of mutations were prepared in order to examine the effect of particular mutations and to maximize the likelihood of identifying a suitable set of mutations for downstream processing (Table 1). The BMS-626529 mimicking and layers 1 and 2 locking mutations were termed the 'F' series while the V3 locking mutations were termed the 'Vt' series. Each mutant was screened via transfection supernatant biolayer interferometry (BLI) in triplicate using, VRC01, PGT145, 17B, and 19B in order to examine gp120 folding, trimer formation, CD4i epitope exposure, and V3 exposure, respectively. Comparison of these results with the differences observed in the same assay for BG505 in the presence and absence of BMS-626529 identified 'F' series mutants F14 and F15 and 'Vt' series Vt-8 as suitable for downstream characterization. The antigenicity profiles of the F14 and F15 mutants did not differ. As F15 is identical to F14 except for one additional mutation, N337L, F14 was used for downstream analysis. This data suggests further exploration of the particular contribution of each mutation in the F14 stabilization of the trimer is warranted, as a further reduced set may confer a similar phenotype. Similarly, Vt8 itself may require only a subset of the mutations it contains.

The full set of tested mutations are listed below (HXB2 numbering) with a brief explanation for each. All were originally placed in BG505 SOSIP. They were then screened via BLI of small scale transfection supernatants. From the BLI data F14, F15 and Vt8 were expressed, purified, and screened for CD4 binding and triggering.

These sets of mutations were then put into CH848 10.17 DT and CH505 M5 SOSIP (F14, Vt8, and F14+Vt8) in addition to a BG505 SOSIP F14+Vt8.

Full Set->Pack the BMS-626529 binding site and lock the layers in place

The set of mutations referred to as F1 are V68I, S115V, A204L, V208L, V255W, N377L, M426W, M434W, and H66S.

Elimination* of N377L, M426W, and M434W may avoid over-packing the area. N377 may be important for folding as it is not totally buried. "Elimination" means that an F2 construct includes all F1 mutations except N337L, M426W, and M434W.

The set of mutations referred to as F2 are: V68I, S115V, A204L, V208L, V255W, and H66S Elimination of S115V may be done if adding a V may be too large for the area where S115 resides.

The set of mutations referred to as F3 are: V68I, A204V, V208L, V255L, and H66S.

Elimination of A204V may be done if adding a V may be too large for the packed region where A204 resides. (Adding E causes opening of the apex.)

The set of mutations referred to as F4 are: V68I, S115V, V208L, V255L, and H66S.

Retention of N377L may be used for the minimal set. The above tested the effect of N377L elimination from the full set and whether N377L stabilizes.

The set of mutations referred to as F5 are: V68I, S115V, A204L, V208L, V255W, N377L, and H66S.

Addition of W69L to minimal set may be done as previous work suggests aromatic residues in position 69 are destabilizing and is tested here.

The set of mutations referred to as F6 are: V68I, S115V, A204L, V208L, V255L, and W69L.

Using W69V instead of W69L may be done to test whether side chain length alters potential stabilizing effect.

The set of mutations referred to as F7 are: V68I, S115V, A204L, V208L, V255L, and W69V.

Using W69A instead of W69L/V may be done to further test whether side chain length alters potential stabilizing effect.

The set of mutations referred to as F8 are: V68I, S115V, A204L, V255L, V208L, and W69A.

Reintroduction of M426W may be done to test a minimally reduced set and the effect of M's.

The set of mutations referred to as F9 are: V68I, S115V, A204L, V208L, V255W, N377L, M426W, and H66S.

Reintroduction of M434W may be done to test a minimally reduced set and the effect of M's.

The set of mutations referred to as F10 are: V68I, S115V, A204L, V208L, V255W, N377L, M434W, and H66S.

Introduction of additional H72P mutation may be done to test if P can favor loop turn stabilizing TRP69 Loop in the W bound state.

The set of mutations referred to as F11 are: V68I, S115V, A204V, V208L, V255L, H72P, and H66S.

Testing minimal set with H66K rather than S may be done if the charge is a better solution to polar switch.

The set of mutations referred to as F12 are: V68I, S115V, V208L, V255L, and H66K.

Elimination of H66S from F1 may be done though H66 may be important for loop configuration.

The set of mutations referred to as F13 are: V68I, S115V, A204L, V208L, V255W, N377L, M426W, and M434W.

The Minimal Set 2 may include the elimination of H66S and swapping of S115V for A204V; H66 could be important for loop and A204 my better stabilize that S115V.

The set of mutations referred to as F14 are: V68I, A204V, V208L, and V255L.

Minimal Set 3 may include adding N377L to test for further stabilization.

The set of mutations referred to as F15 are: V68I, A204L, V208L, V255W, and N377L.

V3 Lock—Full Set

The set of mutations referred to as VT1 are: Y177F, T320L, D180A, Q422L, Y435F, Q203M, E381L, R298M, N302L, and N300L.

Elimination of R298M and E381L may be used to determine whether these two are stabilizing rather than destabilizing.

The set of mutations referred to as VT2 are: Y177F, T320L, D180A, Q422L, Y435F, Q203M, N302L, and N300L.

Elimination of E381L may be used to determine whether this residue is required to stabilize R298.

The set of mutations referred to as VT3 are: Y177F, T320L, D180A, Q422L, Y435F, Q203M, R298M, N302L, and N300L.

Elimination of R298M may be used to determine whether this reside stabilizes E381.

The set of mutations referred to as VT4 are: Y177F, T320L, D180A, Q422L, Y435F, Q203M, E381L, N302L, and N300L.

Retention of Y177F and Y435F may stabilize interior through H-bonding.

The set of mutations referred to as VT5 are: T320L, D180A, Q422L, Q203M, E381L, R298M, N302L, and N300L.

Retention of Y177F and Y435F while eliminating R298M and E381L mutations may be a minimal set avoiding possible problems from charged pair mutations.

The set of mutations referred to as VT6 are: T320L, D180A, Q422L, Q203M, N302L, N300L.

The Dennis Burton Set is a control for comparison.

The set of mutations referred to as VT7 are: R298A, N302F, R304V, A319Y, and T320M.

Elimination of D180A may be done as D180 appears to be destabilizing but may be stabilizing.

The set of mutations referred to as VT8 are: T320M, Q422M, Q203M, N302L, and N300L.

Addition of S174V may be done as S174 is on the periphery but may be stabilizing with a hydrophobe.

The set of mutations referred to as VT9 are: T320M, Q422M, Q203M, N302L, N300L, and S174V.

The Peter Kwong Set (DS-SOSIP.4mut) is an additional control set.

The set of mutations referred to as VT10 are: I201C, A443C, L154M, N300M, N302M, and T320L.

*In the above description, "elimination" means that F #N construct includes all F #N−1 mutations except the mutations identified as eliminated. In some embodiments, "retention" means the identified mutation is included.

Contemplated also are subsets of the mutations within a set. In a non-limiting embodiment, the mutations in Set F14 could be further parsed out to determined if there are fewer mutations or combinations of fewer mutations than in Set 14 which provide stabilization of the trimer.

Contemplated is any HIV envelope incorporating stabilizing mutations of the technology.

In order to examine the ability of these mutants to replicate the effects of BMS, we determined whether CD4 induces exposure of V3 and open state epitopes in the BG505 SOSIP constructs F14, Vt8 and a combined F14/Vt8. Specifically, we investigated CD4 induced 17B and 19B epitope exposure via surface plasmon resonance. The BG505 wild type SOSIP was used as a control with the antibodies immobilized on the chip. SOSIP samples were preincubated with excess CD4. Additionally, we investigated samples preincubated with CD4 and the BMS compound to determine whether BMS further stabilizes the trimer.

The results indicate that, while both the 17B and 19B epitopes are largely masked in all constructs, both epitopes are exposed in the WT protein in the presence of CD4. Both the F14 and F14/Vt8 SOSIPs eliminate triggering while BMS and the Vt8 compound reduce the response markedly with Vt8 increasing the effects of BMS.

The results indicate that the layer-1 and layer-2 locking mutations effectively prevent CD4 triggering. We next asked what structural changes lead to this reduction in triggering. We therefore determined a structure of a VRC01 bound BG505 F14 SOSIP trimer using cryo-electron microscopy.

The class averages in the upper left indicate the roughly eighty-six thousand particles display multiple orientations while the ab initio structure determination based upon these particles clearly identifies the trimeric SOSIP configuration and associated VRC01 Fab molecules. The final resolution of the structure determined via Fourier shell correlation was 4.4 angstroms yielding sufficient resolution in the region of interest for the F14 mutations at the core of the trimer to identify changes leading to the observed phenotype.

The difference between the initial model used in refining the SOSIP coordinates into the cryo-EM map and the final refined map are depicted here. The two regions here suggest a mechanism by which the F14 mutants prevent CD4 induced rearrangements. First, on the left, layer-1, in lime green, has rearranged, shifting tryptophan sixty-nine in its layer-2 pocket, in purple. Second, on the right, tryptophan five-hundred and seventy-one, in the buried gp41 three-helix bundle, has shifted away its pocket between layers 1 and 2. As layers 1 and 2 are known to play a role in allosteric control of the trimer closed to open state equilibrium, this structure suggests the F14 mutations have decoupled the layers from communicating CD4 binding to the gp120 to gp41 interface, which is a major point of contact in the closed state that must break.

The results from the BG505 F14 structure indicate layer-1 and layer-2 have been decoupled from the allosteric network, thus eliminating CD4 induced triggering of the Env. We next asked whether the F14 mutations would eliminate triggering in the chimeric CH848 DT and CH505 M5 SOSIP trimers.

We therefore determined whether CD4 induces exposure of V3 and open state epitopes in a CH848 DT F14/Vt8 mutant as the F14/Vt8 mutant was most effective in the BG505 SOSIP. As multiple SOSIP designs are available for CH848, we determine whether the new designs improve over the previous stabilization methods.

Figure 23A:
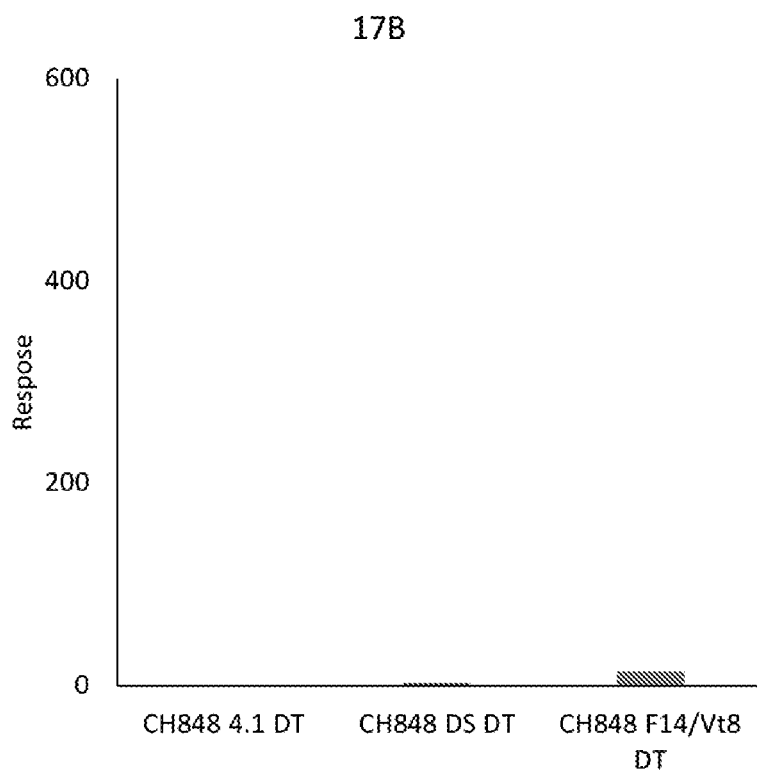
FIG. 23A shows surface plasmon resonance response values for CH848.10.17 DT F14/Vt8 SOSIP, CH848.10.17 DT DS SOSIP and CH848.10.17 DT 4.1 SOSIP trimers comparing the interaction of each with the open state, bridging sheet targeting 17B antibody.
Figure 23B:
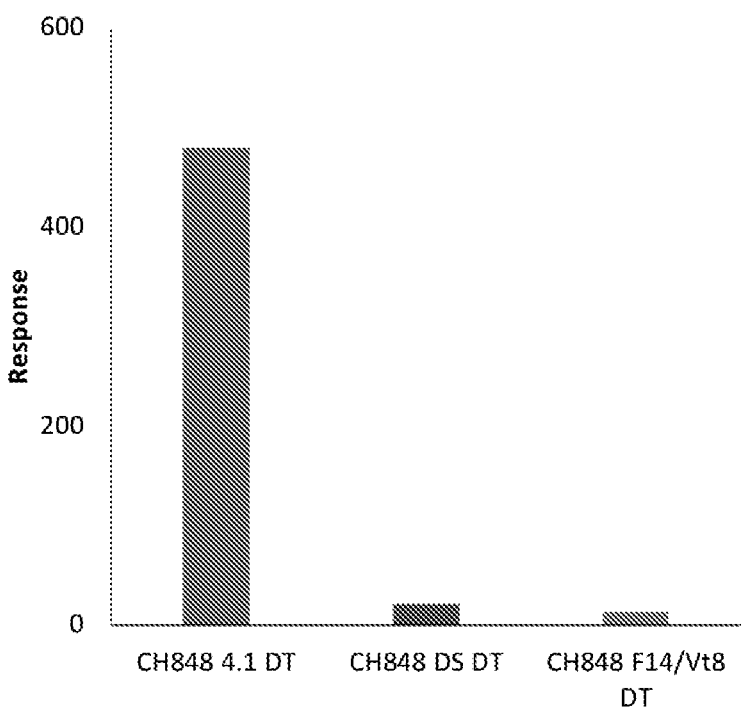
FIG. 23B shows surface plasmon resonance response values for CH848.10.17 DT F14/Vt8 SOSIP, CH848.10.17 DT DS SOSIP and CH848.10.17 DT 4.1 SOSIP trimers in the presence of saturating, open state triggering sCD4 comparing the interaction of each with the open state, bridging sheet targeting 17B antibody.

The results for the CH848 4.1 DT, CH848 DS DT, and the CH848 F14/Vt8 DT mutants indicate that while the 17B epitope is effectively triggered in the 4.1 stabilized mutant, both the DS and F14/Vt8 mutants are unresponsive. The 19B epitope is exposed in the presence of CD4 in the 4.1 and F14/Vt8 constructs with a minimal response from the DS construct. The BMS construct markedly reduces the response observed in the presence of CD4 (FIGS. 23 and 24).

Figure 25A:
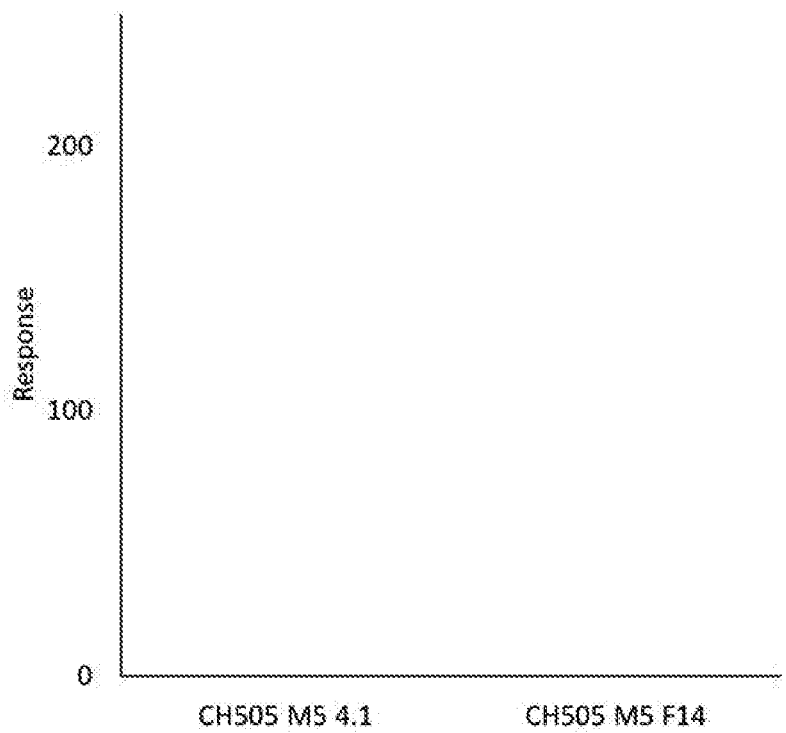
FIG. 25A shows Surface plasmon resonance response values for CH505 M5 G458Y F14 GNTI-SOSIP and CH505 M5 G458Y 4.1 GNTI-SOSIP trimers comparing the interaction of each with the open state, bridging sheet targeting 17B antibody.
Figure 25B:
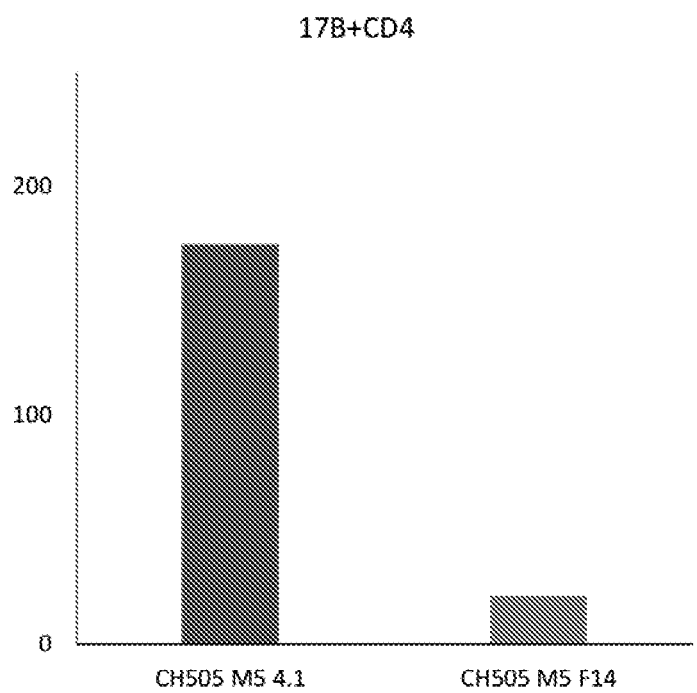
FIG. 25B shows B surface plasmon resonance response values CH505 M5 G458Y F14 GNTI-SOSIP and CH505 M5 G458Y 4.1 GNTI-SOSIP trimers in the presence of saturating, open state triggering sCD4 comparing the interaction of each with the open state, bridging sheet targeting 17B antibody.
Figure 26A:
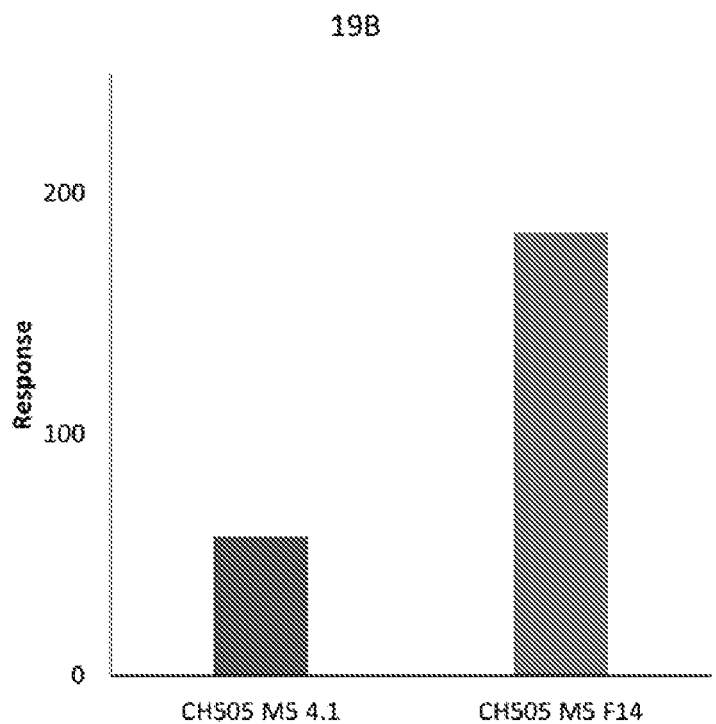
FIG. 26A shows surface plasmon resonance response values for CH505 M5 G458Y F14 GNTI-SOSIP and CH505 M5 G458Y 4.1 GNTI-SOSIP trimers comparing the interaction of each with the open state, variable region 3 (V3) targeting 19B antibody.
Figure 26B:
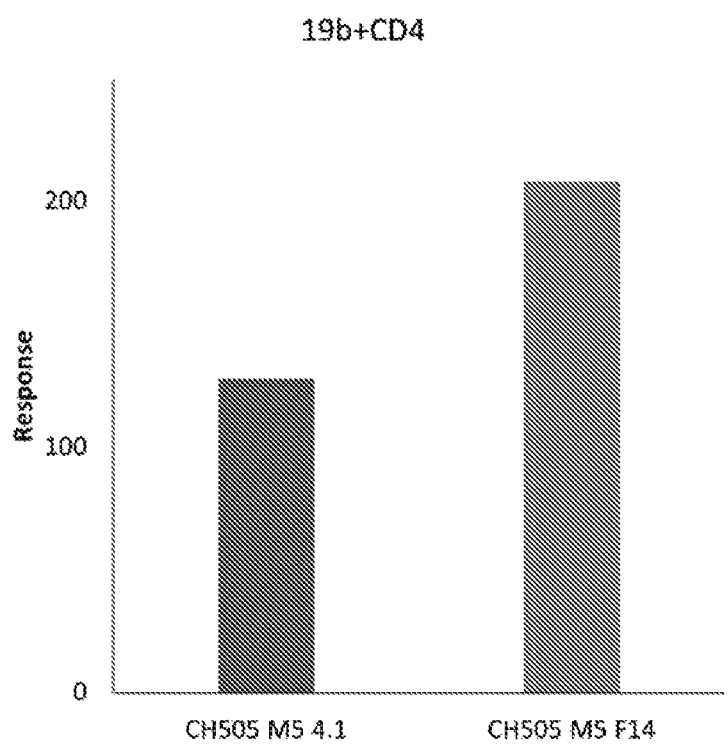
FIG. 26B shows surface plasmon resonance response values for CH505 M5 G458Y F14 GNTI-SOSIP and CH505 M5 G458Y 4.1 GNTI-SOSIP trimers in the presence of saturating, open state triggering sCD4 comparing the interaction of each with the open state, variable region 3 (V3) targeting 19B antibody.
Figure 27A:
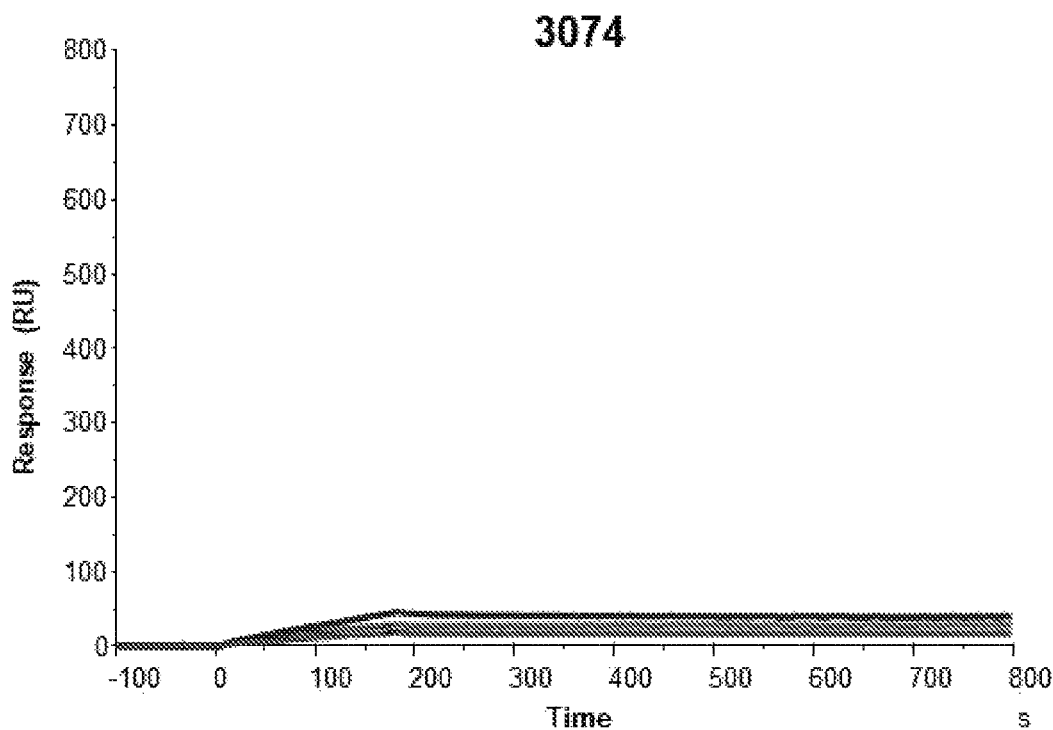
FIGS. 27A-27C show Effects of sCD4 and BMS on V3 binding.
Figure 27B:
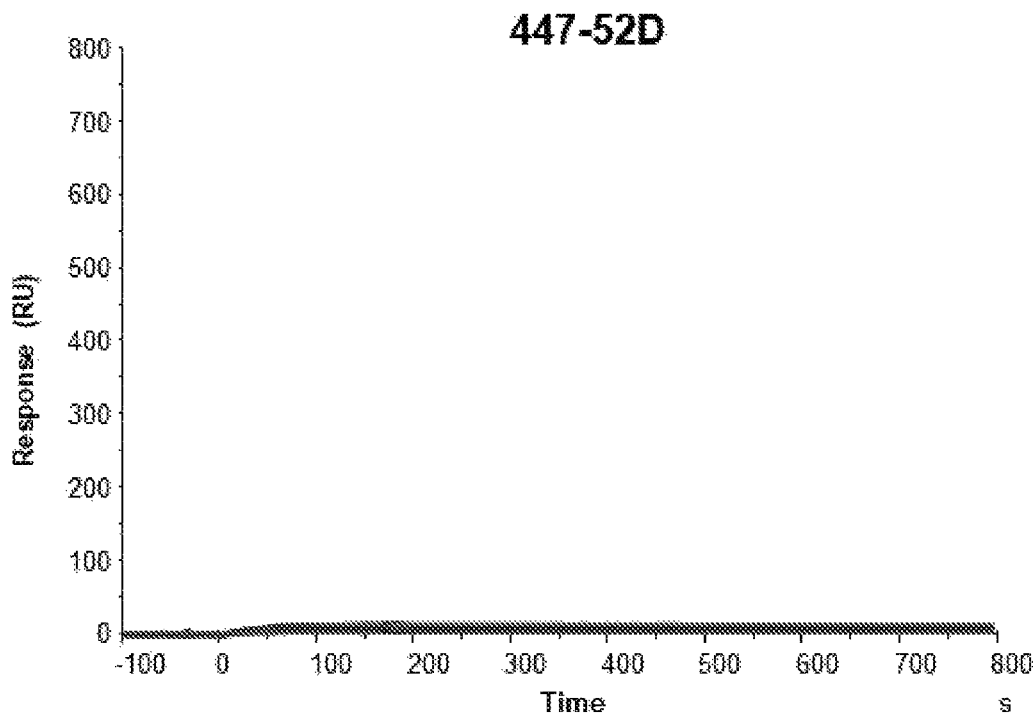
Figure 27C:
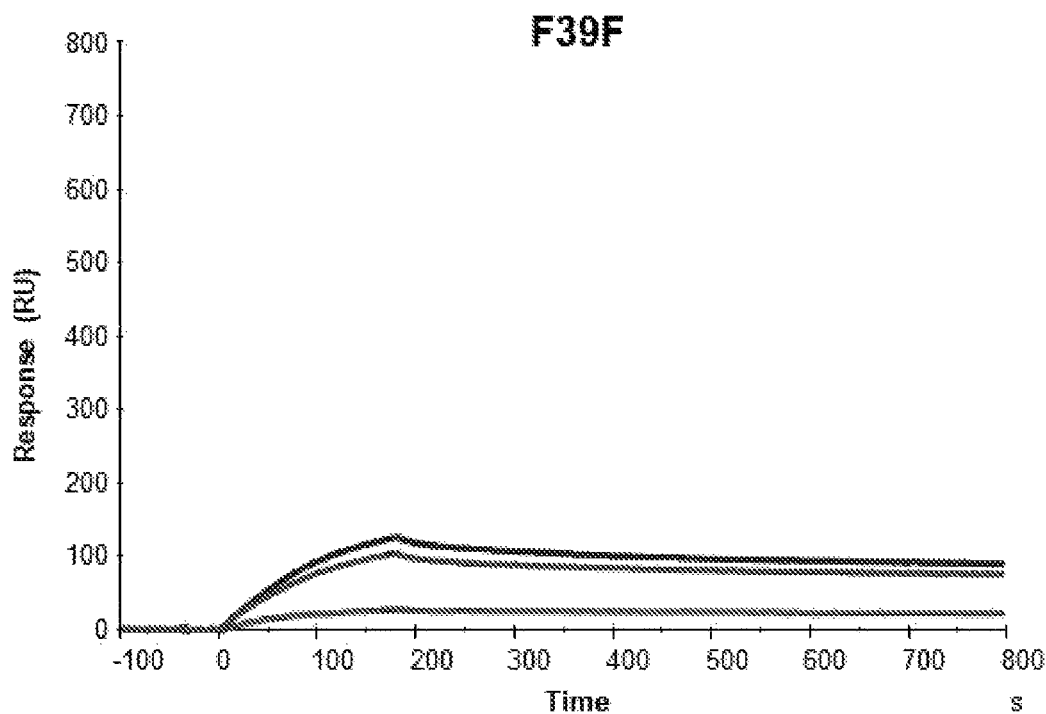
Figure 28A:
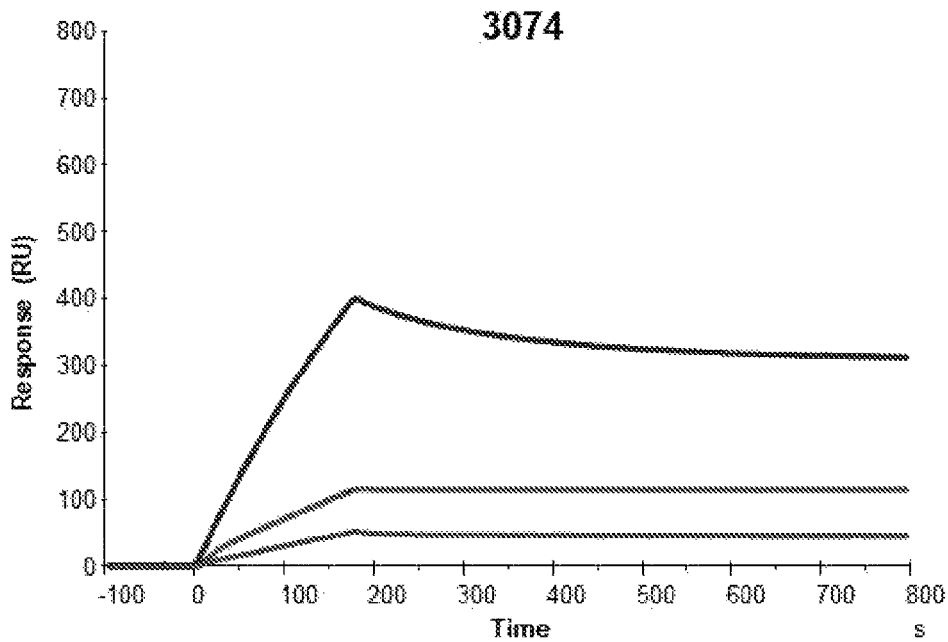
FIGS. 28A-28C show Effects of sCD4 and BMS on V3 binding.
Figure 28B:
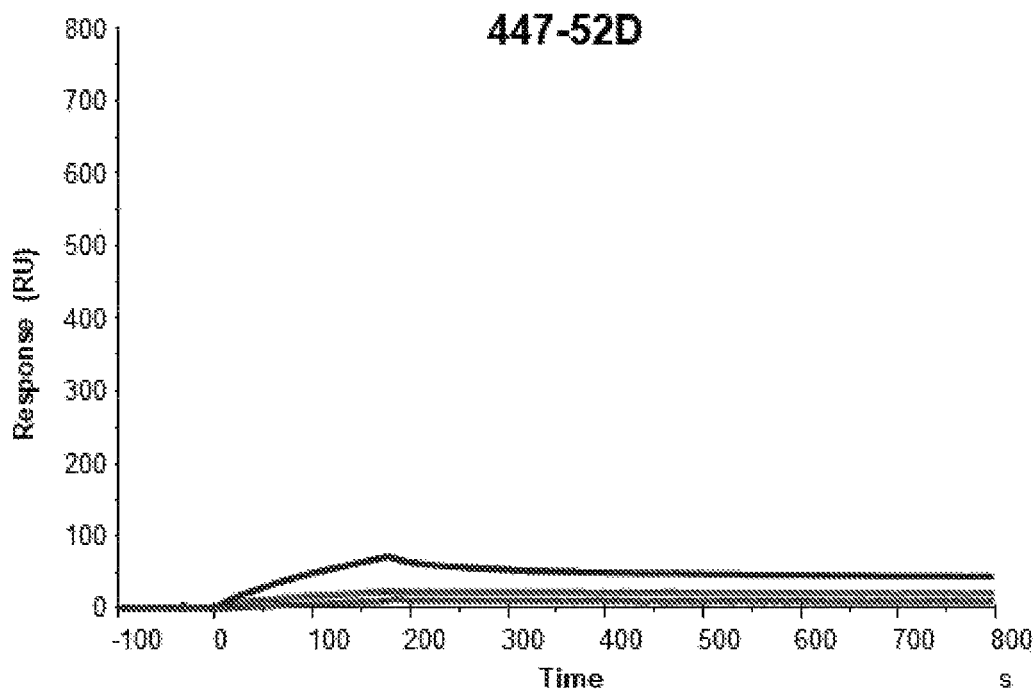
Figure 28C:
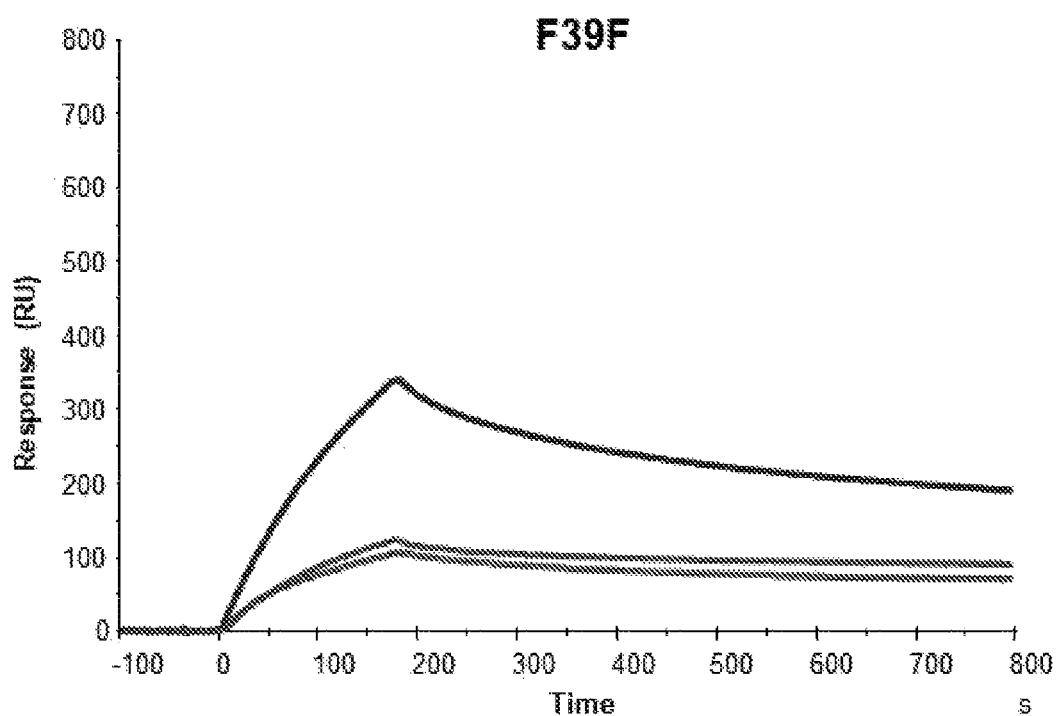
Figure 29A:
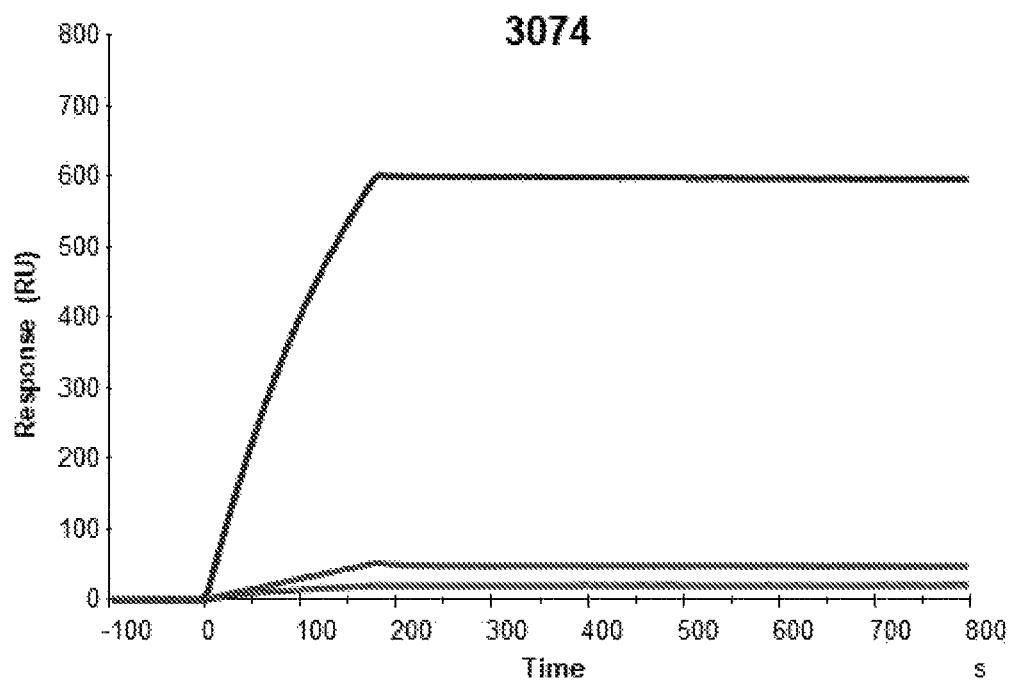
FIGS. 29A-29C shows Effects of sCD4 and BMS on V3 binding.
Figure 29B:
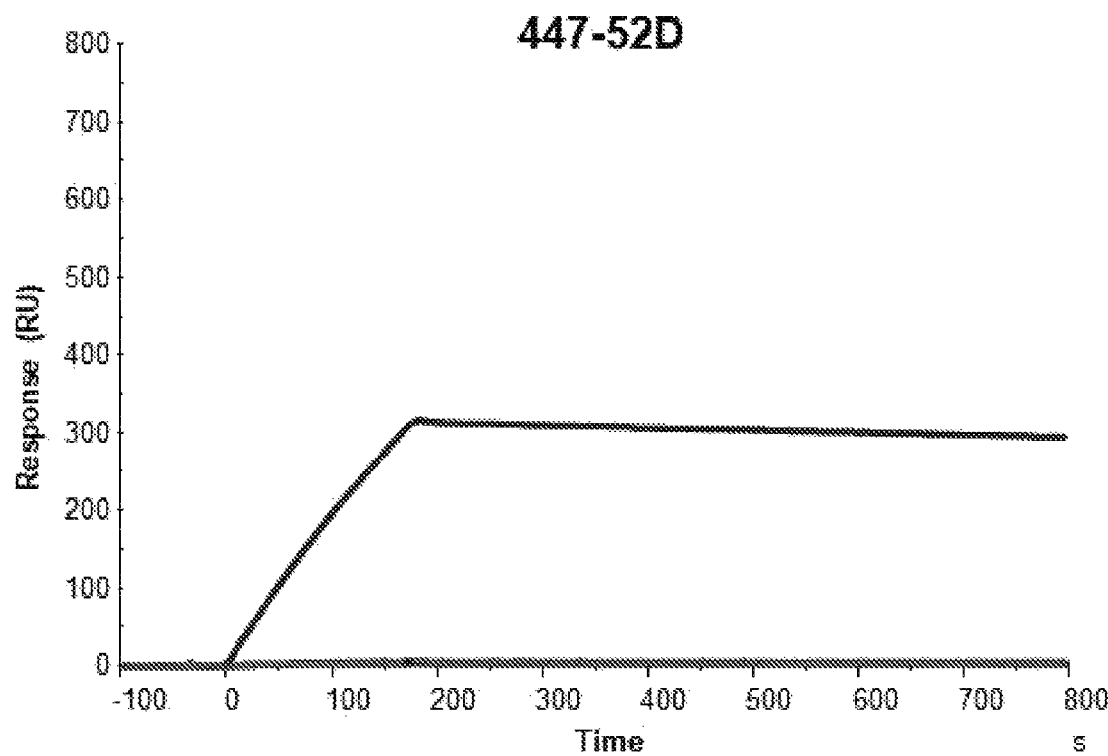
Figure 29C:
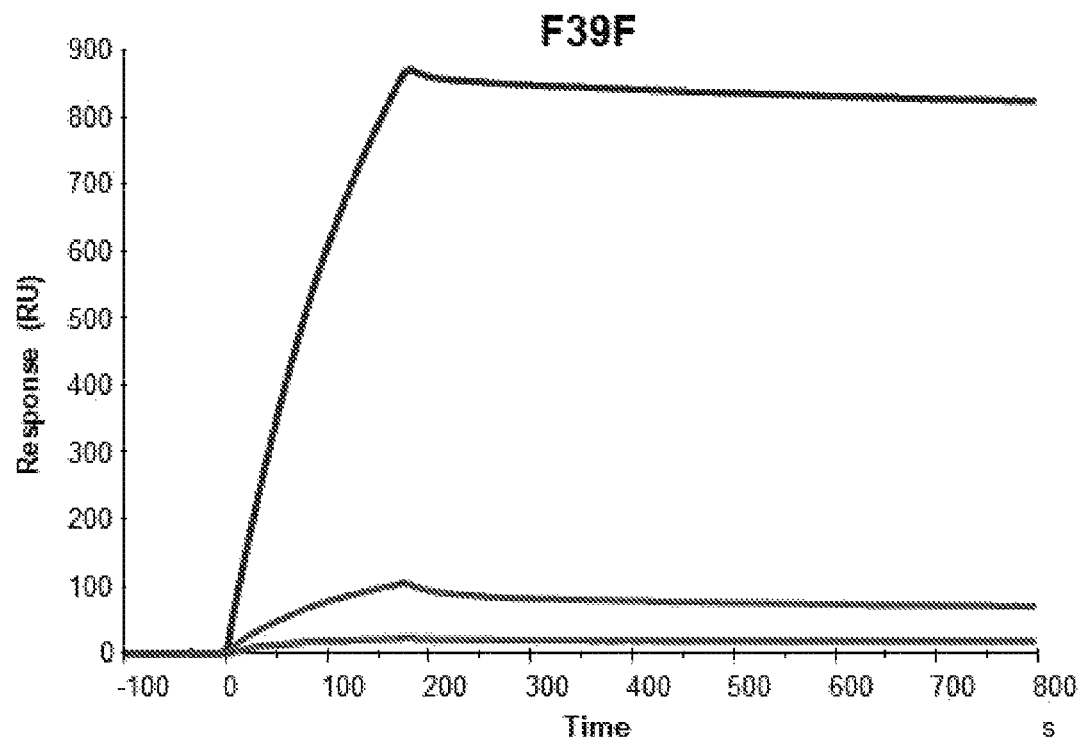
Figure 30A:
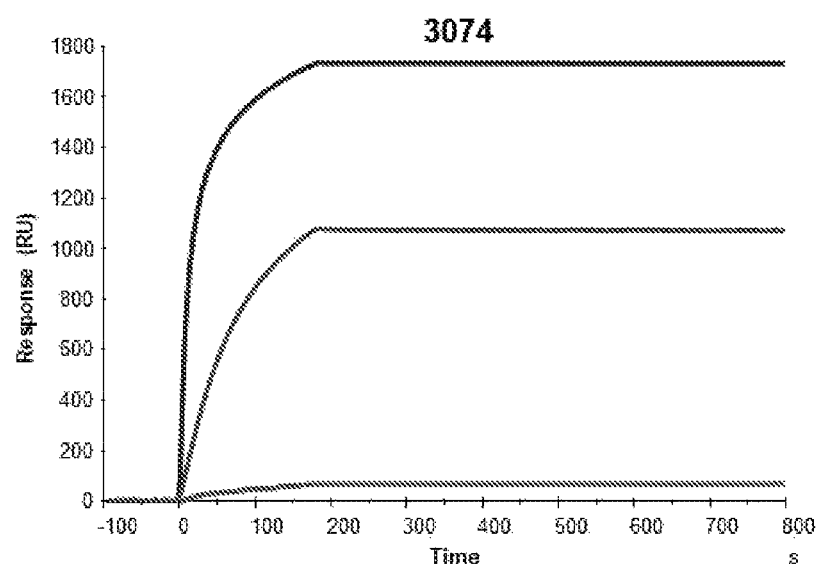
FIGS. 30A-30C shows Effects of sCD4 and BMS on V3 binding.
Figure 30B:
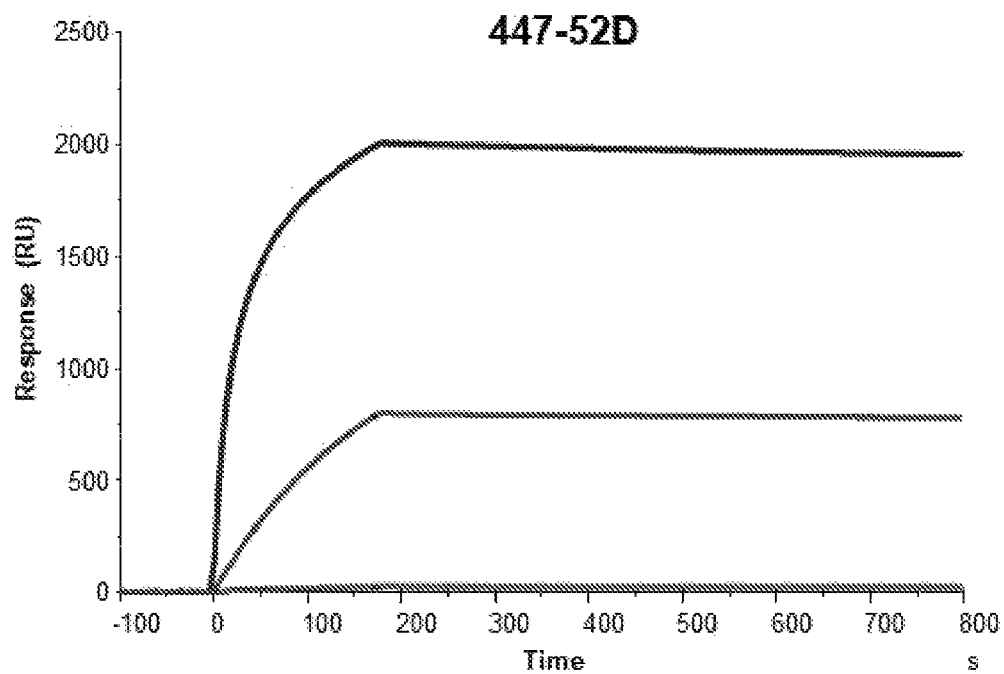
Figure 30C:
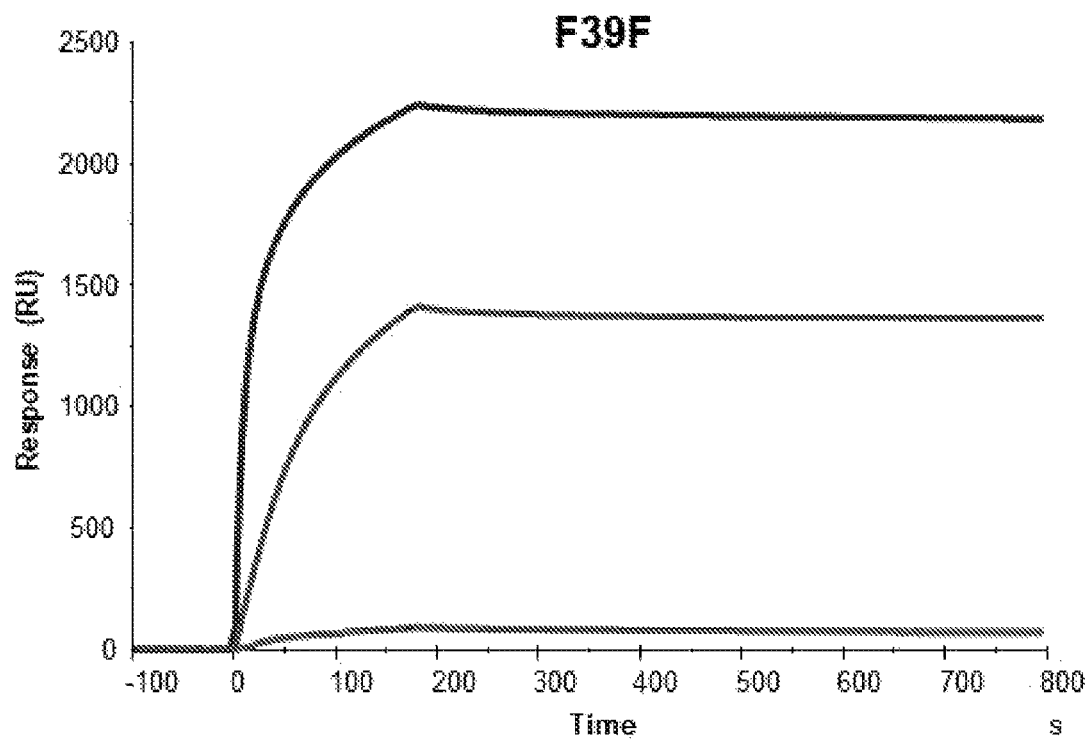
Figure 31A:
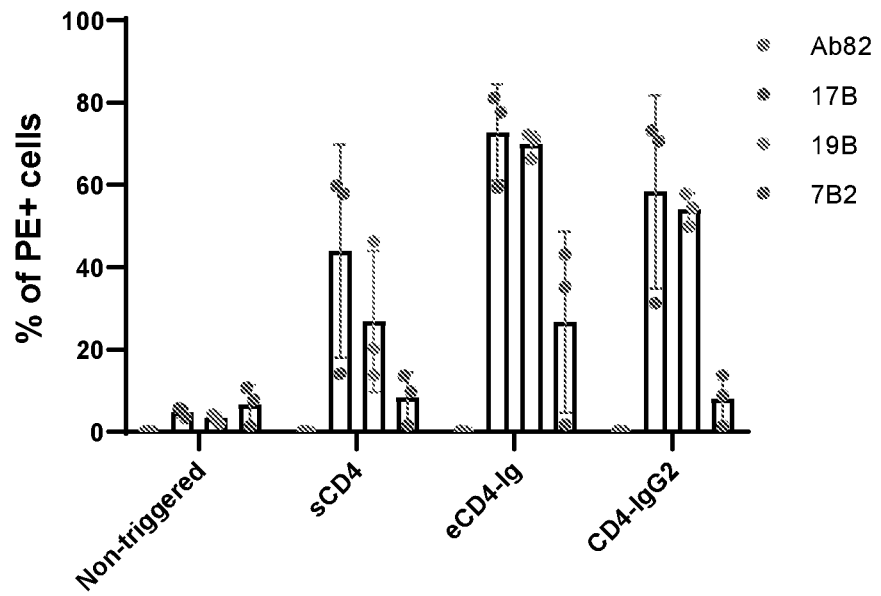
FIGS. 31A-D show percentage of full length Env gp160 HEK293 cells testing positive for interaction with antibodies Ab82 (control), open state, bridging sheet targeting 17B, V3 open state targeting 19B, and 7B2 in the absence and presence of sCD4, eCD4-Ig, or CD4-IgG2.
Figure 31B:
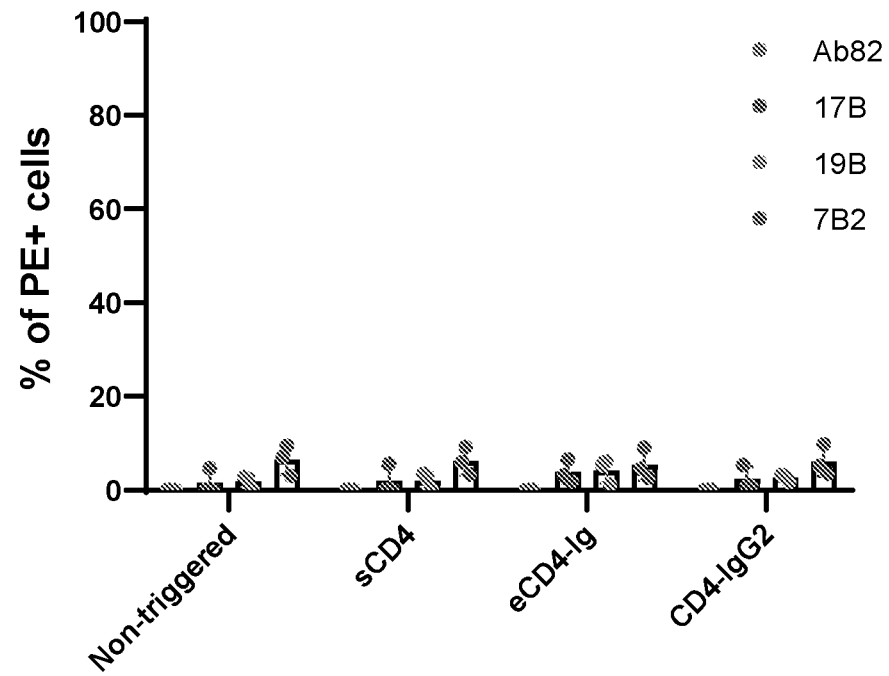
Figure 31C:
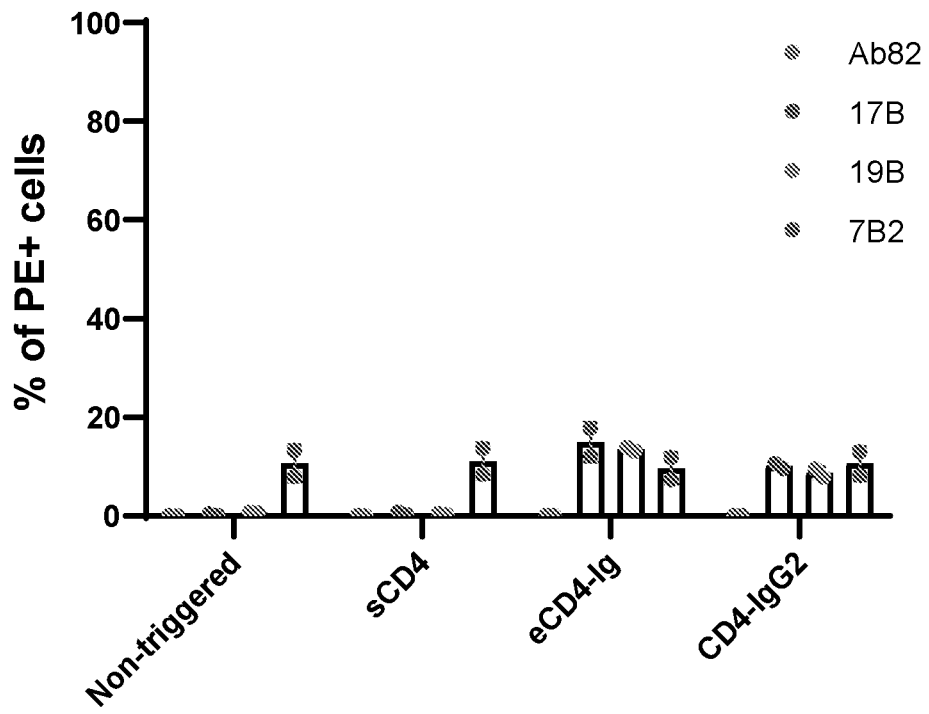
Figure 31D:
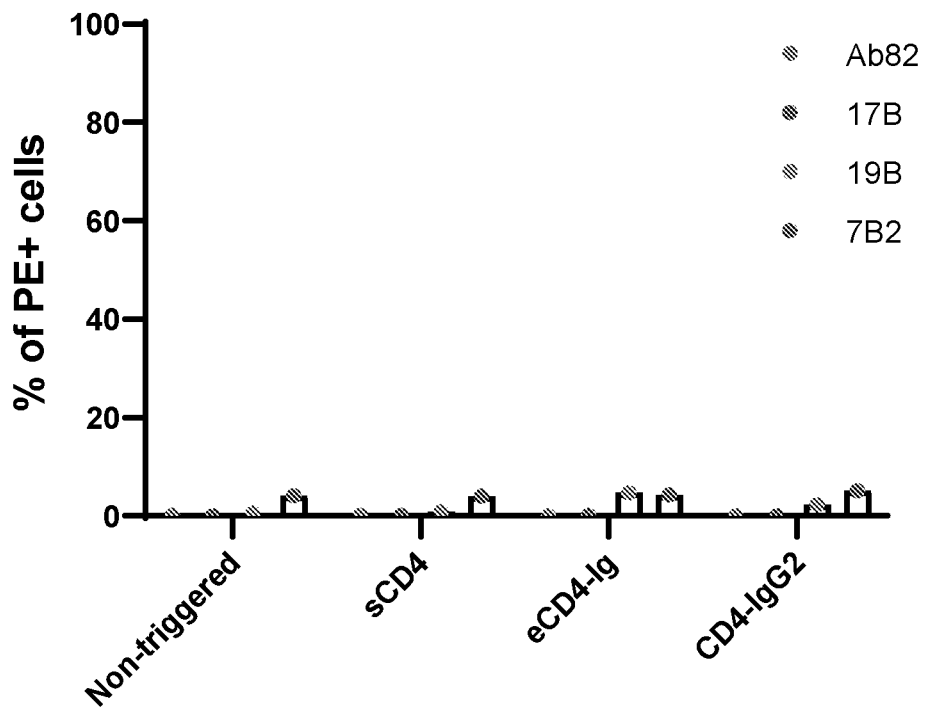
Figure 32A:
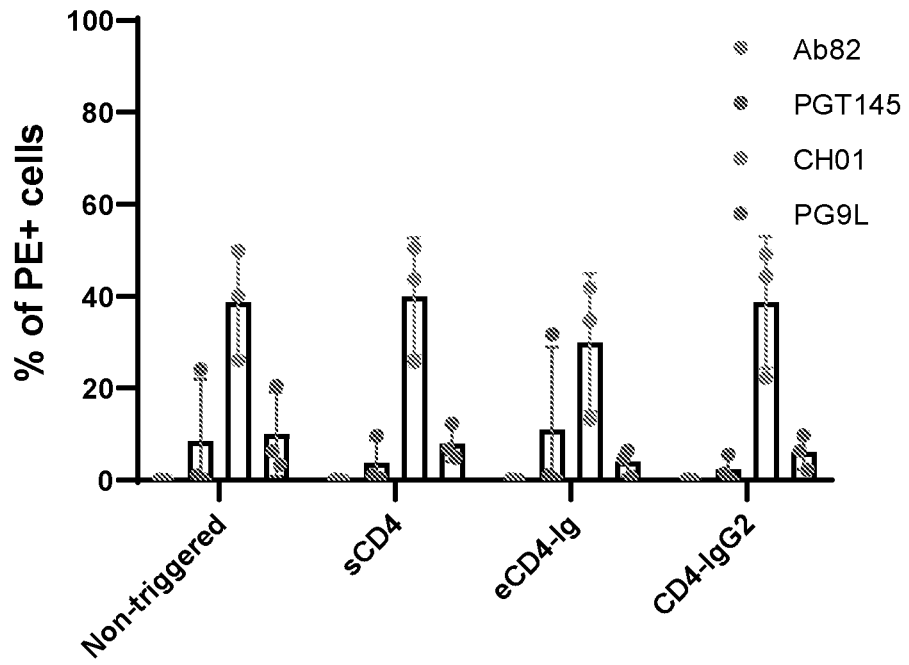
FIGS. 32A-D show percentage of full length Env gp160 HEK293 cells testing positive for interaction with antibodies Ab82 (control), trimer apex targeting, quaternary specific PGT145, and V2 targeting CH01 and PG9L in the absence and presence of sCD4, eCD4-Ig, or CD4-IgG2.
Figure 32B:
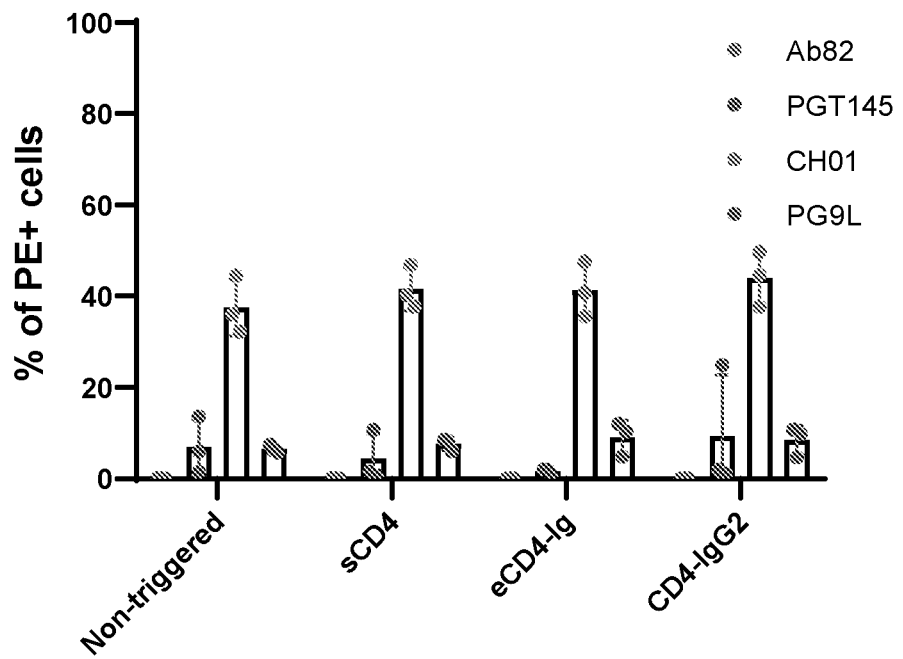
Figure 32C:
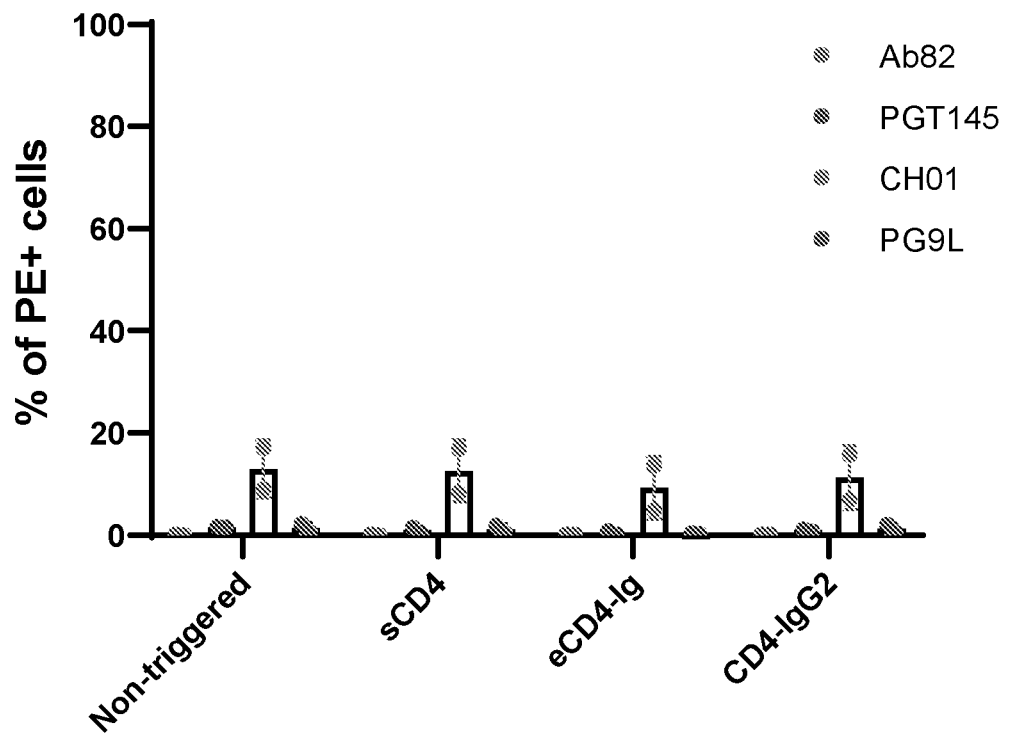
Figure 32D:
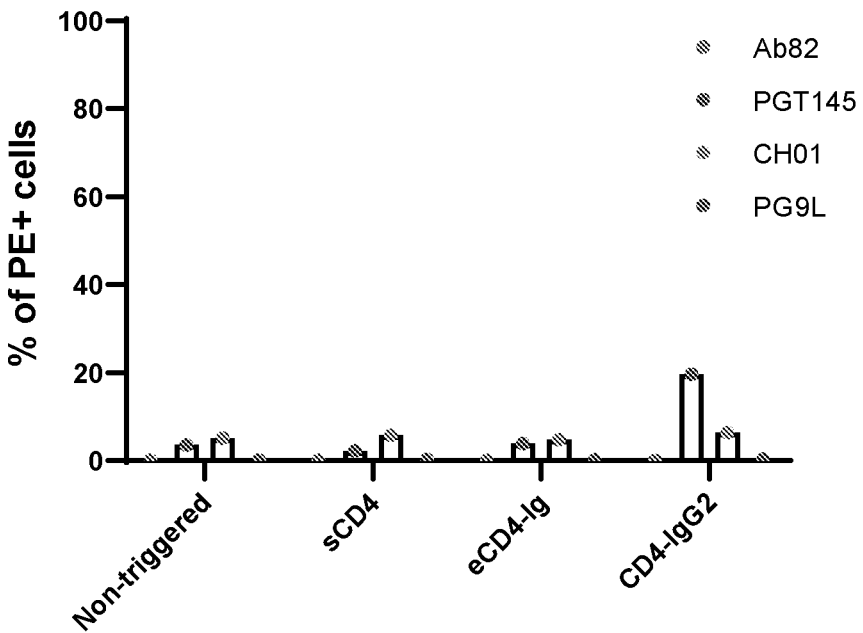
Figure 33A:
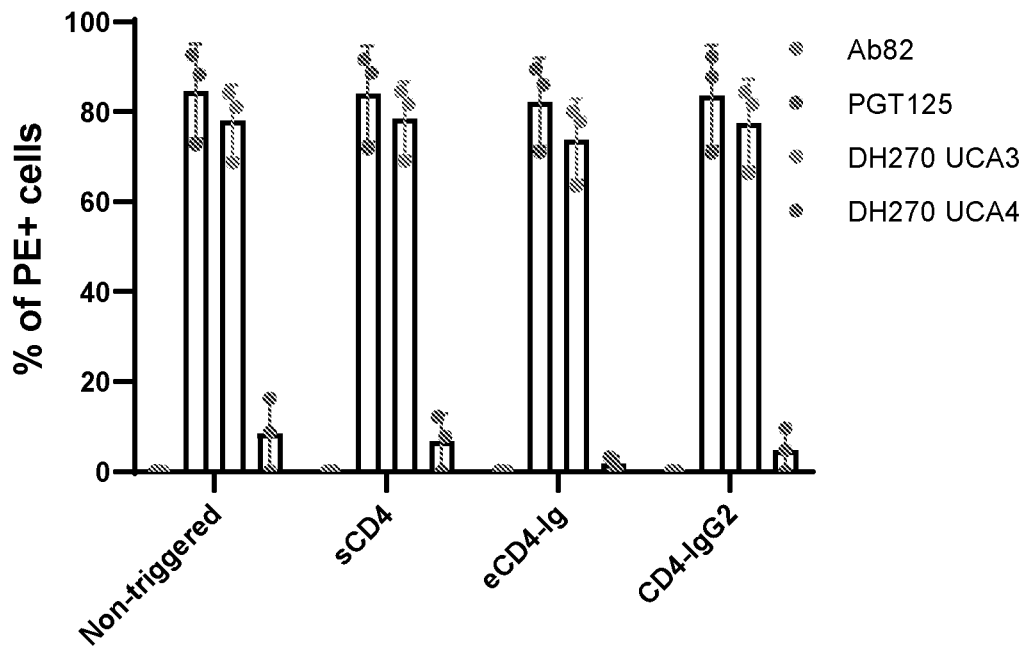
FIGS. 33A-D show Percentage of full length Env gp160 HEK293 cells testing positive for interaction with antibodies Ab82 (control) and V3-glycan targeting antibodies PGT125, DH270 UCA3, and DH270 UCA4 in the absence and presence of sCD4, eCD4-Ig, or CD4-IgG2.
Figure 33B:
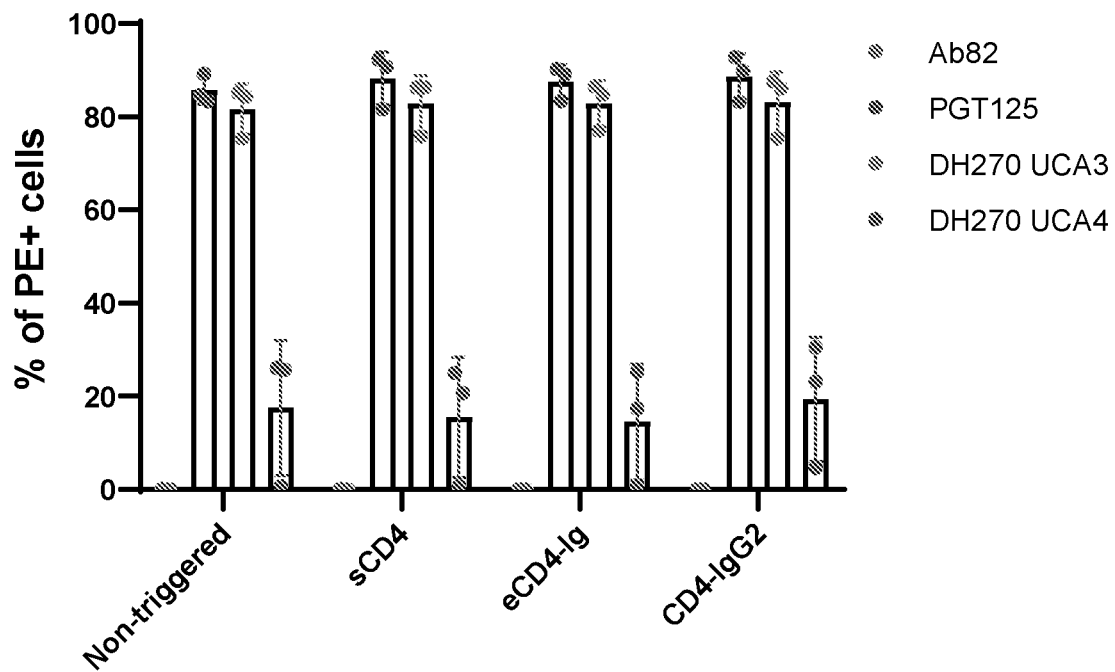
Figure 33C:
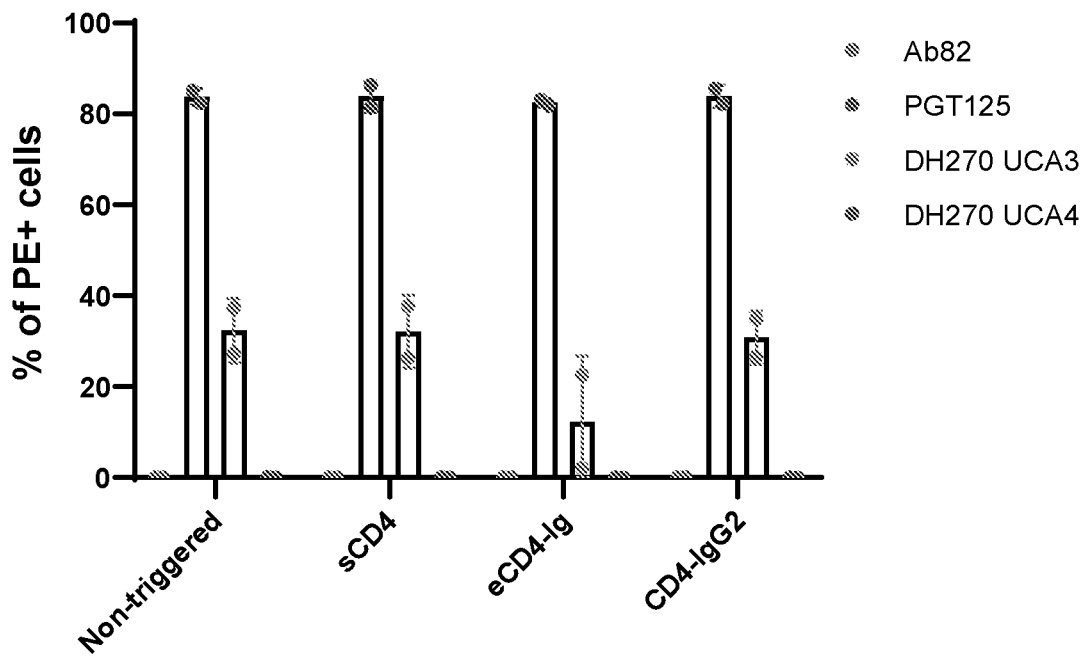
Figure 33D:
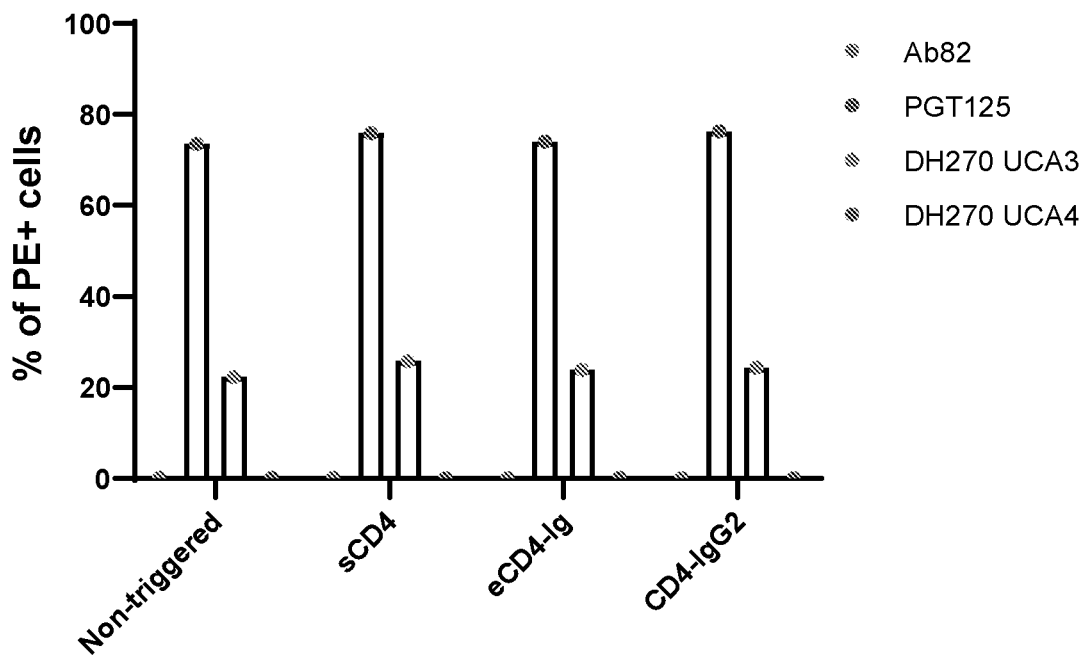

The results for the CH505 M5 4.1 and F14 mutants indicate that, the 4.1 mutant exposes the 17B epitope to a far greater extent than the F14 mutant. Though the 19B epitope is exposed in the 4.1 construct, triggering increases the extent of this exposure. Unusually, the F14 mutant exposes the 19B epitope to a greater extent than the 4.1 mutant and is largely unresponsive to the BMS compound. FIGS. 25 and 26.

The results indicate the F14 mutations effectively reduce exposure of the 17B epitope. However, this stabilization does not necessarily result in reduced 19B epitope exposure. In order to examine the potential effect of these mutations on other regions of the trimer, we next asked what effect these mutations have on the CD4 binding site.

SRP results indicate the F14 and Vt8 stabilizing mutations markedly reduce CD4 binding. It is therefore important to determine whether this effect extends to the CD4 binding site bnAbs. VRC01 binding was evaluated in the presence and absence of both CD4 and BMS.

Figure 34:
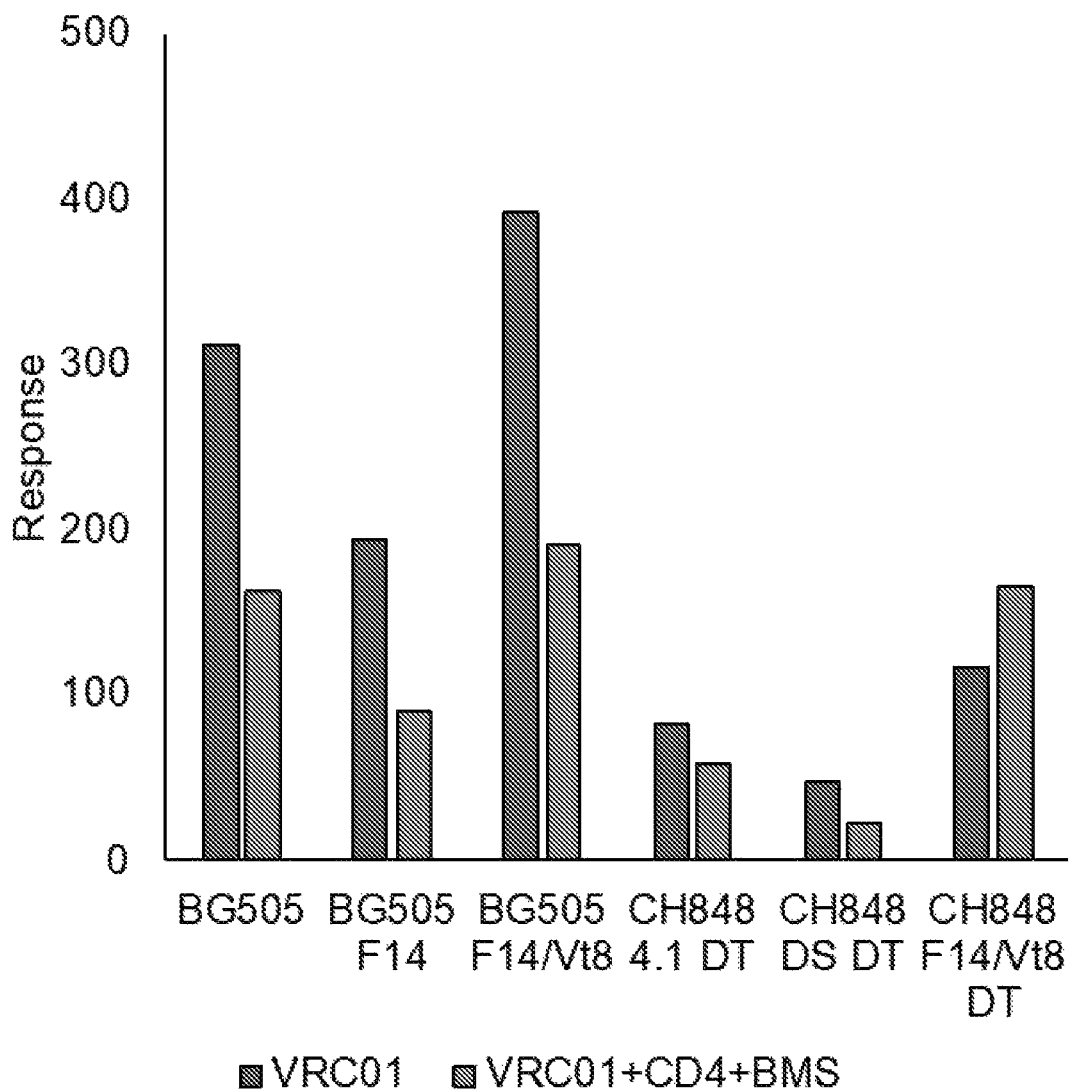
FIG. 34 shows BMS626529 Effect on Mutant Binding with VRC01. Surface plasmon resonance experiments of stabilized and non-stabilized BG505 and CH848 SOSIP trimers interacting with CD4 binding site targeting broadly neutralizing antibody VRC01 in the presence and absence of small molecule, open state inhibiting BMS-626529. With the exception of CH848 F14/Vt8 DT, the presence of BMS-626529 reduces the binding of VRC01.

The results indicate that, while F14 displays a reduction in VRC01 binding in BG505, the F14/Vt8 combination increases this interaction. Interestingly, while addition of BMS in all BG505 constructs as well as the CH848 DS and 4.1 mutants reduces VRC01 interaction, the CH848 F14/Vt8 DT mutant displays an increased affinity for VRC01. FIG. 34.

Figure 35:
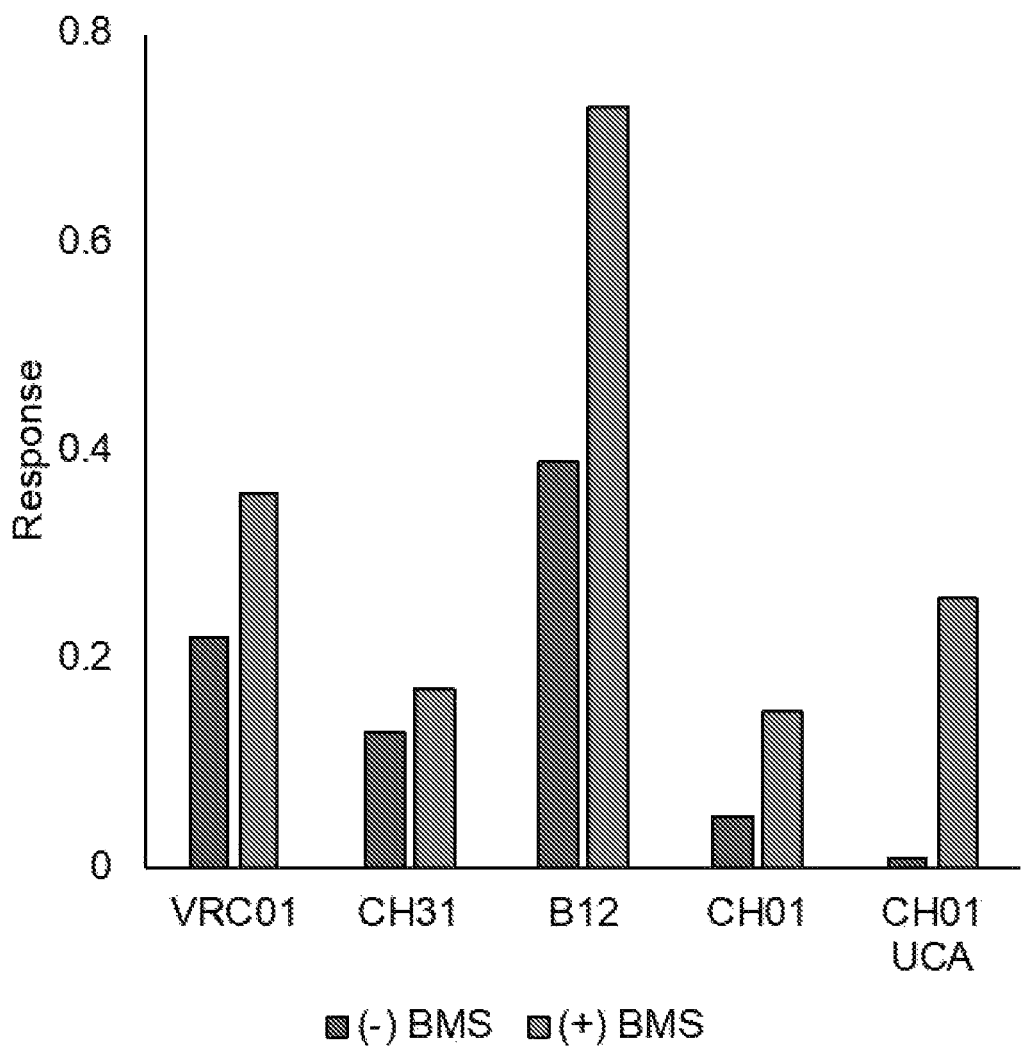
FIG. 35 shows BMS626529 Bound and Unbound CH848 F14/Vt8 Interactions. Surface plasmon resonance experiments of the F14/Vt8 stabilized CH848 SOSIP trimer interacting with bnAbs VRC01, CH31, B12, CH01, and the CH01 unmutated common ancestor antibodies in the presence and absence of small molecule, open state inhibiting BMS-626529. The results indicate that the BMS-626529 molecule enhances the interaction between the SOSIP and antibodies.

The results indicate that while F14 reduces VRC01 binding in BG505, the combined F14/Vt8 mutant increases VRC01 affinity in both BG505 and CH848 DT SOSIPs. Based upon the unusual increase in VRC01 binding of the CH848 F14/Vt8 DT SOSIP in the presence of BMS, we next asked whether this effect extends to other bnAbs. FIG. 35.

The results indicate that CH848 F14/Vt8 DT in the presence of BMS alone indeed increases VRC01 affinity. Additionally, increases are observed in CH31, B12 and CH01. Remarkably, though the CH01 UCA does not bind in the absence of BMS, the UCA interacts with the BMS bound trimer quite well. FIG. 35.

The results indicate the BMS compound is able to sensitize the CH848 F14/Vt8 DT SOSIP to interaction with multiple bnAbs and that the compound can induce interaction with the CH01 UCA.

In conclusion, the F14 and vt8 mutations limit CD4 triggering of the 17B and 19B epitopes in BG505 while the combined F14/Vt8 construct eliminates triggering. The F14/Vt8 mutations eliminate 17B exposure in CH848 DT and limit 19B exposure in the presence of CD4. Additionally, the CH848 F14/Vt8 construct displays a remarkable affinity increase in certain bnAbs in the presence of BMS. Finally, the F14/Vt8 mutations eliminate CD4 induced exposure of the 17B epitope though the 19B epitope remains exposed.

Example 2

Additional sequences comprising stabilizing modifications described herein are provided in WO2014/042669, WO/2017151801, WO/2017152146 and WO/2018161049.

These include sequences of envelopes designed to bind to UCAs of V1V2 and V3, such as but not limited to envelope 19CV3, which comprises the sequence of envelope CH0848.3.d1305.10.19 except for the V3 region which is derived from CH0848 D949.10.17. See FIGS. 52-53.

Example 3

Additional designs examining sub-combinations within a set may be designed to further reduce the number of amino acid changes. In a non-limiting example, set "F14" mutations may be reduced in designs as subsets comprising one, two or three combination of the four mutation currently included in set "F14".

Example 4

Animal studies can be conducted to test the immunogenicity of the various immunogens.

Below is a sample protocol for a rabbit study using one of the immunogens of the technology.

Rabbit Study R47: BG505 gp140 SOSIP F14 x6 (IM) Immunization #1-6:
  Immunogen: BG505gp140SOSIP.T332N.F14
  Adjuvant: GLA-SE @ 0.1 mg/ml GLA, 4% SE (EM-107)
  Rabbit #'s: M519, M520, M521, B514 (New Zealand White females)

Immunogen Dose: 100 μg per animal×5 animals (1 extra dose)=500 μg total

Adjuvant Dose: 25 μg GLA/2% oil per animal×5 animals=125 μg total GLA

Total Volume Needed: 500 μl per animal×5 doses=2.5 ml total

Procedure:
1. Calculate amount of protein needed based on concentration.
2. Add saline as needed to protein for an antigen volume of 1.25 ml
3. Add 1.25 ml antigen to 1.25 ml adjuvant for $V_{final}$=2.5 ml.

Inject 500λ per rabbit 250λ×2 sites IM (lumbar)
Prebleed
Immunization #1 (Week 0)
Post-Immune 1 bleed (Week 2)
Immunization #2 (Week 4)
Post-Immune 2 bleed (Week 6)
Immunization #3 (Week 8)
Post-Immune 3 bleed (Week 10)
Immunization #4 (Week 12)
Post-Immune 4 bleed (Week 14)
Immunization #5 (Week 16)
Post-Immune 5 bleed (Week 18)
Immunization #6 (Week 20)
Post-Immune 6 bleed (Week 22)

Samples from the various time points collected in this study are analyzed for binding, neutralization, etc.

Example 5

Based upon the similarity between the F14 and F14/Vt8 structures and those of the fusion peptide-antibody bound SOSIP trimers, we asked whether the F14 trimer would preferentially induce FP region antibodies in rabbits. That is, though immunization with SOSIP timer alone is unlikely to induce an FP targeting response[7], was asked whether the stabilization of this region by the F14 mutations would induce phenotypically more homogeneous responses to the FP region at the gp120/gp41 interface relative to responses induced by a WT SOSIP trimer. Immunizations were carried out in four rabbits each using 100 ug per dose of either the BG505 WT SOSIP or the BG505 F14 SOSIP at time intervals of four weeks for a total of five immunizations using GLA-SE as an adjuvant. Pre-immunization sera were collected prior to the first immunization with post-immunization sera collected two weeks after each immunization.

Figure 36A:
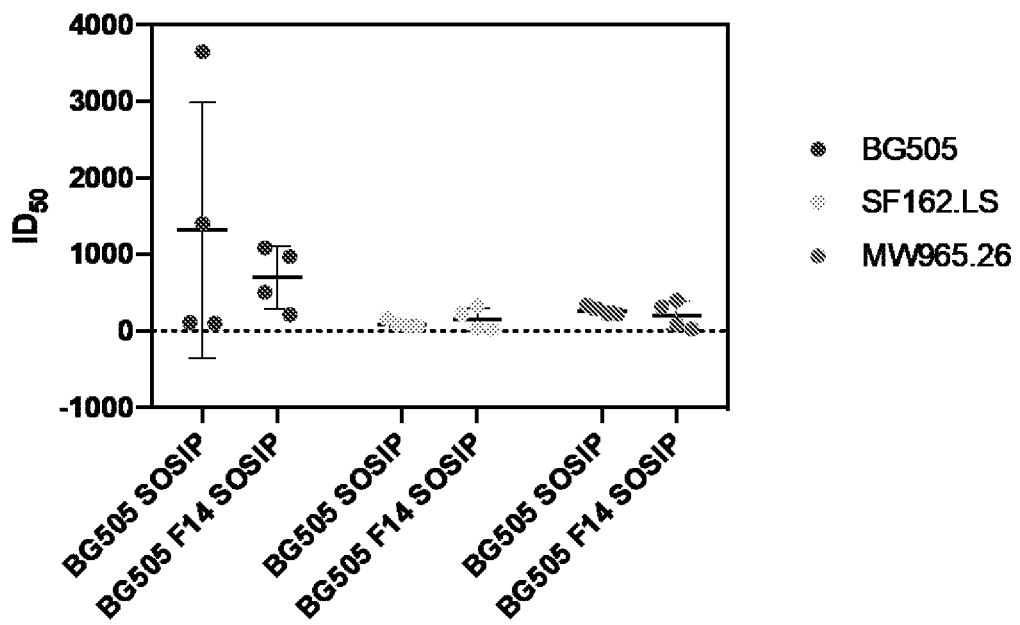
FIGS. 36A-D show Domain organization and immunogenicity of the BG505 (Rabbit study R41) and BG505 F14 (Rabbit study R47) SOSIP.

All four rabbits produced autologous tier-2 neutralizing responses in both the WT and F14 SOSIP immunized rabbits with geometric mean $ID_{50}$s of 495 and 583, respectively, after five immunizations (FIG. 36A, FIG. 38), while neutralization of the easy-to-neutralize tier-1 viruses SF162.LS and MW965.26 was minimal (FIG. 36A, FIG. 39). Though the F14 immunized group displayed a relatively tight titer distribution, the WT rabbits displayed widely disparate titers. Serum neutralization of autologous BG505 virus was observed in three out of five rabbits in a rabbit immunization study using BG505 F14/Vt8 as an immunogen (FIG. 40; data from post 4$^{th}$ immunization sera). As not all rabbits produced autologous neutralizing antibodies, the BG505 F14/Vt8 SOSIP immunized rabbit sera was not further examined.

Figure 36B:
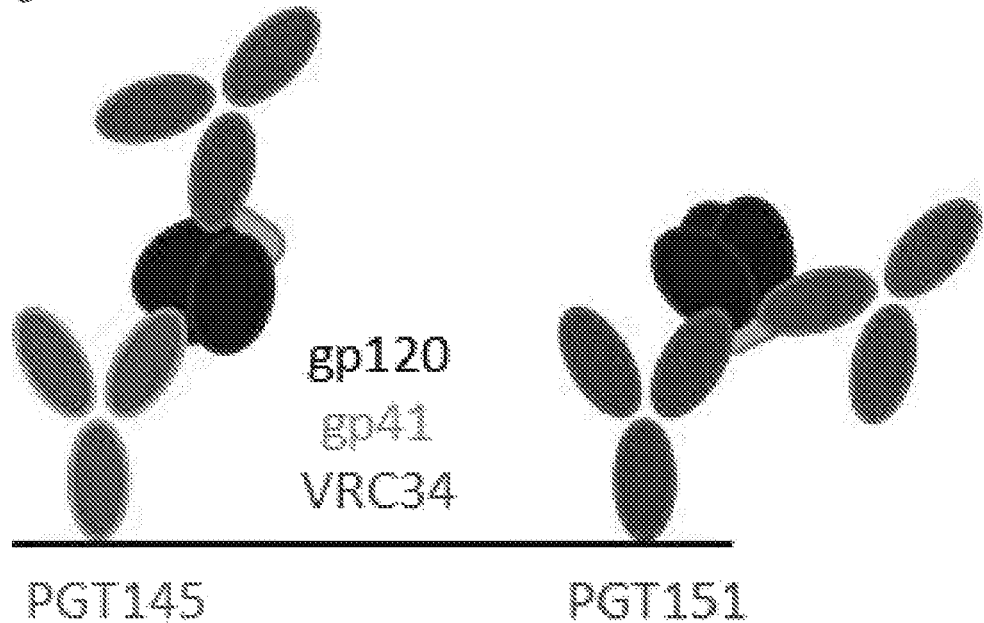
Figure 36C:
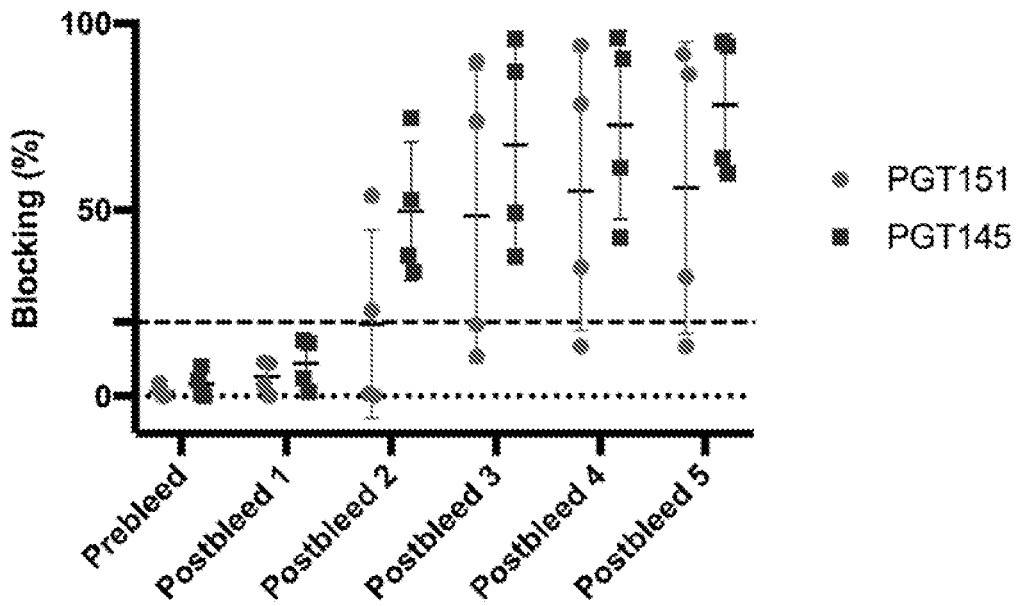
Figure 36D:
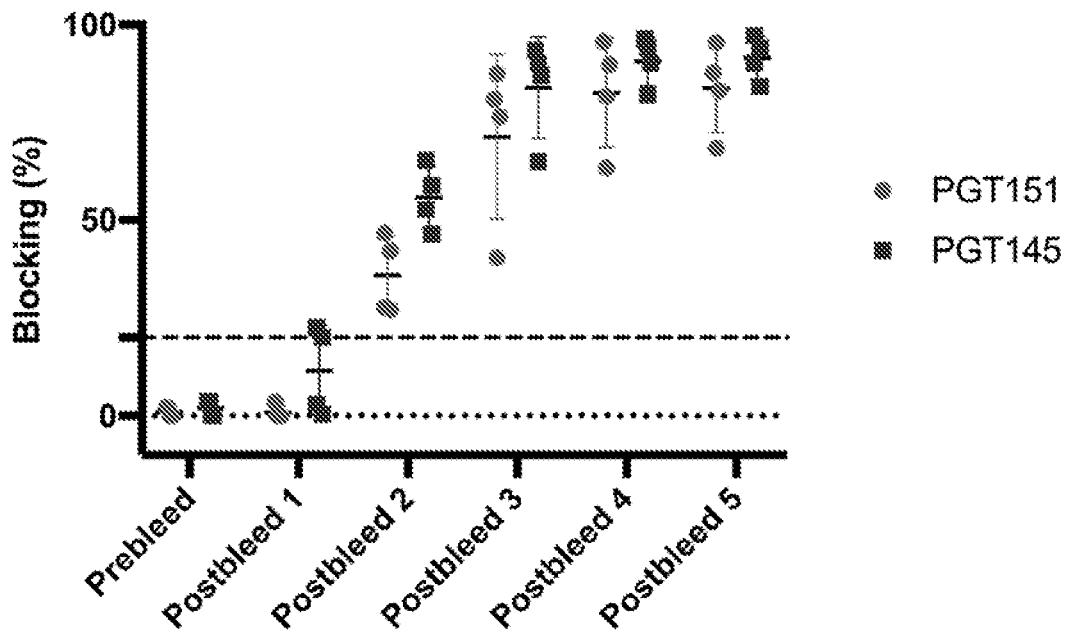
Figure 37:
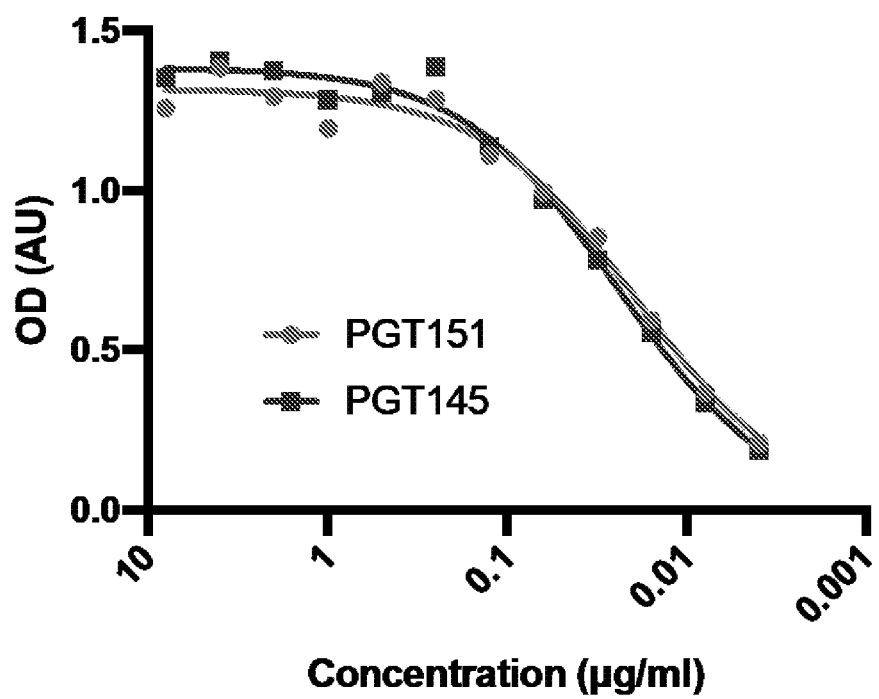
FIG. 37 shows VRC34 ELISA binding to PGT145 and PGT151 capture BG505 F14 SOSIP. Interaction of VRC34 measured at increasing concentration. Curve fit using one site specific interaction model.

In order to compare the relative induction of FP region targeting immune responses in the BG505 WT and BG505 F14 SOSIP immunized rabbits, we next examined N123-VRC34.01 (VRC34) blocking of polyclonal post-immune sera binding to BG505 F14 SOSIP captured on ELISA plates by either PGT151 or PGT145 bnAbs. VRC34 is a broadly neutralizing FP antibody isolated from a HIV-1-infected individual that partially competes for the PGT151 Env gp41-gp120 epitope. We reasoned that phenotypically distinct binding responses would yield differential blocking of VRC34 when the SOSIP was captured using the apex targeting PGT145 vs. the gp120-gp41 interface targeting PGT151 as PGT151 is known to alter the gp120/gp41 interfacial conformation of all three protomers (FIG. 36B). Binding of VRC34 to BG505 F14 SOSIP captured by PGT151 and PGT145 revealed no effect of the capture method on the VRC34 interaction in our assay (FIG. 37). The WT immunized rabbits did not show blocking after the first immunization rising to ~50% blocking after the second. Interestingly, while two rabbits in the WT immunization developed ~95% blocking, two rabbits remained near ~50% blocking (FIG. 36C). After the first immunization, two F14 immunized rabbits displayed weak blocking by VRC34 on PGT145 capture SOSIP rising to ~50% blocking in all four rabbits after the second immunization and plateauing at ~95% blocking after 3 immunizations in 3 rabbits and ~83% blocking in one rabbit after 3 immunizations (FIG. 36D). Blocking of VRC34 on PGT151 captured SOSIP was not observed in either group after the first immunization, rising to ~55% in 4 of 4 of the F14 immunized rabbits after the second immunization at which point only two WT immunized rabbits showed blocking (FIGS. 36C and D). The F14 immunized rabbits reached a PGT151 capture plateau at ~95% blocking after the third immunization with the exception of one rabbit which plateaued at ~75% after the fourth immunization (FIG. 36D). Two of the WT immunized rabbits displayed a similar plateau at ~95% blocking. The two WT immunized rabbits which displayed weaker blocking using PGT145 capture displayed only weak blocking using PGT151 capture at a single time point each. Interestingly, the two low neutralization titer WT-immunized rabbits were those that displayed lower VRC34 blocking with sensitivity to PGT151 capture (FIG. 36D). Together, these data suggested that the BG505 F14 SOSIP presents a more homogenous, immunogenic configuration at this important site of Env vulnerability.

Example 6

Disruption of the HIV-1 Envelope Allosteric Network Blocks CD4-Induced Rearrangements The trimeric HIV-1 Envelope protein (Env) mediates viral-host cell fusion via a network of conformational transitions, with allosteric elements in each protomer orchestrating host receptor-induced exposure of the co-receptor binding site and fusion elements. To understand the molecular details of this allostery, we introduced Env mutations aimed to prevent CD4-induced rearrangements in the HIV-1 BG505 Env trimer. Binding analysis performed on the soluble ectodomain BG505 SOSIP Env trimers, cell-surface expressed BG505 full-length trimers and single-molecule Forster Resonance Energy Transfer (smFRET) performed on the full-length virion-bound Env confirmed that these mutations prevented CD4-induced transitions of the HIV-1 Env. Structural analysis by single-particle cryo-electron microscopy performed on the BG505 SOSIP mutant Env proteins revealed rearrangements in the gp120 topological layer contacts with gp41. Specifically, a conserved tryptophan at position 571 (W571) was displaced from its typical pocket at the interface of gp120 topological layers 1 and 2 by lysine 567, disrupting key gp120-gp41 contacts and rendering the Env insensitive to CD4 binding. Vector based analysis of closed Env SOSIP structures revealed the newly designed trimers exhibited a quaternary structure distinct from that typical of SOSIPs and residing near a cluster of Env trimers bound to vaccine-induced fusion peptide-directed antibodies (vFP Mabs). These results reveal the critical function of W571 as a conformational switch in Env allostery and receptor-mediated viral entry and provide insights on Env conformation that are relevant for vaccine design.

Host cell entry of HIV-1 is accomplished by the envelope glycoprotein (Env) spike. HIV-1 Env is a trimer of heterodimers comprised of gp120 and gp41 protomers, and exists in a metastable conformation capable of transitioning from a prefusion closed configuration to a fusion-competent open state upon triggering by CD4.[1,2] The C-terminal gp41 domain contains a single transmembrane helix and the membrane fusion elements of the trimer.[3-5] The gp120 segment binds the primary receptor CD4, triggering conformational changes leading to the binding of co-receptor CCR5/CXCR4 that causes global rearrangements in the trimer structure leading to viral and cell membrane fusion and gp120 shedding.[6-8] While many studies have sought to understand the nature of the communication between the CD4 binding site, the coreceptor binding site and the fusogenic elements of the HIV-1 Env, a complete understanding of the allosteric mechanism and metastability in HIV-1 Env remains lacking.

The design of a soluble, stabilized ectodomain Env (SOSIP), containing an engineered gp120 to gp41 disulfide (SOS) and an HR1 helix breaking I to P mutation, has revealed structural details regarding broadly neutralizing antibody (bnAb) epitopes and as an immunogen has induced autologous neutralizing antibodies.[2,9] The Env open state presents highly immunogenic, conserved fusion elements that typically induce poorly neutralizing antibody responses with limited heterologous breadth.[10] Indeed, design efforts to improve the Env SOSIP by further stabilizing the closed Env conformation have resulted in multiple prefusion stabilized trimer designs capable of inducing improved autologous, difficult-to-neutralize tier 2 virus antibody responses.[11-14] However, to date, no trimer design has successfully induced robust heterologous antibody responses.

Both the soluble and membrane-bound forms of the Env display an intrinsic ability to transition between multiple conformational states.[2,15-17] In the pre-fusion, closed state, typical of SOSIP trimers, the gp120 domains surround a bundle of three gp41 helices, protecting conserved fusion elements of the trimer (FIG. 1A). Interprotomer gp120 contacts exist at the trimer apex and form a cap that further encloses the gp41 three-helix bundle. This cap is composed of three sequence variable loop regions termed V1/V2 and V3 (FIG. 1A).[3,9,18] Global CD4-induced conformational changes result in dissociation of V1/V2 and V3 from the gp120 core toward a relatively disordered state as well as separation of gp120 from the gp41 three-helix bundle. This results in exposure of the three-helix bundle and fusion elements of the Env trimer.[19,20] A layered architecture of the gp120 inner domain has been described[21], with topological layers 1 and 2 contacting the gp41 subunit and shown, via mutagenesis coupled with cell-cell fusion and neutralization assays, to be important modulators of the CD4-bound conformation.[22] Structures of the CD4-induced open state of the SOSIP Env, determined using cryo-electron microscopy (cryo-EM), showed that three gp120 tryptophan residues, W69, W112, and W427, form contacts from the CD4 binding site β20-β21 loop through to an intermediate helix, containing a portion of layer-2, to the distant gp120 layer-1 loop that is in contact with the gp41 three-helix bundle in the closed state (FIG. 7).[20] In the open state structures, rearrangement of the layer-1 loop, which contains W69, further suggested that layer-1 plasticity plays a role in conformational transitions.[20] Indeed, each loop has been implicated in the regulation of Env conformational transitions.[22,23] Additional structural information from antibody-stabilized, closed-to-open state intermediates in SOSIP trimers suggests trimer opening occurs through ordered conformational transitions.[24]

Despite these advances in our understanding of Env transitions, atomic level details of the allosteric mechanism by which CD4 induces transitions in the Env has remained elusive, thus limiting our ability to leverage such a mechanism for the development of vaccine immunogens. To investigate the allosteric mechanism of CD4-induced Env opening and to design SOSIP and membrane bound Env trimers that are resistant to CD4-induced structural changes, we aimed to interrupt the allosteric network responsible for CD4-induced triggering. The small molecule BMS-626529 is an attachment inhibitor that stabilizes the Env SOSIP in its prefusion closed state preventing CD4 binding and triggering.[25,26] BMS-626529 neutralizes Env pseudoviuruses with nanomolar (nM) IC50, and has shown efficacy in blocking HIV-1 infection in vitro and in vivo.[25] Further, BMS-626529 is known to stabilize membrane Env gp160 in its closed, functional state[26], which is an important target in Env immunogen design efforts. Based upon the known allosteric control elements in the Env[20,21,23] and atomic level details of the binding site of the BMS-626529 inhibitor[26], we designed mutations that disrupted the Env allosteric network and rendered it unresponsive to CD4-induced structural rearrangements. Structure determination via single particle cryo-EM revealed key details regarding how allosteric elements downstream from the gp120-CD4 contact control transitions of the trimer between the Env closed and open states. These results provide a means by which to control the Env conformational ensemble and reveal new details required for understanding the conformational plasticity of the HIV-1 Env.

Results

Design of an Allosterically Decoupled, Conformationally Stabilized Env Construct.

Figure 8A:
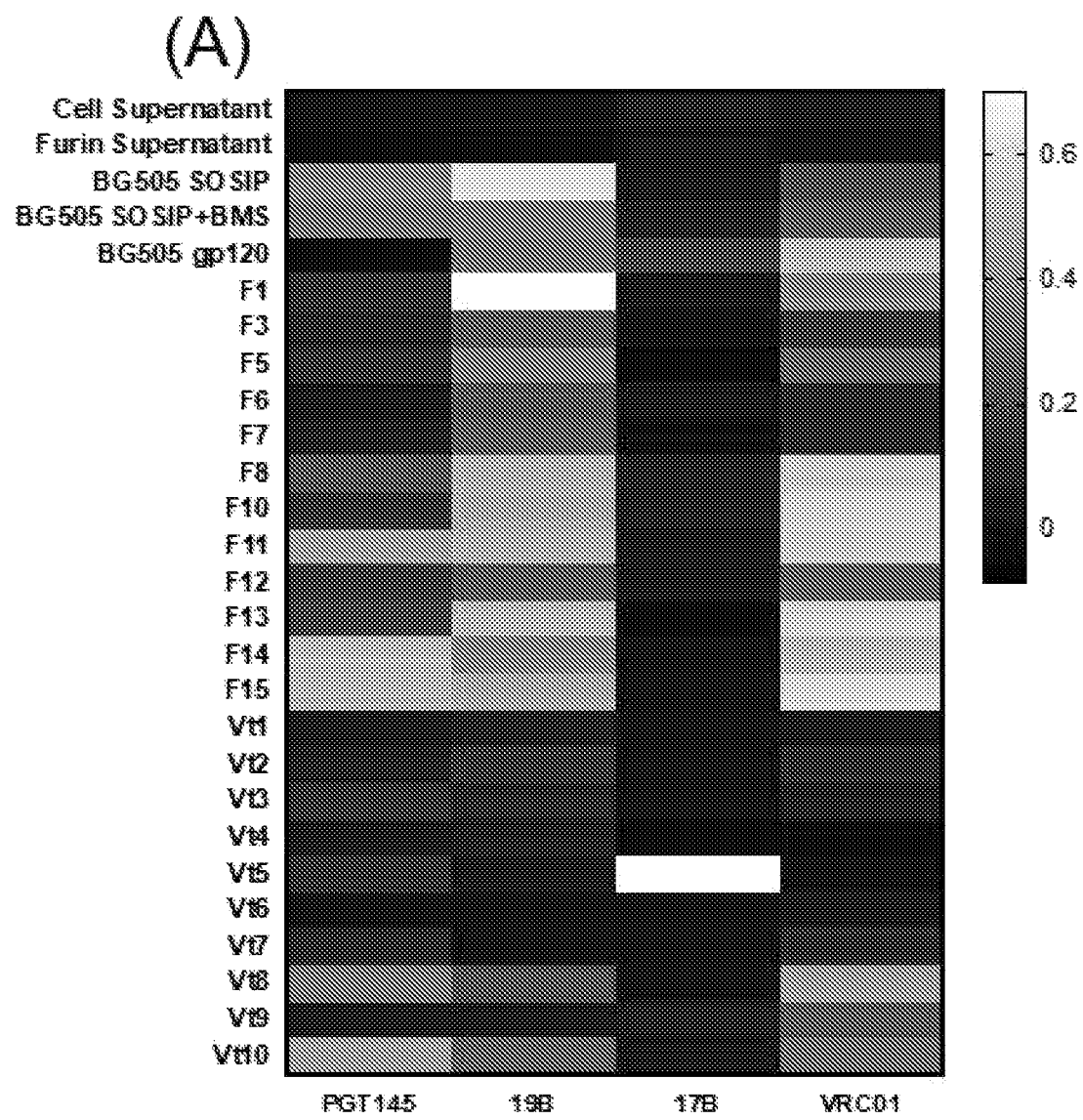
FIGS. 8A-8C show BG505 SOSIP Mutant Screening Results.

The small molecule HIV-1 entry inhibitor BMS-626529 has been shown to prevent sCD4-induced rearrangements in both soluble gp140 SOSIP trimers and native virion bound Env gp160.[25,26] We reasoned that design of stabilized Env trimers based on an understanding of BMS-626529-mediated stabilization could lead to novel mutations that inhibit CD4 triggering for both the soluble SOSIP and membrane-bound Envs. A recent structure of a BG505 SOSIP in complex with BMS-626529 revealed that the compound resides in an induced pocket between the β20-β21 loop and the layer-2 α-1 helix, thus acting to separate the inner and outer domains (FIG. 1A).[26] The BMS-626529 compound appears to interrupt CD4 interaction by sequestering three key CD4 contact residues, N425, M426, and W427, thus impeding CD4 interaction and associated downstream rearrangements. Based upon the BMS-626529 contact region and neighboring residues in this structure, we selected clade A BG505 Env outer domain residues V255 and N377 and β20-β21 residues M426 and M434 for mutagenesis. (FIG. 1A). In combination with these residues, additional sites were selected in layer-1 residues V68, H66, W69, and H72, layer-2 residue S115, and V1/V2 region residues A204 and V208 in order to prevent transitions in these conformationally plastic regions (FIG. 1A). Together, this set of mutation sites, termed the F-series (FIG. 15), included residues spanning the entire allosteric network region of gp120 from the CD4 binding site to the closed state site of gp120 contact with gp41 HR1. While the F-series mutations were designed to block CD4-triggering, we reasoned that V3 exposure may occur even in the absence of full triggering of the Env[27] and examined residues in the V1/V2 to V3 contact region for mutagenesis to lock V3 in its prefusion, V1/V2-coupled state. We selected outer-domain residues E381 and Q422, V1/V2 region residues Q203, D180, and Y177, V3 residues R298, N300, N302 and T320, and residue Y435 for mutagenesis (FIG. 1A). This set of mutations, termed the Vt-series (FIG. 15), was introduced to prevent V3 exposure in a manner similar to previous stabilization strategies.[13,28] Hydrophobic and/or space-filling mutations were made at each site for both the F-series and Vt-series sites. Beginning from a construct containing all sites in each series, smaller sets of mutations were prepared in order to examine the effect of particular mutations and to maximize the likelihood of identifying a suitable set of mutations for downstream processing (FIG. 15). In order to examine their effect on the SOSIP trimer, each BG505 SOSIP mutant and the unmutated BG505 SOSIP (BG505 SOSIP) was transfected in HEK Freestyle293 (293F) cells followed by cell culture supernatant screening via biolayer interferometry (BLI) (FIG. 8A). The antibodies used in this screening included PGT145, 17B, 19B, and VRC01 in order to assess trimer quaternary conformation, CD4i epitope exposure, V3 exposure, and gp120 folding, respectively.

Figure 1D:
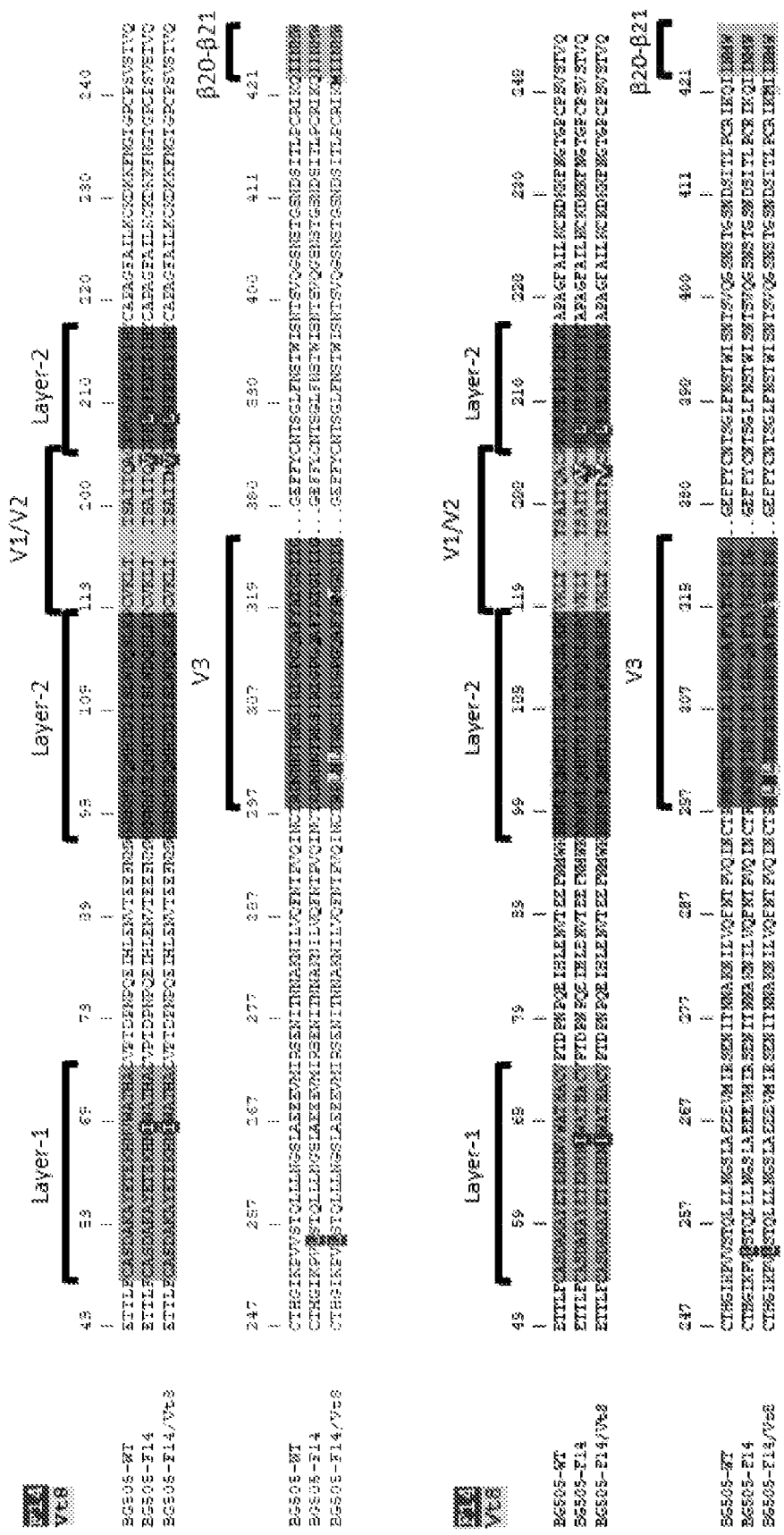

Comparison of these results with the differences observed in the same assay for BG505 SOSIP in the presence and absence of BMS-626529 identified the 'F' series mutants F11, F14, and F15 as well as the 'Vt' series mutant Vt-8 as candidates for replicating the effects of the BMS-626529 compound. Each construct displayed a higher binding response to PGT145 and VRC01, no apparent 17B binding, and reduced 19B binding relative to the BG505 SOSIP (FIG. 8A; mutations from [13] included for comparison). The Vt8 mutations consisted of the V1/V2 mutation Q203M, V3 mutations N300L, N302L, and T320M, and the outer-domain mutation Q422M (FIGS. 1B and D). The F14 mutations consisted of the layer-1 mutation V68I, layer-2 mutations A204V and V208L, and the outer-domain mutation V255L (FIGS. 1C and D). The F15 mutant included the F14 mutations in addition to a gp120 outer-domain mutation N377L with F11 including mutations S115V, H72P, and H66S in addition to the F15 mutations. We selected the F14 construct for further characterization as it possessed the fewest number of mutations relative to F11 and F15. Since the F14 mutations were primarily in the layer 1 and 2 regions and were predicted to block the transition after CD4-induced destabilization of V1/V2 and V3, we combined F14 and Vt8 (F14/Vt8) in order to minimize V3 exposure (FIG. 1D).

Trimer Formation, Antigenicity, and Soluble CD4 (sCD4) Triggering of the Redesigned SOSIP Constructs.

Figure 8B:
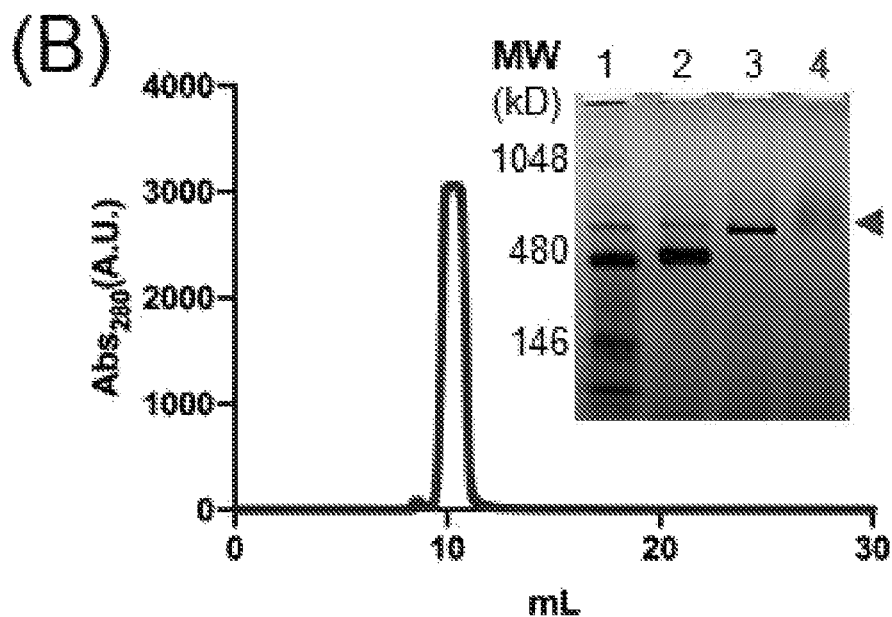
Figure 8C:
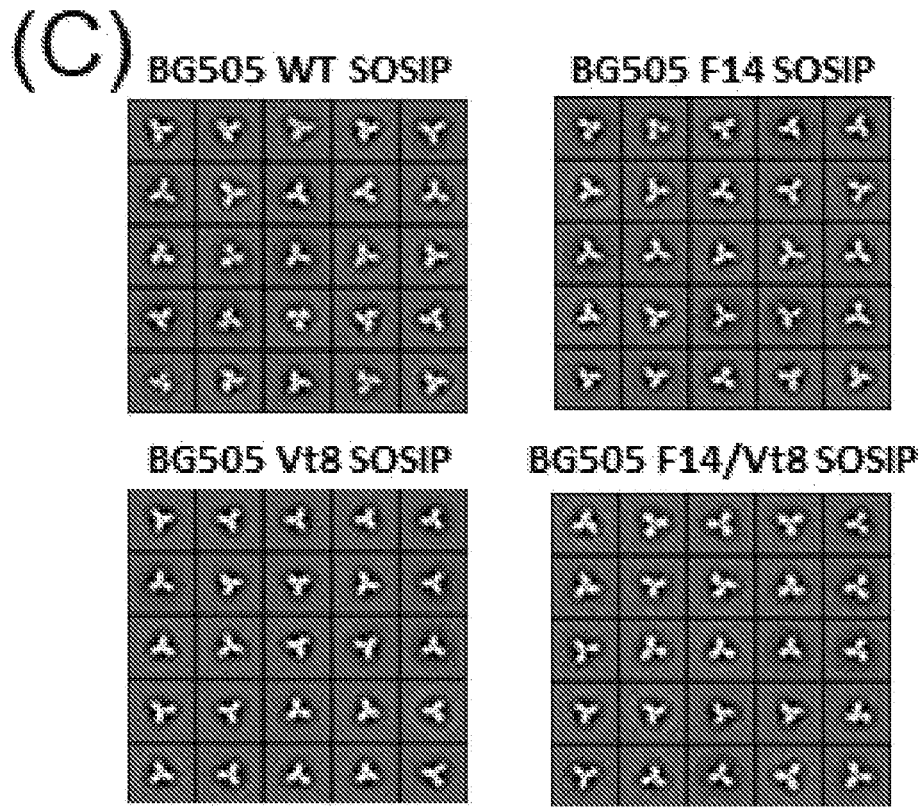

To evaluate the antigenicity of the designed Env mutants, we produced and purified the BG505 and mutant SOSIP Env variants by transient transfection in 293F cell culture followed by PGT145 affinity chromatography to select for well-folded trimers. The PGT145 purified material was further purified via size exclusion chromatography which resulted in a homogenous peak corresponding to the SOSIP trimer yielding a gp140 band when analyzed by non-reducing SDS-PAGE gel (FIG. 8B). We verified trimer formation for each construct by negative stain (NS) electron microscopy. The NS 2D-class averages of each construct confirmed that the mutants adopted a trimeric configuration similar to that of the BG505 SOSIP trimer (FIG. 8C).

Figure 1E:
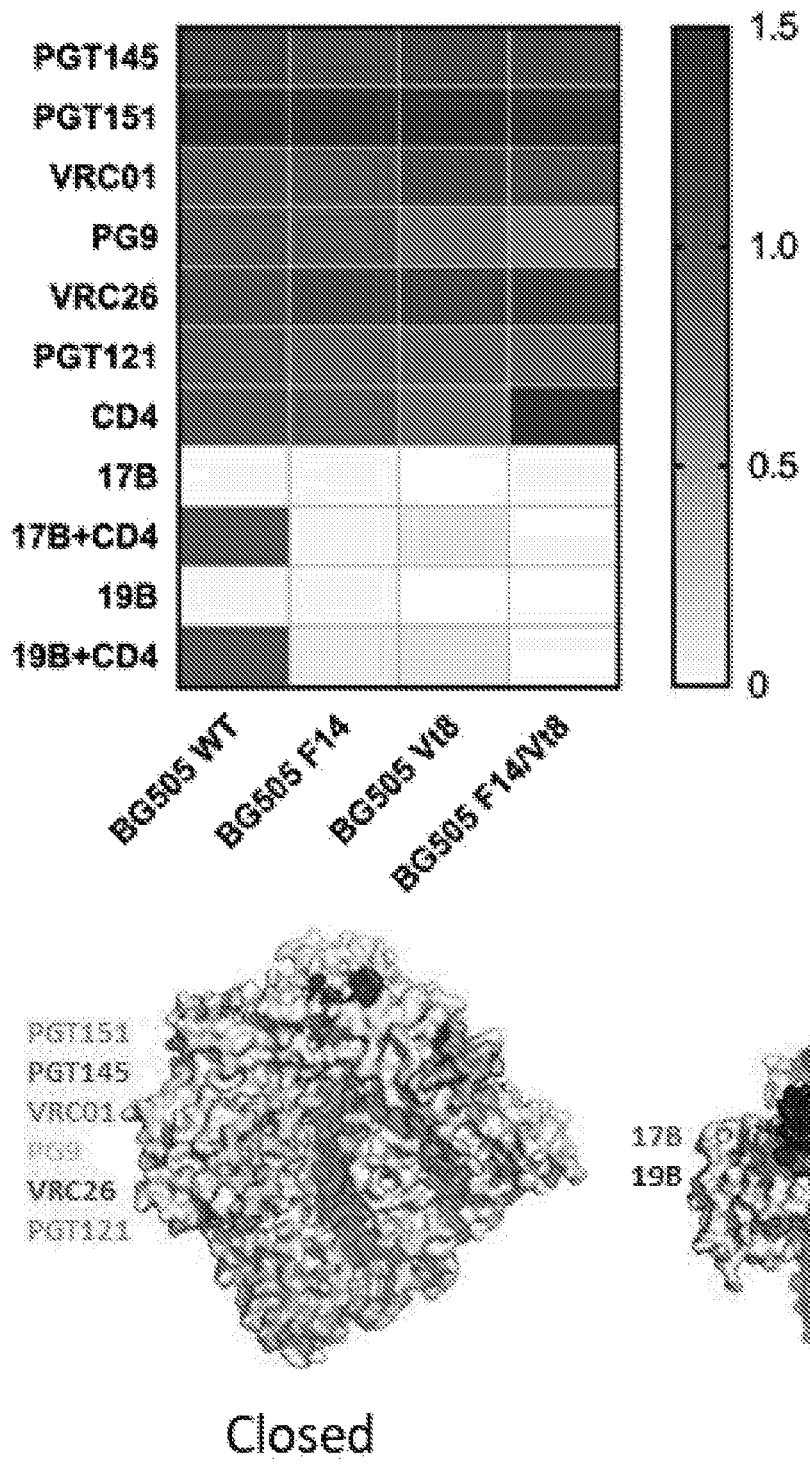
Figure 9A:
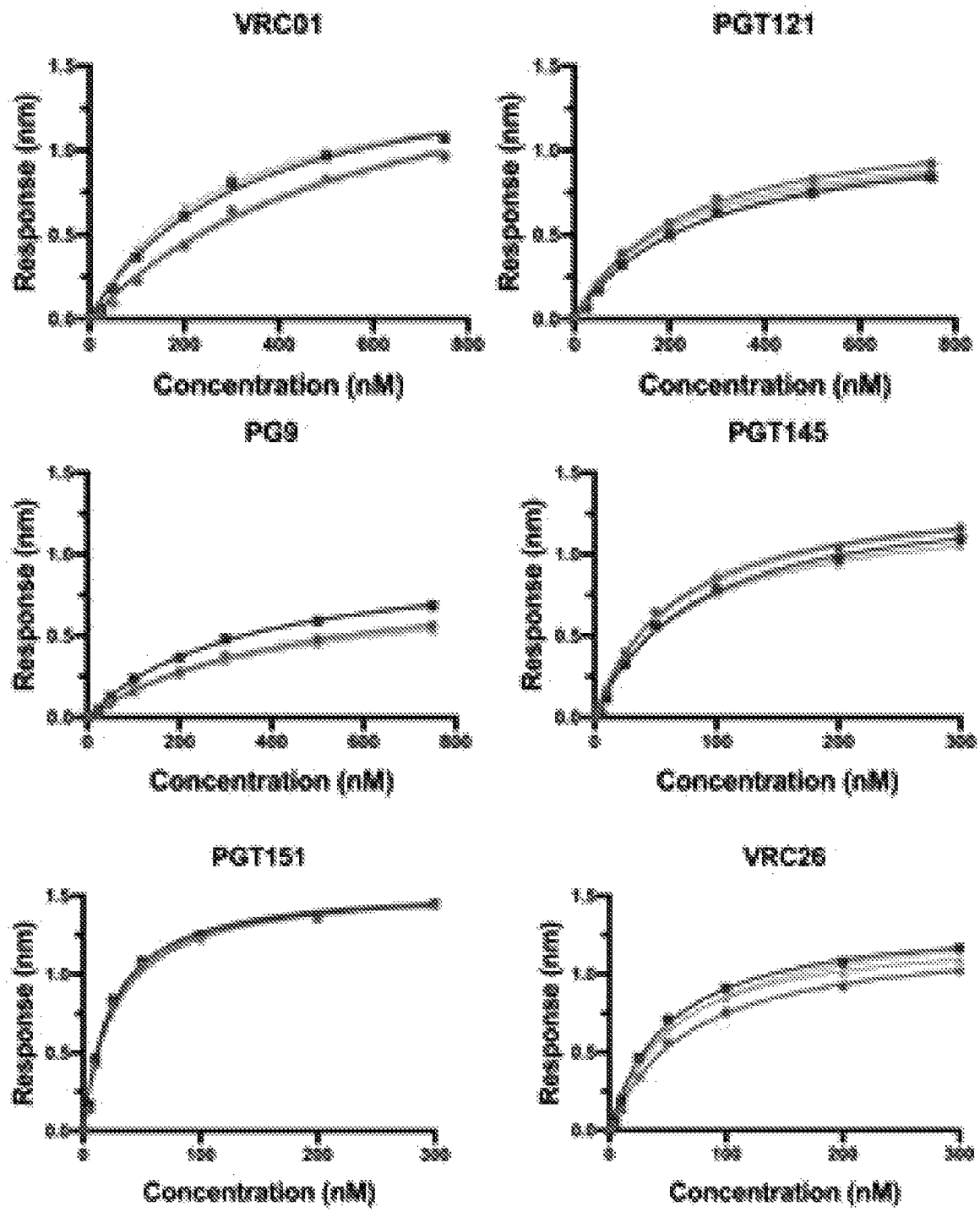
FIGS. 9A-9C show BG505 SOSIP Mutant bnAb Binding, CD4 binding, and CD4 Triggering.

We next examined the antigenicity of key bnAb epitope specificities for the redesigned SOSIPs via BLI using VRC01, PGT121, PG9, PGT145, PGT151, and VRC26 bnAbs, having CD4 binding site, glycan-V3, glycan-V1/V2, trimer apex, gp120/gp41 interface, and V1/V2 epitope specificities, respectively (FIG. 1E). VRC01 binding indicated a ~2-fold enhanced affinity for both Vt8 and F14/Vt8 relative to the BG505 SOSIP (FIG. 1E, FIG. 17, FIG. 9A). Fitting of the dose response curves for PGT121, PG9, PGT145, PGT151, and VRC26 indicated the mutations did not alter the affinity of the trimer for these important bnAb epitope specificities with nominal fold changes on the order of 1.0-1.3 (FIG. 1E, FIG. 17, FIG. 9A). These results indicated that the mutant designs presented a native, well-folded SOSIP trimer configuration and effectively presented multiple bnAb epitope specificities.

Figure 9B:
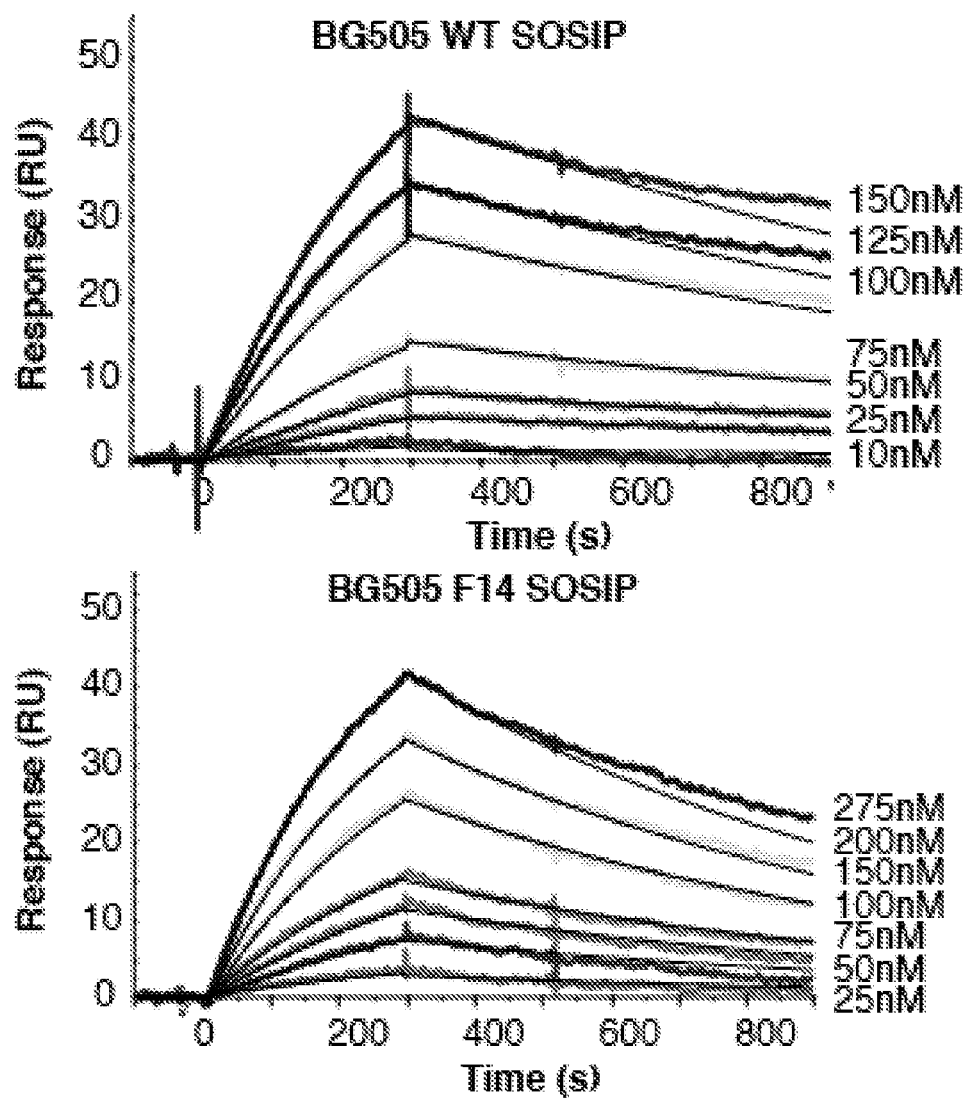
Figure 9B:
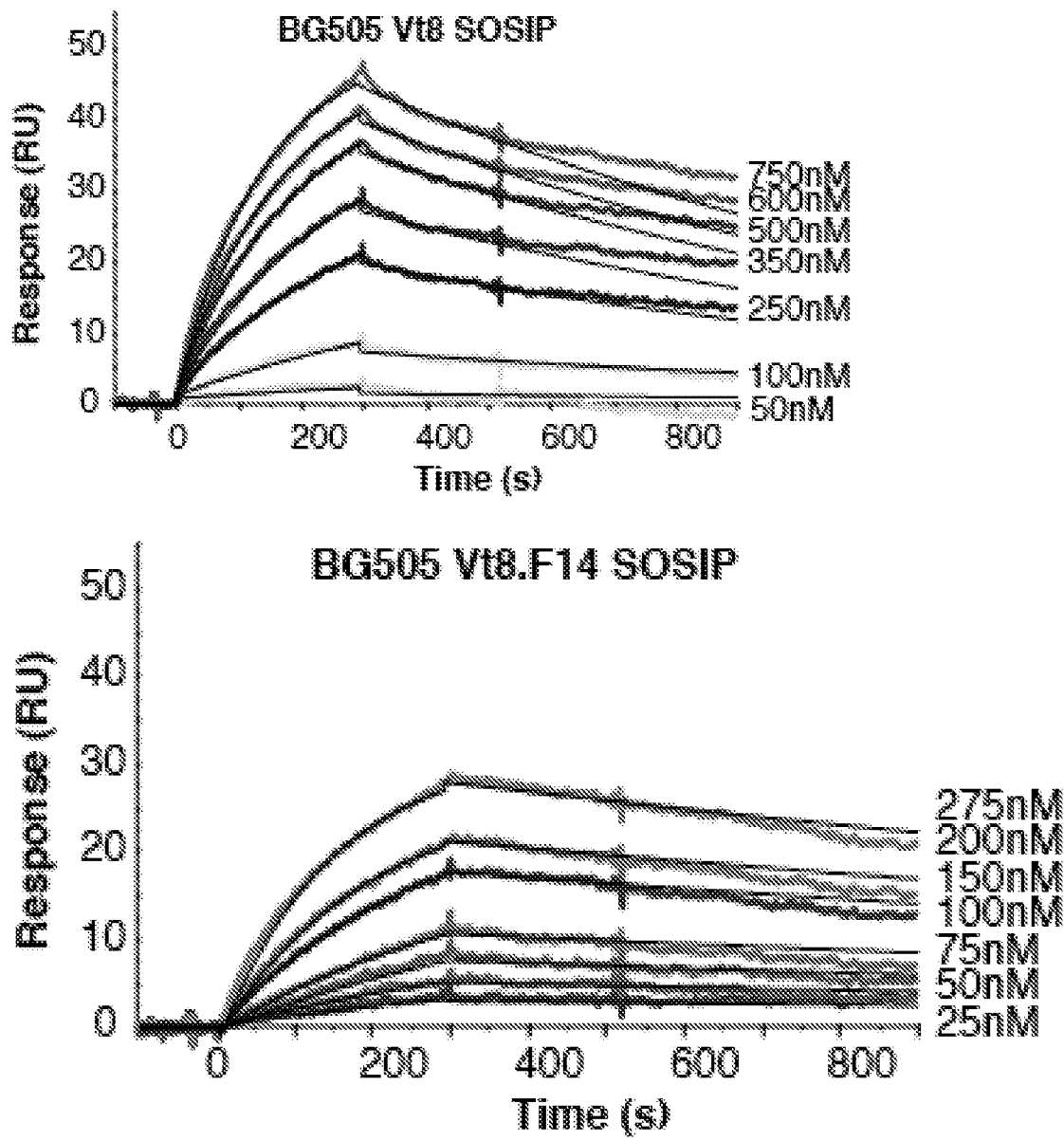
Figure 9C:
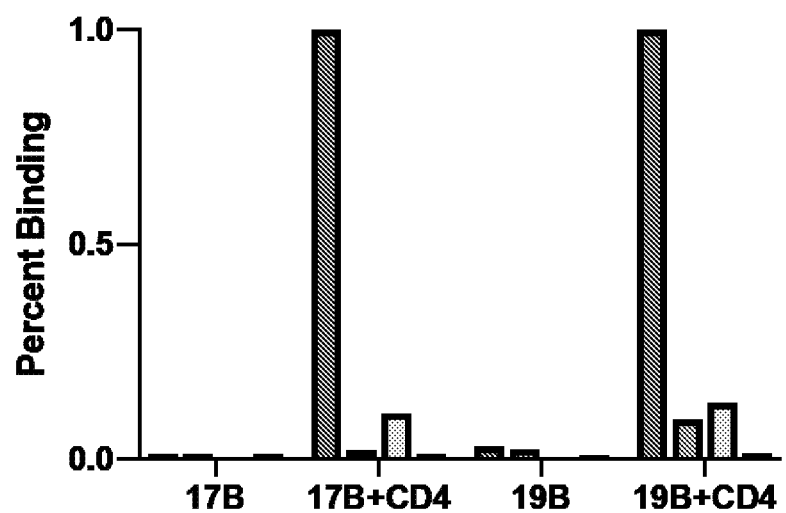

We next asked whether these mutations altered sCD4 binding. We determined the apparent affinity of each mutant construct and BG505 SOSIP for sCD4 via surface plasmon resonance (SPR). The affinities to CD4 determined for the F14 and Vt8 mutant SOSIPs matched that of BG505 SOSIP closely with $K_{DS}$ of 73.0 nM±26.2 nM, 83.9 nM±12.6 nM, and 67.9 nM ±26.4 nM, respectively (FIG. 1E, FIG. 16, FIG. 9B). The BG505 F14/Vt8 SOSIP construct displayed a ~4-fold enhanced CD4 affinity compared to BG505 SOSIP with a $K_D$ of 15.6 nM±0.4 nM primarily as a result of an enhanced association rate (FIG. 1E, FIG. 16, FIG. 9B). As each construct bound CD4, we next asked whether sCD4 triggering was inhibited by the F14, Vt8, and F14/Vt8 mutations relative to the BG505 SOSIP. The CD4i antibody 17B and V3-targeting antibody 19B were used to monitor triggering of the coreceptor binding site and V3 exposed states, respectively. The results for the F14 construct indicated that sCD4 triggering of the open state is nearly eliminated based upon the lack of 17B response together with a ~11-fold reduction in V3 response (FIG. 1E, FIG. 9C). The Vt8 mutations similarly reduced 19B epitope exposure by ~7-fold with triggering of the 17B epitope reduced by ~9-fold (FIG. 1E, FIG. 9C). Importantly, the combined F14/Vt8 construct eliminated CD4-induced exposure of both epitopes (FIG. 1E, FIG. 9C).

Thermal Stability of F14 and F14 Vt8 SOSIPs

Figures 2A, 2B, 2C, 2D:
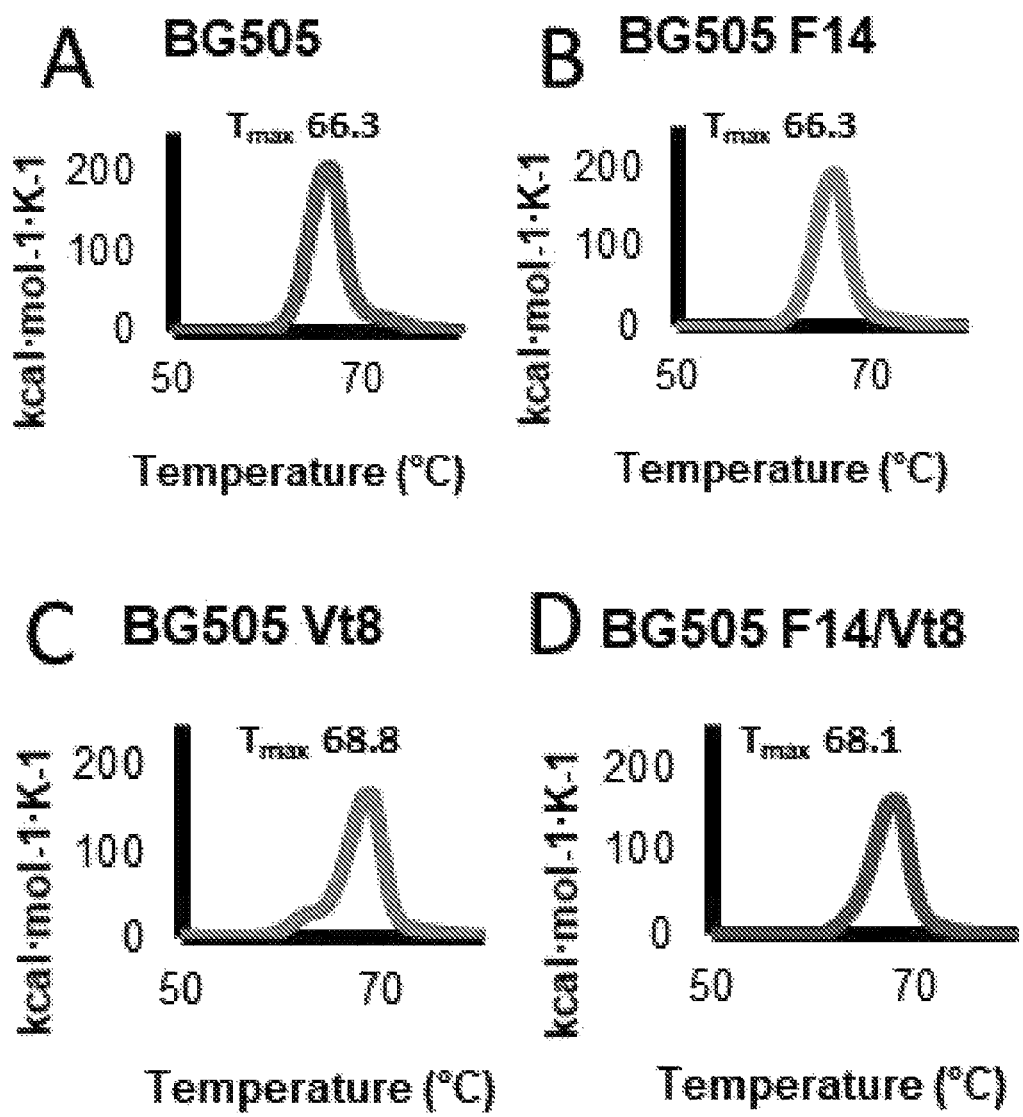
FIGS. 2A-D show physical stability of BG505 SOSIP.664 and mutants. Differential scanning calorimetry data for BG505 parent, F14, Vt8, and F14/Vt8 SOSIPs. Data presented are representative of three independent measures.

To assess the thermal stability of the F14, Vt8 and F14/Vt8 SOSIP trimers, and to compare them with BG505 SOSIP, we determined thermal denaturation maxima ($T_{max}$) using differential scanning calorimetry (DSC), which showed that that the F14 mutations did not alter trimer thermal stability with $T_{max}$ values of 66.3° C.±0.02 and 66.3° C.±0.06 for the BG505 and F14 constructs, respectively (FIG. 2). The Vt8 and F14/Vt8 constructs displayed a 2.5° C. 0.02 and 1.8° C.±0.05 increase in $T_{max}$, respectively, indicating the Vt8 mutations slightly improved thermal stability of the SOSIP trimer (FIG. 2).

Cryo-EM Structures of the BG505 F14 and F14 Vt8 SOSIPs.

Figure 3A:
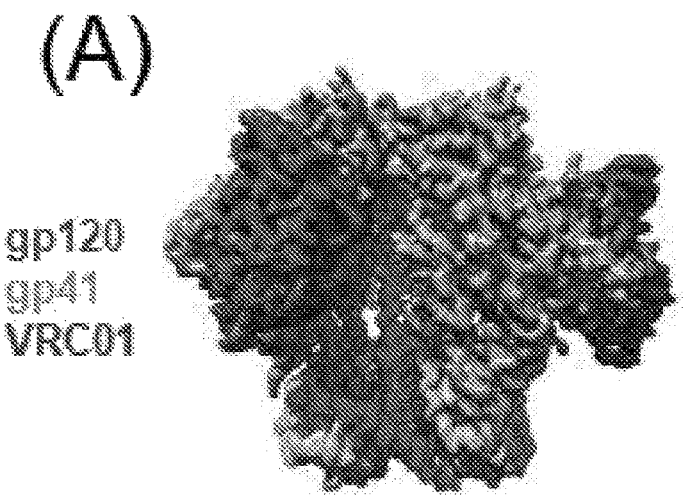
FIGS. 3A-3J shows structural details of BG505 F14 SOSIP and BG505 F14/Vt8 SOSIP.
Figure 3B:
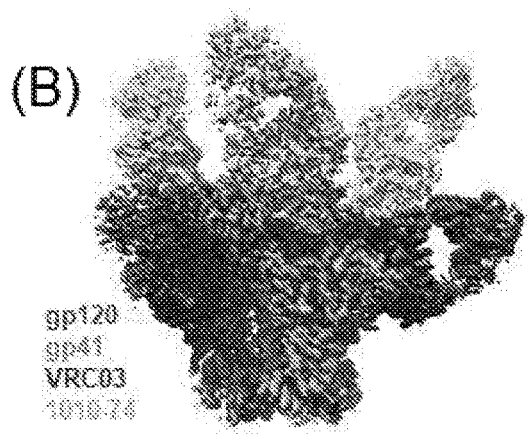
Figure 3C:
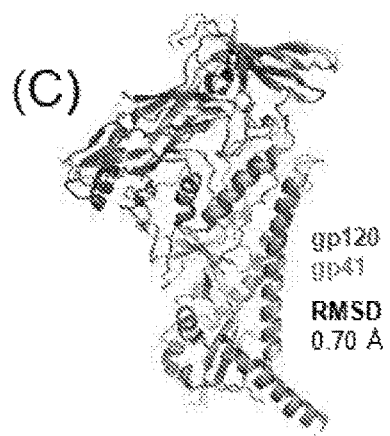
Figure 3D:
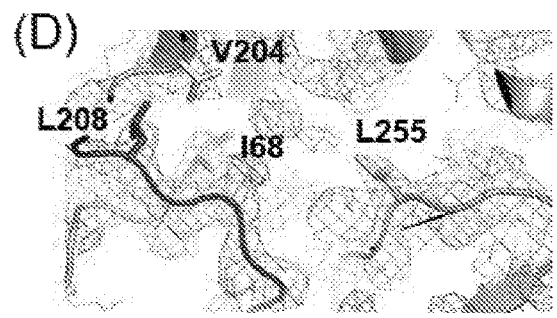
Figure 3E:
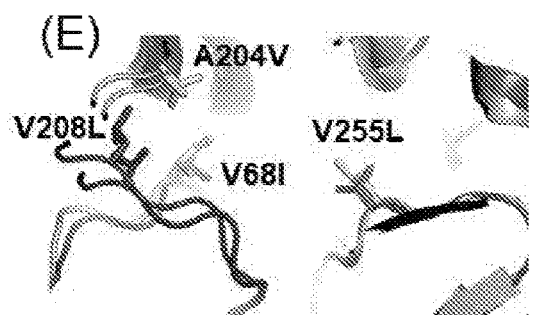
Figure 3F:
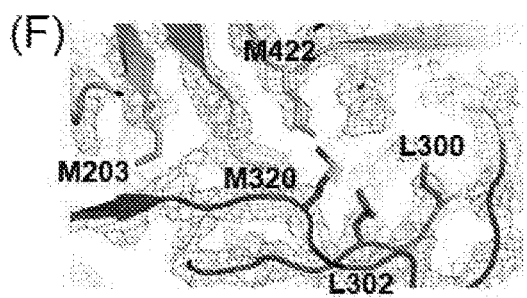
Figure 3G:
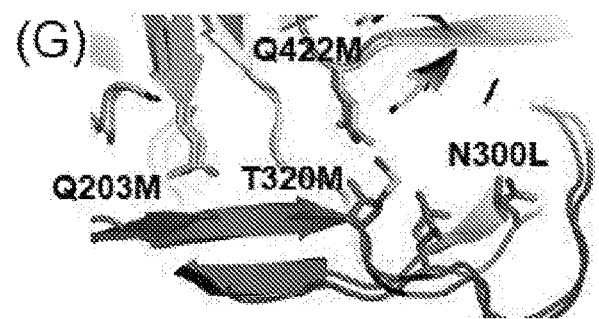
Figures 10A, 10B, 10C, 10D, 10E, 10F, 10G, 10H, 10I, 10J:
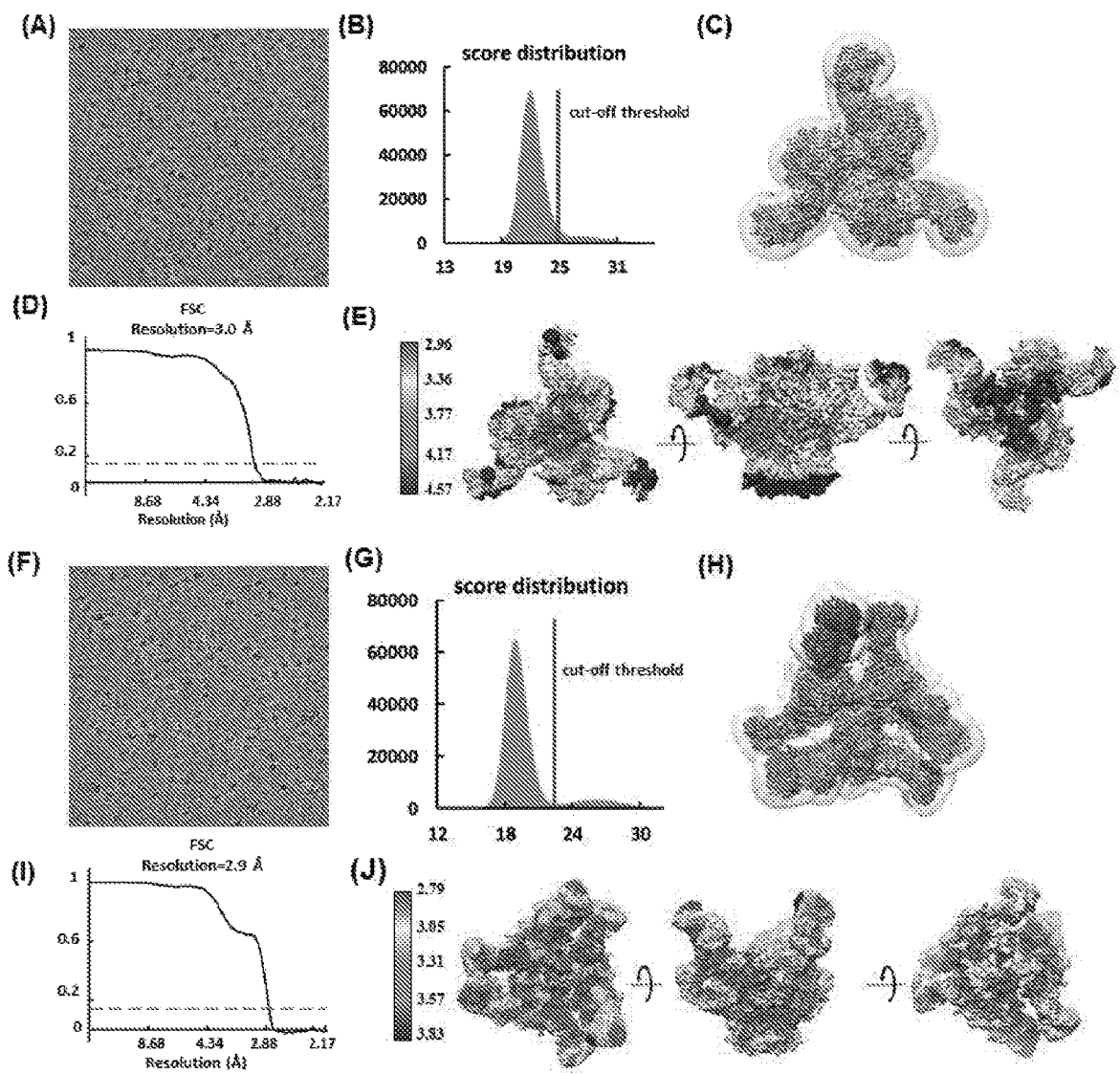
FIGS. 10A-10J show cryo-EM data analysis for BG505 F14 and F14/Vt8 SOSIP datasets.
Figure 11A:
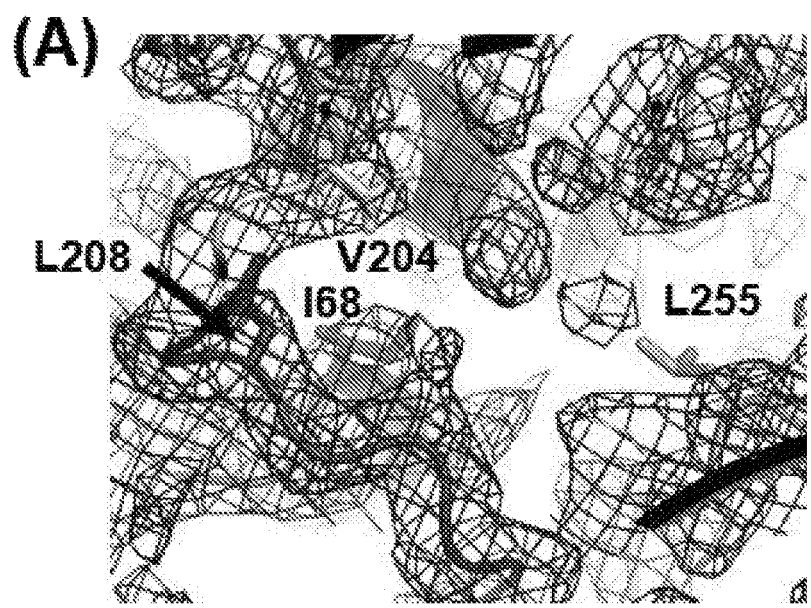
FIGS. 11A-11D show Cryo-EM fit of BG505 F14 mutations.
Figure 11B:
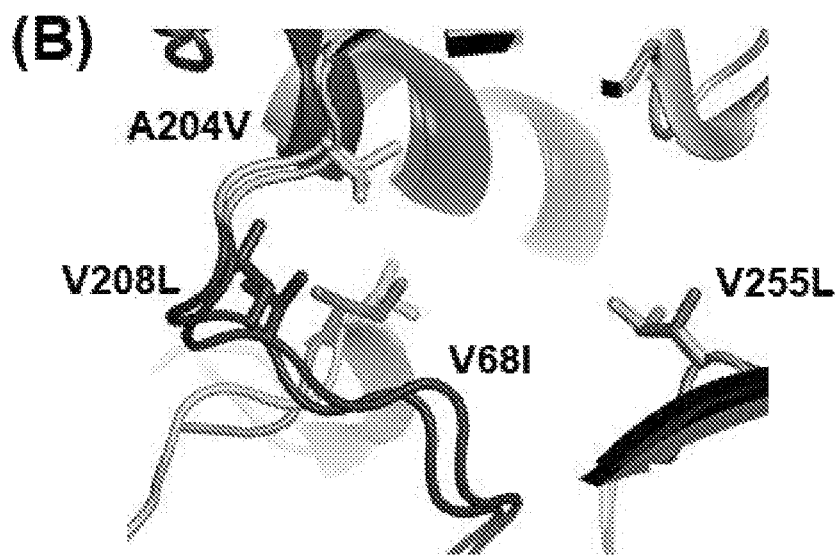
Figure 11C:
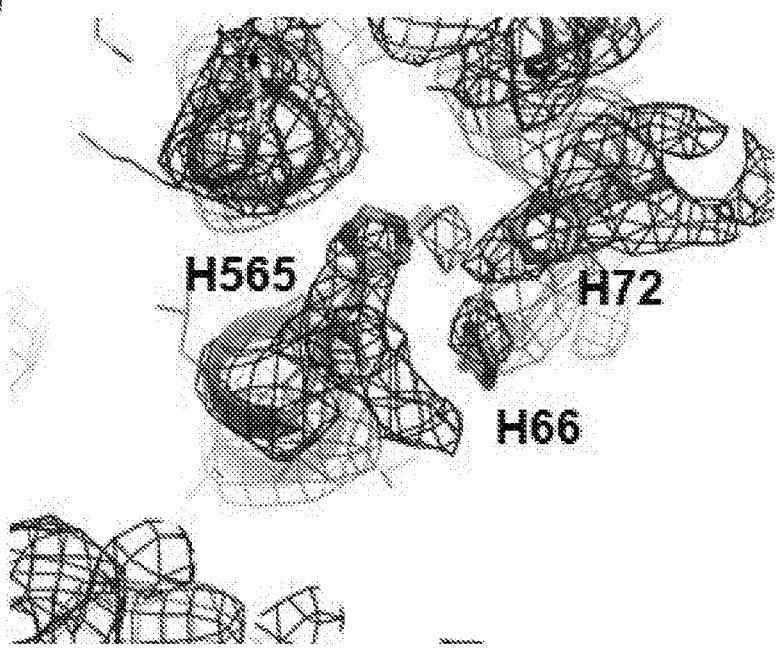
Figure 11D:
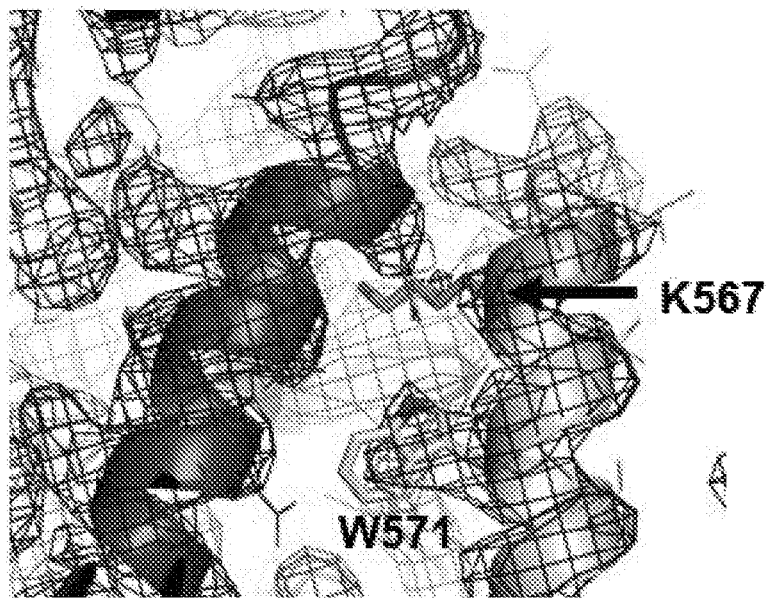

To understand the structural basis for the observed lack of CD4-induced conformational rearrangements, we determined structures of the F14 SOSIP trimer in complex with VRC01 (FIG. 3A) and the F14/Vt8 SOSIP trimer in complex with VRC03 and 10-1074 (FIG. 3B) via single particle cryo-electron microscopy (cryo-EM). Map reconstruction was initially carried out in cryoSPARC[29] followed by further refinement outside of cryoSPARC as described in the methods section (FIG. 10, FIG. 18). A total of 77,632 and 84,378 particles yielded final map resolutions of 3.0 Å and 2.9 Å, respectively (FIG. 10). Fitting of atomic coordinates into each map revealed similar overall structures for both BG505 F14 and F14/Vt8 SOSIPs with a root mean square deviation of 0.70 Å for gp140 alignment (FIG. 3C). The F14 mutations predominantly reside in V1/V2 near the apical region of layer-2 and in layer-1 near the gp120 contact with gp41 HR1 (FIG. 1A-C, 3D-G). Clear densities for the F14 and Vt8 mutations were observed in both structures revealing minimal change in their positions relative to their typical SOSIP positions (FIGS. 3D and F, FIG. 11).

Figure 3H:
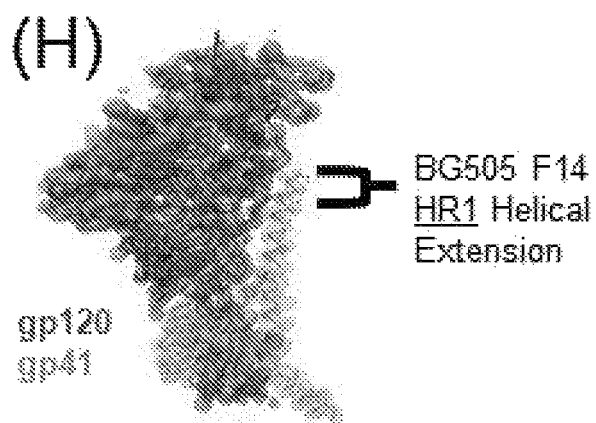
Figure 3I:
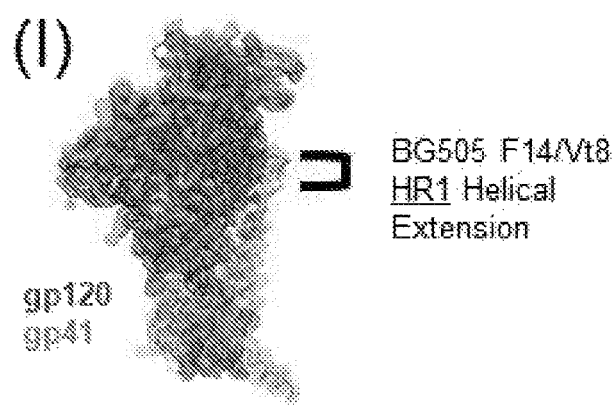
Figure 3J:
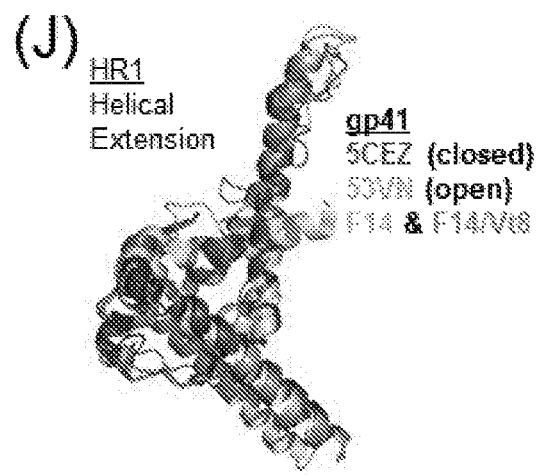
Figures 4A, 4B, 4C, 4D:
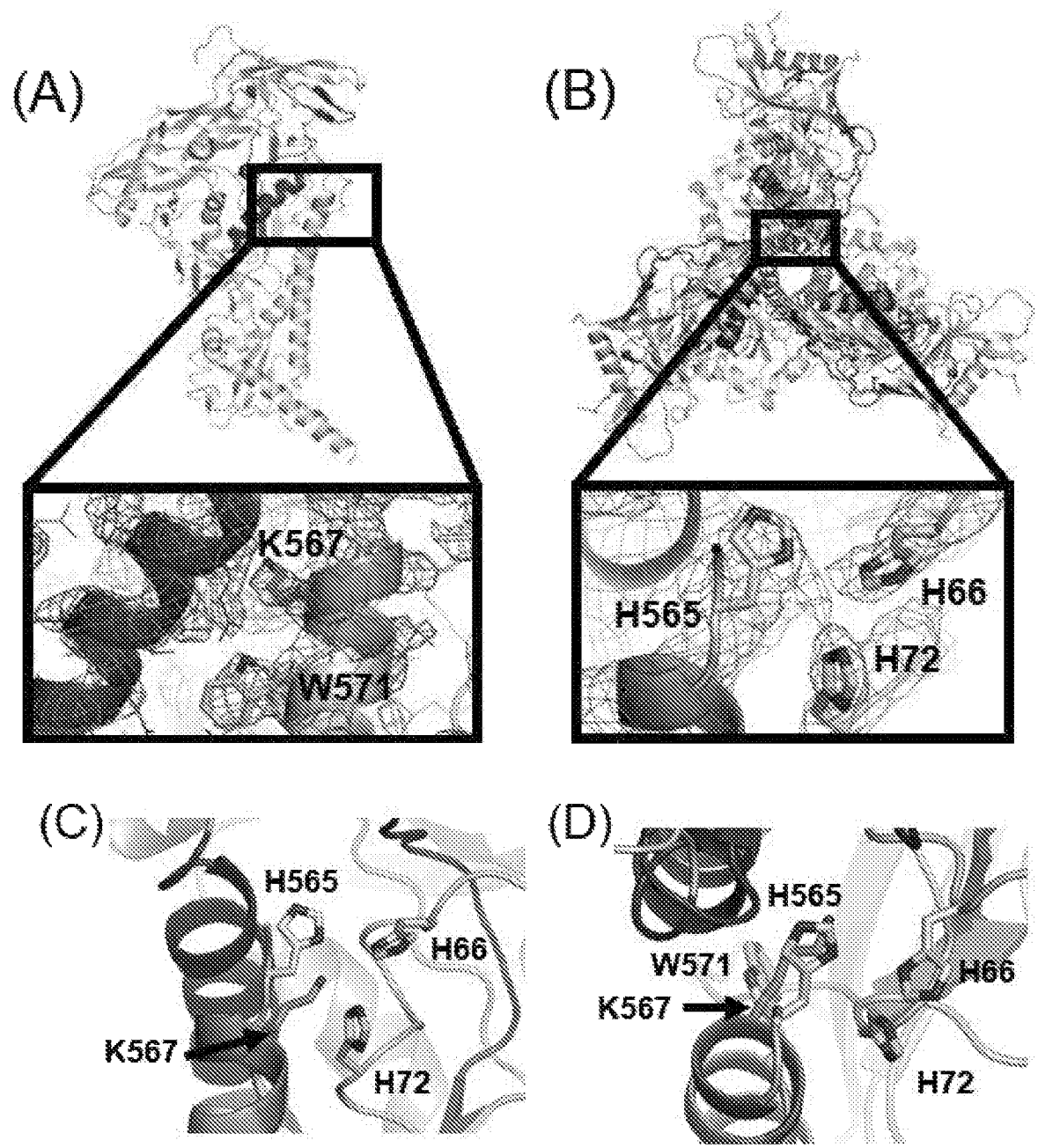
FIGS. 4A-4F show atomic level structural details of BG505 F14/Vt8 SOSIP.
Figures 4E, 4F:
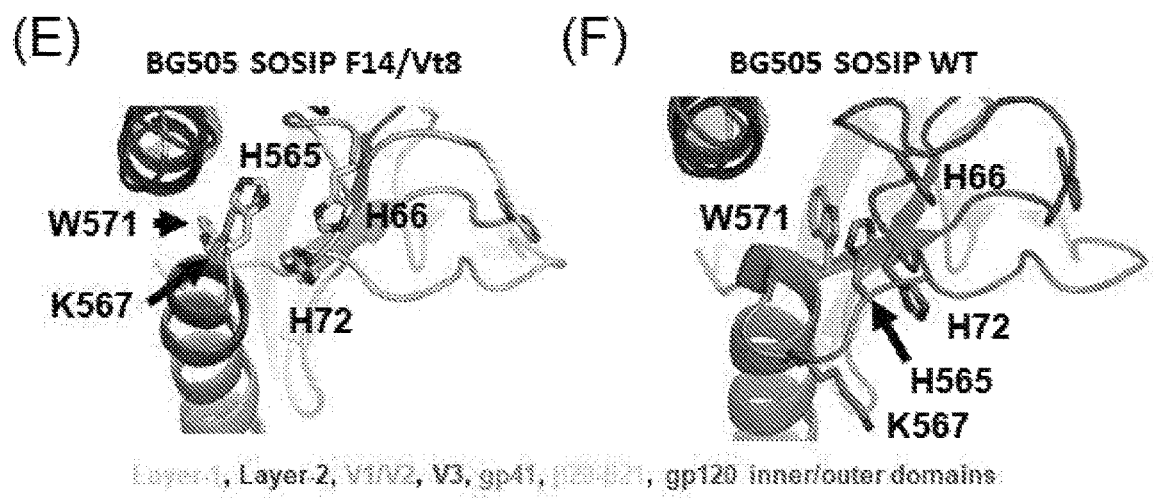

However, map densities in the C-terminal portion of HR-1 in both F14 and F14/Vt8 trimers displayed a helical extension of the buried three helix bundle toward the trimer apex, a feature that resembles the extension observed in open and partially open SOSIP structures (FIGS. 3H, I, and J).[20,24] As a result of this gp41 restructuring, residue K567 displaced W571 from the layer-1/layer-2 pocket that was formed by residues F43, C54, W69, T71, A73, C74, D107, L111, and T217 (FIGS. 4A and D). In the F14/Vt8 structure, this restructuring was associated with a rearrangement in layer-1 that reoriented residues H66 and H72 resulting in the formation of a potentially water mediated histidine triad configuration with gp41 HR1 H565 (FIG. 4B, C, D). Interestingly, the F14 map displayed layer-1 loop densities suggestive of multistate behavior. Specifically, density corresponding to H66 and H72 in a configuration similar to that of the F14/Vt8 structure appeared alongside additional distinct densities, which may correspond to differing H72 sidechain configurations (FIG. 11). This suggested that the addition of the Vt8 mutations in the F14/Vt8 construct further stabilized the topological layer region facilitating the observed reduction in sCD4 triggering. Together, these results showed that structural changes in the region of gp120 contact with the C-terminal portion of gp41 HR1 caused by the F14 mutations effectively decoupled key allosteric control elements in the HIV-1 Env SOSIP trimer.

Comparison of F14 and F14 Vt8 to Previously Determined Env Trimer Structures

Figure 5A:
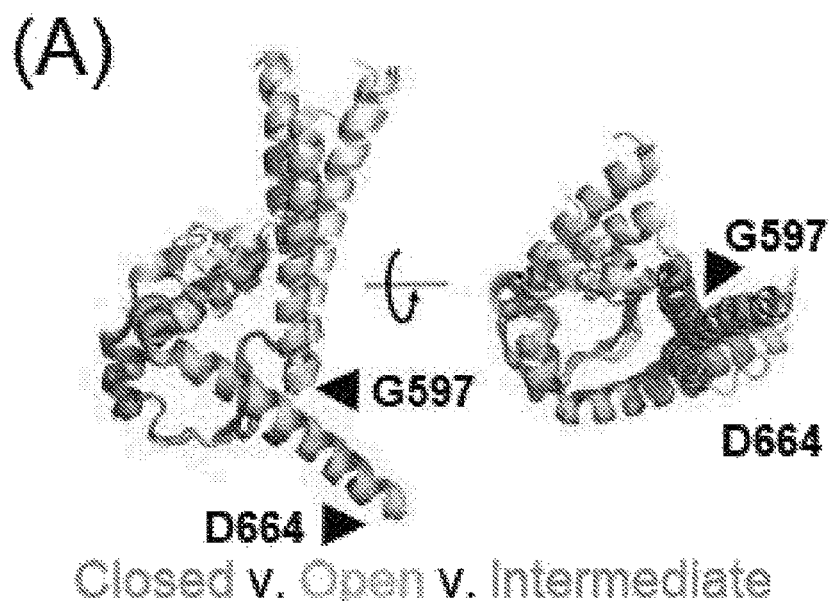
FIGS. 5A-5F show domain organization and immunogenicity of the BG505 F14 and BG505 F14/Vt8 SOSIP
Figure 5B:
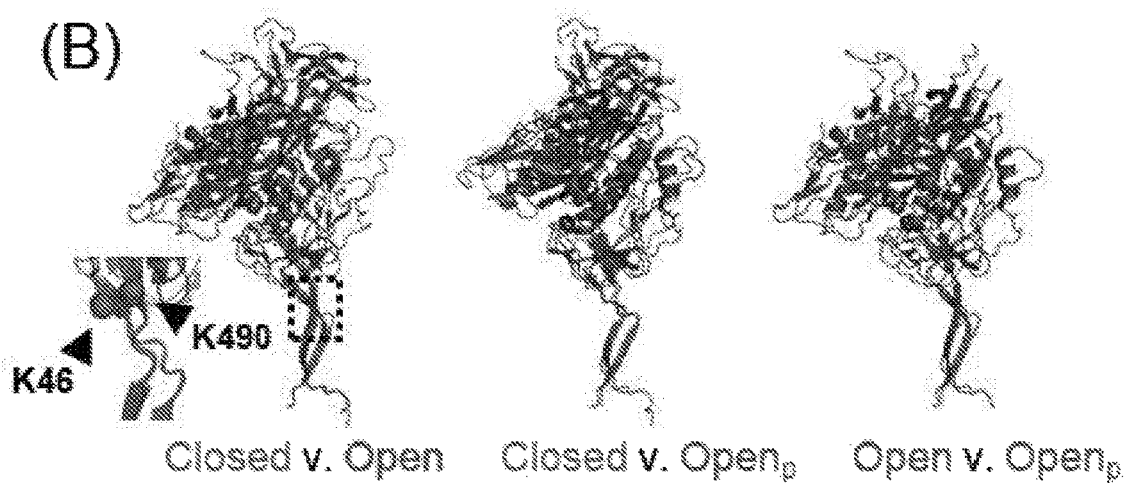

To understand the effect of the F14 and F14/Vt8 mutations on the overall structure of the SOSIP Env trimers, we examined regions of the structures distant from the F14 mutations. The individual domain coordinates of the mutant SOSIP trimer domains were found to be largely unperturbed indicating that the effects of the F14 and Vt8 mutations were localized. The gp120 domains within the Env Trimer are capable of rigid body movement relative to one another and to the gp41 three-helix bundle.[30] We therefore devised a set of reference positions in gp120 and gp41 capable of describing structural rearrangements associated with rigid body movement in gp120 and gp41 (FIG. 5). By comparing the closed[31] and open state[21] SOSIP trimer structures we identified two key points in the trimer about which the distance and angular disposition of the relevant domains could be described. Specifically, alignment of closed and open state (PDB IDs 5CEZ and 5VN3, respectively) gp41 residues G597-D664 that occur at the C-terminal end of the three-helix bundle helix demonstrated that the conformational transition from closed to open state yields a similar structure in this region with an RMSD of 0.721 Å (FIG. 5A). This identified W596 as a hinge point about which the gp41 C-terminus rotates relative to the three-helix bundle helix. Comparing the position of the gp120 domains from this alignment revealed an additional trimer hinge-point between the gp120 N-terminal K46 and C-terminal K490 about which gp120 rotates (FIG. 5B).

Figure 5C:
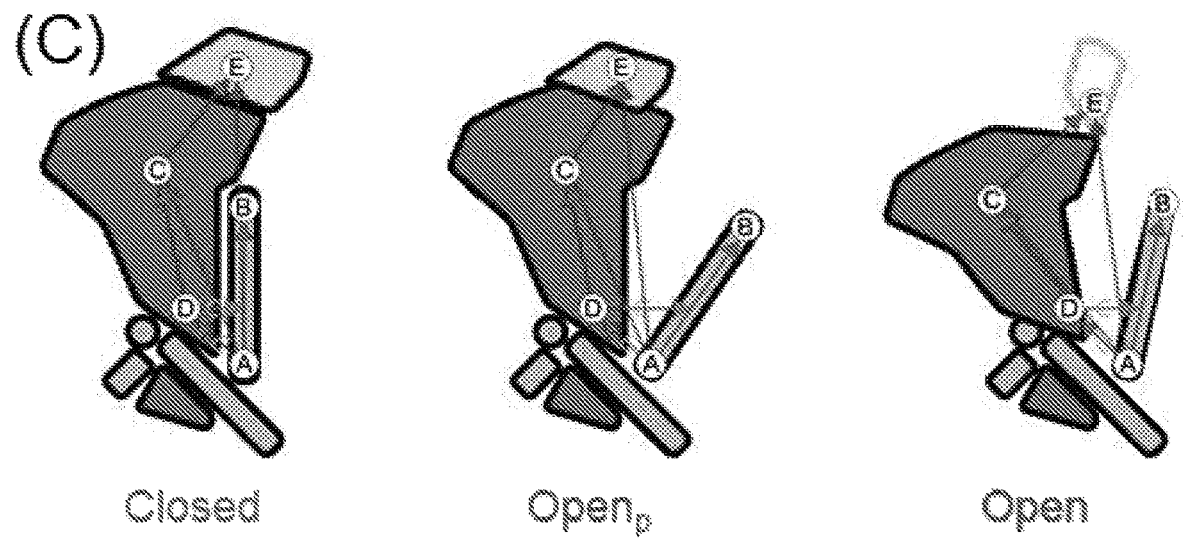
Figure 5D:
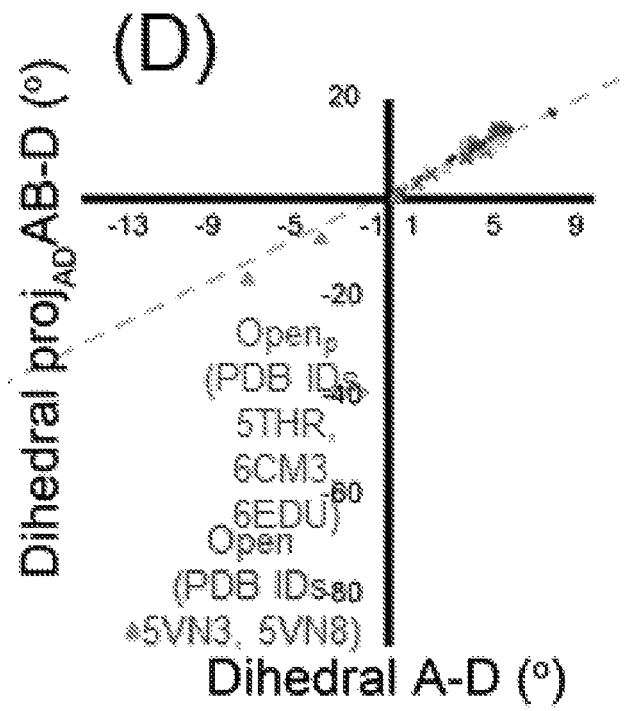
Figure 5E:
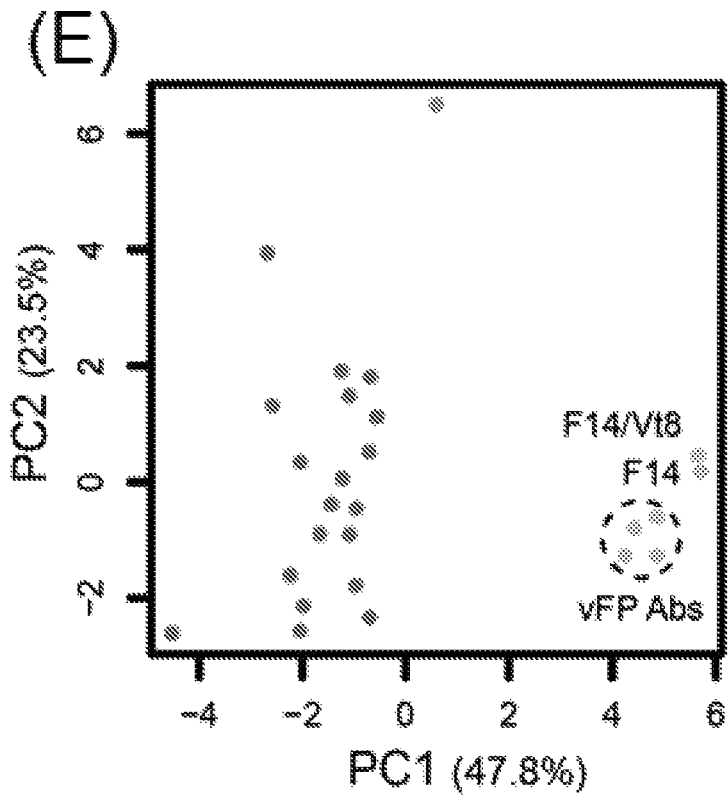

We therefore devised a set of vectors connecting key points of the various trimer elements, including the W596 (A) and W571 (B) c-αs, a gp120 c-α centroid (C), a K46-K490 c-α centroid (D), and a V1/V2 c-α centroid (E), to enable comparison of the relative dispositions of the trimers in the closed, open and partially open (Open$_p$) states (FIG. 5C). Analysis of the dihedrals formed by the W571 to W596, W596 to K46-K490 c-α centroid, and the K46-K490 c-α centroid to gp120 c-α centroid vectors and the W571 to W596/K46-K490 projection, W596 to K46-K490 c-α centroid, and the K46-K490 c-α centroid to gp120 c-α centroid vectors resulted in a linear relationship between the dihedral values for the closed state SOSIP Envs clustered at positive values ($R^2$=0.98) (FIG. 5D). Partially open states lie on the same line but have negative values for both dihedrals while two open state structures occupy negative positions far from the linear fit to closed state structures (FIG. 5D).

Figure 5F:
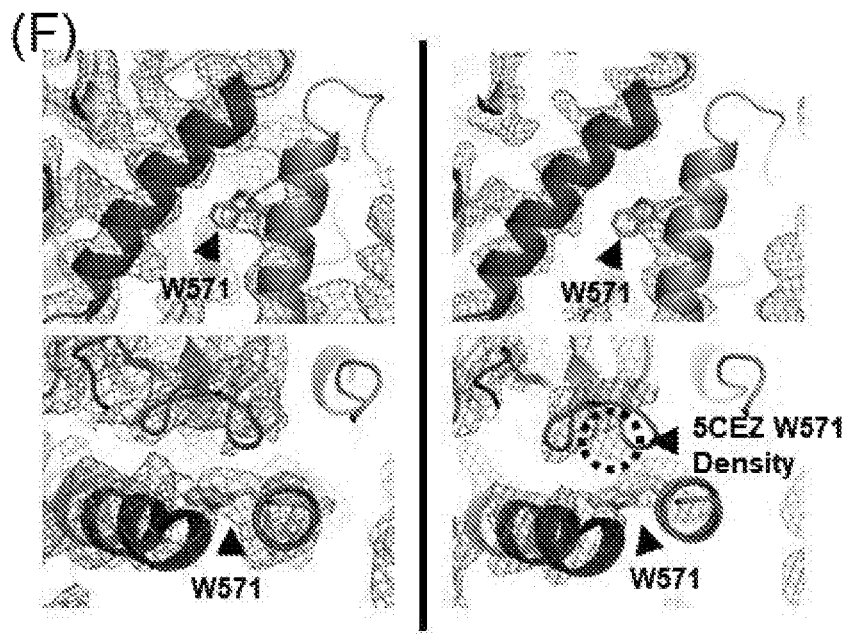
Figure 12A:
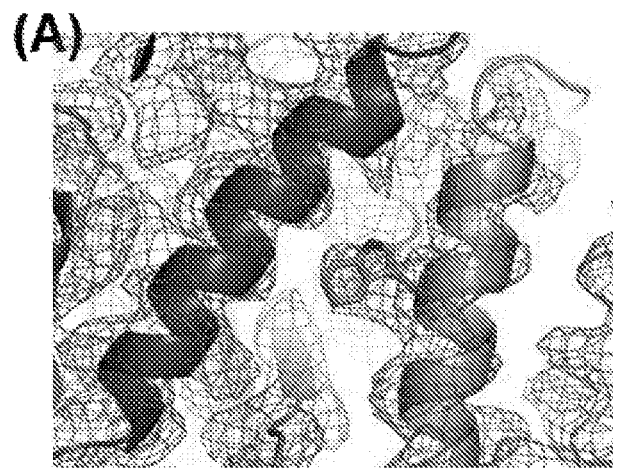
FIGS. 12A-12C show Cryo-EM fit of BG505 F14/Vt8 SOSIP coordinates to vFP bound BG505 DS SOSIP cryo-EM maps.
Figure 12B:
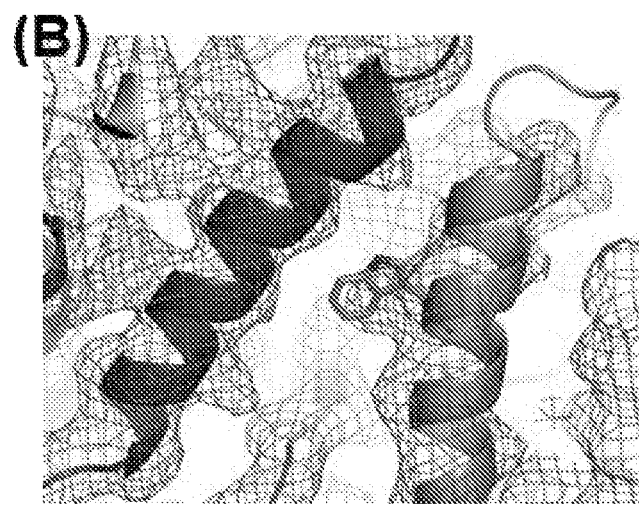
Figure 12C:
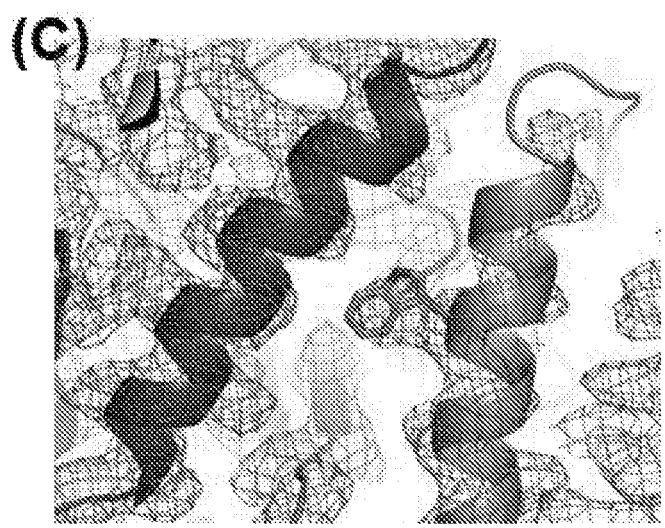

The ability to discern closed, intermediate open, and fully open state structures confirmed that both dihedrals effectively reported on the relative disposition of gp120 to the gp41 three-helix bundle. We therefore examined whether the distance and angle terms between vectors connecting the key points, in combination with the dihedral terms, further characterized structural similarity between various antibody bound trimers. The spread in the angle and distance distributions limited direct analysis. Therefore, we employed the principal components analysis method to reduce the dimensionality of the dataset to enable clustering of similar SOSIP Env structures. The results indicated that the F14 and F14/Vt8 structures indeed differ from the majority of the available SOSIP structures, residing instead near a small cluster of fusion peptide-directed antibody-bound SOSIP structures (FIG. 5E).[32] This finding indicated that the changes observed in the layer1/2 contact region with gp41 indeed altered the overall orientation of gp120 relative to gp41, and showed that these changes were structurally similar to those induced by fusion peptide-directed antibodies. We next examined the structure of the vFP antibodies in the region of the F14 conformational changes. All four vFP-bound, stabilized BG505 SOSIP trimers displayed density consistent with the helical extension and W571 rearrangement suggesting the rearrangement in the F14 and F14/Vt8 structures represents a functionally accessible state of the Env and that vFP antibodies may neutralize via inhibition of HIV-1 Env triggering (FIG. 5F, FIG. 12). Together, these results demonstrated the F14 and F14/Vt8 mutations induced global rearrangements in the SOSIP that may represent an accessible state to the native Env.

Antigenicity, CD4 Triggering, and Conformational Distribution of the Redesigned Gp160 Trimers To determine whether the effects of the F14/Vt8 mutations observed in the soluble SOSIP trimers translated to native, membrane-bound gp160 trimers, we used two measures: 1) we assessed the antigenicity and CD4-triggering of cell surface Env gp160s using 293F cells displaying full length trimers on their surface and 2) we performed smFRET experiments on BG505 Env on the virion surface.

Figure 6A:
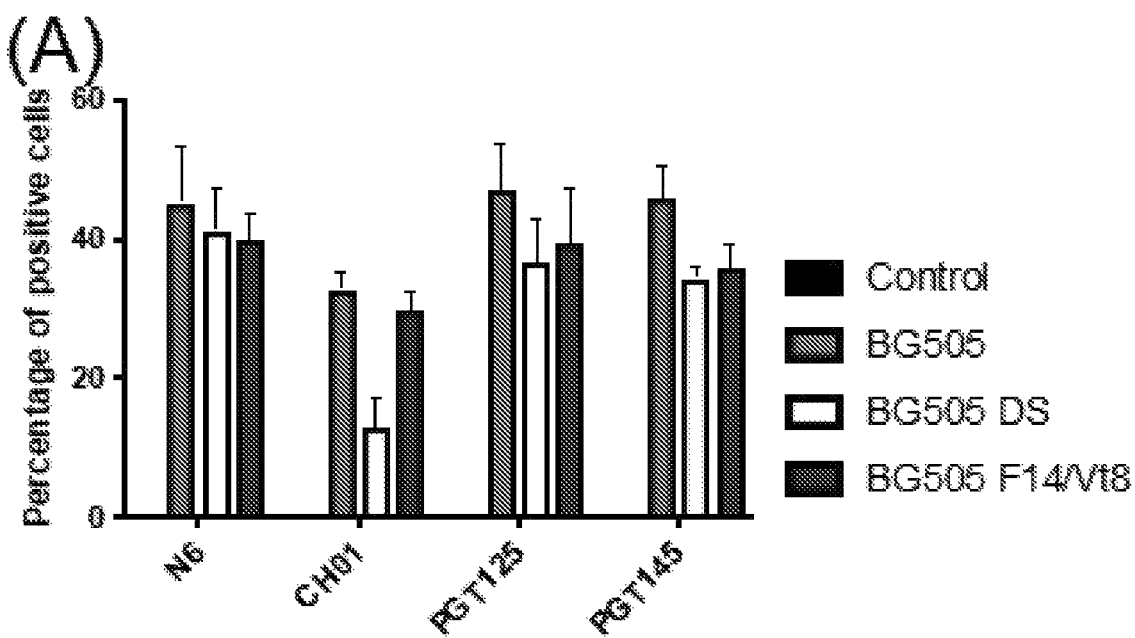
Figure 13:
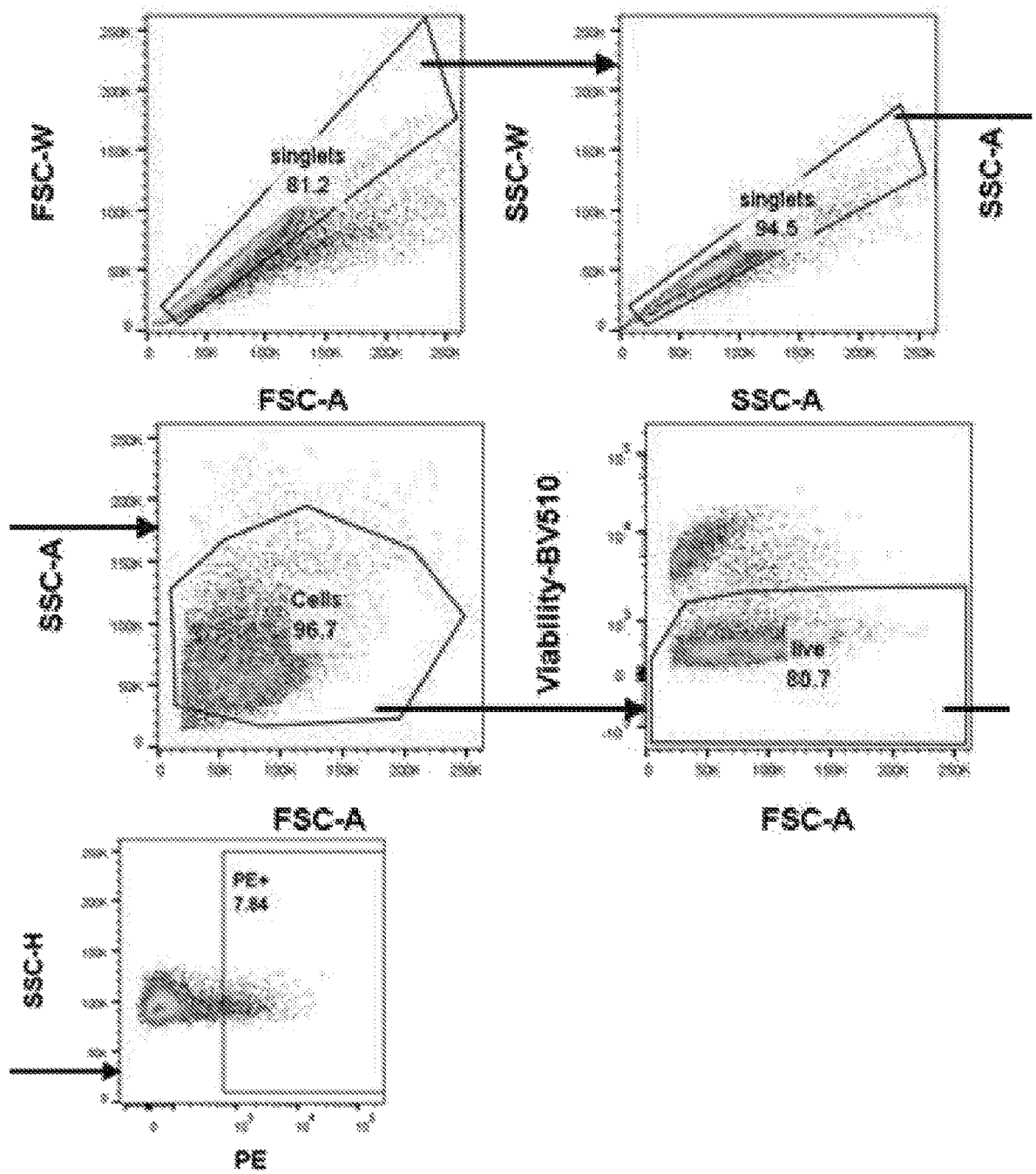
FIG. 13 shows flow cytometry gating strategy. Example data depicting the gating strategy used to assess Env cell surface expressed gp160 trimer binding to bnAbs and non-bnAbs.
Figure 14A:
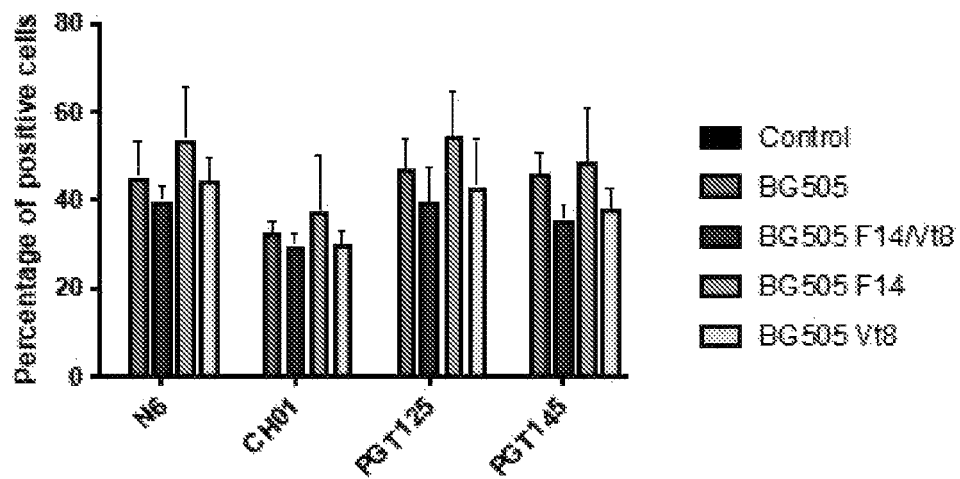
FIGS. 14A-G show antigenicity and triggering of BG505 gp160 construct cell-surface expressed trimer.
Figure 14B:
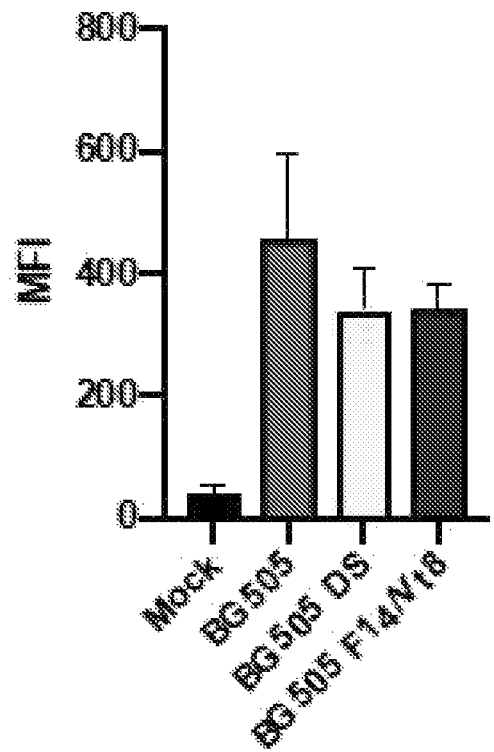
Figure 14C:
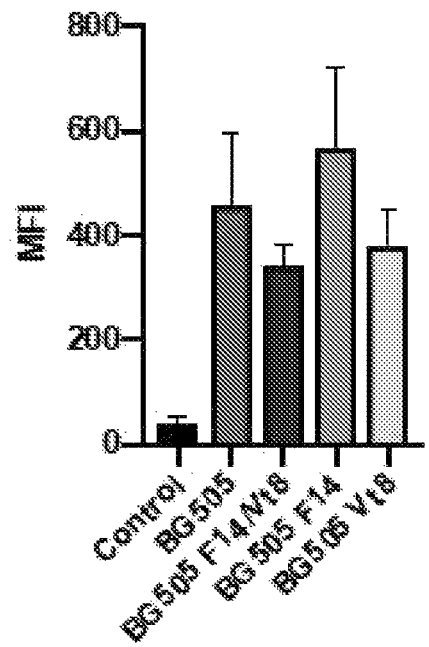

In the assay using cell surface Env gp160s, BG505, a previously engineered BG505 stabilized design termed BG505 DS[18], and BG505 F14/Vt8, BG505 F14, and BG505 Vt8 were first tested for binding to bnAbs N6, CH01, PGT125, and PGT145 targeting CD4bs, V1/V2, glycan-V3, and trimer apex epitopes, respectively. Binding to cell surface expressed Env trimer was assessed via flow cytometry to determine the percentage of positive cells and mean fluorescence intensities (MFI) for bnAb binding (FIG. 13). The percentage of cells testing positive for binding to each bnAb were similar in each construct with the exception of BG505 DS binding to CH01, which displayed a marked reduction in cells positive for CH01 binding (FIG. 6A, FIG. 14A, FIG. 19). We next examined binding of non-bnAbs 19B and 17B, which target the open state V3-tip and bridging sheet epitopes, respectively. Binding to these open state preferring antibodies was tested in the presence and absence of sCD4 or potently neutralizing eCD4-Ig, a coreceptor-mimetic peptide fused eCD4-Ig[33]. In order to ensure comparable levels of Env surface expression between constructs, the near-pan neutralizing bnAb N6[34] was used as a benchmark yielding comparable binding for all constructs tested with MFIs of 457.3±137.9, 338.0±72.6, 341.3±43.2, 568.0±152.6, and 378.3±73.1 for BG505, BG505 DS, BG505 F14/Vt8, BG505 F14, and BG505 Vt8, respectively (FIGS. 14B and C, FIG. 20).

Figure 6B:
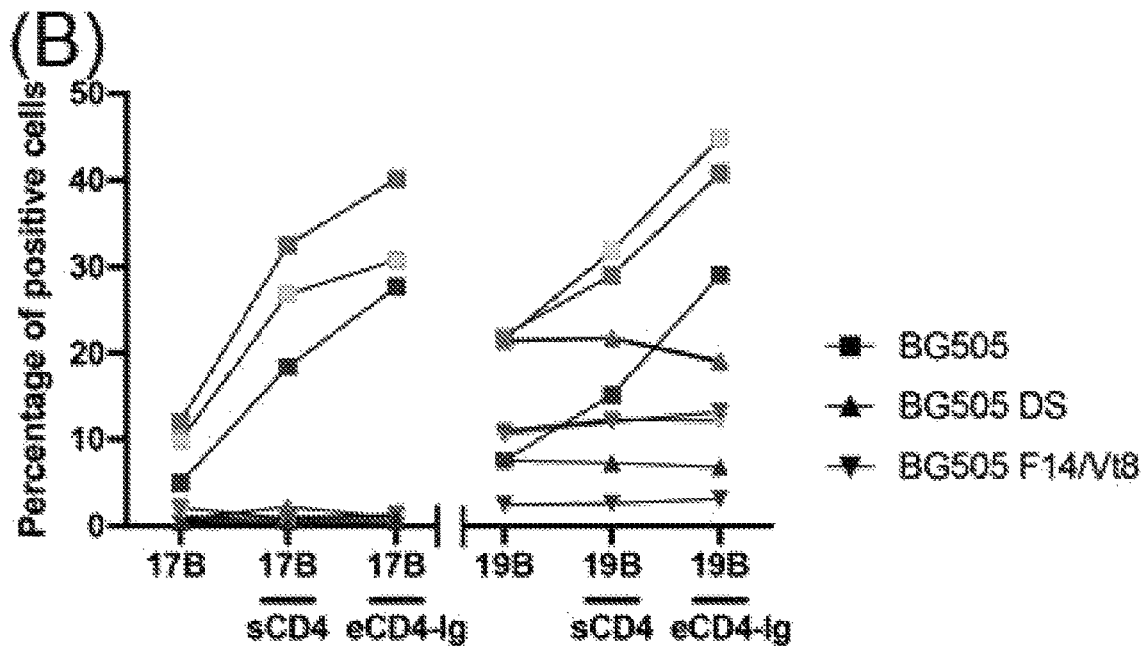
Figure 14D:
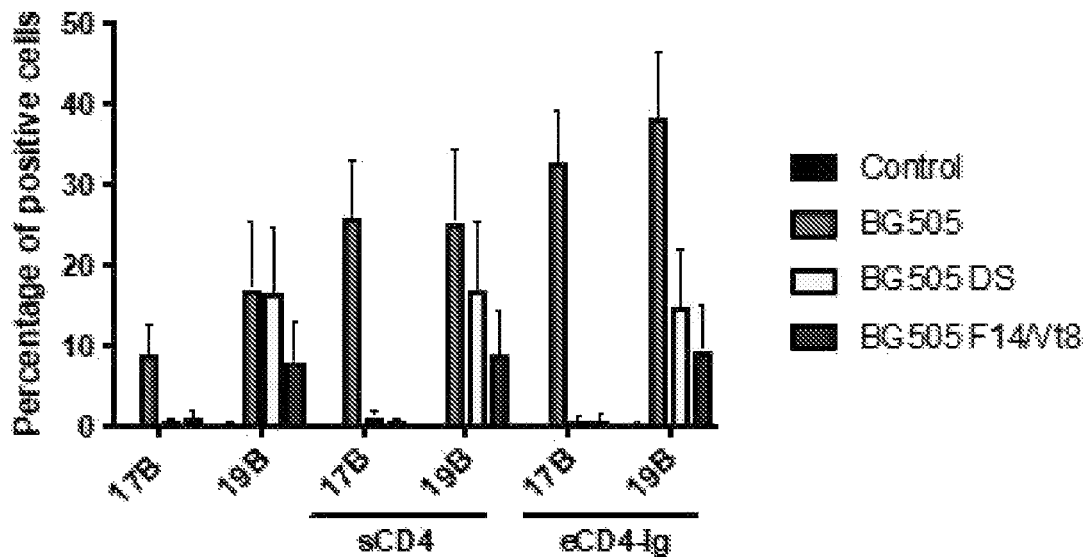
Figure 14E:
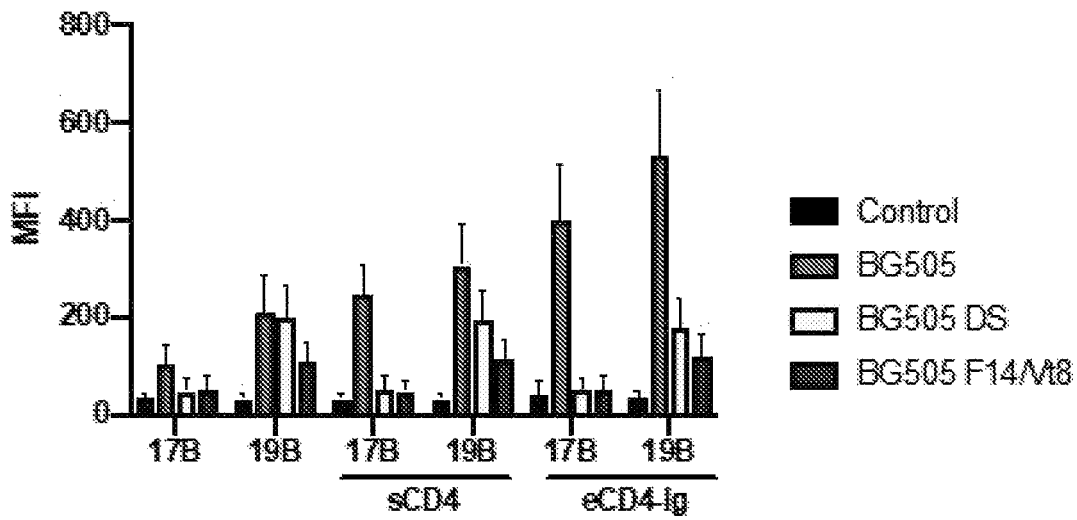

Pairwise percentage positive cell comparison of each construct in each replicate experiment demonstrated a consistent reduction of intrinsic exposure of the 17B open state epitope in both the BG505 DS and BG505 F14/Vt8 stabilized gp160 trimers as compared to BG505 gp160 (FIG. 6B, FIGS. 14D and E, FIG. 19). Intrinsic exposure of the V3 tip targeting 19B epitope was relatively similar between BG505 and BG505 DS gp160s while the BG505 F14/Vt8 gp160 displayed a consistent ~2-fold reduction in 19B epitope exposure relative to BG505 gp160 (FIG. 6B, FIGS. 14D and E, FIG. 19). On incubating the cells with either sCD4 or eCD4-Ig, distinct increases in both the 17B and 19B percentage of positive cells were observed for BG505 gp160, as expected (FIG. 6B, FIGS. 14D and E, FIG. 19).

Figure 14F:
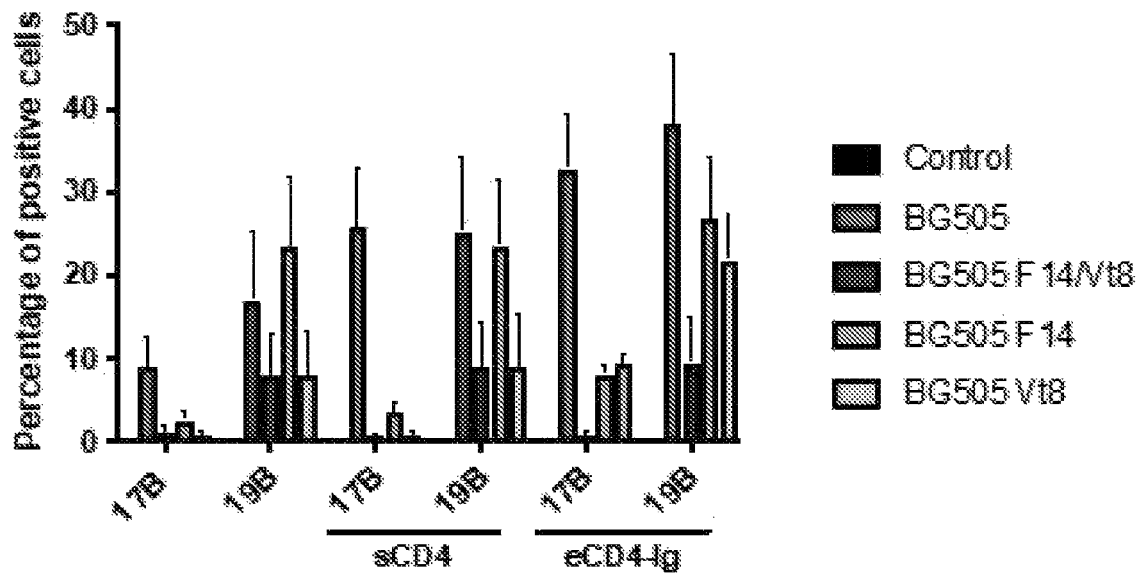
Figure 14G:
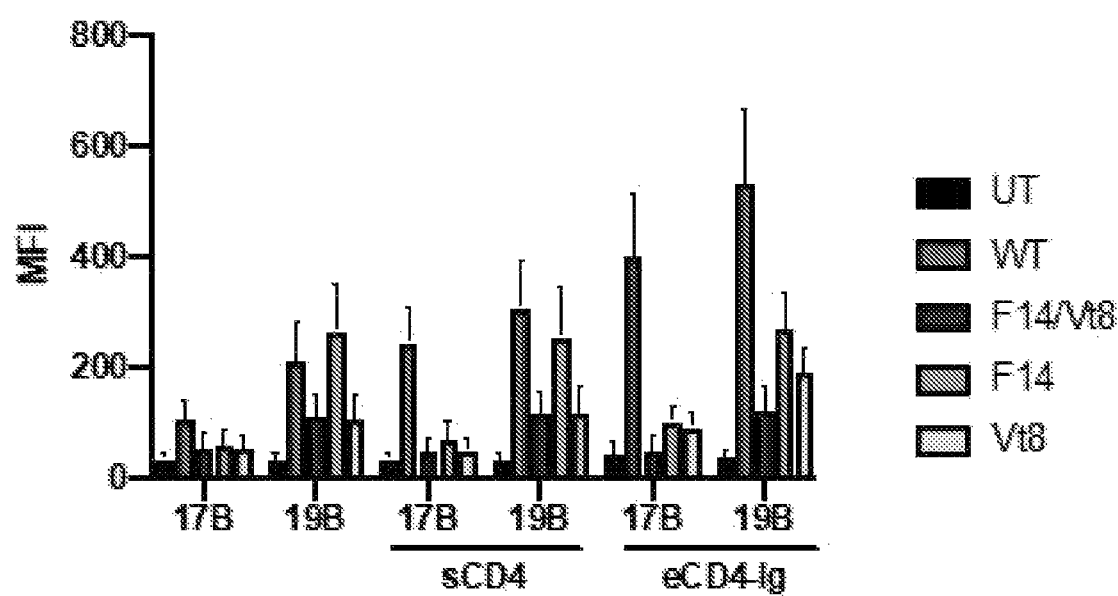
Figures 22A, 22B:
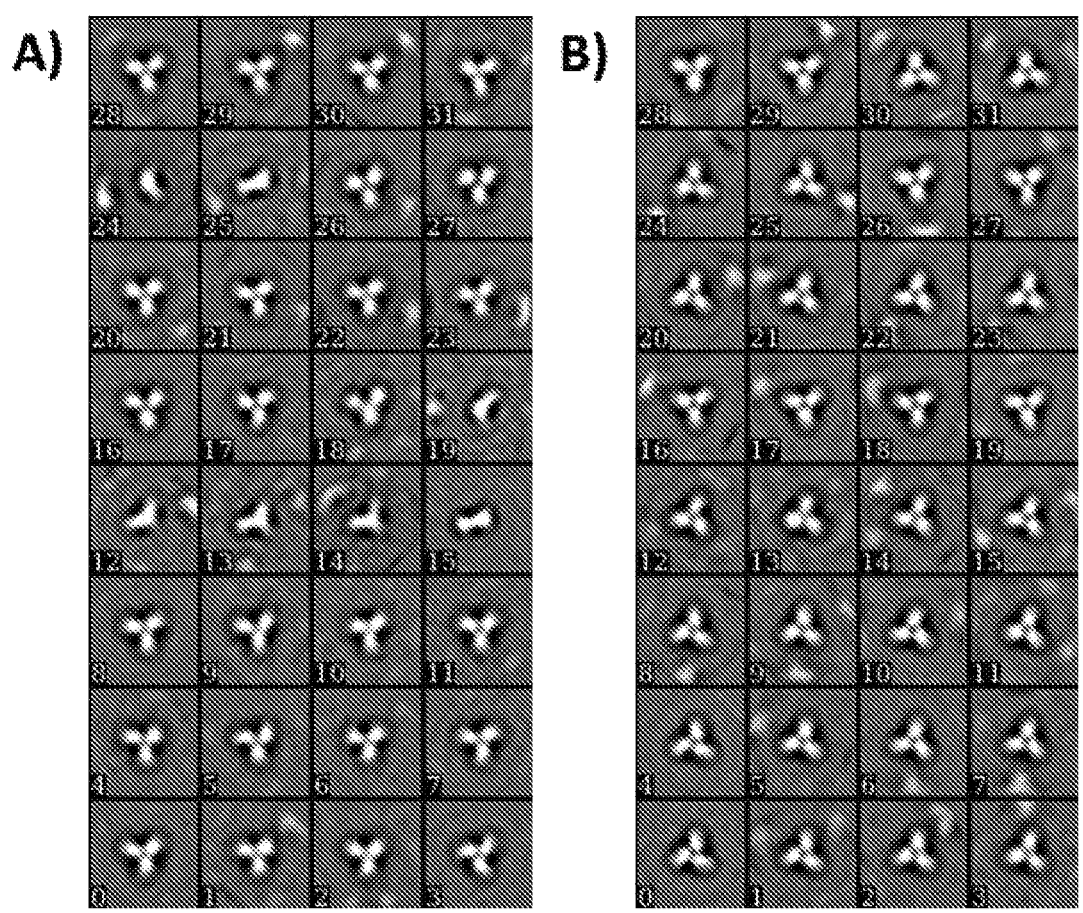
FIG. 22A shows negative stain electron microscopy 2-dimensional class averages of the CH848.10.17 DT F14/Vt8 SOSIP trimer demonstrating the formation of intact trimer.
FIG. 22B shows negative stain electron microscopy 2-dimensional class averages of the CH505 M5 G458Y F14 GNTI-SOSIP trimer demonstrating the formation of intact trimer.

Conversely, binding to these CD4-induced epitope-targeting antibodies was not observed for BG505 DS or F14/Vt8 stabilized gp160 trimers in the presence of either sCD4 or eCD4-Ig (FIG. 6B, FIGS. 14D and E, FIG. 19). Triggering of the 17B epitope was not observed in BG505 F14 or BG505 Vt8 gp160s in the presence of sCD4, although 19B epitope exposure was observed in each (FIGS. 14F and G, FIG. 19). Additionally, both 17B and 19B epitope exposure was observed in the presence of eCD4-Ig (FIGS. 14F and G, FIG. 19). These results showed that the F14, Vt8, and F14/Vt8 mutations allowed presentation of key bnAb epitopes and that the combined F14/Vt8 mutations were necessary for the minimization of intrinsic non-bnAb epitope exposure and the prevention of CD4 induced rearrangement of the surface expressed gp160 Env.

We also used the smFRET assay developed by Munro et. al[17], to examine the conformational landscape and CD4-induced effects on the virion bound F14/Vt8 Env as compared to the BG505 Env. Specifically, we examined the FRET distributions of the BG505 and F14/Vt8 BG505 Envs to determine a) whether the mutations alter the unliganded FRET distribution relative to BG505 Env and b) whether the mutations prevent dodecameric CD4 (sCD4D1D2-Igαtp) induced rearrangements. smFRET studies previously revealed that native Env on virus predominantly resides in in a conformational state termed State 1 but has spontaneous access to two more conformational states, termed states 2 and 3. In response to CD4 binding, wild-type Env opens into State 3 through one necessary intermediate (State 2).[17,35]

Figure 6C:
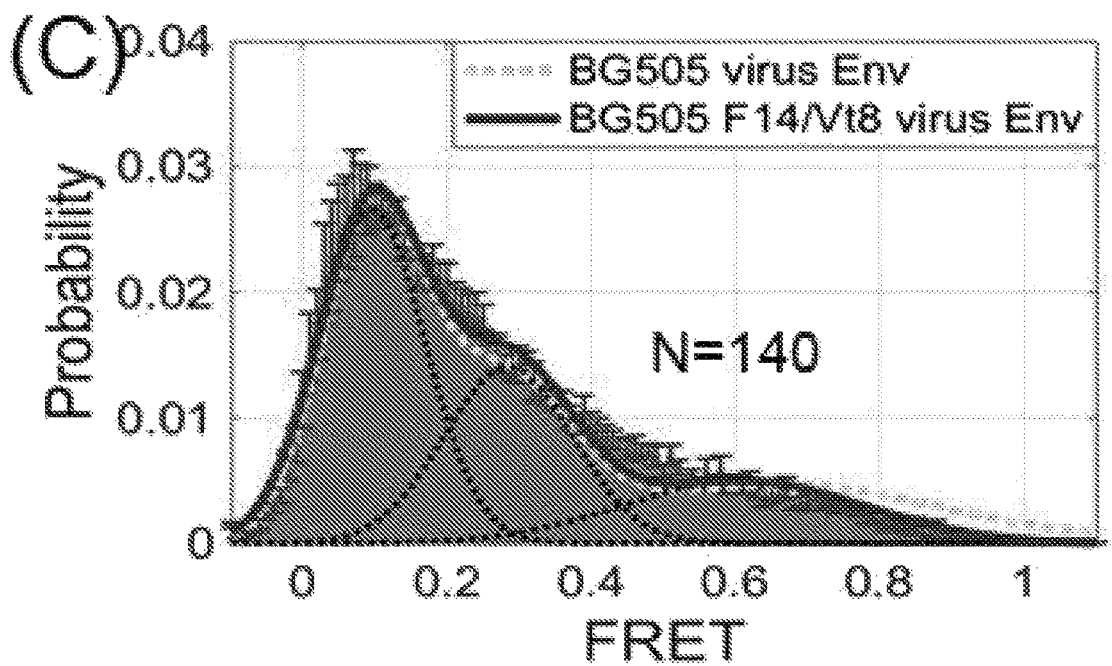
Figure 6D:
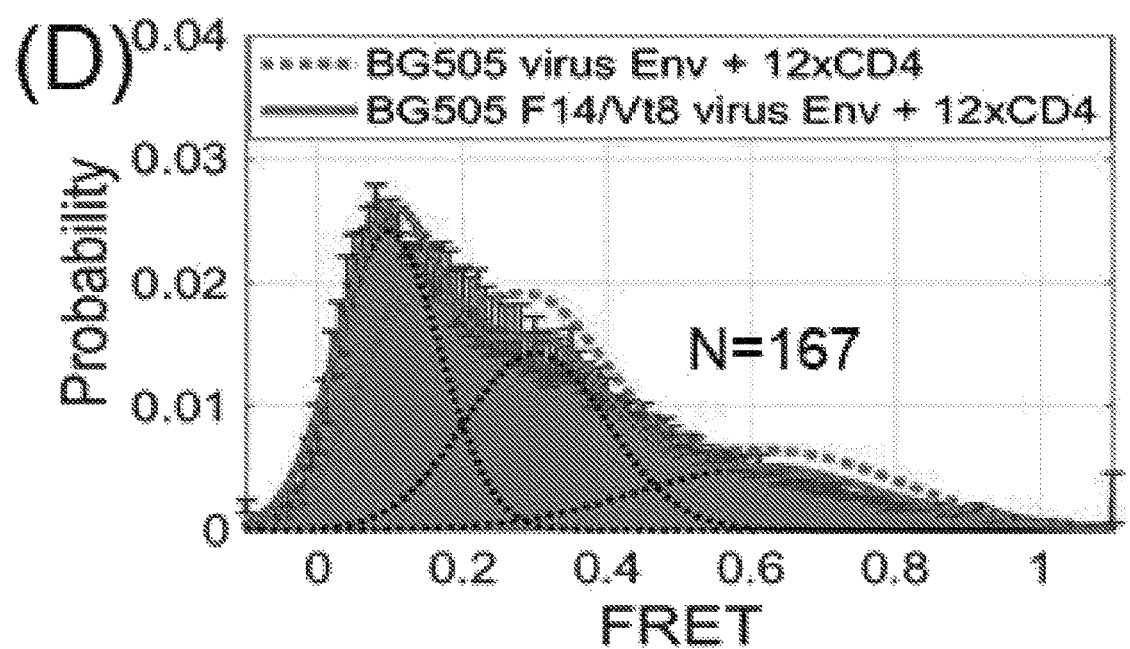

Comparison of the unbound Envs indicated that both unliganded Envs displayed similar distributions, with the predominant State 1 peak at low FRET, yielding State 1 occupancies of ~46% and ~49% for the BG505 and F14/Vt8 Envs, respectively (FIGS. 6C and D, FIG. 21). Both trimers also displayed similar occupancies of State 2 and State 3. Addition of CD4 resulted in a shift in the distribution for the BG505 Env toward increased high and mid-FRET states corresponding to the asymmetric intermediate State 2 configuration and the open State 3 configuration, respectively (FIGS. 6C and D, FIG. 21). Unlike the BG505 Env, however, the F14/Vt8 Env did not respond to addition of dodecameric CD4, displaying the same relative distribution of the three FRET states in the presence of CD4 as were seen in the absence of CD4, and consistent with the observed resistance to CD4-induced changes in the BG505 F14/Vt8 SOSIP Env (FIGS. 6C and D, FIG. 21). Together, results for the cell and viral membrane associated gp160 Env F14/Vt8 mutant trimer are consistent with observations for these mutations in the soluble SOSIP trimer indicating the mutations designed to disable Env allostery effectively blocked CD4-induced rearrangements while maintaining efficient bnAb interaction.

DISCUSSION

The HIV-1 Env is an intricate conformational machine that propagates receptor-mediated structural changes from a neutralization-resistant closed conformation to a fusion-competent open conformation that exposes immunodominant epitopes for non-neutralizing antibodies. The closed conformation of the HIV-1 Env is of interest for vaccine design since it presents the epitopes for broadly neutralizing antibodies, and the expectation is that effective presentation of the native, closed conformation of the Env by vaccination is essential to elicit broadly neutralizing antibodies. Indeed, many studies have succeeded in stabilizing the closed conformation of the HIV-1 Env both in the soluble Env format, as well on the cell surface, with varying levels of success in eliciting autologous and heterologous neutralization.[11-14]

In this study we combined structural and mechanistic information to construct a mutant Env that is no longer responsive to triggering by the CD4 receptor. Two strategies were employed, each aimed at shifting the equilibrium of Env dynamics towards its closed state. The first strategy that led to the F14 series of mutations identified the conserved W571 as a conformational switch and effectively disabled a communication network that relied on the movement of topological layers 1 and 2 to transmit structural changes from the CD4 binding site. The second path aimed to prevent V3 exposure via mutation of buried hydrophilic to hydrophobic residues in order to prevent the infiltration of water into the space between V3 and V1/V2. Together, the findings presented here indicated close coupling of sCD4 induced internal rearrangements in gp120 and the N-terminal portion of the gp41 three-helix bundle.

Figure 7A:
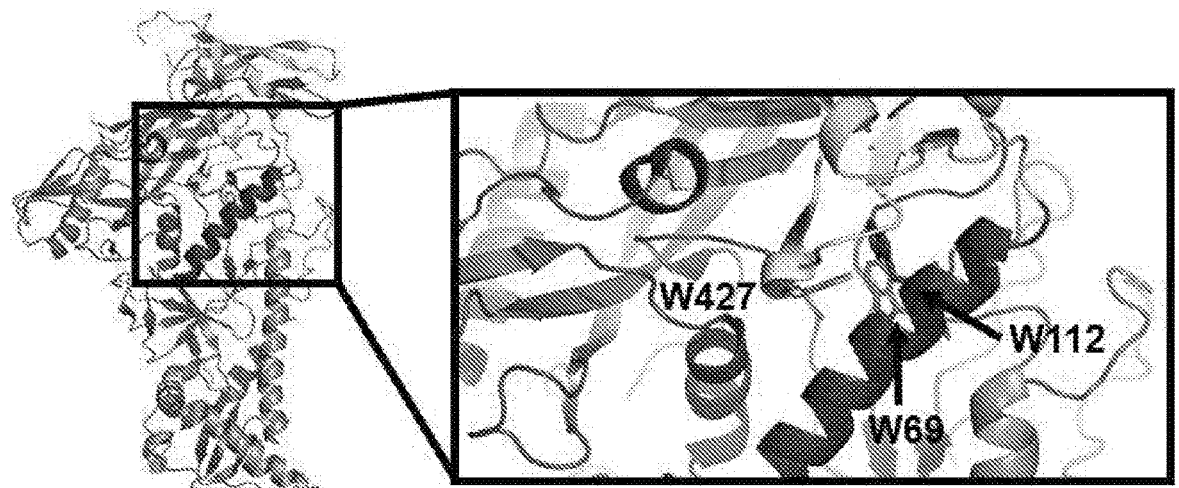
FIGS. 7A-7B show structure of a closed and open state HIV-1 Env gp140 SOSIP protomer.
Figure 7B:
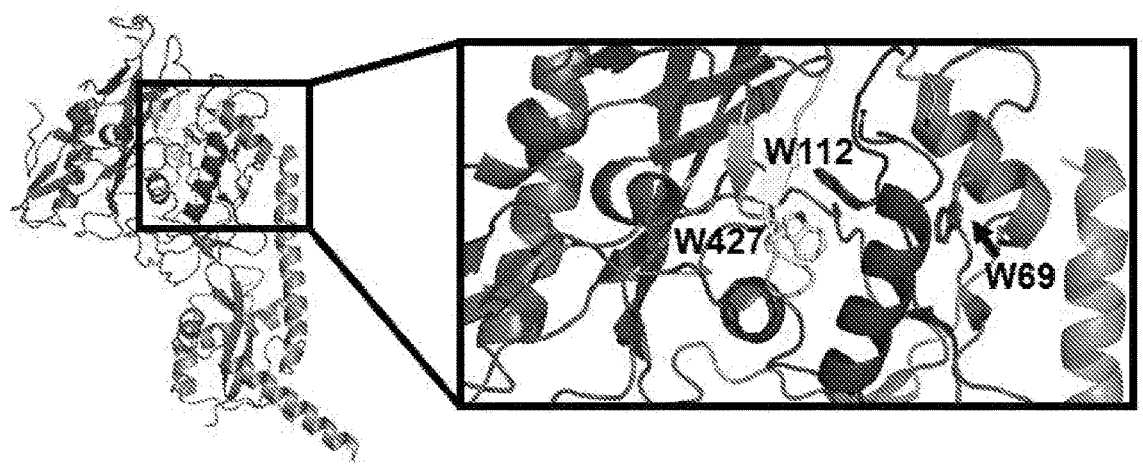

While these designs were made and tested in the context of the soluble SOSIP env, the observed effects translated to the Env on the native virion surface, suggesting that despite the differences between the native Env and the engineered SOSIPs, an allosteric network that was common to both formats was disabled by the mutations.[36] Indeed, the structure of a PGT151-bound full length Env trimer that was purified by detergent solubilization of cell surface expressed gp160 demonstrated contacts between the topological layers of gp120 and the gp41 three-helix bundle consistent with this proposal.[37] Differences between this structure and a full-length virion-bound Env outside of this region notwithstanding, we propose a sequential mechanism by which the Env transitions from the prefusion closed state to a fully open, fusion-competent state through a series of sequential steps (FIG. 7D). Beginning from a closed state in which the trimer apex and topological layers surround the gp41 three-helix bundle[38], engagement of a single CD4 induces β20-β21 loop rearrangement and is associated with Env triggering via residue 1432 in β20-β21 and residue L193 in V1/V2.[23]

Instability in V1/V2 associated with these changes would allow V3 exposure[27,39] and initial apex dissociation of a single gp120 protomer from the gp41 three-helix bundle[24]. Internal configurational changes in V1/V2 could then propagate to layers-1 and 2, thereby releasing W571, thus lowering the potential energy barrier to full gp120-gp41 three-helix bundle dissociation resulting in a single gp120 open, asymmetric trimer configuration.[35] Indeed, viruses with substitution of W571 are replication deficient and non-infectious due to abolished membrane fusion activity despite effective cell surface expression, processing, and retention of CD4 binding, demonstrating the importance of this residue in downstream CD4-induced changes.[40,41] Absent a stable trimeric apex interface, the remaining two closed state protomers could then decay toward the open state, potentially assisted by CD4 quaternary contacts.[20,38,42] Together, with the mechanistic insights provided by the observed structural rearrangements in the SOSIP Env, the results from this study indicate direct manipulation of the Env allosteric network allows for fine-tuned conformational control of Env structure that can assist in the development and refinement of the next generation of Env vaccine immunogens.

Methods

Recombinant HIV-1 Envelope SOSIP Gp140 Production.

Antibodies and antibody Fabs were produced as described previously.[43] BG505 N332 SOSIP gp140 envelopes were expressed as previously described with minor modifications.[44] Envelope production was performed with Freestyle293 cells (Invitrogen). On the day of transfection, Freestyle293 were diluted to $1.25 \times 10^6$ cells/mL with fresh Freestyle293 media up to 1 L total volume. The cells were co-transfected with 650 µg of SOSIP expressing plasmid DNA and 150 µg of furin expressing plasmid DNA complexed with 293Fectin (Invitrogen). On day 6 cell culture supernatants were harvested by centrifugation of the cell culture for 30 min at 3500 rpm. The cell-free supernatant was filtered through a 0.8 µm filter and concentrated to less than 100 mL with a single-use tangential flow filtration cassette and 0.8 µm filtered again. Trimeric Env protein was purified with monoclonal antibody PGT145 affinity chromatography. PGT145-coupled resin was packed into Tricorn column (GE Healthcare) and stored in PBS supplemented with 0.05% sodium azide. Cell-free supernatant was applied to the column at 2 mL/min using an AKTA Pure (GE Healthcare), washed, and protein was eluted off of the column with 3M $MgCl_2$. The eluate was immediately diluted in 10 mM Tris pH8, 0.2 µm filtered, and concentrated down to 2 mL for size exclusion chromatography. Size exclusion chromatography was performed with a Superose6 16/600 column (GE Healthcare) in 10 mM Tris pH8, 500 mM NaCl. Fractions containing trimeric HIV-1 Env protein were pooled together, sterile-filtered, snap frozen, and stored at −80° C.

Biolayer Interferometry

Cell supernatant mAb binding and dose response curves were obtained using biolayer interferometry (BLI; OctetRed96, FortéBio). Antibodies were immobilized on anti-Human IgG Fc capture (AHC; FortéBio) sensor tips via immersion in 20 µg/ml mAb in phosphate buffered saline (PBS) for 300 s followed by washing in PBS for 60 s at 1000 rpm. For the cell supernatant assays, the mAb captured sensor tips were then immersed in 200 µl of the transfection supernatant for 400 s at 1000 rpm for the association phase after which the sensor tips were immersed in PBS for 600 s for the dissociation phase. The sensor tips were regenerated using glycine pH 2.0 for an immersion time of 20 s between measurements. For the dose response experiments, the sensor tips were immersed in the SOSIP-containing wells for 180 s for the association and 60 s for dissociation phase using a shake speed of 1000 rpm beginning from the lowest SOSIP concentration. Regeneration was not performed between measurements of increase SOSIP concentration. A longer, final dissociation phase of 600 s was measured for the highest concentration SOSIP containing well. Non-specific binding was accounted for via subtraction of sensorgrams obtained using the anti-Flu Hemagglutinin Ab82 control mAb. Reported binding corresponds to values and the end of the association phase. Data was evaluated using the Octet Data Analysis 10.0 software (FortéBio) with dose response curves fitted in GraphPad Prism using the one site specific binding model.

Surface Plasmon Resonance

Triggering of SOSIP gp140 Envs by soluble CD4 (sCD4) was monitored via surface Plasmon resonance and was performed on a BIAcore 3000 instrument (GE Healthcare). Antibodies were immobilized using direct immobilization using amine coupling on CM3 sensor chips (GE Healthcare) at ~5000 RU. The SOSIP concentration in the presence and absence of a 1:3 mixture of sCD4 was 200 nM. Samples were injected over at a rate of 30 µl/min for a total of 90 µl using the high performance kinject injection mode with a dissociation phase of 600 s over four flow cells containing 17B, 19B, VRC01, or the Ab82 control. The chip surface was regenerated between measurements using two injections of 20 µl of glycine pH 2.0 at a flow rate of 50 µl/min. The resulting response curves were processed using the BIAevaluation 4.1 (GE Healthcare) software using a double reference subtraction. Reported response values were determined taking the average response from 170-175 seconds after the start of the injection.

Thermal Denaturation

Thermal denaturation experiments were performed using the NanoDSC platform (TA Instruments). Samples were dialyzed into HEPES buffered saline (HBS; 10 mM HEPES, 150 mM NaCl, pH 7.4), diluted in dialysate to 0.2 to 0.4 mg/ml, and degassed for 15 minutes. Following condition of the DSC cells in dialysate, samples were loaded and heated from 20° C. to 100° C. at 3 atm of pressure at a rate of 1° C./min using the dialysate as a reference. The obtained denaturation profiles were buffer subtracted and base line corrected using a $6^{th}$-order polynomial using the NanoAnalyze software (TA Instruments). The reported $T_{max}$ corresponds to the average maximum observed heat capacity from three independent measures.

Cryo-EM Sample Preparation

The BG505 F14 and F14/Vt8 SOSIP trimers complexes were prepared using a stock solution of 2 mg/ml trimer incubated with a six-fold molar excess of VRC01 or VRC03 and 10-1074, respectively. To prevent interaction of the trimer complexes with the air-water interface during vitrification, the samples were incubated in 0.085 mM n-dodecyl β-D-maltoside (DDM). Samples were applied to plasma-cleaned QUANTIFOIL holey carbon grids (EMS, R1.2/1.3 Cu 300 mesh) followed by a 30 second adsorption period and blotting with filter paper. The grid was then plunge frozen in liquid ethane using an EM GP2 plunge freezer (Leica, 90-95% relative humidity).

Cryo-EM Data Collection

Cryo-EM imaging was performed on a FEI Titan Krios microscope (Thermo Fisher Scientific) operated at 300 kV. Data collection images were acquired with a Falcon 3EC Direct Electron Detector operated in counting mode with a calibrated physical pixel size of 1.08 Å with a defocus range between −1.0 and −3.5 µm using the EPU software (Thermo Fisher Scientific). No energy filter or $C_s$ corrector was installed on the microscope. The dose rate used was ~0.8 $e^-/Å^2 \cdot s$ to ensure operation in the linear range of the detector. The total exposure time was 60 s, and intermediate frames were recorded every 2 s giving an accumulated dose of ~42 $e^-/Å^2$ and a total of 30 frames per image. A total of 2,350 images for BG505-F14-SOSIP and 2,060 images for BG505-F14/Vt8-SOSIP were collected over two days, respectively.

Data Processing

Cryo-EM image quality was monitored on-the-fly during data collection using automated processing routines. Initial data processing was performed within cryoSPARC[29] including particle picking, multiple rounds of 2D classification, ab initio reconstruction, homogeneous map refinement and non-uniform map refinement, yielding 3.5 Å and 3.7 Å maps for the BG505-F14-SOSIP and the BG505-F14/Vt8-SOSIP complexes, respectively. Further processing was done outside of cryoSPARC as described next. Movie frame alignment was carried out using UNBLUR[45], and CTF determination using CTFFIND4[46]. Particles were picked automatically using a Gaussian disk of 90 Å in radius as the search template. For the BG505-F14-SOSIP dataset, 1,518,046 particles were picked from 2,350 micrographs, extracted using a binning factor of 2 and subjected to 8 rounds of refinement in cisTEM[47], using an ab-initio model generated with cryoSPARC[29]. The distribution of scores assigned to each particle by cisTEM showed a clear bi-modal distribution and only particles in the group containing the higher scores were selected for further processing (FIG. 10). This subset of 77,632 particles was re-extracted without binning and subjected to 10 rounds of local refinement followed by 5 additional rounds using a shape mask generated with EMAN2[48]. Per-particle CTF refinement was then conducted until no further improvement in the FSC curve was observed. At this point, particle frames were re-extracted from the raw data and subjected to per-particle motion correction using all movie frames and applying a data-driven dose weighting scheme as described previously.[49] The per-particle refinement procedure was iterated two additional times using the newly generated map as a reference and at that point no further improvement was observed. The resolution of the final map was 3.0 Å measured according to the 0.143-cutoff FSC criteria. A b-factor of –120 Å$^2$ was applied to the reconstruction for purposes of visualization. For the BG505—F14/Vt8-SOSIP dataset, 869,323 particles were picked from 2,060 micrographs, and a subset of 84,378 particles was used for further local refinement using a similar strategy as that used to process the BG505-F14-SOSIP dataset. The estimated resolution for the final map in this case was 2.9 Å according to the 0.143-cutoff FSC criteria.

Cryo-EM Structure Fitting

Structure fitting of the cryo-EM maps was performed in Chimera[50] using the gp120 and gp41 segments from PDB ID 5CEZ (chains G and B, respectively) with F14 and Vt8 mutations added using PyMol. Coordinates for VRC01, VRC03, and 10-1074 were obtained from PDB ID 3NGB (chains H and L), PDB ID 3SE8 (chains H and L), and PDB ID 5T3Z (chains H and L), respectively. Initial coordinate refinement was performed using Rosetta.[51] The best fit from 110 models was then iteratively with manual refinement in Coot[52] followed by real-space refinement in Phenix.[51] Structure fit and map quality statistics were determined using MolProbity[54] and EMRinger[5], respectively. Structure and map analyses were performed using a combination of PyMol[56] and Chimera.

Vector Based Structure Analysis

Centroids for the vectors in the analysis included a K46-K490 Ca centroid, W571 and W596 c-αs, c-αs of gp120 excluding variable loops the V1/V1 region residues, and the N- and C-termni, and a V1/V2+V3 c-α centroid Vectors between these reference positions were generated and included a projection of the W596 to K46-K490 centroid vector on to the W596 to W571 vector. Angles, distances, and dihedrals between these vectors were then compiled for a set of available crystal and cryo-EM structures with resolutions better than 4.5 Å (PDB IDs for closed state structures 4TVP[57], 4ZMJ[18], 5ACO[58], 5CEZ[31], 5CJX[59], 5D9Q[60], 5FYJ[61], 5FYK[61], 5FYL[61], 5T3X[62], 5T3Z[62], 5U7M[26], 5U70[26], 5UTF[13], 5V7J[63], 5V8L[64], 5V8M[64], 6CDE[32], 6CDI[32], 6CH7[65], 6CH8[65], 6CUE[66], 6CUF[67], and 6DE7[12]; Open and partially open state structures 5THR[19] chains A and E, 5VN3[20] chains A and G, 5VN8[59] chains A and G, 6CM3[24] chains A and E, and 6EDU[24] chains A and D; PGT151 bound structures, 5FUU[68] chains A and B, C and D, and E and F, 6DCQ[37] chains A and B, C and D, and E and F, 6MAR[69] chains A and B, C and D, and E and F) in addition to a single CD4 bound SOSIP trimer (PDB ID 5U1F[42] chains A and B, C and E, and D and F), as well as the BG505 F14 and F14/Vt8 SOSIP structures determined in this study. A single protomer was analyzed for each structure with the exception of PGT151 and single CD4 bound structures for which each protomer was analyze. Vector based structural analysis was performed using the VMD[70] Tcl interface. Principal component analysis of the resulting vectors, angles, and torsions was performed using R[71].

Cell-Surface Expressed Env gp160 Antigenicity

FreeStyle 293F cells (ThermoFisher, catalog #R79007) (1×10$^6$ cells/ml, 0.5 ml per well of a 12-well plate) were transfected using a mixture of 1 μg HIV Env gp160s DNA in 75 μl jetPRIME buffer (Polyplus-transfection) with 2 μl jetPRIME transfection reagent (Polyplus-transfection) following the manufacturer's protocol. Transfected cells were cultured in Freestyle 293 Expression Medium (Invitrogen Inc.) at 120 rpm for 48 hours before flow cytometry staining.

293F cells were counted using trypan blue and then were rinsed with PBS containing 1% BSA, pelleted at 250×g for 3 min. Cells were incubated with wither sCD4 or eCD4-Ig[33] at a final concentration of 10 μg/mL for 20 min at 4° C. Human anti-HIV Env Abs at a final concentration of 10 μg/mL were used to stain 0.4×10$^6$ cells per well in 40 μL PBS containing 1% BSA of in V bottom 96-well plates, 30 min at RT in the dark. Cells were then washed once with 200 μL PBS containing 1% BSA and incubated with PE conjugated Goat F(ab')2 Anti-Human IgG-(Fab')2 secondary antibody (abcam, Cambridge, MA) at a final concentration of 2.5 μg/ml in 100 μL PBS containing 1% BSA per well. After 30 min incubation at 4° C. in the dark, cells were washed once, and stained with 200 μL aqua viability dye (1:1000 in PBS) for 20 min at RT in the dark, then washed twice with PBS containing 1% BSA. Flow cytometric data were acquired on a LSRII using FACSDIVA software (BD Biosciences) and were analyzed with FlowJo software (FlowJo). FACSDIVA software (BD Biosciences) and were analyzed with FlowJo software.

Preparation and smFRET Analysis of Dye-Labeled HIV-1BG505 Virus Env.

Dye-labeled wild-type and mutant F14Vt8 HIV-1$_{BG505}$ virus Env were prepared and imaged as previously described.[36] Briefly, peptides-tagged Envs in the context of full-length virus were constructed by introducing two labeling tag peptides (GQQQLG (SEQ ID NO: 9); GDSLDM-LEWSLM (SEQ ID NO: 10)) into variable loops V1 and V4 of gp120 subunit on both wild-type and F14Vt8 BG505 Env in the context of a replication competent clade A virus carrying the Q23 as the backbone. Wild-type and mutant BG505 virus Env for smFRET imaging was prepared by co-transfecting HEK293 cells with mixed plasmids consisting of a 40:1 ratio of replication-incompetent (RT deleted) wild-type vs. peptides-tagged HIV-$1_{BG505}$ virus Env. The viruses were harvested 40-hour post-transfection, filtered, concentrated, and labeled with donor dye Cy3B(3S)-cadaverine (0.5 μM) and acceptor dye LD650-CoA (0.5 μM, Lumidyne Technologies) in the presence of transglutaminase (0.65 μM, Sigma Aldrich) and AcpS (5 μM) at room temperature overnight. PEG2000-biotin (0.02 mg/ml, Avanti Polar Lipids) was then added to above labeling solutions the next day and incubated for 30 minutes prior to purification. Labeled viruses were further purified by ultracentrifugation at 40,000 rpm over a 6%-18% Optiprep (Sigma Aldrich) gradient for 1 hour.

Dye-labeled virus Envs were immobilized on a streptavidin-coated quartz microscopy slide for smFRET imaging. smFRET movies were acquired on a prism-based total internal reflection fluorescence microscope, and FRET traces were extracted and analyzed by using a customized software package based on LabView and Mathworks.[72] The evanescent field generated by a 532 nm CW laser (Opus, Laser Quantum) was used to excite donor dye. Fluorescence from both donor and acceptor dyes that are labeled on HIV-$1_{BG505}$ virus Env was firstly collected, then spectrally split, and later simultaneously detected by two synchronized sCMOS cameras (ORCA-Flash4.0v2, Hamamatsu). The dynamics of fluorescently labeled Env on virus was traced by monitoring fluorescence signals with 40 milliseconds time-resolution for 80 seconds in imaging buffer containing 50 mM Tris pH 7.4, 50 mM NaCl, a cocktail of triplet-state quenchers, and oxygen scavenger consisted of 2 mM protocatechuic acid with 8 nM protocatechuic-3,4-dioxygenase. In the case of ligands binding experiments, fluorescently labeled wild-type or F14Vt8 mutant virus Env was pre-incubated with 10 μg/ml sCD4D1D2-Igαtp (12×CD4) for 30 min at room temperature before imaging.

FRET (presented as efficiency/value) traces in real time were derived from fluorescence signals traces based on the equation $FRET=I_A/(\gamma I_D+I_A)$, where $I_D$ and $I_A$ are the fluorescence intensities of donor ($I_D$) and acceptor ($I_A$), and γ is the correlation ecoefficiency. FRET traces that pass through the stringent filters of signal-to-noise (S/N) ratio as well as anti-correlated features between $I_D$ and $I_A$ were used to build FRET histograms. On the basis of the observations from original FRET traces and the idealization by hidden Markov modeling, FRET histograms were further fitted into the sum of three Gaussian distributions. Relative state occupancy of each FRET state was estimated as the area under each Gaussian curve, where standard errors was calculated from thousands of individual data points that corresponds to the indicated number (N) of molecules in FRET histogram.

BIBLIOGRAPHY FOR EXAMPLES

Tran, E. E. H. et al. Structural Mechanism of Trimeric HIV-1 Envelope Glycoprotein Activation. *PLOS Pathogens* 8, e1002797, doi:10.1371/journal.ppat.1002797 (2012).

2 Ward, A. B. & Wilson, I. A. The HIV-1 envelope glycoprotein structure: nailing down a moving target. *Immunological Reviews* 275, 21-32 (2017).

3 Ward, A. B. & Wilson, I. A. Insights Into the Trimeric HIV-1 Envelope Glycoprotein Structure. *Trends in biochemical sciences* 40, 101-107, doi:10.1016/j.tibs.2014.12.006 (2015).

4 Chan, D. C. & Kim, P. S. HIV Entry and Its Inhibition. *Cell* 93, 681-684, doi:https://doi.org/10.1016/S0092-8674(00)81430-0 (1998).

5 Weissenhorn, W., Dessen, A., Harrison, S. C., Skehel, J. J. & Wiley, D. C. Atomic structure of the ectodomain from HIV-1 gp41. *Nature* 387, 426-430, doi:10.1038/387426a0 (1997).

6 Shaik, M. M. et al. Structural basis of coreceptor recognition by HIV-1 envelope spike. *Nature* 565, 318-323, doi:10.1038/s41586-018-0804-9 (2019).

7 Kwong, P. D. et al. Structure of an HIV gp120 envelope glycoprotein in complex with the CD4 receptor and a neutralizing human antibody. *Nature* 393, 648-659 (1998).

8 Harrison, S. C. Viral membrane fusion. *Nature Structural & Amp; Molecular Biology* 15, 690, doi:10.1038/nsmb.1456 (2008).

9 Sanders, R. W. et al. A Next-Generation Cleaved, Soluble HIV-1 Env Trimer, BG505 SOSIP.664 gp140, Expresses Multiple Epitopes for Broadly Neutralizing but Not Non-Neutralizing Antibodies. *PLOS Pathogens* 9, e1003618, doi:10.1371/journal.ppat.1003618 (2013).

10 de Taeye, Steven W. et al. Immunogenicity of Stabilized HIV-1 Envelope Trimers with Reduced Exposure of Non-neutralizing Epitopes. *Cell* 163, 1702-1715, doi:https://doi.org/10.1016/j.cell.2015.11.056 (2015).

11 He, L. et al. HIV-1 vaccine design through minimizing envelope metastability. *Science advances* 4, eaau6769-eaau6769, doi:10.1126/sciadv.aau6769 (2018).

12 Zhang, P. et al. Interdomain Stabilization Impairs CD4 Binding and Improves Immunogenicity of the HIV-1 Envelope Trimer. *Cell Host & Microbe* 23, 832-844.e836, doi:https://doi.org/10.1016/j.chom.2018.05.002 (2018).

13 Chuang, G.-Y. et al. Structure-Based Design of a Soluble Prefusion-Closed HIV-1 Env Trimer with Reduced CD4 Affinity and Improved Immunogenicity. *Journal of Virology* 91, doi:10.1128/JVI.02268-16 (2017).

14 Torrents de la Pena, A. et al. Improving the Immunogenicity of Native-like HIV-1 Envelope Trimers by Hyperstabilization. *Cell reports* 20, 1805-1817, doi:10.1016/j.celrep.2017.07.077 (2017).

15 Munro, J. B. & Mothes, W. Structure and Dynamics of the Native HIV-1 Env Trimer. *Journal of Virology* 89, 5752-5755 (2015).

16 Pugach, P. et al. A Native-Like SOSIP.664 Trimer Based on an HIV-1 Subtype B env Gene. *Journal of Virology* 89, 3380-3395, doi:10.1128/JVI.03473-14 (2015).

17 Munro, J. B. et al. Conformational dynamics of single HIV-1 envelope trimers on the surface of native virions. *Science* 346, 759, doi:10.1126/science.1254426 (2014).

18 Kwon, Y. D. et al. Crystal structure, conformational fixation, and entry-related interactions of mature ligand-free HIV-1 Env. *Nature structural & molecular biology* 22, 522-531, doi:10.1038/nsmb.3051 (2015).

19 Wang, H. et al. Cryo-EM structure of a CD4-bound open HIV-1 envelope trimer reveals structural rearrangements of the gp120 V1V2 loop. *Proceedings of the National Academy of Sciences* 113, E7151-E7158, doi:10.1073/pnas.1615939113 (2016).

20 Ozorowski, G. et al. Open and closed structures reveal allostery and pliability in the HIV-1 envelope spike. *Nature* 547, 360-363, doi:10.1038/nature23010

21 Pancera, M. et al. Structure of HIV-1 gp120 with gp41-interactive region reveals layered envelope architecture and basis of conformational mobility. *Proceedings of the National Academy of Sciences* 107, 1166, doi:10.1073/pnas.0911004107 (2010).

22 Finzi, A. et al. Topological Layers in the HIV-1 gp120 Inner Domain Regulate gp41 Interaction and CD4-Triggered Conformational Transitions. *Molecular cell* 37, 656-667, doi:10.1016/j.molcel.2010.02.012 (2010).

23 Herschhorn, A. et al. The β20-β21 of gp120 is a regulatory switch for HIV-1 Env conformational transitions. *Nature Communications* 8, 1049, doi:10.1038/s41467-017-01119-w (2017).

24 Wang, H., Barnes, C. O., Yang, Z., Nussenzweig, M. C. & Bjorkman, P. J. Partially Open HIV-1 Envelope Structures Exhibit Conformational Changes Relevant for Coreceptor Binding and Fusion. *Cell Host & Microbe* 24, 579-592.e574, doi:https://doi.org/10.1016/j.chom.2018.09.003 (2018).

25 Meanwell, N. A. et al. Inhibitors of HIV-1 Attachment: The Discovery and Development of Temsavir and its Prodrug Fostemsavir. *Journal of Medicinal Chemistry* 61, 62-80, doi:10.1021/acs.jmedchem.7b01337 (2018).

26 Pancera, M. et al. Crystal structures of trimeric HIV envelope with entry inhibitors BMS-378806 and BMS-626529. *Nature Chemical Biology* 13, 1115, doi:10.1038/nchembio.2460 https://www.nature.com/articles/nchembio.2460#supplementary-information (2017).

27 Zolla-Pazner, S. et al. Structure/Function Studies Involving the V3 Region of the HIV-1 Envelope Delineate Multiple Factors That Affect Neutralization Sensitivity. *Journal of virology* 90, 636-649, doi:10.1128/JVI.01645-15 (2015).

28 Kulp, D. W. et al. Structure-based design of native-like HIV-1 envelope trimers to silence non-neutralizing epitopes and eliminate CD4 binding. *Nature Communications* 8, 1655, doi:10.1038/s41467-017-01549-6 (2017).

29 Punjani, A., Rubinstein, J. L., Fleet, D. J. & Brubaker, M. A. cryoSPARC: algorithms for rapid unsupervised cryo-EM structure determination. *Nature Methods* 14, 290, doi:10.1038/nmeth.4169 https://www.nature.com/articles/nmeth.4169#supplementary-information (2017).

30 Lemmin, T., Soto, C., Stuckey, J. & Kwong, P. D. Microsecond Dynamics and Network Analysis of the HIV-1 SOSIP Env Trimer Reveal Collective Behavior and Conserved Microdomains of the Glycan Shield. *Structure* 25, 1631-1639.e1632, doi:10.1016/j.str.2017.07.018 (2017).

31 Garces, F. et al. Affinity Maturation of a Potent Family of HIV Antibodies Is Primarily Focused on Accommodating or Avoiding Glycans. *Immunity* 43, 1053-1063, doi:10.1016/j.immuni.2015.11.007 (2015).

32 Xu, K. et al. Epitope-based vaccine design yields fusion peptide-directed antibodies that neutralize diverse strains of HIV-1. *Nature Medicine* 24, 857-867, doi:10.1038/s41591-018-0042-6 (2018).

33 Gardner, M. R. et al. AAV-expressed eCD4-Ig provides durable protection from multiple SHIV challenges. *Nature* 519, 87-91, doi:10.1038/nature14264 (2015).

34 Huang, J. et al. Identification of a CD4-Binding-Site Antibody to HIV that Evolved Near-Pan Neutralization Breadth. *Immunity* 45, 1108-1121, doi:10.1016/j.immuni.2016.10.027 (2016).

35 Ma, X. et al. HIV-1 Env trimer opens through an asymmetric intermediate in which individual protomers adopt distinct conformations. *eLife* 7, e34271, doi:10.7554/eLife.34271 (2018).

36 Lu, M. et al. Associating HIV-1 envelope glycoprotein structures with states on the virus observed by smFRET. *Nature* 568, 415-419, doi:10.1038/s41586-019-1101-y (2019).

37 Rantalainen, K. et al. Co-evolution of HIV Envelope and Apex-Targeting Neutralizing Antibody Lineage Provides Benchmarks for Vaccine Design. *Cell Reports* 23, 3249-3261, doi:https://doi.org/10.1016/j.celrep.2018.05.046 (2018).

38 Liu, J., Bartesaghi, A., Borgnia, M. J., Sapiro, G. & Subramaniam, S. Molecular architecture of native HIV-1 gp120 trimers. *Nature* 455, 109-113, doi:10.1038/nature07159 (2008).

39 Powell, R. L. R. et al. Plasticity and Epitope Exposure of the HIV-1 Envelope Trimer. *Journal of Virology* 91, e00410-00417, doi:10.1128/JVI.00410-17 (2017).

40 Cao, J. et al. Effects of amino acid changes in the extracellular domain of the human immunodeficiency virus type 1 gp41 envelope glycoprotein. *Journal of virology* 67, 2747-2755 (1993).

41 Mo, H. et al. Conserved residues in the coiled-coil pocket of human immunodeficiency virus type 1 gp41 are essential for viral replication and interhelical interaction. *Virology* 329, 319-327, doi:https://doi.org/10.1016/j.virol.2004.08.025 (2004).

42 Liu, Q. et al. Quaternary contact in the initial interaction of CD4 with the HIV-1 envelope trimer. *Nature Structural & Amp; Molecular Biology* 24, 370, doi:10.1038/nsmb.3382 https://www.nature.com/articles/nsmb.3382#supplementary-information (2017).

43 Saunders, K. O. et al. Vaccine Elicitation of High Mannose-Dependent Neutralizing Antibodies against the V3-Glycan Broadly Neutralizing Epitope in Nonhuman Primates. *Cell Reports* 18, 2175-2188, doi:https://doi.org/10.1016/j.celrep.2017.02.003 (2017).

44 Saunders, K. O. et al. Vaccine Induction of Heterologous Tier 2 HIV-1 Neutralizing Antibodies in Animal Models. *Cell Reports* 21, 3681-3690, doi:https://doi.org/10.1016/j.celrep.2017.12.028 (2017).

45 Grant, T. & Grigorieff, N. Measuring the optimal exposure for single particle cryo-EM using a 2.6 Å reconstruction of rotavirus VP6. *eLife* 4, e06980, doi:10.7554/eLife.06980 (2015).

46 Rohou, A. & Grigorieff, N. CTFFIND4: Fast and accurate defocus estimation from electron micrographs. *Journal of Structural Biology* 192, 216-221, doi:https://doi.org/10.1016/j.jsb.2015.08.008 (2015).

47 Grant, T., Rohou, A. & Grigorieff, N. cisTEM, user-friendly software for single-particle image processing. *eLife* 7, e35383, doi:10.7554/eLife.35383 (2018).

48 Tang, G. et al. EMAN2: An extensible image processing suite for electron microscopy. *Journal of Structural Biology* 157, 38-46, doi:http://dx.doi.org/10.1016/j.jsb.2006.05.009 (2007).

49 Bartesaghi, A. et al. Atomic Resolution Cryo-EM Structure of β-Galactosidase. *Structure* 26, 848-856.e843, doi:https://doi.org/10.1016/j.str.2018.04.004 (2018).

50 Pettersen, E. F. et al. UCSF Chimera—A visualization system for exploratory research and analysis. *Journal of Computational Chemistry* 25, 1605-1612, doi:10.1002/jcc.20084 (2004).
51 Wang, R. Y.-R. et al. Automated structure refinement of macromolecular assemblies from cryo-EM maps using Rosetta. *eLife* 5, e17219, doi:10.7554/eLife.17219 (2016).
52 —Features and development of Coot.—*Acta crystallographica. Section D, Biological crystallography* —66, -486-501, doi:-(2010).
53 Afonine, P. V. et al. Real-space refinement in PHENIX for cryo-EM and crystallography. *Acta Crystallographica Section D* 74, 531-544, doi:10.1107/S2059798318006551 (2018).
54 Chen, V. B. et al. MolProbity: all-atom structure validation for macromolecular crystallography. *Acta Crystallogr D Biol Crystallogr* 66, 12-21, doi:10.1107/S0907444909042073 (2010).
55 Barad, B. A. et al. EMRinger: side chain-directed model and map validation for 3D cryo-electron microscopy. *Nature Methods* 12, 943, doi:10.1038/nmeth.3541 https://www.nature.com/articles/nmeth.3541#supplementary-information (2015).
56 Schrodinger, L. The PyMOL Molecular Graphics System. (2015).
57 Pancera, M. et al. Structure and immune recognition of trimeric pre-fusion HIV-1 Env. *Nature* 514, 455, doi:10.1038/nature13808 https://www.nature.com/articles/nature13808#supplementary-information (2014).
58 Lee, Jeong H., de Val, N., Lyumkis, D. & Ward, Andrew B. Model Building and Refinement of a Natively Glycosylated HIV-1 Env Protein by High-Resolution Cryoelectron Microscopy. *Structure* 23, 1943-1951, doi:https://doi.org/10.1016/j.str.2015.07.020 (2015).
59 Scharf, L. et al. Broadly Neutralizing Antibody 8ANC195 Recognizes Closed and Open States of HIV-1 Env. *Cell* 162, 1379-1390, doi:https://doi.org/10.1016/j.cell.2015.08.035 (2015).
60 Jardine, J. G. et al. Minimally Mutated HIV-1 Broadly Neutralizing Antibodies to Guide Reductionist Vaccine Design. *PLOS Pathogens* 12, e1005815, doi:10.1371/journal.ppat.1005815 (2016).
61 Stewart-Jones, Guillaume B. E. et al. Trimeric HIV-1-Env Structures Define Glycan Shields from Clades A, B, and G. *Cell* 165, 813-826, doi:10.1016/j.cell.2016.04.010.
62 Gristick, H. B. et al. Natively glycosylated HIV-1 Env structure reveals new mode for antibody recognition of the CD4-binding site. *Nature Structural & Amp; Molecular Biology* 23, 906, doi:10.1038/nsmb.3291 https://www.nature.com/articles/nsmb.3291#supplementary-information (2016).
63 Zhou, T. et al. Quantification of the Impact of the HIV-1-Glycan Shield on Antibody Elicitation. *Cell Reports* 19, 719-732, doi:https://doi.org/10.1016/j.celrep.2017.04.013 (2017).
64 Lee, J. H. et al. A Broadly Neutralizing Antibody Targets the Dynamic HIV Envelope Trimer Apex via a Long, Rigidified, and Anionic β-Hairpin Structure. *Immunity* 46, 690-702, doi:https://doi.org/10.1016/j.immuni.2017.03.017 (2017).
65 Barnes, C. O. et al. Structural characterization of a highly-potent V3-glycan broadly neutralizing antibody bound to natively-glycosylated HIV-1 envelope. *Nature Communications* 9, 1251, doi:10.1038/s41467-018-03632-y (2018).
66 Dingens, A. S. et al. Complete functional mapping of infection- and vaccine-elicited antibodies against the fusion peptide of HIV. *PLOS Pathogens* 14, e1007159, doi:10.1371/journal.ppat.1007159 (2018).
67 Tria, G., Mertens, H. D. T., Kachala, M. & Svergun, D. I. Advanced ensemble modelling of flexible macromolecules using X-ray solution scattering. *IUCrJ* 2, 207-217, doi:doi:10.1107/S205225251500202X (2015).
68 Lee, J. H., Ozorowski, G. & Ward, A. B. Cryo-EM structure of a native, fully glycosylated, cleaved HIV-1 envelope trimer. *Science* 351, 1043, doi:10.1126/science.aad2450 (2016).
69 Cao, L. et al. Differential processing of HIV envelope glycans on the virus and soluble recombinant trimer. *Nature Communications* 9, 3693, doi:10.1038/s41467-018-06121-4 (2018).
70 Humphrey, W., Dalke, A. & Schulten, K. VMD: Visual molecular dynamics. *Journal of Molecular Graphics* 14, 33-38, doi:https://doi.org/10.1016/0263-7855(96)00018-5 (1996).
71 Team, R. C. R: A Language and Environment for Statistical Computing. (2017).
72 Juette, M. F. et al. Single-molecule imaging of non-equilibrium molecular ensembles on the millisecond timescale. *Nature methods* 13, 341-344, doi:10.1038/nmeth.3769 (2016).

What is claimed is:

1. A modified recombinant HIV-1 envelope comprising a valine to isoleucine mutation at amino acid position 68, an alanine to valine mutation at amino acid position 204, a valine to leucine mutation at amino acid position 208, and a valine to leucine mutation at amino acid position 255, wherein the amino acid positions refer to HXB2 numbering in an unmodified HIV-1 envelope.

2. The modified recombinant HIV-1 envelope of claim 1, wherein the modified recombinant HIV-1 envelope is a gp120 envelope, a gp140 envelope, or a gp160 envelope.

3. The modified recombinant HIV-1 envelope of claim 1, further comprising a threonine to methionine mutation at amino acid position 320, a glutamine to methionine mutation at amino acid position 422, a glutamine to methionine mutation at amino acid position 203, an asparagine to leucine mutation at amino acid position 302, and an asparagine to leucine mutation at amino acid position 300, wherein the amino acid positions refer to HXB2 numbering in an unmodified HIV-1 envelope.

4. The modified recombinant HIV-1 envelope of claim 1 or 3, wherein the unmodified HIV-1 envelope is an envelope selected from: CH505 M5G458mut envelope, BG505, CONs, JRFL, CH505 T/F, w.53., CH505 M5, CH505 M11, CH848 10.17 DT, or 19CV3.

5. The modified recombinant HIV-1 envelope of claim 1, wherein the modified recombinant HIV-1 envelope further comprises additional stabilizing mutations selected from the group consisting of: a valine to tryptophan mutation at amino acid position 255 and an asparagine to leucine mutation at amino acid position 377, wherein the amino acid positions refer to HXB2 numbering in an unmodified HIV-1 envelope.

6. The modified recombinant HIV-1 envelope of claim 1, wherein the modified recombinant HIV-1 envelope is a CH505 M5G458mut envelope comprising the amino acid sequence of SEQ ID NO: 51.

7. An immunogenic composition comprising:
the modified recombinant HIV-1 envelope according to any of claims 1, 3, or 4 and a carrier.

8. The immunogenic composition of claim 7 further comprising an adjuvant.

9. The immunogenic composition of claim 7, wherein the modified recombinant HIV-1 envelope is comprised in a nanoparticle.

10. A method of inducing an immune response in a subject, the method comprising administering the immunogenic composition of claim 7.

11. The immunogenic composition of claim 8, wherein the modified recombinant HIV-1 envelope is comprised in a nanoparticle.

12. A method of inducing an immune response in a subject, the method comprising administering the immunogenic composition of claim 8.

* * * * *